(12) United States Patent
Borgman et al.

(10) Patent No.: US 11,540,964 B2
(45) Date of Patent: Jan. 3, 2023

(54) PATIENT SUPPORT SURFACE CONTROL, END OF LIFE INDICATION, AND X-RAY CASSETTE SLEEVE

(71) Applicant: Hill-Rom Services, Inc., Batesville, IN (US)

(72) Inventors: Darrell L. Borgman, Batesville, IN (US); Douglas E. Borgman, Brookville, IN (US); Arpit Shah, Batesville, IN (US); Wui Hsien Wong, Singapore (SG); Keith Moores, Milan, IN (US); Jason M. Gilreath, Cincinnati, OH (US); Michael R. Montini, Batesville, IN (US); Charles A. Lachenbruch, Batesville, IN (US); Eric R. Meyer, Batesville, IN (US); Frank E. Sauser, Cincinnati, OH (US); Catherine M. Wagner, Osgood, IN (US); Rachel L. Williamson, Batesville, IN (US); Brandon P. Fisk, Brookville, IN (US); Jason B. Grace, Cincinnati, OH (US); Brian Guthrie, Greensburg, IN (US);
(Continued)

(73) Assignee: Hill-Rom Services, Inc., Batesville, IN (US)

( * ) Notice: Subject to any disclaimer, the term of this patent is extended or adjusted under 35 U.S.C. 154(b) by 866 days.

(21) Appl. No.: 16/285,608

(22) Filed: Feb. 26, 2019

(65) Prior Publication Data
US 2019/0262201 A1    Aug. 29, 2019

Related U.S. Application Data

(60) Provisional application No. 62/635,749, filed on Feb. 27, 2018, provisional application No. 62/667,769,
(Continued)

(51) Int. Cl.
*A61G 7/057*  (2006.01)
*A47C 21/04*  (2006.01)
(Continued)

(52) U.S. Cl.
CPC ........ *A61G 7/05784* (2016.11); *A47C 21/042* (2013.01); *A61B 6/0407* (2013.01);
(Continued)

(58) Field of Classification Search
CPC ............ A61G 7/05784; A61G 7/05769; A61G 7/015; A61G 7/018; A47C 21/042
See application file for complete search history.

(56) References Cited

U.S. PATENT DOCUMENTS

| | | |
|---|---|---|
| 1,332,933 A | 3/1920 | Sylvester |
| 2,886,834 A | 5/1959 | Gilbertson |

(Continued)

FOREIGN PATENT DOCUMENTS

| | | |
|---|---|---|
| CN | 1146329 A | 4/1997 |
| CN | 102497844 A | 6/2012 |

(Continued)

OTHER PUBLICATIONS

Decision of Dismissal of Amendment from corresponding Japanese Appln. No. 2019-032881, dated Jan. 6, 2021 (English translation included).
(Continued)

*Primary Examiner* — Peter M. Cuomo
*Assistant Examiner* — Adam C Ortiz
(74) *Attorney, Agent, or Firm* — Barnes & Thornburg LLP

(57) ABSTRACT

A patient support apparatus may include a support surface configured to conduct air along a top face of the support surface so that heat and moisture from a patient lying on the
(Continued)

support surface are drawn away from the top face of the support surface. An opening may be formed in a side of the support surface. A cavity may extend from the opening into the support surface. An inlet port may be positioned within the cavity and fluidly coupled to the top face. A blower assembly may be configured to position within the cavity. The blower assembly may have an outlet port that couples to the inlet port when the blower assembly is positioned within the cavity. The blower assembly may conduct air through the inlet port to the top face of the support surface.

17 Claims, 66 Drawing Sheets

(72) Inventors: Nicole Johannigman, Greensburg, IN (US); Gregory J. Shannon, Indianapolis, IN (US); David C. Newkirk, Lawrenceburg, IN (US); Michael Churilla, Harrison, OH (US); Jnanesha Ramegowda, Batesville, IN (US);Taylor Franklin, Batesville, IN (US); Kathryn R. Smith, Batesville, IN (US); John G. Byers, Batesville, IN (US); Frederick K. Schultz, Bringhurst, IN (US); Andrew R. Wager, Indianapolis, IN (US); Sridhar Karimpuzha Seshadri, Blue Ash, OH (US); Gary R. Gibbons, Batesville, IN (US); Scott M. Corbin, Sunman, IN (US); John Goewert, Batesville, IN (US); Thomas L. Simpson, Brookville, IN (US); Faron L. Blessing, Batesville, IN (US); James D. Voll, Columbus, IN (US); Kin Meng Choi, Batesville, IN (US); Stephen S. Amrhein, Batesville, IN (US); Herve Gautier, Plumergat (FR); Jean-Francois Lellig, Auray (FR); Philippe Kaikenger, Pluvigner (FR); Matthieu Guetta, St. Pierre Quiberon (FR)

Related U.S. Application Data filed on May 7, 2018, provisional application No. 62/793,668, filed on Jan. 17, 2019.

(51) Int. Cl.
| | | |
|---|---|---|
| *A61G 7/018* | (2006.01) | |
| *A61G 7/075* | (2006.01) | |
| *A61B 6/00* | (2006.01) | |
| *A61B 6/04* | (2006.01) | |
| *G01T 1/16* | (2006.01) | |
| *A61G 7/015* | (2006.01) | |

(52) U.S. Cl.
CPC .......... *A61B 6/4283* (2013.01); *A61B 6/4423* (2013.01); *A61G 7/018* (2013.01); *A61G 7/05769* (2013.01); *A61G 7/05792* (2016.11); *A61G 7/0755* (2013.01); *G01T 1/16* (2013.01); *A61G 7/015* (2013.01); *A61G 2210/50* (2013.01); *A61G 2210/70* (2013.01)

(56) References Cited

U.S. PATENT DOCUMENTS

| | | |
|---|---|---|
| 3,551,923 A | 1/1971 | Franklin |
| 3,639,927 A | 2/1972 | Munch |
| 3,742,528 A | 7/1973 | Muench |
| 3,864,766 A | 2/1975 | Prete |
| 4,114,230 A | 9/1978 | MacFarland |
| 4,127,906 A | 12/1978 | Zur |
| 4,156,145 A | 5/1979 | Weatherholt |
| 4,169,295 A | 10/1979 | Darling |
| 4,306,322 A | 12/1981 | Young et al. |
| 4,644,597 A | 2/1987 | Walker |
| 4,665,573 A | 5/1987 | Fiore |
| 4,665,574 A | 5/1987 | Filips et al. |
| 4,679,264 A | 7/1987 | Mollura |
| 4,688,283 A | 8/1987 | Jacobson et al. |
| 4,706,313 A | 11/1987 | Murphy |
| 4,724,560 A | 2/1988 | Christie |
| 4,766,628 A | 8/1988 | Walker |
| 4,788,729 A | 12/1988 | Walker |
| 4,803,744 A | 2/1989 | Peck et al. |
| 4,807,313 A | 2/1989 | Ryder et al. |
| 4,839,512 A | 6/1989 | Speck |
| 4,843,663 A | 7/1989 | Horvat et al. |
| 4,893,323 A | 1/1990 | Cook |
| 4,914,762 A | 4/1990 | Perali et al. |
| 4,953,247 A | 9/1990 | Hasty |
| 4,962,552 A | 10/1990 | Hasty |
| 4,982,466 A | 1/1991 | Higgins et al. |
| 4,995,124 A | 2/1991 | Wridge et al. |
| 5,016,268 A | 5/1991 | Lotman |
| 5,060,174 A | 10/1991 | Gross |
| 5,097,552 A | 3/1992 | Viesturs |
| 5,117,518 A | 6/1992 | Schild |
| 5,142,717 A | 9/1992 | Everard et al. |
| 5,144,708 A | 9/1992 | Pekar |
| 5,161,271 A | 11/1992 | Gronbach |
| 5,180,619 A | 1/1993 | Landi et al. |
| 5,243,722 A | 9/1993 | Gusakov |
| 5,249,319 A | 10/1993 | Higgs |
| 5,269,030 A | 12/1993 | Pahno et al. |
| 5,323,500 A | 6/1994 | Roe et al. |
| 5,325,551 A | 7/1994 | Tappel et al. |
| 5,444,881 A | 8/1995 | Landi et al. |
| 5,450,638 A | 9/1995 | Johnson |
| 5,469,592 A | 11/1995 | Johnson |
| 5,471,687 A | 12/1995 | Vierra |
| 5,473,783 A | 12/1995 | Allen |
| 5,539,942 A | 7/1996 | Melou |
| 5,596,781 A | 1/1997 | Graebe |
| 5,634,224 A | 6/1997 | Gates |
| 5,638,565 A | 6/1997 | Pekar |
| 5,652,985 A | 8/1997 | Wilkinson et al. |
| 5,689,845 A | 11/1997 | Sobieralski |
| 5,731,062 A | 3/1998 | Kim et al. |
| 5,774,917 A | 7/1998 | Liu |
| 5,802,646 A | 9/1998 | Stolpmann et al. |
| 5,817,391 A | 10/1998 | Rock et al. |
| 5,833,321 A | 11/1998 | Kim et al. |
| 5,840,400 A | 11/1998 | Landi et al. |
| 5,845,352 A | 12/1998 | Matsler et al. |
| 5,851,930 A | 12/1998 | Bessey et al. |
| 5,870,785 A | 2/1999 | Hoorens |
| 5,873,137 A | 2/1999 | Yavets-Chen |
| 5,882,322 A | 3/1999 | Kim et al. |
| 5,896,680 A | 4/1999 | Kim et al. |
| 5,917,180 A | 6/1999 | Reimer et al. |
| 5,918,336 A | 7/1999 | Lee et al. |
| 5,926,884 A | 7/1999 | Biggie et al. |
| D412,685 S | 8/1999 | Bar et al. |
| 5,954,402 A | 9/1999 | McInturff |
| 5,970,789 A | 10/1999 | Meyer et al. |
| 5,972,477 A | 10/1999 | Kim et al. |
| 5,984,418 A | 11/1999 | McInturff |
| 6,014,346 A | 1/2000 | Malone |
| 6,085,369 A | 7/2000 | Feher |
| 6,095,611 A | 8/2000 | Bar et al. |
| 6,145,142 A | 11/2000 | Rechin et al. |
| 6,165,142 A | 12/2000 | Bar |
| 6,182,315 B1 | 2/2001 | Lee |
| 6,202,239 B1 | 3/2001 | Ward et al. |
| 6,212,718 B1* | 4/2001 | Stolpmann .......... A61G 7/05776 285/914 |
| 6,223,369 B1 | 5/2001 | Maier et al. |

(56) References Cited

U.S. PATENT DOCUMENTS

| | | |
|---|---|---|
| 6,269,504 B1 | 8/2001 | Romano et al. |
| 6,286,167 B1 | 9/2001 | Stolpmann |
| 6,306,483 B1 | 10/2001 | Bessey et al. |
| 6,337,836 B1 | 1/2002 | Eidelson |
| 6,378,948 B1 | 4/2002 | Macher et al. |
| 6,398,409 B1 | 6/2002 | Brooks |
| 6,403,196 B1 | 6/2002 | Bessey et al. |
| 6,430,766 B1 | 8/2002 | Henley et al. |
| 6,463,610 B1 | 10/2002 | Shulte et al. |
| 6,474,743 B1 | 11/2002 | Harker et al. |
| 6,487,739 B1 | 12/2002 | Harker |
| 6,560,804 B2 | 5/2003 | Wise et al. |
| 6,564,410 B2 | 5/2003 | Graebe et al. |
| 6,568,273 B2 | 5/2003 | Reimer |
| 6,584,628 B1 | 7/2003 | Kummer et al. |
| 6,623,080 B2 | 9/2003 | Clapper |
| 6,646,556 B1 | 11/2003 | Smith et al. |
| 6,652,140 B1 | 11/2003 | Taber et al. |
| 6,687,936 B2 | 2/2004 | Graebe et al. |
| 6,782,574 B2 | 8/2004 | Totton et al. |
| 6,893,156 B2 | 5/2005 | Sharpensteen et al. |
| 7,065,816 B2 | 6/2006 | McGettigan |
| 7,100,978 B2 | 9/2006 | Ekern et al. |
| 7,469,432 B2 | 12/2008 | Chambers |
| 7,523,515 B2 | 4/2009 | Allen et al. |
| 7,652,581 B2 | 1/2010 | Gentry et al. |
| 7,712,164 B2 | 5/2010 | Chambers |
| 7,731,423 B2 | 6/2010 | Caminade et al. |
| 8,286,282 B2 | 10/2012 | Kummer et al. |
| 8,531,307 B2 * | 9/2013 | Lachenbruch ..... A61G 7/05784 340/665 |
| 8,595,873 B2 | 12/2013 | Hornbach et al. |
| 8,856,993 B2 | 10/2014 | Richards et al. |
| 8,918,930 B2 | 12/2014 | Stroh et al. |
| 8,939,379 B2 | 1/2015 | Myers et al. |
| 9,030,331 B2 | 5/2015 | Lachenbruch |
| 9,131,780 B2 | 9/2015 | Lachenbruch et al. |
| 9,131,781 B2 | 9/2015 | Zaiss et al. |
| 9,138,064 B2 | 9/2015 | Tursi, Jr. et al. |
| 9,233,038 B2 | 1/2016 | Gibson et al. |
| 9,254,231 B2 | 2/2016 | Vrzalik et al. |
| 9,326,903 B2 | 5/2016 | Locke |
| 9,392,875 B2 | 7/2016 | Weyl |
| 9,433,300 B2 | 9/2016 | Gibson et al. |
| 9,462,893 B2 | 10/2016 | Romano et al. |
| 9,504,620 B2 | 11/2016 | Soltani et al. |
| 9,773,436 B2 | 9/2017 | Myers et al. |
| 9,835,344 B2 | 12/2017 | Vrzalik et al. |
| 9,907,719 B2 | 3/2018 | Stiff |
| 10,172,470 B1 | 1/2019 | Vrzalik et al. |
| 2002/0116766 A1 | 8/2002 | Stolpmann |
| 2003/0029062 A1 | 2/2003 | Esterman |
| 2003/0115672 A1 | 6/2003 | Newkirk |
| 2004/0031103 A1 | 2/2004 | Wyatt et al. |
| 2004/0141589 A1 | 7/2004 | Sharpensteen et al. |
| 2004/0261183 A1 | 12/2004 | Tsai |
| 2005/0086739 A1 | 4/2005 | Wu |
| 2005/0273941 A1 | 12/2005 | Stolpmann et al. |
| 2006/0271011 A1 * | 11/2006 | Mock ................ A61M 15/0075 604/500 |
| 2007/0091726 A1 | 4/2007 | Stauffer et al. |
| 2007/0101499 A1 | 5/2007 | Kobuss et al. |
| 2008/0095322 A1 | 4/2008 | Caminade et al. |
| 2009/0222996 A1 | 9/2009 | Balonick et al. |
| 2010/0071127 A1 | 3/2010 | Koger et al. |
| 2010/0072097 A1 | 3/2010 | Khan |
| 2010/0095461 A1 | 4/2010 | Romano et al. |
| 2010/0122417 A1 | 5/2010 | Vrzalik et al. |
| 2011/0047710 A1 | 3/2011 | Beard |
| 2011/0173756 A1 | 7/2011 | Chung et al. |
| 2011/0219548 A1 | 9/2011 | Vrzalik et al. |
| 2012/0078421 A1 | 3/2012 | Shaw |
| 2012/0317713 A1 | 12/2012 | Eytan et al. |
| 2013/0219627 A1 | 8/2013 | Myers |
| 2014/0201919 A1 | 7/2014 | Albero et al. |
| 2014/0023771 A1 | 8/2014 | Prakash et al. |
| 2014/0237719 A1 | 8/2014 | Brykalski et al. |
| 2015/0121625 A1 * | 5/2015 | Myers ....................... G09F 3/00 5/636 |
| 2015/0296992 A1 | 10/2015 | Ghanei et al. |
| 2016/0196403 A1 | 7/2016 | Jellum |
| 2017/0252245 A1 | 9/2017 | O'Reagan |

FOREIGN PATENT DOCUMENTS

| | | |
|---|---|---|
| DE | 29502025 U1 | 6/1996 |
| DE | 10316162 A1 | 10/2004 |
| DE | 10333742 A1 | 2/2005 |
| EP | 853918 A2 | 7/1998 |
| EP | 1915948 A2 | 4/2008 |
| EP | 2520200 A1 | 11/2012 |
| GB | 2473661 A | 3/2011 |
| JP | S59-178869 | 11/1984 |
| JP | H01-500488 A | 10/1993 |
| JP | H07-508446 A | 10/1993 |
| JP | 2002055074 A | 2/2002 |
| JP | 2004144454 A | 5/2004 |
| JP | 3113107 | 9/2005 |
| JP | 2007175476 A | 7/2007 |
| JP | 2001517491 B2 | 4/2009 |
| JP | 2007525266 B2 | 1/2010 |
| JP | 2008114061 B2 | 6/2010 |
| JP | 2003527205 B2 | 10/2012 |
| JP | 2013-526972 | 6/2013 |
| JP | 2015-504741 | 2/2015 |
| JP | 2011067626 B2 | 5/2015 |
| JP | S58-073403 B2 | 3/2016 |
| WO | 9602167 A1 | 2/1996 |
| WO | 03041538 A1 | 5/2003 |
| WO | 2009071614 A1 | 6/2009 |
| WO | 2011026040 A1 | 3/2011 |
| WO | 2016059116 A1 | 4/2016 |

OTHER PUBLICATIONS

Australian Examination Report No. 1 for Application No. 2019201323, dated Aug. 14, 2019, 5 pages.
European Office Action for Application No. 19159476.1, dated Apr. 21, 2021, 18 pages.
Chinese Office Action for Application No. 201910147457.8, dated Aug. 5, 2020, 10 pages.
Extended European Search Report for Application No. 19159476.1, dated Sep. 26, 2019, 12 pages.
Partial European Search Report for Application No. 19159476.1, dated Jul. 18, 2019, 13 pages.
Office Action from corresponding Chinese Appln. No. 201910147457.8, dated Feb. 9, 2021 (English translation included).
Japanese Office Action for Application No. 2019-032881, dated Oct. 13, 2020, 3 pages.

* cited by examiner

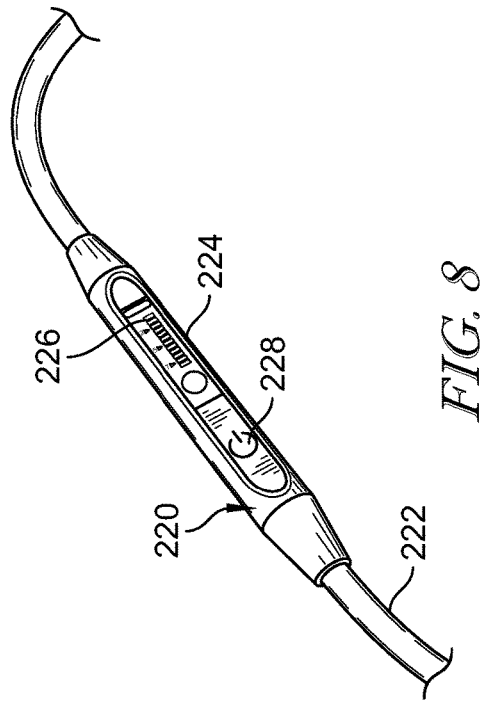
FIG. 7
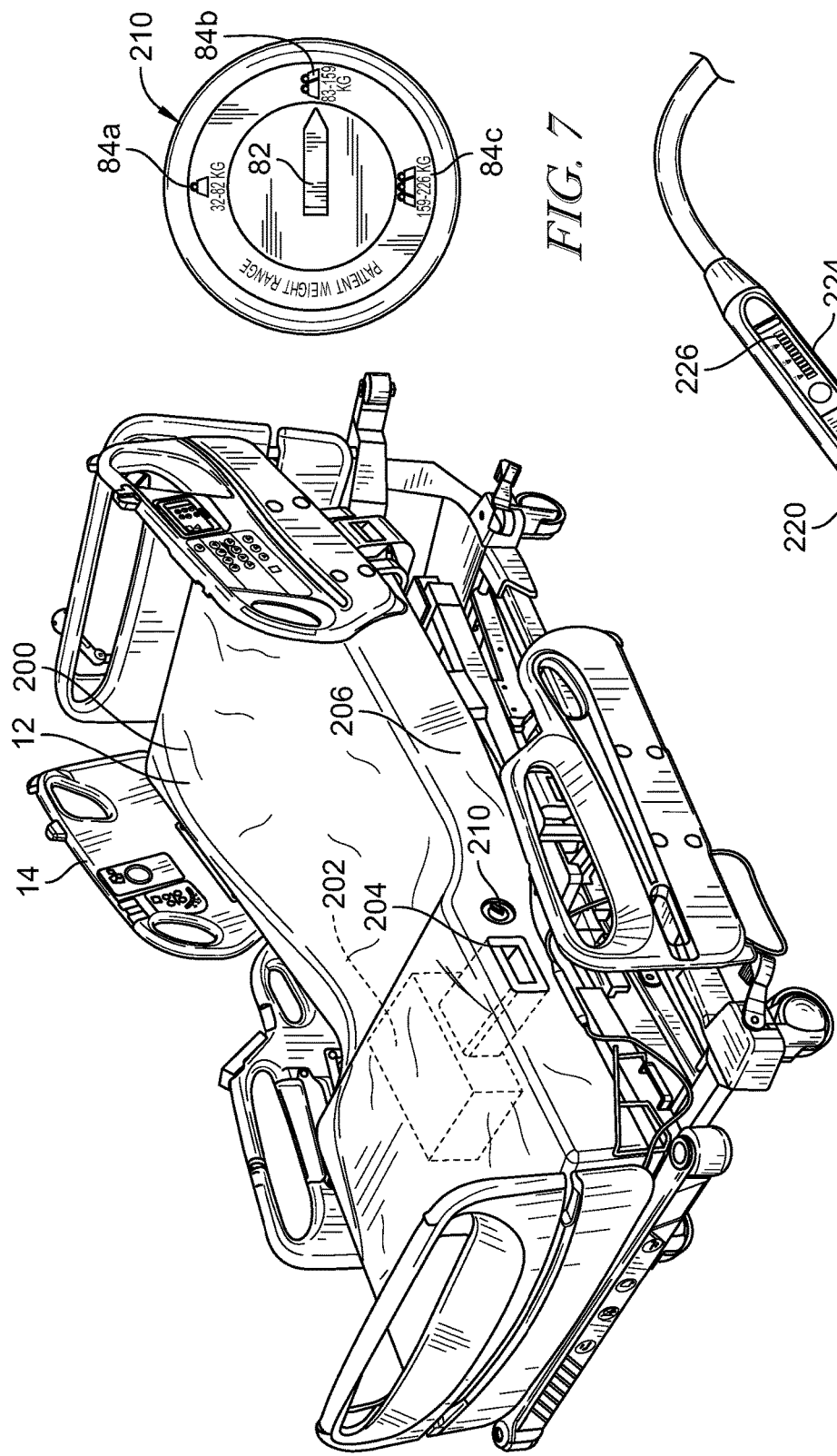
FIG. 8
FIG. 6

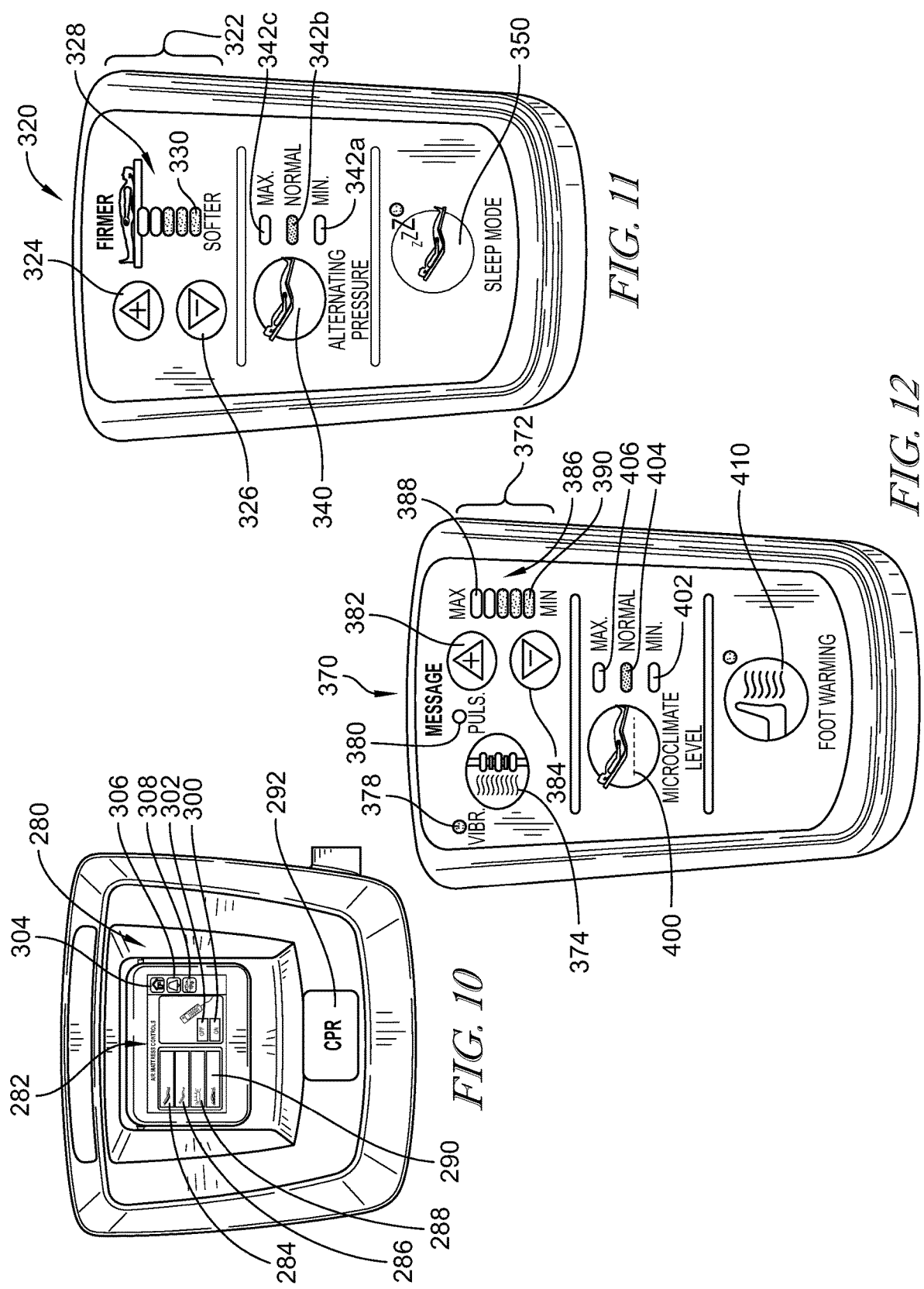

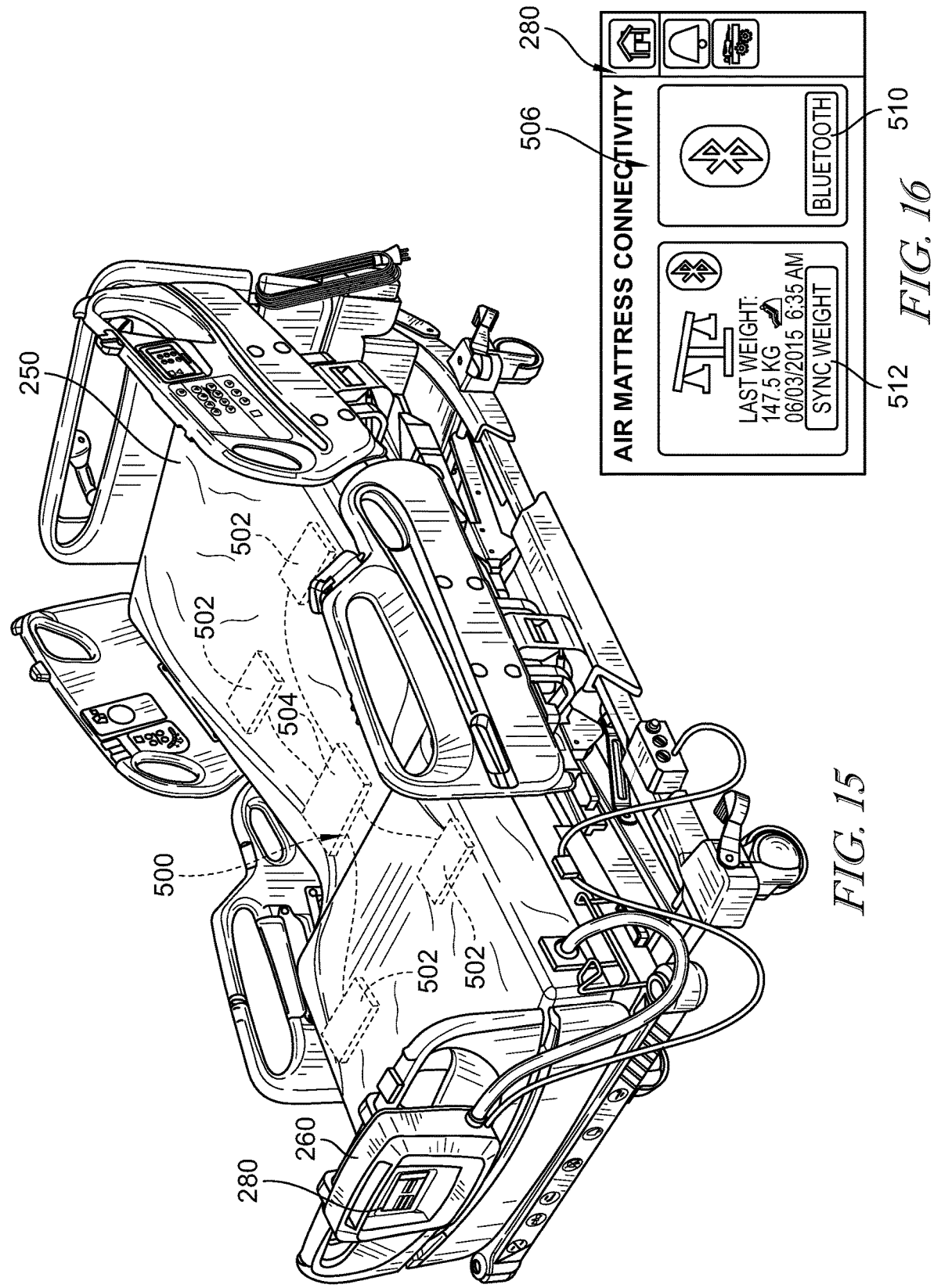

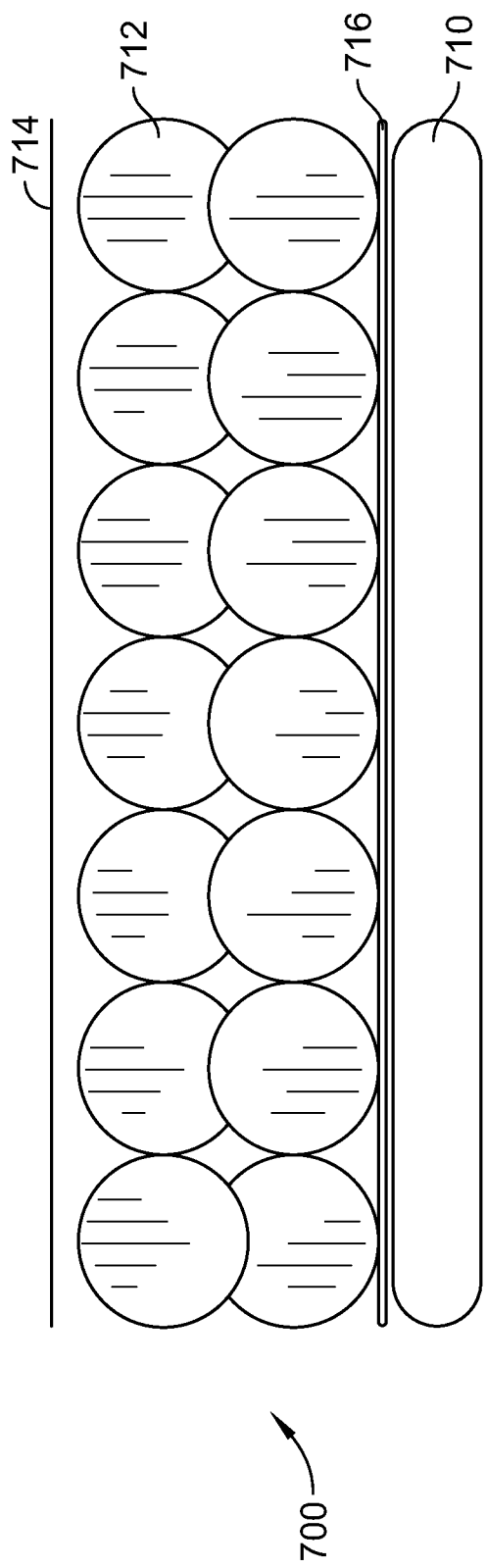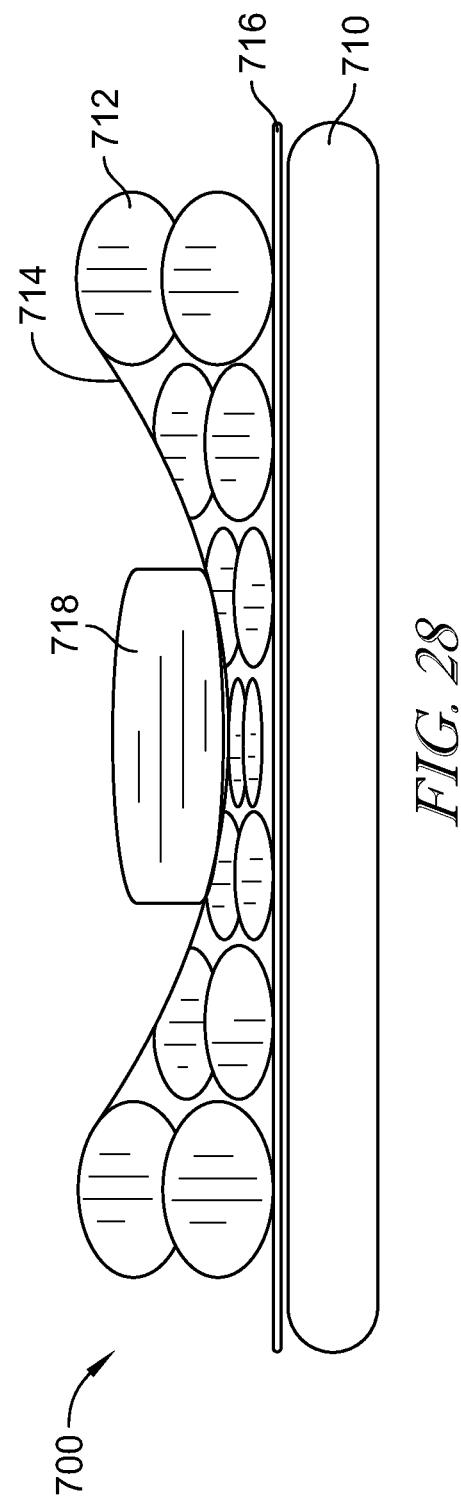

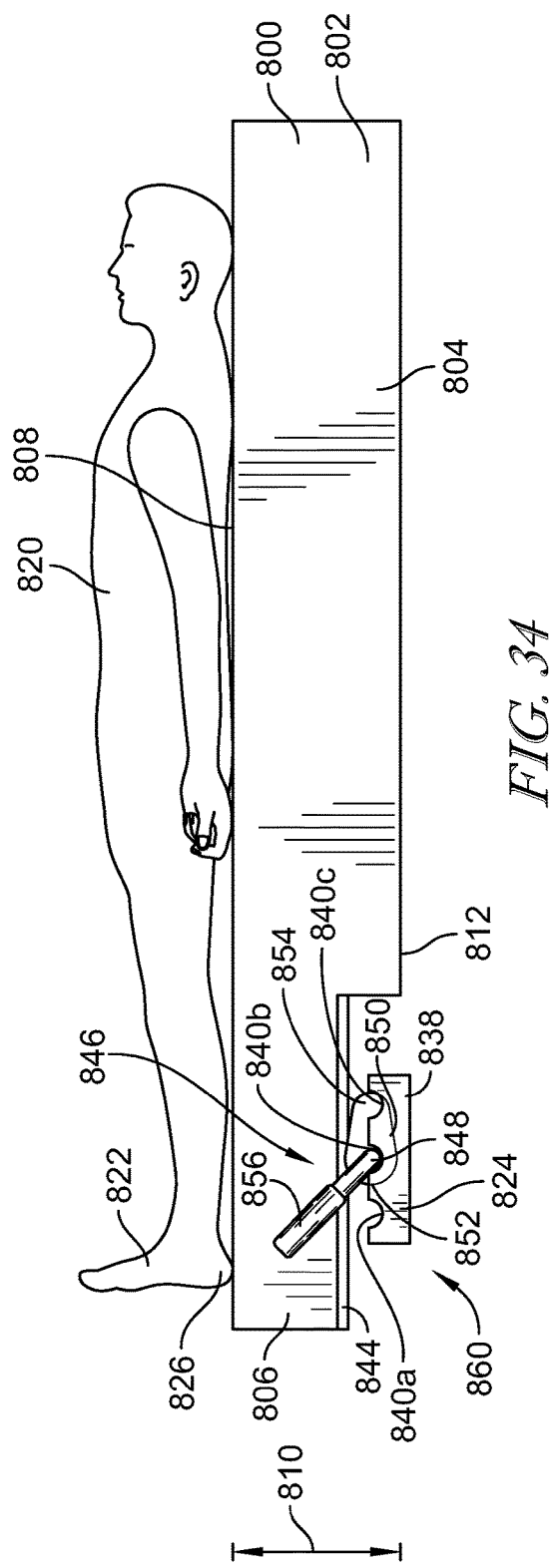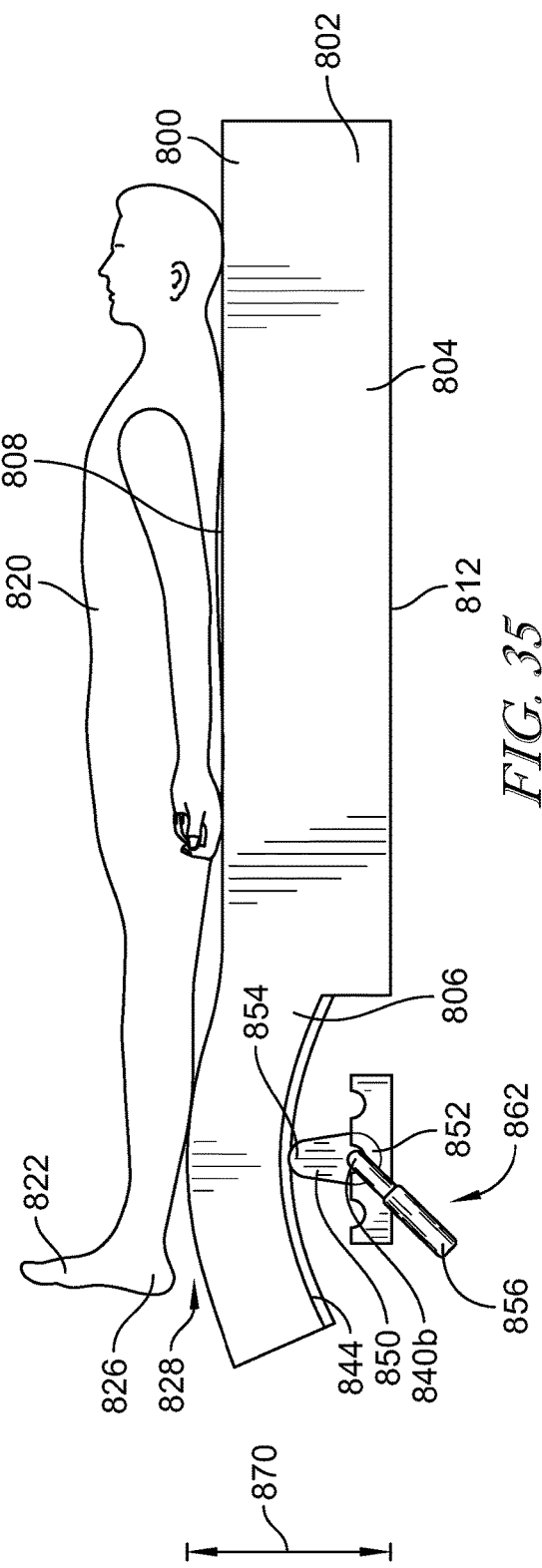

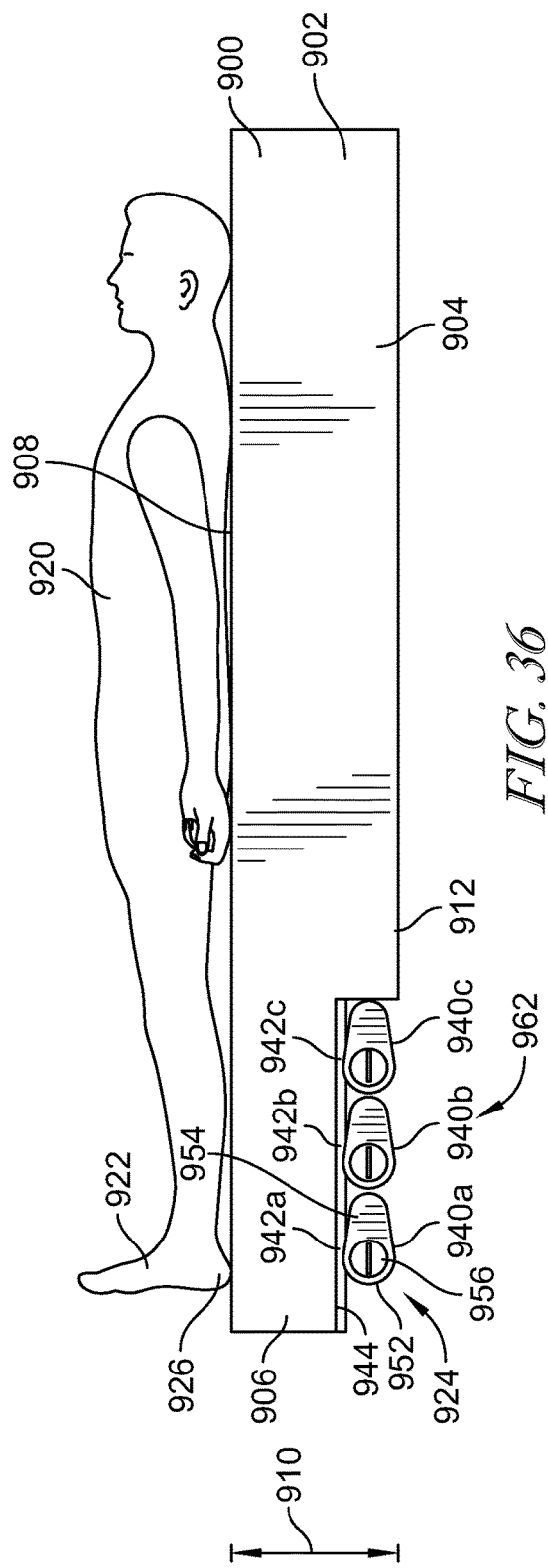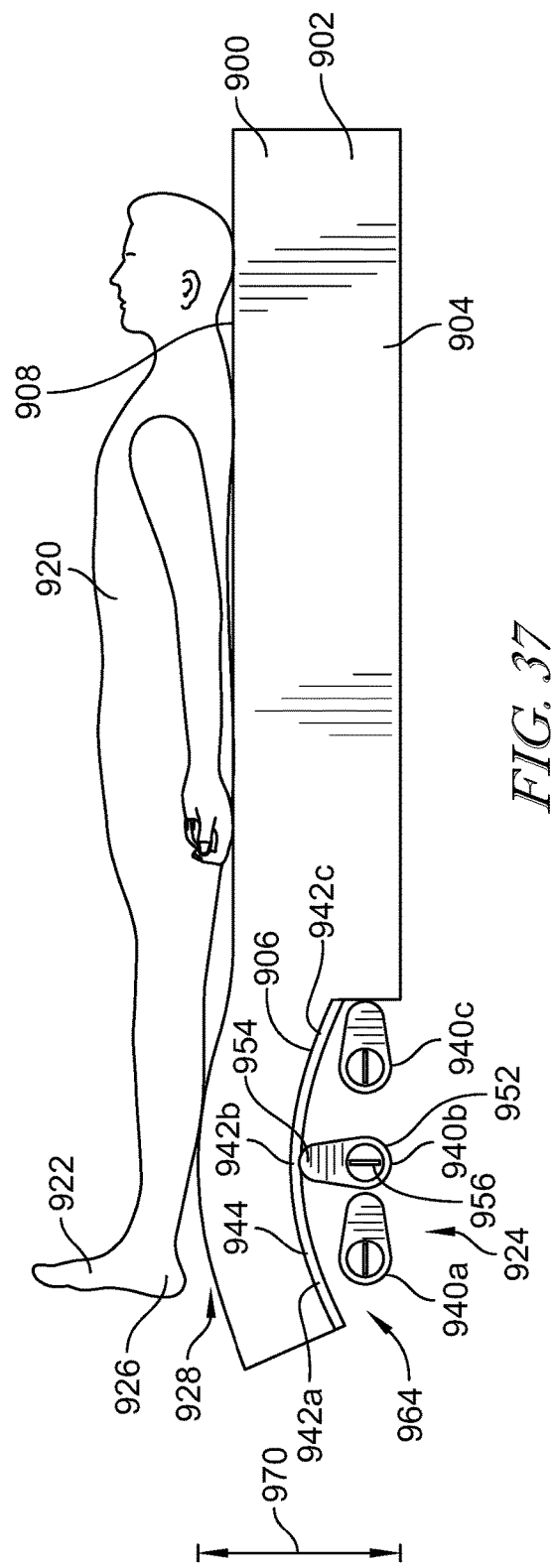

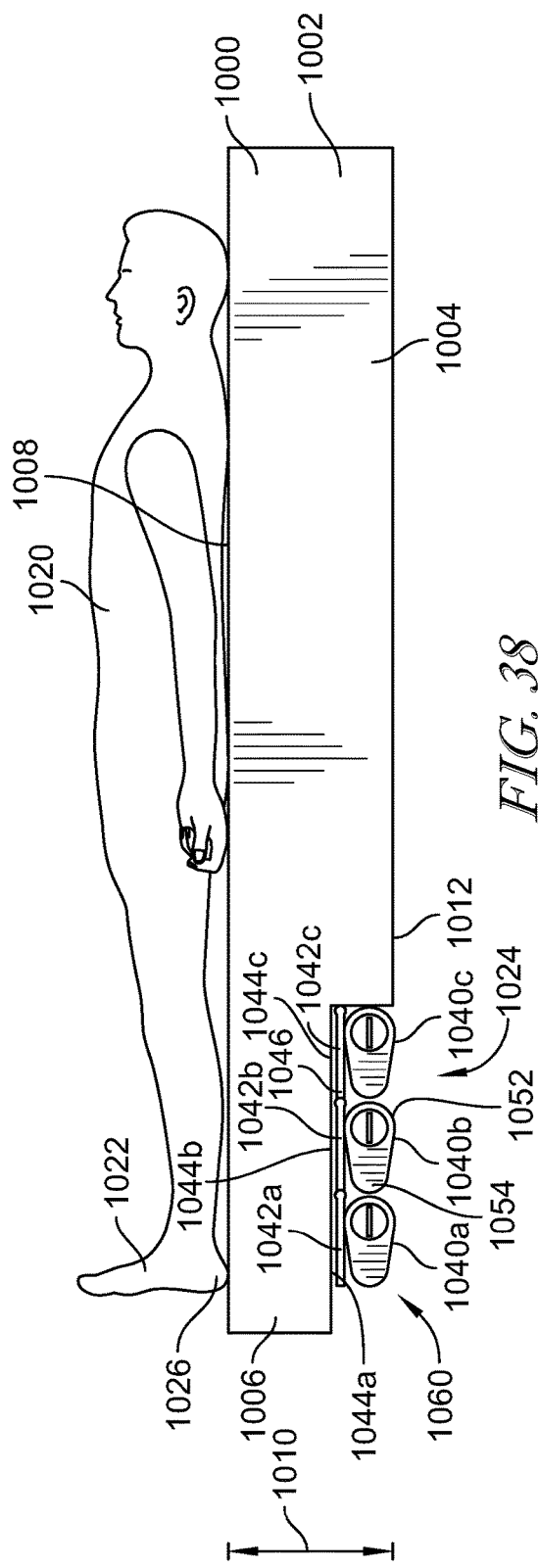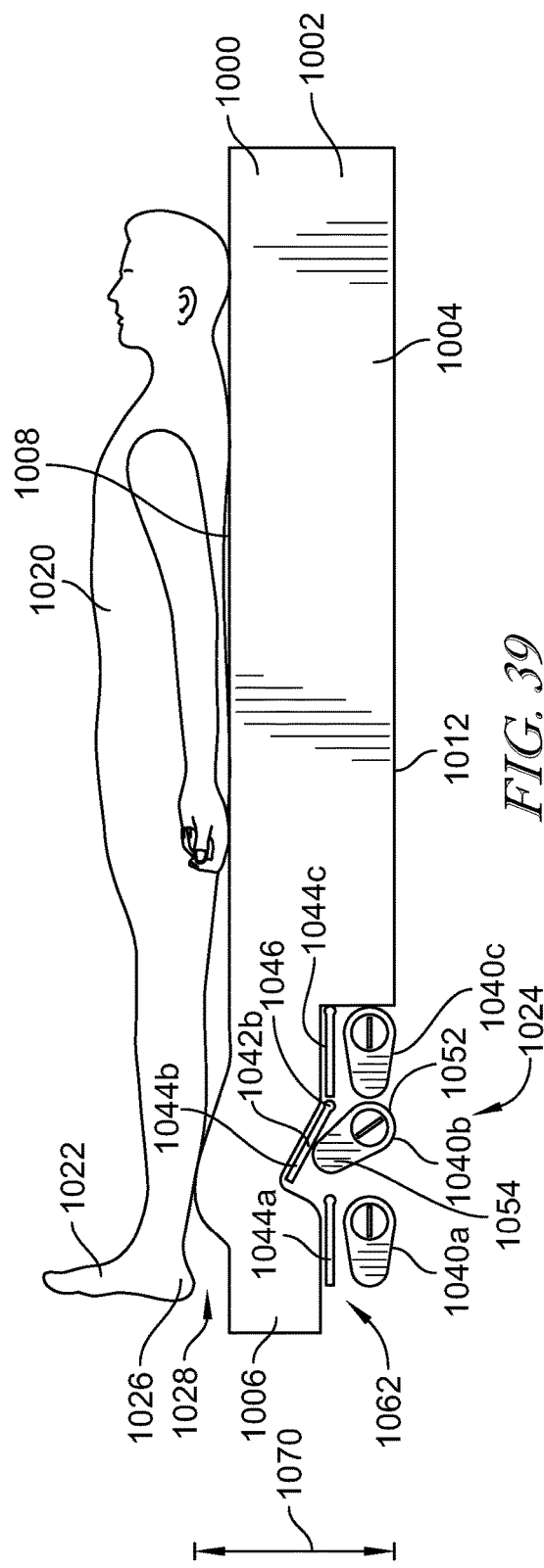

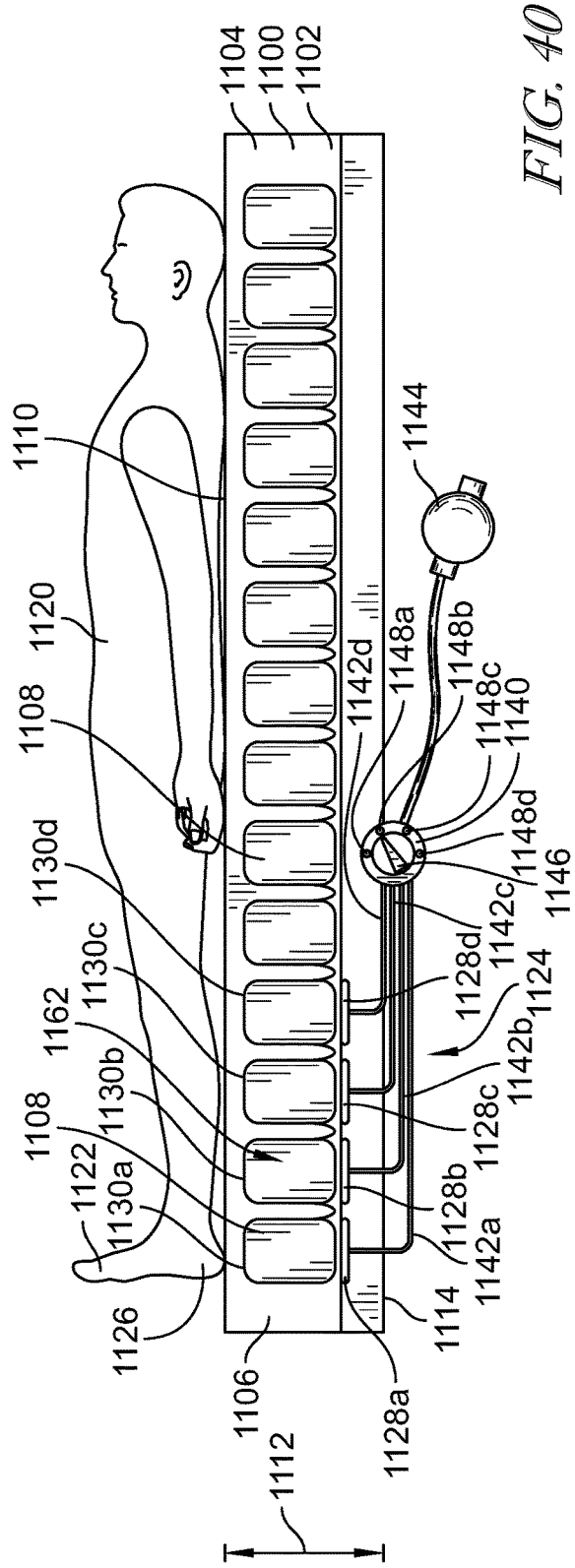
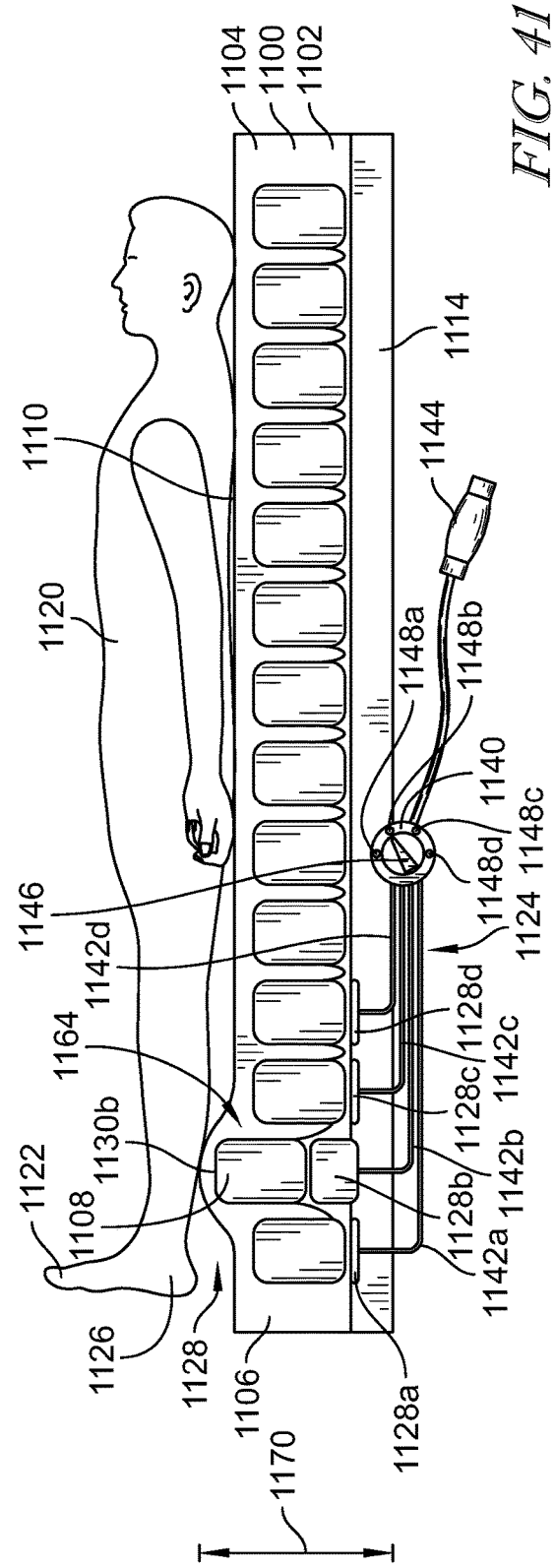

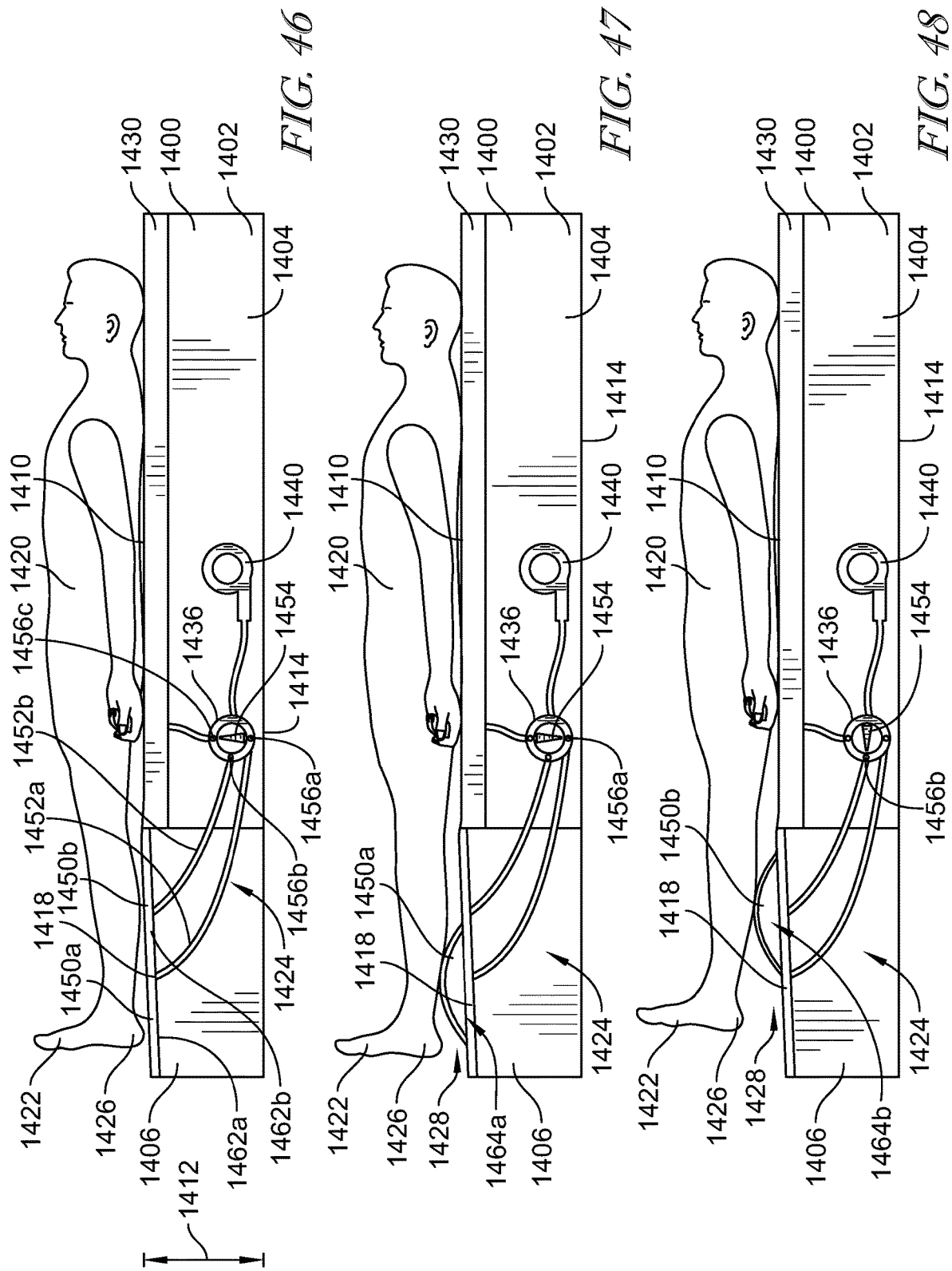

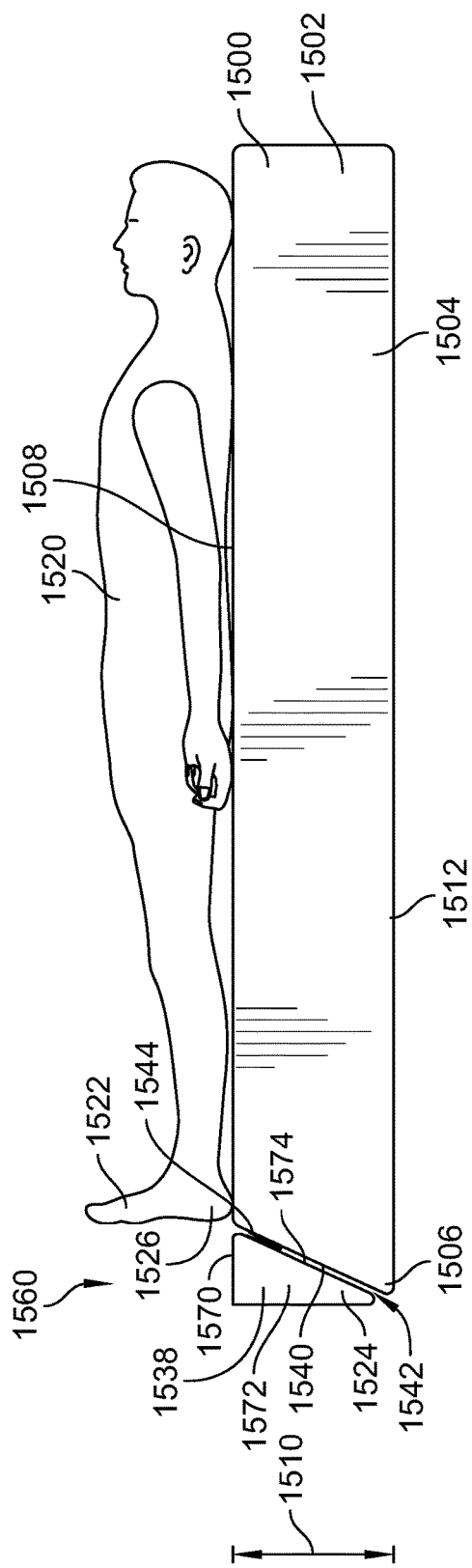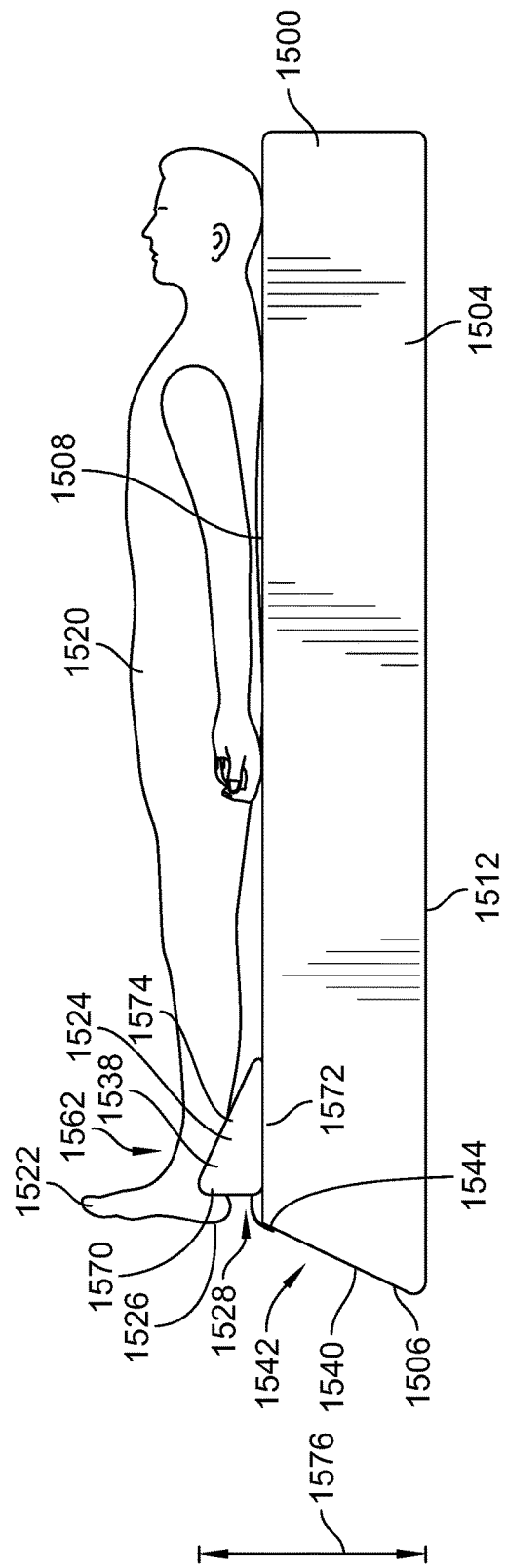

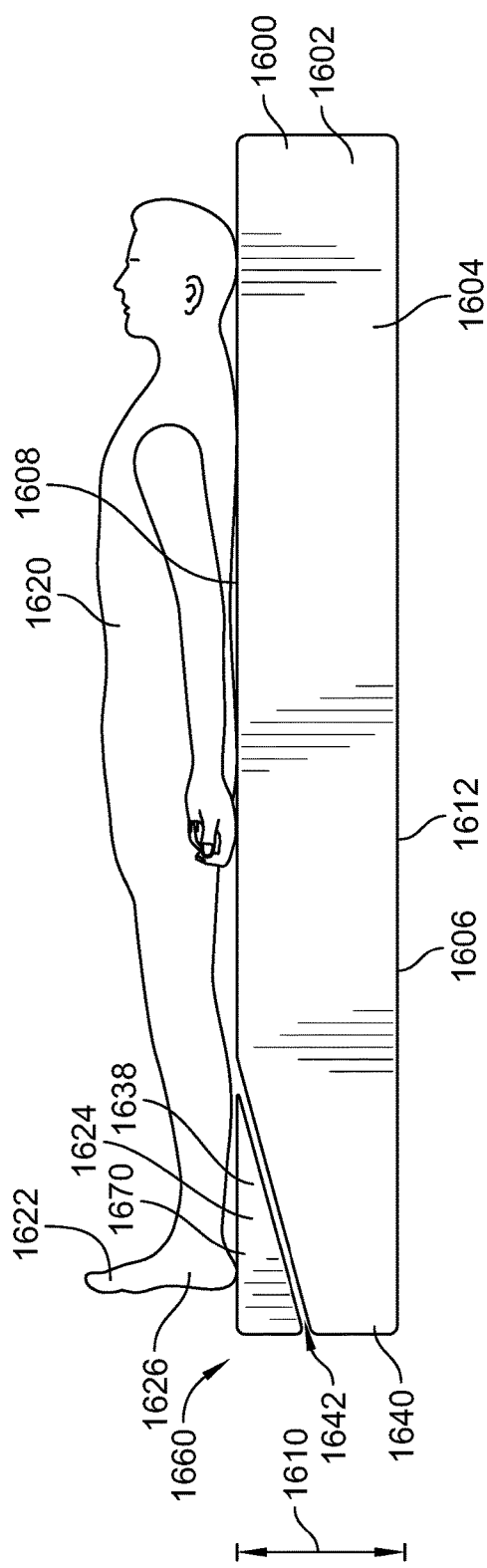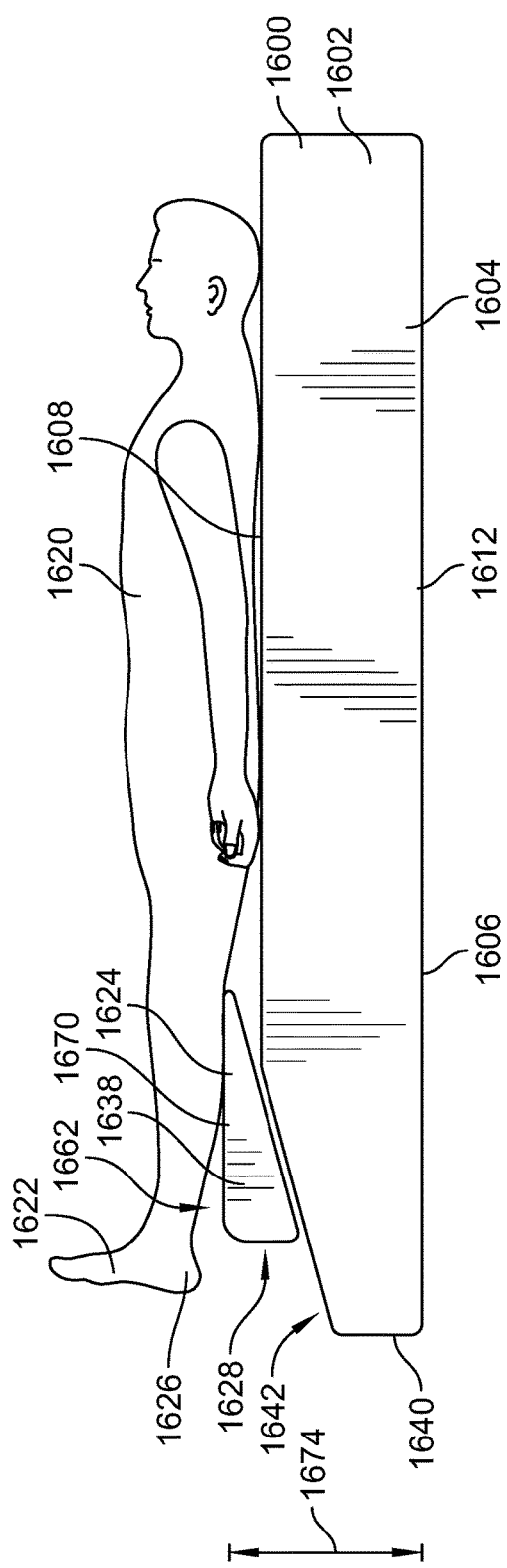

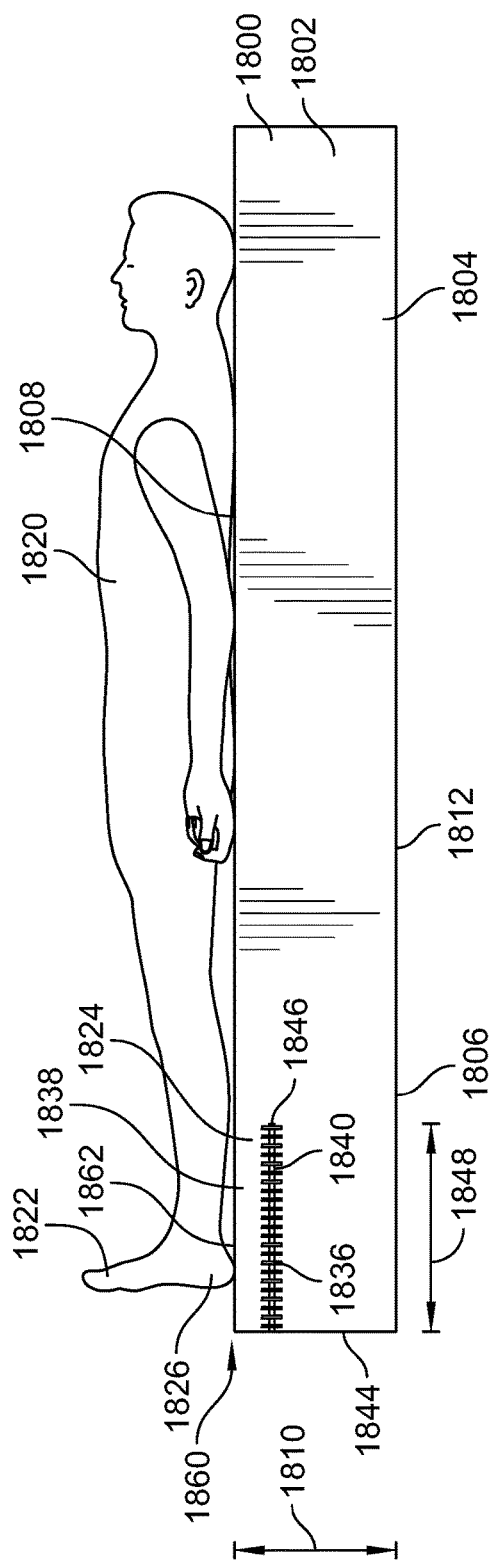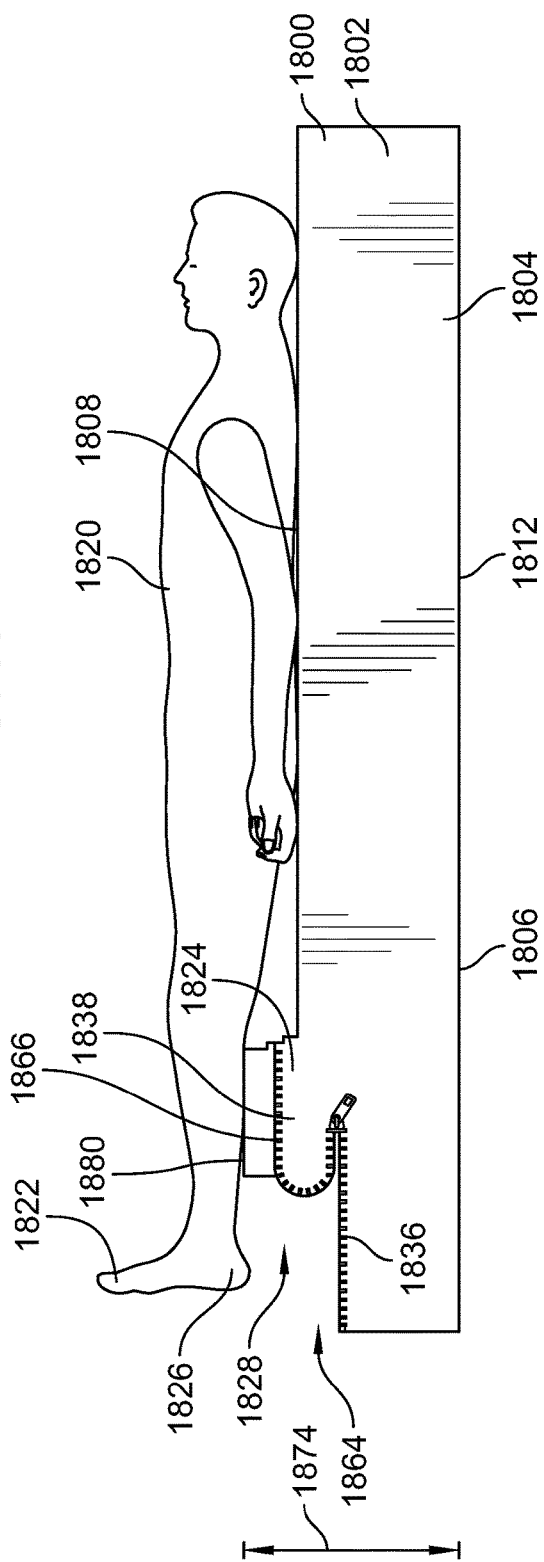

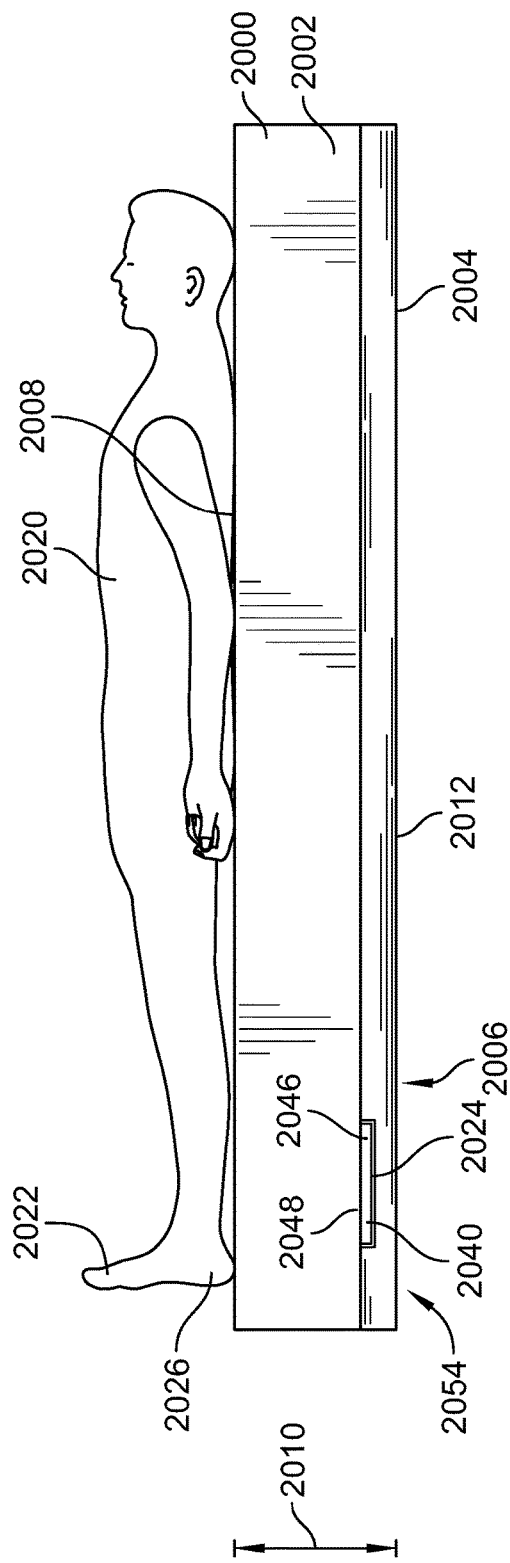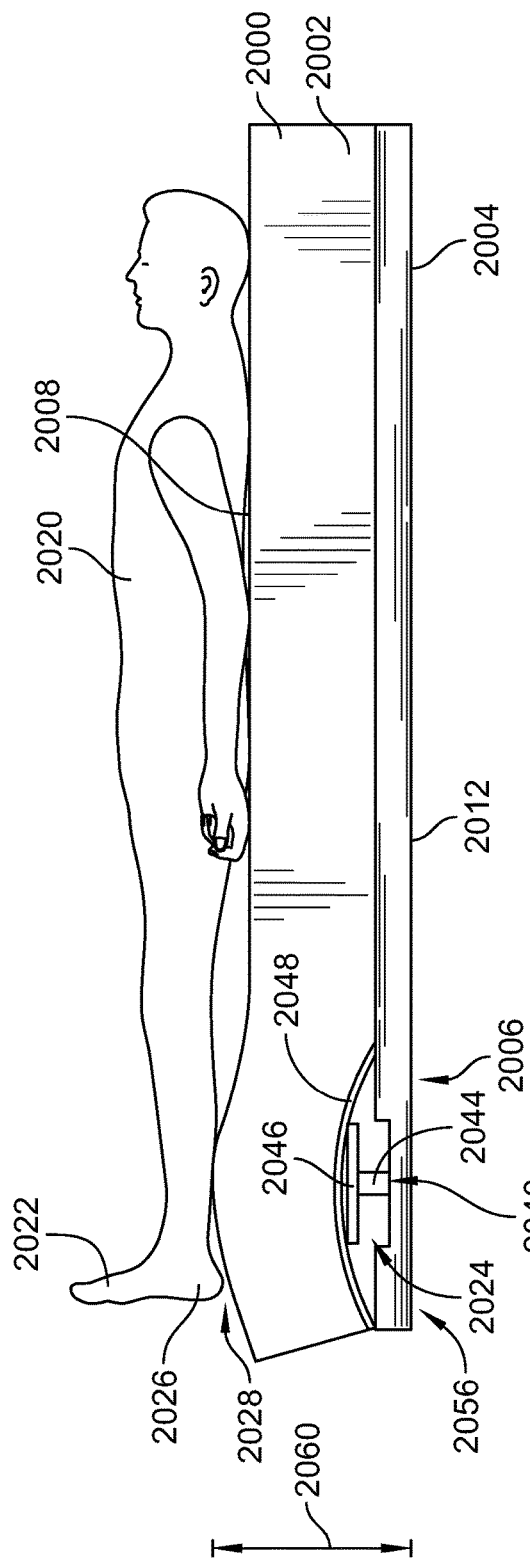

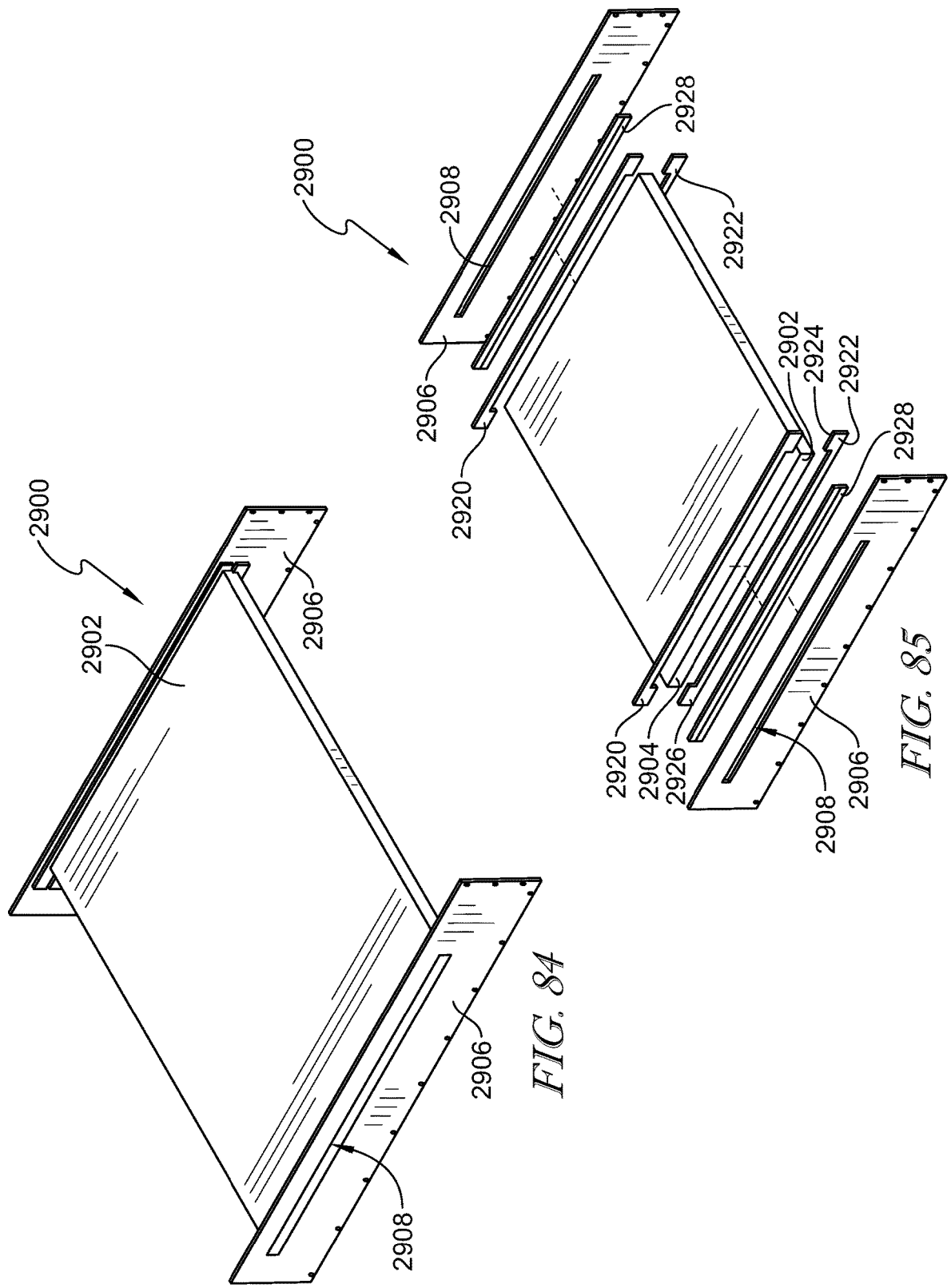

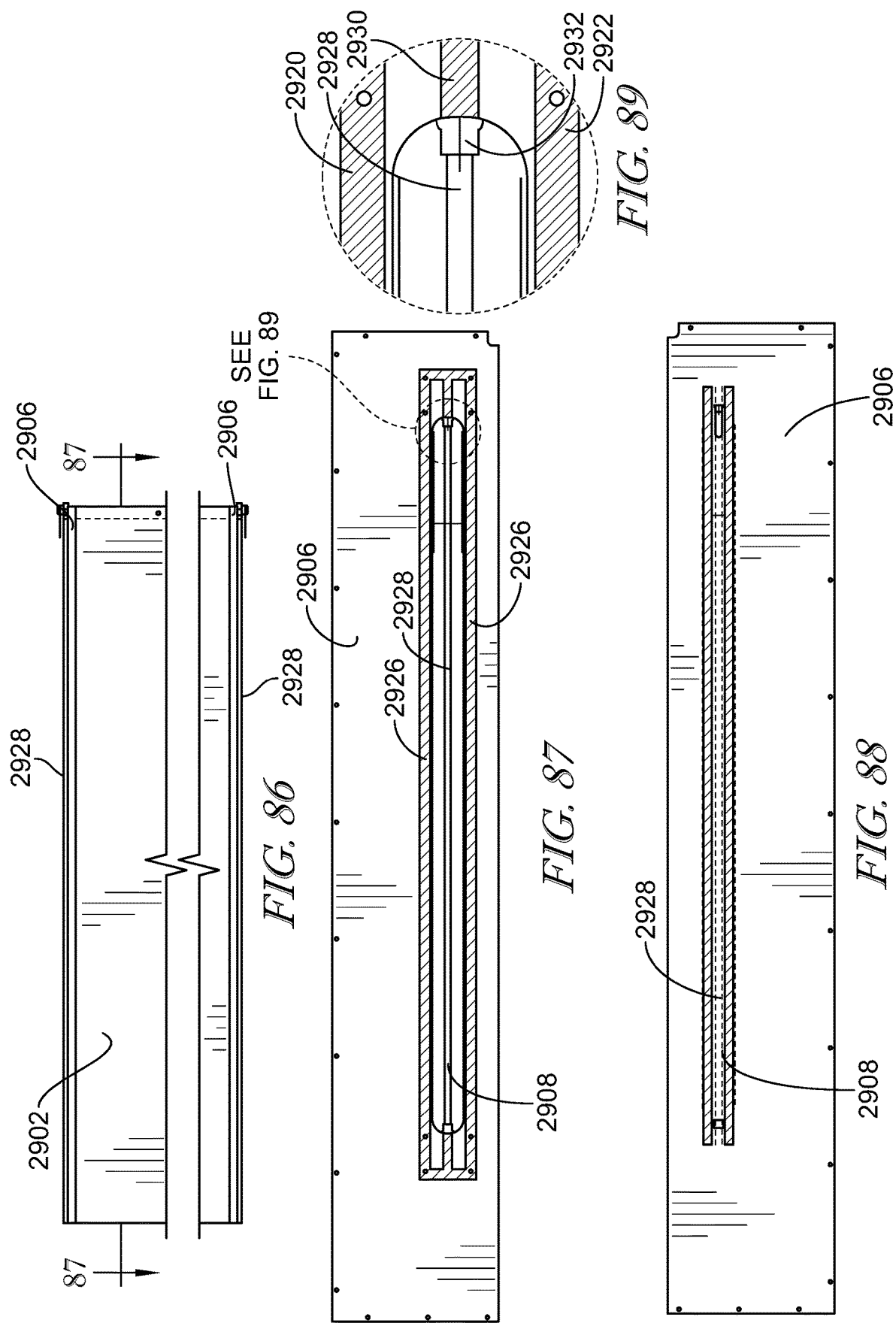

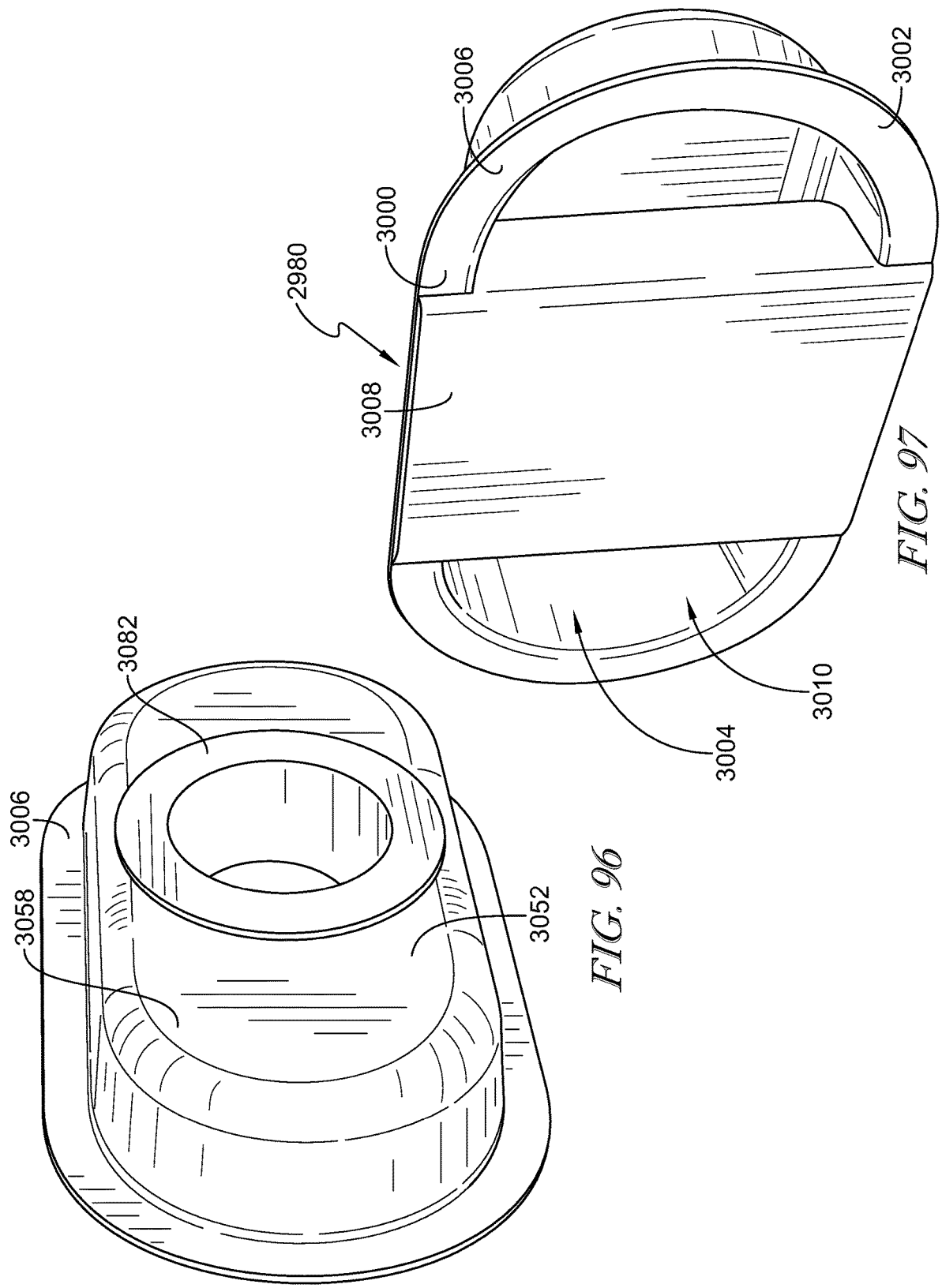

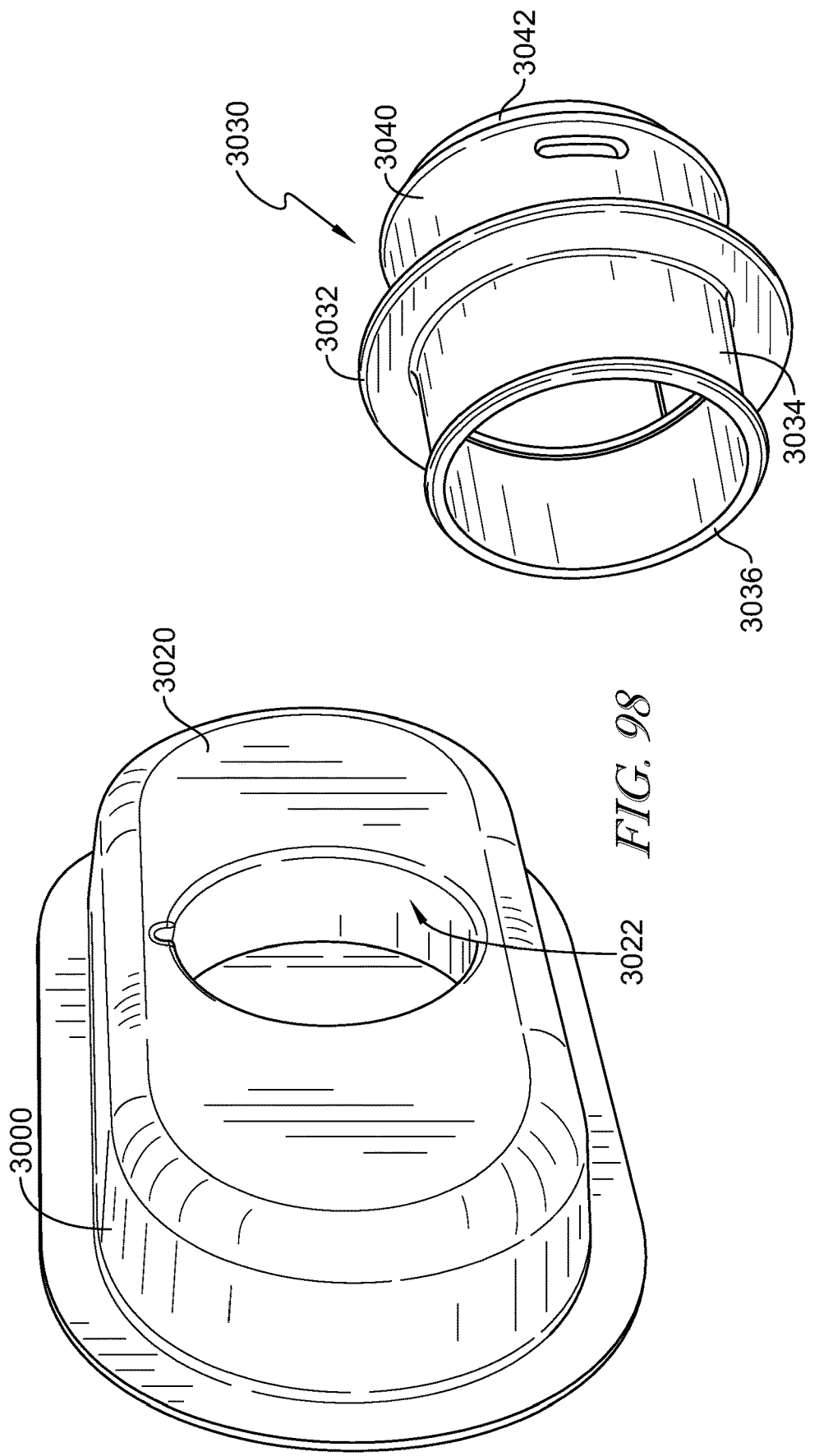

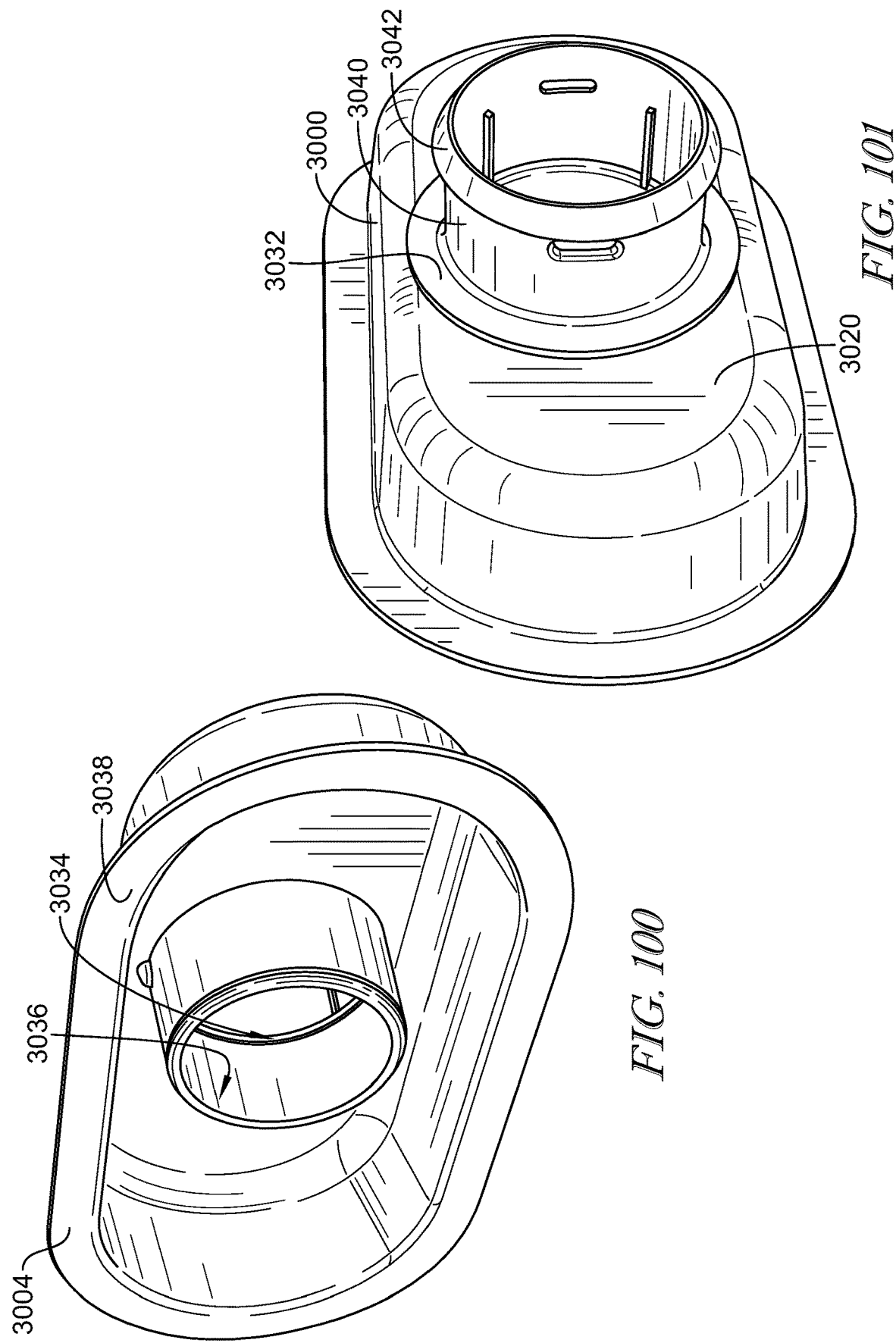

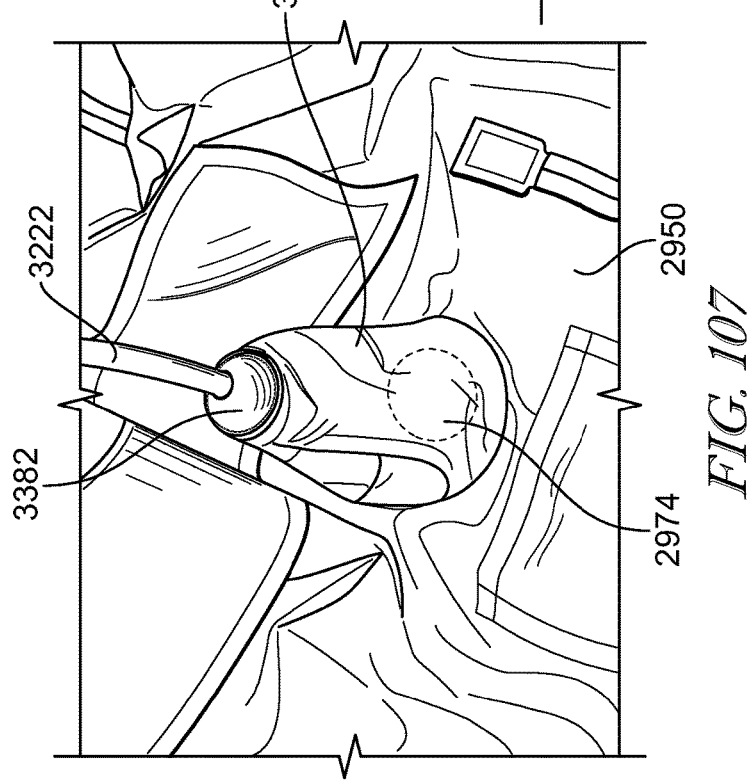
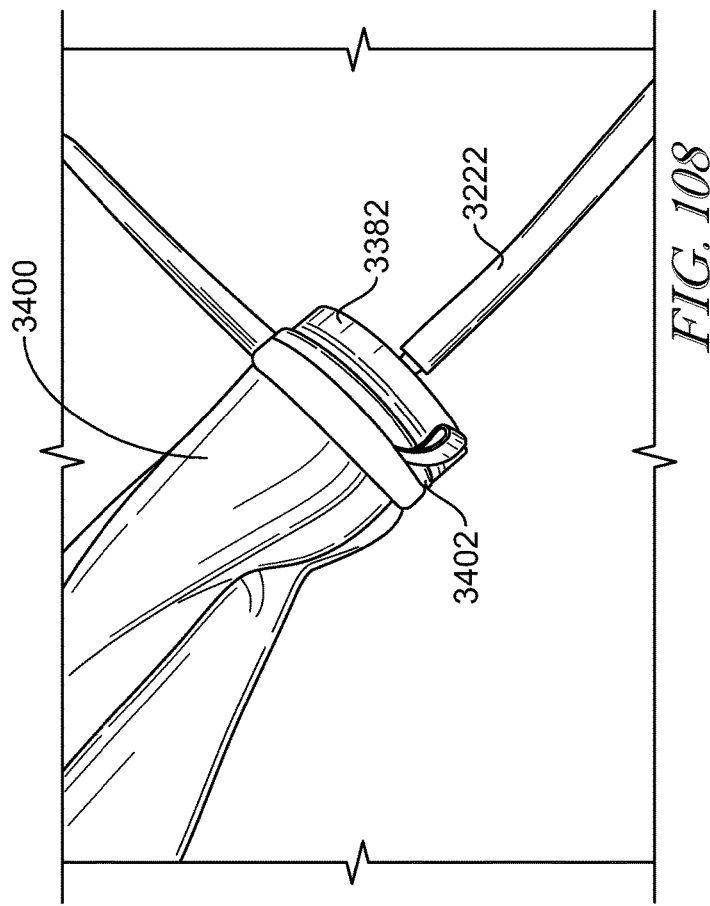

PATIENT SUPPORT SURFACE CONTROL, END OF LIFE INDICATION, AND X-RAY CASSETTE SLEEVE

CROSS-REFERENCE TO RELATED APPLICATIONS

This application claims priority under 35 U.S.C. § 119(e) to U.S. Provisional Patent Application Ser. No. 62/635,749, filed Feb. 27, 2018, U.S. Provisional Patent Application Ser. No. 62/667,769, filed May 7, 2018, and U.S. Provisional Patent Application Ser. No. 62/793,668, filed Jan. 17, 2019, all of which are expressly incorporated by reference herein.

BACKGROUND

The present disclosure relates to controllers for patient beds and features of bed frames of patient beds that are typically found in healthcare facilities such as hospitals and nursing homes. More particularly, the present disclosure relates to support surfaces having enhanced patient and caregiver interaction such as controlling overall bed functionality and patient therapy.

The present disclosure is also related to a microclimate structure for hospital beds, medical beds, or other types of beds in which the microclimate structures are designed to cool and dry a patient's skin around targeted therapeutic regions. In a care facility, such as a hospital or a nursing home, patients are often placed on patient support apparatuses for an extended period of time. Patients who are positioned on the patient support apparatus often have a risk of developing certain skin conditions, such as bed sores (also known as pressure sores or decubitus ulcers), due to heat and moisture along the interface of the patient with the surface of the bed mattress. In an effort to mitigate or prevent such conditions, some bed mattresses have a built-in microclimate structure. The microclimate structure may conduct air along the interface of a patient with the surface to keep the patient's skin cool and dry. Some microclimate structures require a large volume of air to be supplied to them in order to provide an effective amount of cooling and drying to a patient's skin. Accordingly, some microclimate structures require a pneumatic box that is fluidly coupled to the microclimate structure and positioned within the patient room, thereby occupying space within the patient's room.

Typical powered air surfaces or microclimate structures generally rely on a separate pump and control to provide wound treatment therapy. Accordingly, users must locate an available pump module within the healthcare facility to operate the structure. Also, separate pumps get lost in healthcare facilities, thereby reducing the number of pumps available in the facility and increasing the difficulty of finding an available pump. Often, this results in a delay in providing treatment to the patient and not all patients have access to a microclimate system. Moreover, the hose attachments of typical pumps provide an unreliable connection and can become dirty, thereby requiring cleaning of the hoses and pumps after each use. Failure to clean the hoses and pumps may result in the spread of infection and other diseases.

The present disclosure also relates to monitoring the use of support surfaces of patient support apparatuses and mitigating the use of a support surface that has degraded. Support surfaces wear in response to patient loads being applied to the support surfaces over time. Use of support surfaces beyond their useful lives may degrade the support surfaces and reduce the effectiveness of the support provided by the support surfaces to patients supported thereby. Degradation of the support surfaces may increase the likelihood of skin breakdown and pressure ulcers caused by support surfaces that have reached the end of their useful life. Support surfaces should be replaced once their useful lives have expired to minimize the likelihood of skin breakdown and pressure ulcers. By doing so, the substantial costs associated with treating skin breakdown and damage resulting from patient stays on support surfaces in service beyond their useful lives may be avoided.

Generally, notifying caregivers that a support surface is nearing the end of its life span is important to reduce patient safety hazards. A support surface life is dependent on several factors including how long it is used, the number of cleanings and disinfections it undergoes, ambient conditions, and storage conditions. Additionally, if a first support surface is only used with 100 pound patients for 5,000 hours, and a second support surface is used only with 500 pound patients for 5,000 hours, the performance of first support surface and the performance of the second support surface will be dramatically different over time.

The present disclosure also relates to x-ray sleeves. Generally, x-ray sleeves are installed in toppers. However, many support surfaces do not include a topper and, therefore, cannot accept an x-ray sleeve. Also, many x-ray sleeves only allow access to the x-ray sleeve from one of the sides of the support surface. Accordingly, a caregiver may have difficulty installing an x-ray cassette. Housekeepers may also be required to take the support surface out of service to clean the x-ray sleeve. Another downfall to current x-ray sleeves is that many x-ray sleeves are not fluid resistant. As a result, fluids, such as bodily fluids may contaminate the x-ray cassette or internal surface components.

The present disclosure also relates to determining if a patient has bottomed out on the support surface. Bottoming out occurs when the patient has immersed all the way through the support surface and is no longer supported by the support surface in a therapeutic pressure range that results in high interface pressure. Bottoming out reduces the effectiveness of patient therapy, may be uncomfortable to patients, and/or may injure the patient, for example causing pressure ulcers, bruises, poor circulation, or the like. Bottoming out may occur in a support surface having air bladders, when there is insufficient air in the bladders. Such bottoming out, if detected, may be corrected by inflating the bladders. Bottoming out may also occur when the air bladders have become worn and cannot retain air any longer. In a support surface having foam, bottoming out may occur when the foam becomes worn and the support surface has reached its end of life. Generally, bottoming out is detected by the caregiver performing a "hand check," wherein the caregiver positions his/her hand under the patient. However, hand checks are intrusive and may be uncomfortable to the patient.

The present disclosure also relates to heel suspension in a patient support apparatus. Often, caregivers desire the ability to suspend the heels of a patient to ensure that new or worsening pressure ulcers do not occur on the foot. Typically, the caregiver needs to suspend the heel in a manner that creates an air gap between the support surface and the heel. This is usually accomplished by the use of foam heel wedges that are placed on top of the support surface underneath the patient's calf. These accessories are separate from the bed and are often misplaced. In cases where the accessory cannot be located, the caregiver must use towels and/or pillows to accomplish the same task.

The present disclosure also relates to determining when a mattress cover has been soiled. There is currently no automated method for detecting fluid ingress into a mattress. Generally, hospital personnel perform hand and visual checks of the mattress core on a sometimes-yearly basis to determine if fluid ingress has occurred. In some cases the hospital personnel may be unable to tell that the mattress cover has been compromised, thereby posing a significant risk to the patient for infections.

The present disclosure also relates to therapeutic mattresses. Generally, a patient support apparatus in a healthcare facility includes a foam mattress. However, in situations where the patient may be susceptible to pressure ulcers, the patient may be positioned on a mattress having inflatable air bladders. The air bladders may be inflated or deflated based on the patient's comfort and condition. Typically, the type of patient support apparatus used in determined at the time that the patient is admitted to the healthcare facility. Accordingly, is a patient is admitted to a foam mattress and later develops pressure ulcers, the patient must be moved to mattress having inflatable air bladders. Depending on the patient's condition, moving the patient to another support apparatus may be dangerous and detrimental to the patient's overall health.

The present disclosure also relates to developing air flow paths and a pneumatic system to generate adequate air flow for a microclimate management system on a medical mattress. Air flow may be required to be directed to the specific human body location on a medical mattress system. The air flow may be required to be controlled and any blockage to the intake and exhaust system detected. Control of air flow and detection of blockages may reduce safety concerns with mattress contamination due to fluid ingress.

SUMMARY

The present disclosure includes one or more of the features recited in the appended claims and/or the following features which, alone or in any combination, may comprise patentable subject matter.

In one aspect of the disclosed embodiments, a patient support apparatus may include a support surface including a topper. The topper may be configured to conduct air along a top face of the support surface so that heat and moisture from a patient lying on the support surface are drawn away from the top face of the support surface. An opening may be formed in a side of the support surface. A cavity may extend from the opening into the support surface. An inlet port may be positioned within the cavity and fluidly coupled to the topper. A pneumatic blower may be removably positioned within the cavity. The pneumatic blower may have an outlet port that couples to the inlet port when the pneumatic blower is positioned within the cavity. The pneumatic blower may conduct air through the inlet port to the topper.

It may be contemplated that the cavity is formed in a thigh section of the support surface. A controller may be provided to control the flow of air from the pneumatic blower to the topper. The support surface may include a plurality of bladders. Each of the plurality of bladders may be fluidly coupled to the pneumatic blower. The controller may control the flow of air from the pneumatic blower to each of the plurality of bladders to inflate and deflate each of the plurality of bladders. Each of the plurality of bladders may be inflated or deflated to control a comfort level of the support surface. Each of the plurality of bladders may be inflated and deflated to control pulsation of the support surface. A compression sleeve may be fluidly coupled to the pneumatic blower. The controller may control the flow of air to the compression sleeve. The support surface may be positioned on a bed frame. The controller may be coupled to the bed frame. An electrical plug may extend from the pneumatic blower. The controller may be positioned on the electrical plug.

In some embodiments, the controller may be a patient pendant. The patient support may include a plurality of bladders. The patient pendant may control a pulsation intensity of the plurality of bladders. The patient support may include a microclimate system having a flow control. The patient pendant may control the flow control of the microclimate system. The patient support may include a foot warmer. The patient pendant may control the foot warmer. The patient pendant may control one or more of a pulsation intensity of the support surface, a microclimate management flowrate of the topper, and a foot warmer positioned within a foot section of the support surface. The patient pendant may control two or more of a pulsation intensity of the support surface, a microclimate management flowrate of the topper, and a foot warmer positioned within a foot section of the support surface. The patient pendant may control each of a pulsation intensity of the support surface, a microclimate management flowrate of the topper, and a foot warmer positioned within a foot section of the support surface.

Optionally, an interface may be provided on a side of the support surface. The interface may include a dial to select a patient weight range. A plurality of bladders within the support surface may be inflated or deflated to adjust the support surface according to the patient weight range. The interface may also include an end of life indicator that monitors a remaining life span of the support surface. The end of life indicator may include a chemical strip that erodes or grows over time. The end of life indicator may include a timer that tracks how long the support surface has been in use. The end of life indicator may include a timer that tracks a total time that the support surface receives power.

It may be desired that an end of life indicator is positioned within the support surface. The end of life indicator may monitor a remaining life span of the support surface. The end of life indicator may include a transmitter to transmit a signal indicating a remaining life span of the support surface to a user interface.

Alternatively or additionally, the support surface may include a bottom ticking coupled to an upper ticking with a first zipper. An x-ray cassette sleeve may have an opening that is sealed by a second zipper positioned between the first zipper and the top face of the support surface. The second zipper may have a different appearance from the first zipper. The opening of the x-ray cassette sleeve may extend at least partially around two sides of the support surface and entirely across a head end of the support surface. The topper may extend over the upper ticking. A fluid resistant material may be welded over a rip stop material of the second zipper to fluidly seal the opening of the x-ray cassette sleeve.

In some embodiments, a sensor may be positioned below the support surface. The sensor may determine when a patient is within a predetermined range of the sensor. An indicator may provide an alert when the sensor determines that the patient is within a predetermined range of the sensor. A sensor may be positioned below the support surface. A conductive material may be positioned below the topper. The sensor may determine when the conductive material is within a predetermined range of the sensor. An indicator may provide an alert when the sensor determines that the conductor is within a predetermined range of the sensor.

In another aspect of the disclosed embodiments, a patient support apparatus may include a support surface including a topper. The topper may be configured to conduct air along a top face of the support surface so that heat and moisture from a patient lying on the support surface are drawn away from the top face of the support surface. An inlet port may be positioned within the support surface and fluidly coupled to the topper. A pneumatic blower may be positioned within the support surface. The pneumatic blower may have an outlet port that couples to the inlet port when the pneumatic blower is positioned within the support surface. The pneumatic blower may conduct air through the inlet port to the topper.

It may be desired that the pneumatic blower is positioned within a thigh section of the support surface. A controller may be provided to control the flow of air from the pneumatic blower to the topper. The support surface may include a plurality of bladders. Each of the plurality of bladders may be fluidly coupled to the pneumatic blower. The controller may control the flow of air from the pneumatic blower to each of the plurality of bladders to inflate and deflate each of the plurality of bladders. Each of the plurality of bladders may be inflated or deflated to control a comfort level of the support surface. Each of the plurality of bladders may be inflated and deflated to control pulsation of the support surface. A compression sleeve may be fluidly coupled to the pneumatic blower. The controller may control the flow of air to the compression sleeve. The support surface may be positioned on a bed frame. The controller maybe coupled to the bed frame. An electrical plug may extend from the pneumatic blower. The controller may be positioned on the electrical plug. The controller may include a patient pendant. The patient pendant may control one or more of a pulsation intensity of the support surface, a microclimate management flowrate of the topper, and a foot warmer positioned within a foot section of the support surface. The patient pendant may control two or more of a pulsation intensity of the support surface, a microclimate management flowrate of the topper, and a foot warmer positioned within a foot section of the support surface. The patient pendant may control each of a pulsation intensity of the support surface, a microclimate management flowrate of the topper, and a foot warmer positioned within a foot section of the support surface.

Alternatively, or additionally, an interface may be provided on a side of the support surface. The interface may include a dial to select a patient weight range. A plurality of bladders within the support surface may be inflated or deflated to adjust the support surface according to the patient weight range. The interface may also include an end of life indicator that monitors a remaining life span of the support surface. The end of life indicator may include a chemical strip that erodes or grows over time. The end of life indicator may include a timer that tracks how long the support surface has been in use. The end of life indicator may include a timer that tracks a total time that the support surface receives power. An end of life indicator may be positioned within the support surface. The end of life indicator may monitor a remaining life span of the support surface. The end of life indicator may include a transmitter to transmit a signal indicating a remaining life span of the support surface to a user interface.

In some embodiments, the support surface may include a bottom ticking coupled to an upper ticking with a first zipper. An x-ray cassette sleeve may have an opening that is sealed by a second zipper positioned between the first zipper and the top face of the support surface. The second zipper may have a different appearance from the first zipper. The opening of the x-ray cassette sleeve may extend at least partially around two sides of the support surface and entirely across a head end of the support surface. The topper may extend over the upper ticking. A fluid resistant material may be welded over a rip stop material of the second zipper to fluidly seal the opening of the x-ray cassette sleeve.

Optionally, a sensor is positioned below the support surface. The sensor determines when a patient is within a predetermined range of the sensor. An indicator may provide an alert when the sensor determines that the patient is within a predetermined range of the sensor. A sensor may be positioned below the support surface. A conductive material may be positioned below the topper. The sensor may determine when the conductive material is within a predetermined range of the sensor. An indicator may provide an alert when the sensor determines that the conductor is within a predetermined range of the sensor.

In yet another aspect of the disclosed embodiments, a patient support apparatus may include a support surface including a topper. The topper may be configured to conduct air along a top face of the support surface so that heat and moisture from a patient lying on the support surface are drawn away from the top face of the support surface. A pneumatic blower may have an outlet port that couples to an inlet port of the support surface. The pneumatic blower may conduct air through the inlet port to the topper. An end of life indicator may be coupled to the support surface to indicate when the support surface has reached an end of a useful life of the support surface.

Optionally, the end of life indicator includes a chemical strip that erodes or grows over time. The end of life indicator may include a timer that tracks how long the support surface has been in use. The end of life indicator may include a timer that tracks a total time that the support surface receives power. The end of life indicator may include a transmitter to transmit a signal indicating a remaining life span of the support surface to a user interface.

It may be contemplated that an interface is provided on a side of the support surface. The interface may include a dial to select a patient weight range. A plurality of bladders within the support surface may be inflated or deflated to adjust the support surface according to the patient weight range. The interface may include the end of life indicator.

In some embodiments, the end of life indicator may include a sensor positioned below the support surface. The sensor may determine when a patient is within a predetermined range of the sensor. The end of life indicator may provide an end of life alert when the sensor determines that the patient is within a predetermined range of the sensor. The end of life indicator may include a sensor positioned below the support surface. A conductive material may be positioned below the topper. The sensor may determine when the conductive material is within a predetermined range of the sensor. The end of life indicator may provide an end of life alert when the sensor determines that the conductor is within a predetermined range of the sensor.

In a further aspect of the disclosed embodiments, patient support apparatus may include a support surface including a topper. The topper may be configured to conduct air along a top face of the support surface so that heat and moisture from a patient lying on the support surface are drawn away from the top face of the support surface. The support surface may include a bottom ticking coupled to an upper ticking with a first zipper. A pneumatic blower may have an outlet port that couples to an inlet port of the support surface. The pneumatic blower may conduct air through the inlet port to the topper. An x-ray cassette sleeve may have an opening that is sealed by a second zipper positioned between the first zipper and the top face of the support surface.

Alternatively, or additionally, the second zipper may have a different appearance from the first zipper. The first zipper may have a first color that is different from a second color of the second zipper. The first zipper may have a first size that is different from a second size of the second zipper.

It may be desired that the opening of the x-ray cassette sleeve extends at least partially along three sides of the support surface. The opening of the x-ray cassette sleeve may extend at least partially around both sides of the support surface and entirely across a head end of the support surface.

In some embodiments, a fluid resistant material may be welded over a rip stop material of the second zipper to fluidly seal the opening of the x-ray cassette sleeve. The fluid resistant material may be welded with ultrasonic welding. The fluid resistant material may be welded with radio-frequency welding.

In a further aspect of the disclosed embodiments, a patient support apparatus may include a support surface including a topper. The topper may be configured to conduct air along a top face of the support surface so that heat and moisture from a patient lying on the support surface are drawn away from the top face of the support surface. The support surface may include a bottom ticking coupled to an upper ticking. A pneumatic blower may have an outlet port that couples to an inlet port of the support surface. The pneumatic blower may conduct air through the inlet port to the topper. An x-ray cassette sleeve may have an opening that is sealed by a sleeve zipper that extends at least partially along three sides of the support surface.

Optionally, the bottom ticking may be coupled to the upper ticking with a ticking zipper. The sleeve zipper may have a different appearance from the ticking zipper. The sleeve zipper may have a first color that is different from a second color of the ticking zipper. The sleeve zipper may have a first size that is different from a second size of the ticking zipper.

It may be desired that the sleeve zipper extends at least partially around both sides of the support surface and entirely across a head end of the support surface.

In some embodiments, a fluid resistant material is welded over a rip stop material of the sleeve zipper to fluidly seal the opening of the x-ray cassette sleeve. The fluid resistant material may be welded with ultrasonic welding. The fluid resistant material may be welded with radio-frequency welding.

In another aspect of the disclosed embodiments, a patient support apparatus may include a support surface having a head end and a foot end. The support surface may have a top face at a first height. The top face may extend from the head end to the foot end. A heel support mechanism may be built into the foot end of the support surface. The heel support mechanism may be configured to alter a height of the top face at the foot end of the support surface to a second height that is different than the first height. The second height may be greater than the first height. The second height may be less than the first height.

It may be desired that the heel support mechanism includes a plate positioned below the foot end of the support surface. The plate may have at least one groove. A rod may be positioned within the groove and have a cam attached thereto. A handle may extend from the rod to rotate the rod. The rod may be rotatable between a lowered position, wherein the cam holds the top face of the foot end at a first height, and a raised position, wherein the cam raises the top face of the foot end to the second height. The plate may have a plurality of grooves. The rod may be moveable between the plurality of grooves to adjust a section of the foot end actuated by the cam.

Optionally, the heel support mechanism may have an air bladder positioned within the foot end of the support surface to alter the height of the top face of the foot end. The air bladder may be inflatable to raise the top face of the foot end to the second height. The second height may be greater than the first height. The air bladder may be deflatable to lower the top face of the foot end to the second height. The second height may be less than the first height. The air bladder may be inflated and deflated with a hand pump. The air bladder may be inflated and deflated with a pump of a microclimate system. The heel suspension mechanism may include a plurality of air bladders. Each air bladder of the plurality of air bladders may be positioned under one of a plurality of sections of the foot end. One of the air bladders of the plurality of air bladders may be actuated to alter the height of the corresponding section of the foot end.

Alternatively or additionally, the heel suspension mechanism may have a foam wedge coupled to the foot end and movable to alter the height of the top face of the foot section. The foam wedge may be rotated relative to the foot end to position the foam wedge at the second height. The foam wedge may be translated along the foot end to position the foam wedge at the second height.

In some embodiments, the heel suspension mechanism may have at least one cam positioned under the foot end. A membrane may be positioned between the at least one cam and the foot end. The cam may be rotatable to move the membrane. The membrane may alter the height of the top face of the foot end when the membrane is moved. The heel suspension mechanism may have a plurality of cams. At least one of the plurality of cams may be rotatable to move the membrane. The membrane may have a hinged plate. The cam may rotate the hinged plate when the cam is rotated. The heel suspension mechanism may have a plurality of hinged plates and a plurality of cams. Each cam may be positioned under one of the plurality of hinges plates and rotatable to rotate the corresponding hinged plate.

It may be contemplated that the support surface includes a base surface and the heel suspension mechanism includes a top surface positioned over the base surface at the foot end. The top surface may be configured to roll into a rolled configuration to alter the height of the top face of the foot end. A fastening mechanism may be provided to secure the top surface to the base surface.

It may be desired that the heel suspension mechanism has a jack positioned under the foot end. The jack may be actuated to alter the height of the top face of the foot end. The jack may a hydraulic jack or hand operated.

In some embodiments, the heel suspension mechanism may be a telescoping member positioned under the foot end. The telescoping member may be adjustable to alter the height of the top face of the foot end. The telescoping member may be hydraulic or hand operated.

In another aspect of the disclosed embodiments, a patient support apparatus may include a support surface including a mattress having a top cover and at least one support element. A flexible substrate may be positioned beneath the top cover and above the at least one support element. A first conductive trace may be carried by the flexible substrate, and a second conductive trace may be carried by the flexible substrate adjacent to the first conductive trace. An open circuit may be formed between the first conductive trace and the second conductive trace when the flexible substrate is dry. The presence of a threshold amount of liquid on the flexible substrate may form a closed circuit with the first conductive trace and the second conductive trace due to the flexible substrate being wet.

It may be contemplated that the first conductive trace and the second conductive trace include conductive threads woven into the flexible substrate. The first conductive trace and the second conductive trace may include conductive ink printed on the flexible substrate.

In some embodiments, an impedance between the first conductive trace and the second conductive trace may change when the flexible substrate is wet.

Optionally, the flexible substrate may be a plastic sheet. The first conductive trace and the second conductive trace may be woven into the plastic sheet.

Alternatively or additionally, an alarm may be activated when an impedance between the first conductive trace and the second conductive trace changes. The alarm may be a visual alarm. The alarm may be an audible alarm. The alarm may be located remotely from the support surface.

In some embodiments, a passive RFID tag may be situated on the flexible substrate and in electrical communication with the first conductive trace and the second conductive trace. An antenna may receive wireless energy emitted by the passive RFID tag indicating whether the flexible substrate is dry or wet. A reader may supply power to the antenna. The reader may receive signals from the antenna and transmit a notification message in response to at least one of the signals from the antenna indicating that the flexible substrate is wet. The reader may be communicatively coupled to a network of a healthcare facility. The reader may be configured to communicate wirelessly with the network.

It may be desired that the flexible substrate is generally rectangular in shape and the RFID tag is mounted closer to an edge of the flexible substrate than to a middle of the flexible substrate.

Optionally, the first conductive trace includes first trace segments and the second conductive trace includes second trace segments. The first trace segments may be spaced from and interleaved with the second trace segments.

In some embodiments, the flexible substrate includes a plastic film and the first conductive trace and the second conductive trace are woven into the plastic film. The flexible substrate may include a hydrophobic material and a moisture absorbent material may overlie the first conductive trace and the second conductive trace. The flexible substrate may include a synthetic resin or a thermoplastic polymer material.

According to another aspect of the disclosure, a patient support apparatus may have a support layer. A mattress layer may be positioned on the support layer. A therapeutic layer may be positioned on the mattress layer and may have a plurality of bladders that are configured to inflate. A protective layer may be positioned over the therapeutic layer. A control unit may be configured to inflate the therapeutic layer. In a normal mode, the control unit may not be coupled to the therapeutic layer and the therapeutic layer may be deflated. In a therapeutic mode, the control unit may be coupled to the therapeutic layer to inflate the therapeutic layer.

In some embodiments, each of the plurality of bladders may be individually inflated. The therapeutic layer may be inflated with alternating pressures.

Optionally, the support layer may be positioned on a bed frame. The control unit may be positioned on the bed frame. A hose may extend from the control unit and may be configured to be coupled to the therapeutic layer. The hose may be coupled to an inlet of the therapeutic layer. The control unit may include a pump. The control unit may include user inputs to selectively alter a pressure in the therapeutic layer. The therapeutic layer may deflate when the control unit is disconnected from the therapeutic layer.

Alternatively, or in addition to, the support layer may include foam. The mattress may include foam. The protective layer may include three-dimensional spacers. The protective layer may include a non-woven fabric layer. The protective layer may include foam.

It may be desired that, each of the plurality of bladders is inflatable to a different pressure.

It may be contemplated that a cover encloses the support layer, the mattress layer, the therapeutic layer, and the protective layer. The cover may include a zipper that is configured to seal the cover around the support layer, the mattress layer, the therapeutic layer, and the protective layer.

According to another aspect of the disclosure, a patient support apparatus may include a mattress assembly having a foam support layer. A foam mattress layer may be positioned on the foam support layer. A therapeutic layer may be positioned on the foam mattress layer and may have a plurality of bladders. A protective layer may be positioned over the therapeutic layer. A control unit may be configured to inflate the therapeutic layer. In a normal mode, the control unit may not be coupled to the therapeutic layer and the therapeutic layer may be deflated. In a therapeutic mode, a hose may couple the control unit to the therapeutic layer to inflate the therapeutic layer.

In some embodiments, the therapeutic layer may be inflated with alternating pressures.

Optionally, the support layer may be positioned on a bed frame. The control unit may be positioned on the bed frame. The control unit may include a pump. The control unit may include user inputs to selectively alter a pressure in the therapeutic layer. The therapeutic layer may deflate when the control unit is disconnected from the therapeutic layer.

Alternatively, or additionally, the protective layer may include at least one of three-dimensional spacers, a non-woven fabric layer, or foam.

It may be desired that each of the plurality of bladders is inflatable to a different pressure.

In some embodiments, a cover encloses the mattress assembly.

According to an aspect of the disclosed embodiments, a patient support apparatus may include a first foam layer and a second foam layer positioned on the first foam layer. A manifold may be positioned on the second foam layer. The manifold may have a plurality of apertures. A patient three dimensional spacer may be positioned on the manifold and configured to retain a patient. A blower may be configured to direct air flow into the manifold. The airflow may exit the manifold through the plurality of apertures and enter the patient three dimensional spacer.

It may be desired that the manifold includes a bottom fabric layer and a top fabric layer. A manifold three dimensional spacer may be positioned between the bottom fabric layer and the top fabric layer. The plurality of apertures may be formed in the top fabric layer. The plurality of apertures may be positioned at high pressure points in the patient three dimensional spacer. The plurality of apertures may be positioned in a seat region of the patient three dimensional spacer. The air flow may enter the manifold in the manifold three dimensional spacer. The patient three dimensional spacer may have a smaller thickness than the manifold three dimensional spacer.

Alternatively or additionally, the second foam layer may be a visco foam. The first foam layer may be positioned on a support foam layer.

Optionally, the plurality of apertures may be formed in a seat region so that the air flow flows from the manifold to a seat region of the patient three dimensional spacer. The patient three dimensional spacer may have exit apertures for the air flow to exit the patient three dimensional spacer. The exit apertures may be positioned at a head end of the patient three dimensional spacer. The airflow may enter the patient three dimensional spacer at the seat region and flows to the head end of the patient three dimensional spacer.

It may be contemplated that the blower is positioned in a foot end of the patient support apparatus. The blower may be external to the patient support apparatus and includes hoses to the manifold.

In some embodiments, a blower housing may house the blower. The blower housing may be positioned in a foot end of the patient support apparatus. The blower housing may include a base having a vacuum chamber and a top cover sealed to the base to create a pressurized chamber. An intake of the blower may be sealed to the vacuum chamber.

It may desired that an inlet is in flow communication with the vacuum chamber. A pair of inlets may be in flow communication with the vacuum chamber. The inlet may include an intake extending into an inlet cavity. A ridge may be formed at a bottom of the intake to prevent direct fluid intrusion into the cavity. The ridge may cover a portion of the intake.

Optionally, an outlet of the blower may be in flow communication with the pressurized chamber. An outlet may be formed in the top cover. The outlet may release the air flow from the pressurized chamber to manifold.

In some embodiments, the blower may increase speed to maintain pressure when an inlet of the blower housing is blocked. The blower may decrease speed to maintain pressure when an outlet of the blower housing is blocked According to another aspect of the disclosed embodiments, a blower assembly for a patient support apparatus may include a blower housing having a base that forms a vacuum chamber and a top cover sealed to the base to create a pressurized chamber. A blower may have an inlet and an outlet. The inlet may be sealed to the vacuum chamber. The outlet may be in flow communication with the pressurized chamber. A pair of inlets may be in flow communication with the vacuum chamber.

Optionally, the blower housing may be positioned in a foot end of the patient support apparatus. The blower housing may be external to the patient support apparatus and may include a hose coupling the blower housing to a manifold of the patient support apparatus.

It may be contemplated that each of pair of inlets includes an intake extending into an inlet cavity. A ridge may be formed at a bottom of the intake to prevent direct fluid intrusion into the cavity. The ridge may cover a portion of the intake.

Alternatively or additionally, an outlet may be formed in the top cover. The outlet may release the air flow from the pressurized chamber to a manifold of the patient support apparatus.

It may be desired that the blower increases speed to maintain pressure when an inlet of the blower housing is blocked. The blower may decrease speed to maintain pressure when an outlet of the blower housing is blocked.

According to yet another aspect of the disclosed embodiments, a method of monitoring the operation of a blower assembly may include setting a predetermined speed of a blower in a blower assembly. The method may also include monitoring the speed of the blower in the blower assembly. The method may also include comparing the monitored speed of the blower to the predetermined speed. The method may also include determining whether the blower assembly has a blockage based on the comparison of the monitored speed to the predetermined speed.

Optionally, determining whether the blower assembly has a blockage may include determining that the blower assembly does not have a blockage when the monitored speed is substantially equal to the predetermined speed. Determining whether the blower assembly has a blockage may include determining that an intake of the blower assembly has a blockage when the monitored speed is greater than the predetermined speed. Determining whether the blower assembly has a blockage ay include determining that an outlet of the blower assembly has a blockage when the monitored speed is less than the predetermined speed.

According to a further aspect of the disclosed embodiments, a patient support apparatus may include a first foam layer and a second foam layer positioned on the first foam layer. A manifold may be positioned on the second foam layer. The manifold may include a bottom fabric layer and a top fabric layer. A manifold may be positioned between the bottom fabric layer and the top fabric layer. A plurality of apertures may be formed in the top fabric layer. A patient three dimensional spacer may be positioned on the manifold and configured to retain a patient. Exit apertures may be formed in a head end of the patient three dimensional spacer. A blower may be configured to direct air flow into the manifold three dimensional spacer. The airflow may exit the manifold three dimensional spacer through the plurality of apertures and enter the patient three dimensional spacer. The air flow may flow through the patient three dimensional spacers to the exit apertures.

In some embodiments, the plurality of apertures may be positioned at high pressure points in the patient three dimensional spacer. The plurality of apertures may be positioned in a seat region of the patient three dimensional spacer.

Optionally, the patient three dimensional spacer may have a smaller thickness than the manifold three dimensional spacer. The second foam layer may be a visco foam. The first foam layer may be positioned on a support foam layer.

It may be desired that the blower is positioned in a foot end of the patient support apparatus. The blower may be external to the patient support apparatus and includes hoses to the manifold.

It may be contemplated that a blower housing houses the blower. The blower housing may include a base having a vacuum chamber. A top cover may be sealed to the base to create a pressurized chamber. The blower housing may be positioned in a foot end of the patient support apparatus. An intake of the blower may be sealed to the vacuum chamber. An inlet may be flow communication with the vacuum chamber. The inlet may include an intake extending into an inlet cavity. A ridge may be formed at a bottom of the intake to prevent direct fluid intrusion into the cavity. The ridge may cover a portion of the intake. An outlet of the blower may be in flow communication with the pressurized chamber. An outlet may be formed in the top cover. The outlet may release the air flow from the pressurized chamber to manifold.

Optionally, the blower may increase speed to maintain pressure when an inlet of the blower housing is blocked. The blower may decrease speed to maintain pressure when an outlet of the blower housing is blocked.

According to another aspect of the disclosed embodiments, a patient support apparatus may include a support surface including a topper. The topper may be configured to conduct air along a top face of the support surface so that heat and moisture from a patient lying on the support surface are drawn away from the top face of the support surface. The support surface may include a bottom ticking coupled to an upper ticking with a first zipper. A pneumatic blower may have an outlet port that couples to an inlet port of the support surface. The pneumatic blower may conduct air through the inlet port to the topper. An x-ray cassette sleeve may have openings that extend at least partially along two sides of the support surface. The openings may be sealed by a pair of second zippers. Each second zipper may be positioned between the first zipper and the top face of the support surface.

In some embodiments, each second zipper may have a different appearance from the first zipper. The first zipper may have a first color that is different from a second color of each of the second zippers. The first zipper may have a first size that is different from a second size of each of the second zippers.

Optionally, the opening may not extend along a head of the support surface.

It may be desired that a fluid resistant material is welded over a rip stop material of each of the second zippers to fluidly seal the opening of the x-ray cassette sleeve. The fluid resistant material may be welded with ultrasonic welding. The fluid resistant material may be welded with radio-frequency welding.

According to yet another aspect of the disclosed embodiments, a patient support apparatus may include a support surface including a topper. The topper may be configured to conduct air along a top face of the support surface so that heat and moisture from a patient lying on the support surface are drawn away from the top face of the support surface. The support surface may include a bottom ticking coupled to an upper ticking. A pneumatic blower may have an outlet port that couples to an inlet port of the support surface. The pneumatic blower may conduct air through the inlet port to the topper. An x-ray cassette sleeve may have an opening that is sealed by a pair of sleeve zippers. Each of the pair of sleeve zippers may extends at least partially along a side of the support surface.

In some embodiments, the bottom ticking may be coupled to the upper ticking with a ticking zipper. Each of the sleeve zippers may have a different appearance from the ticking zipper. Each of the sleeve zippers may have a first color that is different from a second color of the ticking zipper. Each of the sleeve zippers may have a first size that is different from a second size of the ticking zipper.

Optionally, a fluid resistant material may be welded over a rip stop material of each of the sleeve zippers to fluidly seal the opening of the x-ray cassette sleeve. The fluid resistant material may be welded with ultrasonic welding. The fluid resistant material may be welded with radio-frequency welding.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

According to another aspect of the disclosed embodiments, a patient support apparatus may include a support surface configured to conduct air along a top face of the support surface so that heat and moisture from a patient lying on the support surface are drawn away from the top face of the support surface. An opening may be formed in a side of the support surface. A cavity may extend from the opening into the support surface. An inlet port may be positioned within the cavity and fluidly coupled to the top face. A pneumatic blower may be configured to position within the cavity. The pneumatic blower may have an outlet port that couples to the inlet port when the pneumatic blower is positioned within the cavity. The pneumatic blower may conduct air through the inlet port to the top face of the support surface.

In some embodiments, an end of life indicator may be coupled to the support surface to indicate when the support surface has reached an end of a useful life of the support surface.

Optionally, the support surface may include a bottom ticking coupled to an upper ticking with a first zipper. The patient support apparatus may also include an x-ray cassette sleeve having an opening that is sealed by a second zipper positioned between the first zipper and the top face of the support surface.

Additionally or alternatively, an x-ray cassette sleeve may have an opening that is sealed by a sleeve zipper that extends at least partially along three sides of the support surface.

It may be desired that a heel support mechanism may be built into a foot end of the support surface. The heel support mechanism may be configured to alter a height of the top face at the foot end of the support surface.

It may be contemplated that the support surface may include at least one support element. The patient support apparatus may also include a flexible substrate positioned above the at least one support element. A first conductive trace may be carried by the flexible substrate. A second conductive trace may be carried by the flexible substrate adjacent to the first conductive trace. An open circuit may be formed between the first conductive trace and the second conductive trace when the flexible substrate is dry. The presence of a threshold amount of liquid on the flexible substrate may form a closed circuit with the first conductive trace and the second conductive trace due to the flexible substrate being wet.

In some embodiments, the support surface may include a therapeutic layer having a plurality of bladders that are configured to inflate. A protective layer may be positioned over the therapeutic layer. A control unit may be configured to inflate the therapeutic layer. In a normal mode, the control unit may not be coupled to the therapeutic layer and the therapeutic layer is deflated. In a therapeutic mode, the control unit may be coupled to the therapeutic layer to inflate the therapeutic layer.

Optionally, the support surface may include a foam support layer. A foam mattress layer may be positioned on the foam support layer. A therapeutic layer may be positioned on the foam mattress layer and have a plurality of bladders. A protective layer may be positioned over the therapeutic layer. A control unit may be configured to inflate the therapeutic layer. In a normal mode, the control unit may not be coupled to the therapeutic layer and the therapeutic layer is deflated. In a therapeutic mode, a hose may couple the control unit to the therapeutic layer to inflate the therapeutic layer.

Additionally or alternatively, the patient support surface may include a first foam layer. A second foam layer may be positioned on the first foam layer. A manifold may be positioned on the second foam layer. The manifold may have a plurality of apertures. A patient three dimensional spacer may be positioned on the manifold and configured to retain a patient. The blower may be configured to direct air flow into the manifold. The airflow exits the manifold through the plurality of apertures and enters the patient three dimensional spacer.

It may be desired that the blower may include a blower housing having a base that forms a vacuum chamber and a top cover sealed to the base to create a pressurized chamber. A fan may be positioned with the pressurized chamber. A fan inlet may be sealed to the vacuum chamber. A fan outlet may be in flow communication with the pressurized chamber. A pair of housing inlets may be in flow communication with the vacuum chamber.

It may be contemplated that the blower may be controlled by setting a predetermined speed of the blower. The speed of the blower may be monitored. The monitored speed of the blower may be compared to the predetermined speed. Whether the blower has a blockage may be determined based on the comparison of the monitored speed to the predetermined speed.

In some embodiments, the support surface may also include a first foam layer. A second foam layer may be positioned on the first foam layer. A manifold may be positioned on the second foam layer. The manifold may include a bottom fabric layer and a top fabric layer. A manifold three dimensional spacer may be positioned between the bottom fabric layer and the top fabric layer. A plurality of apertures may be formed in the top fabric layer. A patient three dimensional spacer may be positioned on the manifold and configured to retain a patient. Exit apertures may be formed in a head end of the patient three dimensional spacer. The blower may be configured to direct air flow into the manifold three dimensional spacer. The airflow may exit the manifold three dimensional spacer through the plurality of apertures and enter the patient three dimensional spacer. The air flow may flow through the patient three dimensional spacers to the exit apertures.

Optionally, an x-ray cassette sleeve may have an openings that extend at least partially along two sides of the support surface.

Additionally or alternatively, an x-ray cassette sleeve may have an opening that is sealed by a pair of sleeve zippers. Each of the pair of sleeve zippers may extend at least partially along a side of the support surface.

It may be desired that an electronics enclosure may be positioned within the support surface. A wire may extend from the electronics enclosure and may be grounded. An overmold may be formed on the wire. A terminal may extend from the wire through the overmold to provide a ground test point.

In some embodiments, a support surface outlet port may extend through the support surface and may be in fluid communication with the outlet port of the blower. The support surface outlet port may have a lip to facilitate preventing the ingress of fluids into the support surface outlet port.

According to a further aspect of the disclosed embodiments, patient support apparatus includes a support surface configured to conduct air along a top face of the support surface so that heat and moisture from a patient lying on the support surface are drawn away from the top face of the support surface. An opening may be formed in a side of the support surface. A cavity may extend from the opening into the support surface. An inlet port may be positioned within the cavity and may fluidly couple to the top face. A blower assembly may be configured to position within the cavity. The blower assembly may have an outlet port that couples to the inlet port when the blower assembly is positioned within the cavity. The blower assembly may conduct air through the inlet port to the top face of the support surface.

According to an aspect of the disclosed embodiments, a patient support apparatus may include a cover having a foot end and an opposite head end. A pair of sides may extend between the foot end and the head end. A cover inlet may extend through the cover. A cover outlet may extend through the cover. A blower assembly may positioned in the cover, the blower assembly may have a blower inlet in flow communication with the cover inlet and a blower outlet. A microclimate management system may be in flow communication with the blower outlet. Air may flow through the cover inlet to the blower assembly and the blower assembly may discharge the air to the microclimate management system. The air may be discharged from the microclimate management system through the cover outlet.

In some embodiments, the cover inlet may be positioned in one of the sides of the cover. Some embodiments may include two cover inlets. Each cover inlet may be positioned in one of the sides of the cover. The blower assembly may include two blower inlets. Each blower inlet may be in fluid communication with one of the cover inlets. The cover outlet may positioned in the head end of the cover. Some embodiments may include a plurality of cover outlets.

Optionally, the cover inlet may include an opening. An inlet cover may partially cover the opening. A plug may be positioned in the opening and may be configured to couple the cover inlet to the blower inlet. The plug may include an opening flange that may be configured to be inserted into the opening. A blower flange may be configured to couple to the blower inlet. A passageway may extend through the plug. The passageway may have an axis that is co-axial to an axis of the opening when the opening flange is inserted into the opening. The cover outlet may include an opening. An outlet cover may partially cover the opening. A plug may be positioned in the opening and may be configured to couple the cover outlet to an outlet of the microclimate management system. The plug may include an opening flange that may be configured to be inserted into the opening. The cover outlet may include a notch and the plug may include a tab. The tab may be received in the notch to prevent rotation of the plug relative to the cover outlet when the opening flange is inserted into the opening. The plug may include a lip that extends from the opening when the opening flange is inserted into the opening.

Additionally or alternatively, a ground plate may be positioned in the blower assembly. A ground wire may extend from the ground plate. The ground wire may extend through the cover. A ground lug may extend from the ground wire. The ground lug may be configured to enable testing of the blower assembly. The ground lug may enable impedance testing of the blower assembly.

It may be desired that a power cord may extend through the cover. The power cord may include an overmold. The cover may include an umbilical. The umbilical may be secured to the overmold to prevent fluid ingress into the cover. The overmold may include a pair of ridges. A notch may be defined between the ridges. The umbilical may be secured to the overmold with at least one of a tie or clamp secured within the notch.

According to another aspect of the disclosed embodiments, a patient support apparatus may include a cover having a foot end and an opposite head end. A pair of sides may extend between the foot end and the head end. A pair of cover inlets may be provided. Each cover inlet may extend through one of the sides of the cover. A plurality of cover outlets may extend through the head end of the cover. A blower assembly may be positioned in the cover. The blower assembly may have a blower inlet in flow communication with the cover inlet and a blower outlet. A microclimate management system may be in flow communication with the blower outlet. Air may flow through the cover inlet to the blower assembly and the blower assembly may discharge the air to the microclimate management system. The air may be discharged from the microclimate management system through the cover outlet.

It may be desired that the blower assembly may include two blower inlets. Each blower inlet may be in fluid communication with one of the cover inlets. The cover inlet may include an opening. An inlet cover may partially cover the opening. A plug may be positioned in the opening and may be configured to couple the cover inlet to the blower inlet. The plug may include an opening flange that may be configured to be inserted into the opening. A blower flange may be configured to couple to the blower inlet. A passageway may extend through the plug. The passageway may have an axis that is co-axial to an axis of the opening when the opening flange is inserted into the opening.

In some embodiments, the cover outlet may include an opening. An outlet cover may partially cover the opening. A plug may be positioned in the opening and may be configured to couple the cover outlet to an outlet of the microclimate management system. The plug may include an opening flange that is configured to be inserted into the opening. The cover outlet may include a notch and the plug may include a tab. The tab may be received in the notch to prevent rotation of the plug relative to the cover outlet when the opening flange is inserted into the opening. The plug may include a lip that extends from the opening when the opening flange is inserted into the opening.

Optionally, a ground plate may be positioned in the blower assembly. A ground wire may extend from the ground plate. The ground wire may extend through the cover. A ground lug may extend from the ground wire. The ground lug may be configured to enable testing of the blower assembly. The ground lug may enable impedance testing of the blower assembly.

Additionally or alternatively, a power cord may extend through the cover. The power cord may include an overmold. The cover may include an umbilical. The umbilical may be secured to the overmold to prevent fluid ingress into the cover. The overmold may include a pair of ridges. A notch may be defined between the ridges. The umbilical may be secured to the overmold with at least one of a tie or clamp secured within the notch.

According to yet another aspect of the disclosed embodiments, a patient support apparatus may include a cover having a foot end and an opposite head end. A pair of sides may extend between the foot end and the head end. A cover inlet may extend through the cover. The cover inlet may have an opening. An inlet cover may partially cover the opening. A plug may be positioned in the opening and configured to couple the cover inlet to a blower assembly positioned within the cover.

It may be desired that the cover inlet may be positioned in one of the sides of the cover. Some embodiments may include two cover inlets. Each cover inlet may be positioned in one of the sides of the cover. A blower assembly may include two blower inlets. Each blower inlet may be in fluid communication with one of the cover inlets. The plug may include an opening flange that may be configured to be inserted into the opening. A blower flange may be configured to couple to the blower assembly. A passageway may extend through the plug. The passageway may have an axis that is co-axial to an axis of the opening when the opening flange is inserted into the opening.

According to a further aspect of the disclosed embodiments, a patient support apparatus may include a cover having a foot end and an opposite head end. A pair of sides may extend between the foot end and the head end. A cover outlet may extend through the cover. The cover outlet may include an opening. An outlet cover may partially cover the opening. A plug may be positioned in the opening and may be configured to couple the cover outlet to a microclimate management system positioned within the cover.

It may be contemplated that the cover outlet may be positioned in the head end of the cover. Some embodiments may include a plurality of cover outlets. The plug may include an opening flange that may be configured to be inserted into the opening. The cover outlet may include a notch and the plug may include a tab. The tab may be received in the notch to prevent rotation of the plug relative to the cover outlet when the opening flange is inserted into the opening. The plug may include a lip that extends from the opening when the opening flange is inserted into the opening.

According to yet a further aspect of the disclosed embodiments, a patient support apparatus may include a cover having a foot end and an opposite head end. A pair of sides may extend between the foot end and the head end. A blower assembly may be positioned in the cover. A ground plate may be positioned in the blower assembly. A ground wire may extend from the ground plate. The ground wire may extend through the cover.

In some embodiments, ground lug may extend from the ground wire. The ground lug may be configured to enable testing of the blower assembly. The ground lug may enable impedance testing of the blower assembly.

Optionally, the blower assembly may include a blower inlet that may be in fluid communication with a cover inlet positioned in the cover. The cover inlet may include an opening. An inlet cover may partially cover the opening. A plug may have an opening flange that may be configured to be inserted into the opening. A blower flange may be configured to couple to the blower inlet. A passageway may extend through the plug. The passageway may have an axis that is co-axial to an axis of the opening when the opening flange is inserted into the opening.

In some embodiments, the blower assembly may include a blower outlet that is in fluid communication with a cover outlet positioned in the cover. The cover outlet may include an opening. An outlet cover may partially cover the opening. A plug may have an opening flange that may be configured to be inserted into the opening. The plug may be configured to couple to an outlet of a microclimate management system. The cover outlet may include a notch and the plug may include a tab. The tab may be received in the notch to prevent rotation of the plug relative to the cover outlet when the opening flange is inserted into the opening. The plug may include a lip that extends from the opening when the opening flange is inserted into the opening.

It may be contemplated that a power cord may extend through the cover. The power cord may include an overmold. The cover may include an umbilical. The umbilical may be secured to the overmold to prevent fluid ingress into the cover. The overmold may include a pair of ridges. A notch may be defined between the ridges. The umbilical may be secured to the overmold with at least one of a tie or clamp secured within the notch. The power cord and the ground wire may be sheathed together.

According to an aspect of the disclosed embodiments, a patient support apparatus may include a cover having a foot end and an opposite head end. A pair of sides may extend between the foot end and the head end. The cover may have an umbilical. A blower assembly may be positioned in the cover. A power cord may extending from the blower assembly and through the cover. The power cord may have an overmold. The umbilical may be secured to the overmold to prevent fluid ingress into the cover.

In some embodiments, the overmold may include a pair of ridges. A notch may be defined between the ridges. The umbilical may be secured to the overmold with at least one of a tie or clamp secured within the notch.

Optionally, a ground plate may be positioned in the blower assembly. A ground wire may extend from the ground plate. The ground wire may extend through the cover. A ground lug may extend from the ground wire. The ground lug may be configured to enable testing of the blower assembly. The ground lug may enable impedance testing of the blower assembly.

Optionally, the blower assembly may include a blower inlet that may be in fluid communication with a cover inlet positioned in the cover. The cover inlet may include an opening. An inlet cover may partially cover the opening. A plug may have an opening flange that may be configured to be inserted into the opening. A blower flange may be configured to couple to the blower inlet. A passageway may extend through the plug. The passageway may have an axis that is co-axial to an axis of the opening when the opening flange is inserted into the opening.

In some embodiments, the blower assembly may include a blower outlet that is in fluid communication with a cover outlet positioned in the cover. The cover outlet may include an opening. An outlet cover may partially cover the opening. A plug may have an opening flange that may be configured to be inserted into the opening. The plug may be configured to couple to an outlet of a microclimate management system. The cover outlet may include a notch and the plug may include a tab. The tab may be received in the notch to prevent rotation of the plug relative to the cover outlet when the opening flange is inserted into the opening. The plug may include a lip that extends from the opening when the opening flange is inserted into the opening.

BRIEF DESCRIPTION OF THE DRAWINGS

The detailed description particularly refers to the accompanying figures in which:

FIG. 6 is a perspective view of the patient support apparatus of FIG. 1 having a support surface in accordance with an embodiment and a pneumatic blower positioned therein;

FIG. 7 is a front elevation view of an interface of the support surface of FIG. 6;

FIG. 8 is a perspective view of a power cord of a pneumatic blower having a controller incorporated therein;

FIG. 10 is a front elevation view of an interface of a pneumatic blower in accordance with an embodiment;

FIG. 11 is a front perspective view of a patient pedant for a support surface formed in accordance with an embodiment;

FIG. 12 is a front perspective view of a patient pedant for a support surface formed in accordance with an embodiment;

FIG. 15 is a perspective view of a patient support apparatus in accordance with an embodiment and having a scale incorporated into a support surface thereof;

FIG. 16 is a schematic view of a screen for monitoring the scale of FIG. 15;

FIG. 27 is a cross-sectional view of one embodiment of the support surface shown in FIG. 26 illustrating the support surface without a patient or load positioned thereon;

FIG. 28 is a cross-sectional view of the support surface similar to the view shown in FIG. 27, wherein a patient is illustrated on the support surface and the support surface has bottomed out;

FIG. 34 is a side elevation view of a support surface having a cam assembly positioned in a foot end, wherein the cam assembly operates as a heel suspension mechanism;

FIG. 35 is a side elevation view similar to FIG. 34, wherein the cam assembly is actuated to raise the foot end of the support surface;

FIG. 36 is a side elevation view of a support surface having another cam assembly positioned in a foot end, wherein the cam assembly operates as a heel suspension mechanism;

FIG. 37 is a side elevation view similar to FIG. 36, wherein the cam assembly is actuated to raise the foot end of the support surface;

FIG. 38 is a side elevation view of a support surface having yet another cam assembly positioned in a foot end, wherein the cam assembly operates as a heel suspension mechanism;

FIG. 39 is a side elevation view similar to FIG. 38, wherein the cam assembly is actuated to raise the foot end of the support surface;

FIG. 40 is a side elevation view of a support surface having a plurality of bladders positioned in a foot end, wherein the plurality of bladders operate as a heel suspension mechanism;

FIG. 41 is a side elevation view similar to FIG. 40, wherein one of the plurality of bladders is actuated to raise the foot end of the support surface;

FIG. 46 is a side elevation view of a support surface having two air bladders positioned in a foot end, wherein the air bladders operate as a heel suspension mechanism;

FIG. 47 is a side elevation view similar to FIG. 46, wherein one of the air bladders is actuated to raise the foot end of the support surface;

FIG. 48 is a side elevation view similar to FIG. 46, wherein another of the air bladders is actuated to raise the foot end of the support surface;

FIG. 49 is a side elevation view of a support surface having a foam wedge positioned in a foot end, wherein the foam wedge operates as a heel suspension mechanism;

FIG. 50 is a side elevation view similar to FIG. 49, wherein the foam wedge is actuated to raise the foot end of the support surface;

FIG. 51 is a side elevation view of a support surface having another foam wedge positioned in a foot end, wherein the foam wedge operates as a heel suspension mechanism;

FIG. 52 is a side elevation view similar to FIG. 51, wherein the foam wedge is actuated to raise the foot end of the support surface;

FIG. 55 is a side elevation view of a support surface having another cutout positioned in a foot end, wherein the cutout operates as a heel suspension mechanism;

FIG. 56 is a side elevation view similar to FIG. 55, wherein the cutout is actuated to raise the foot end of the support surface;

FIG. 59 is a side elevation view of a support surface having an elevating member positioned in a foot end, wherein the elevating member operates as a heel suspension mechanism; and FIG. 60 is a side elevation view similar to FIG. 59, wherein the elevating member is actuated to raise the foot end of the support surface;

FIG. 84 is a top perspective view of an x-ray sleeve that is configured to be inserted into a mattress;

FIG. 85 is an exploded view of the x-ray sleeve shown in FIG. 84;

FIG. 86 is a top partial view of the x-ray sleeve shown in FIG. 84;

FIG. 87 is a cross-sectional view of the x-ray sleeve taken about line A-A in FIG. 86;

FIG. 88 is a side view of the x-ray sleeve shown in FIG. 84;

FIG. 89 is an enlarged view of area B shown in FIG. 87;

FIG. 96 is a rear perspective view of the plug positioned within the opening formed in the outlet;

FIG. 97 is a front perspective view of an inlet of a blower assembly having a cover positioned on a front face of the inlet;

FIG. 98 is a rear perspective view of the inlet having an opening;

FIG. 99 is a front perspective view of a plug that is configured to be inserted into the opening formed in the inlet;

FIG. 100 is a front perspective view of the plug positioned within the opening formed in the inlet;

FIG. 101 is a rear perspective view of the plug positioned within the opening formed in the inlet;

FIG. 107 is a perspective view of the power cord extending through an umbilical formed in a bottom cover of the mattress; and FIG. 108 is a side inside-out view of the power cord extending through an umbilical formed in a bottom cover of the mattress.

DETAILED DESCRIPTION

Figure 1:
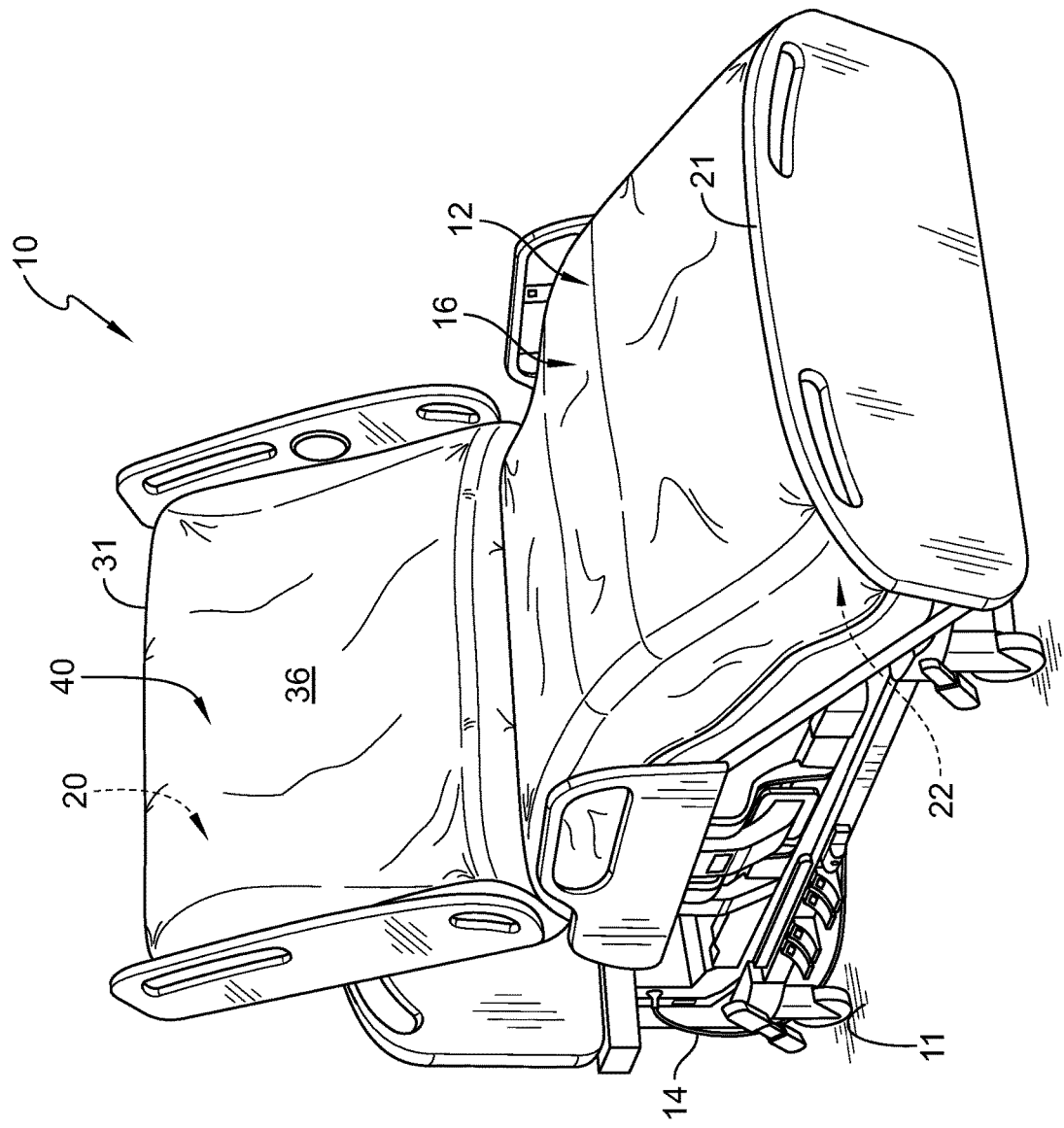
FIG. 1 is perspective view of an illustrative patient support apparatus including a microclimate system supported on a frame structure showing that the microclimate system includes a support surface.

An illustrative patient support apparatus embodied as a hospital bed 10 is shown in FIG. 1. The bed 10 is illustrated as a hospital bed; however, it will be appreciated that the bed 10 may be utilized in any healthcare facility or home. For example, the bed 10 may be utilized in a nursing home or in a patient own home under hospice care. Additionally, although this description is in reference to a bed 10, it will be appreciated that the support surfaces and devices described herein may be equally applicable to other support apparatuses, for example, chairs, wheelchairs, stretchers, etc. The bed 10 includes a microclimate system 12 mounted on a frame structure 14 that supports the microclimate system 12 above a floor 11. The microclimate system 12 is arranged to underlie a patient supported on the bed 10. The microclimate system 12 is configured to cool and dry the interface between a patient and the bed 10 to promote skin health by moving air along the interface when the patient is supported on the bed 10. The microclimate system 12 may include an environmental sensor unit configured to detect information about the environment around the microclimate system 12 so that operation of the microclimate system 12 can be adjusted to account for environmental temperature, humidity, and/or pressure.

Figure 2:
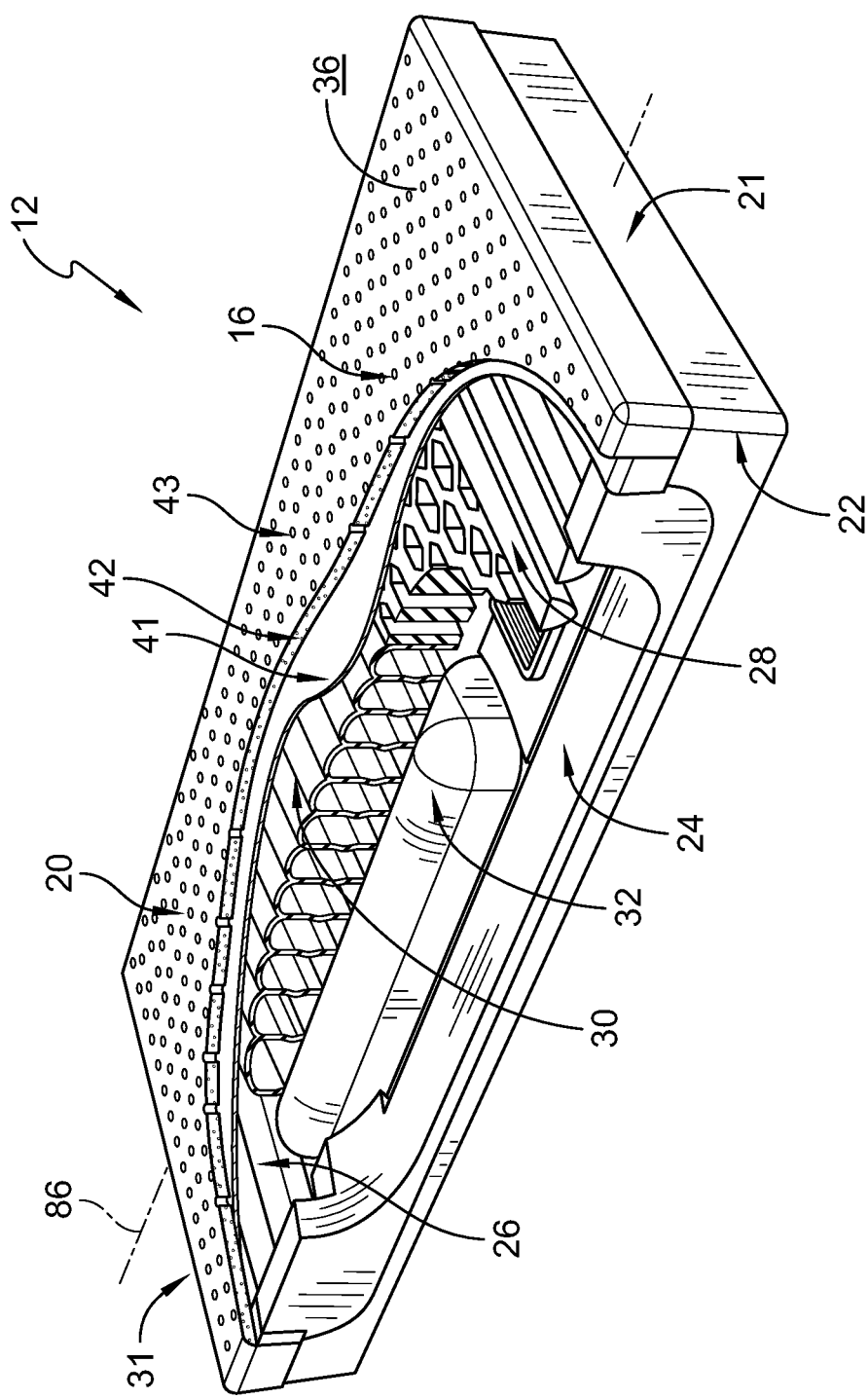
FIG. 2 is a perspective view of the microclimate system of FIG. 1 showing that the support surface includes a topper that cooperates with a lower ticking to enclose the other components of the support surface.

Referring now to FIG. 2, the support surface 16 (sometimes called a mattress) is configured to underlie a patient supported on the bed 10. An air box (not shown) may be coupled to the support surface 16 to provide conditioned air to the support surface 16 in order to cool and dry the interface between a patient and the support surface 16 when the patient is supported on the bed 10.

The support surface 16 includes a topper 20 and a lower ticking 22 that cooperate to encase a foam shell 24, a foam head section 26, a foam foot section 28, body bladders 30, and turn bladders 32 as shown, for example, in FIG. 2. The bladders 30 may be passive or active pressure redistribution bladders. In some embodiments, the bladders 30 may also include heel suspension bladders. A heel suspension feature may be utilized to replace foam wedges typically used in healthcare facilities. Other embodiments of a heel suspension feature may include a portion of the foot section 28 that folds over. In yet another embodiment, a cam may be provided to rotate a portion of the foot section 28 upward for heel suspension. It may be desired that the turn bladders 32 are also configured as passive or active pressure redistribution bladders. A passive pressure redistribution system may utilize a series of pressure release valves and foam filled bladders. The topper 20 forms a top face 36 of the support surface 16 and is configured to conduct conditioned air provided by the air box 18 along the interface between a patient and the support surface 16 when the patient is supported on the bed 10. The foam components 24, 26, 28 and the bladders 30, 32 cooperate to support a patient when the patient is supported on the bed 10. In some embodiments, the support surface 16 may also include a coverlet 40 encasing the topper 20 and the lower ticking 22 as shown in FIG. 1.

The topper 20 illustratively includes a bottom layer 41, a middle layer 42, and a top layer 43 as shown in FIG. 2. The middle layer 42 is illustratively a three-dimensional material that allows conditioned air to flow between the bottom layer 41 and the top layer 43 along the top face 36 of the support surface 16 from a foot end 21 to a head end 31 of the support surface 16. The top layer 43 is made from a perforated material that allows moisture from a patient supported on the topper 20 to pass through the top layer 43 and be carried away for evaporation by conditioned air flowing through the middle layer 42 of the topper 20. In other embodiments, other air-flow cooled toppers may be used with the support surface 16. For example, air-loss toppers, air-fluidized bead toppers, and the like can be used in support surface 16.

Figures 3, 4:
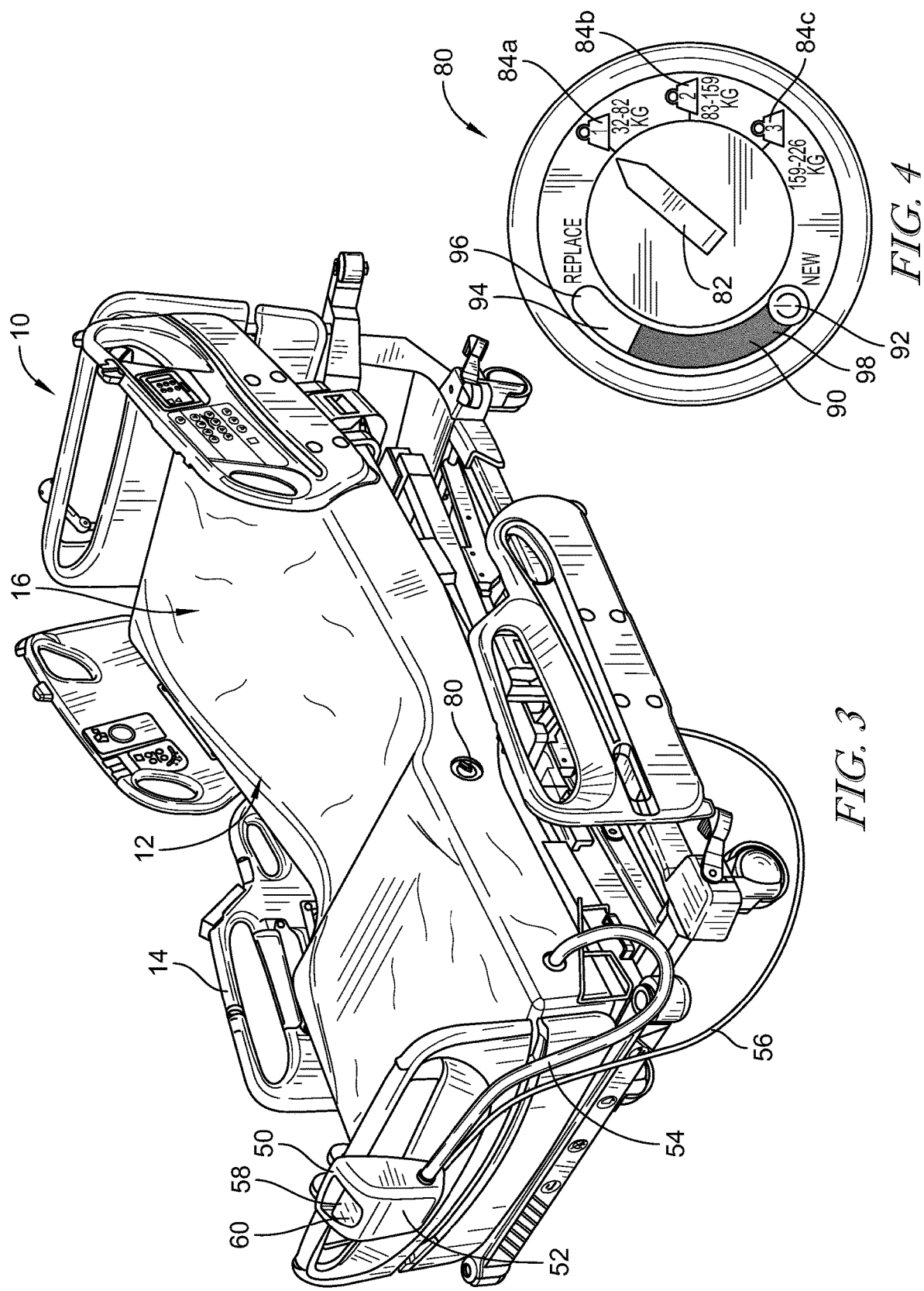
FIG. 3 is a perspective view of the patient support apparatus of FIG. 1 having a support surface in accordance with an embodiment and a pneumatic blower coupled to a foot end thereof.
FIG. 4 is a front elevation view of an interface of the support surface of FIG. 3.

Referring to FIG. 3, an air box or pneumatic blower 50 is illustratively adapted to be mounted on the frame structure 14, but in other embodiments may be integrated into the frame structure 14. By providing a separate blower 50, a cost of the micro-climate system 12 may be reduced if the microclimate system 12 is not needed. Additionally, the external nature of the blower 50 allows additional features to be packaged into the support surface 16, e.g. heel suspension, temperature control, etc. The air box 50 is coupled to the support surface 16 to provide air to the support surface 16. The air box 18 includes a housing 52 (including air handling unit), a connector hose 54, a power cord 56, and a user interface 58. The user interface 58 is coupled to the housing 52 and includes an LCD display 60 and having a number of buttons. The user interface is described in more detail below. The power cord 56 may be electrically coupled to a source of power, e.g. a wall outlet or a power source incorporated into the bed 10. The housing 52 holds an environmental sensor unit and an air handling unit. The connector hose 54 extends from the housing 52 to the support surface 16 to couple the air handling unit to the support surface 16. The connector hose 54 is illustrated as a single hose 54. The connector hose 54 is configured to provide air flow to the microclimate system 12 and the bladders 30, 32. The housing 52 may include a valve system to selectively provide air flow to one of the microclimate system 12 or the bladders 30, 32. Optionally, the connector hose 54 may include a plurality of hoses, wherein each hose connects the air handling unit to one of the microclimate system 12, the bladders 30, and the bladders 32.

An interface 80 is provided on a side of the support surface 16 in a positioned that is not blocked by a siderail of the bed 10. Although the display is illustrated in the side of the support surface 16, the interface 80 may be located at any position along the support surface 16, e.g. at a foot of the support surface 16. An expanded view of the interface 80 is provided in FIG. 4. The interface 80 includes a weight based value control system having a dial 82 and a plurality of indicators 84 that may be selected by the dial 82. In the illustrative embodiment, the indicators 84 include three weight ranges; however, any number of weight ranges may be contemplated. The weight ranges are related to a weight of the patient. By selecting a weight range that corresponds to a weight of the patient, the body bladders 30 are inflated to an appropriate level to provide comfort for the patient. For example, as first indicator 84a provides a range of 32 kg to 82 kg. For patients within this weight range, the body bladders 30 may be inflated to a first firmness. A second indicator 84b provides a weight range of 83 kg to 159 kg. Patients in this weight range may require the body bladders 30 to be inflated to a greater level than the first weight range. That is, when selecting the indicator 84b the body bladders 30 are inflated to a firmness that is greater than the firmness when the indicator 84a is selected. A third indicator 84c provides a weight range of 159 kg to 226 kg. Patients in this weight range may require the body bladders 30 to be inflated to a greater level than the second weight range. That is, when selecting the indicator 84c the body bladders 30 are inflated to a firmness that is greater than the firmness when the indicator 84b is selected. A caregiver may select the appropriate weight range (i.e. indicator 84) prior to the patient being positioned on the support surface 16 or while the patient is on the support surface 16.

The interface 80 also includes an end of life indicator 90. The end of life indicator 90 includes a "new" button 92 that may be selected when the support surface 16 is installed at the healthcare facility. By selecting the "new" button 92, an end of life meter for the support surface 16 is activated. The end of life indicator 90 also includes a meter 94. In the illustrative embodiment, the meter 94 is a liquid crystal display (LED). The meter 94 includes an upper limit 96 and a lower limit 98. When the support surface 16 is first installed and the "new" button 92 is selected, the meter 94 is started at the lower limit 98. As the support surface 16 becomes worn out, the meter 94 raises toward the upper limit 96. In some embodiments, the meter 94 is displayed in different colors. For example, when the meter 94 is near the lower limit 98, the meter 94 may be green. As the meter 94 raises to a position between the upper limit 96 and the lower limit 98, e.g. half way between the upper limit 96 and the lower limit 98, the meter 94 may turn yellow. As the meter 94 approaches the upper limit 96, the meter 94 may turn red. As the meter 94 approaches the upper limit 96, caregivers are alerted that the support surface 16 may have become worn out.

Several embodiments of end of life detectors may be used to determine when the support surface 16 has reached and of life, and to signal to the meter 94 what level of use should be displayed. Some of these embodiments are described in more detail below. In some embodiments, the end of life detector includes a timer that is activated when the support surface 16 is installed. The timer counts down the life of the support surface 16 over a predetermined time, e.g. 3 years, 5 years, and 7 years. For example, an end of life detector for a support surface 16 with a 7 year life span will indicate that the support surface 16 should be replaced 7 years from the date of installation. Some timers may be electronic, whereas other timers may include a chemical that erodes or grows over time. The chemical may be configured to erode entirely from the system within a predetermined time from the date that the chemical is activated.

In some embodiments, the timer may be switched on and off. For example, the timer may track an amount of time that the bed is in use by tracking when a patient enters and exits the support surface 16. When a patient is detected on the support surface 16, the timer is switch on to track an amount of use. When the patient exits the support surface 16, the timer is turned off. In another embodiment, the timer tracks when the support surface 16 has power. For example, when the support surface 16 is plugged in and power is delivered to the support surface 16, the timer switches to an on position to track use. When the support surface 16 is turned off and is not receiving power, the timer switches to an off position and stops tracking the use of the support surface 16 until power is restored.

Figure 5:
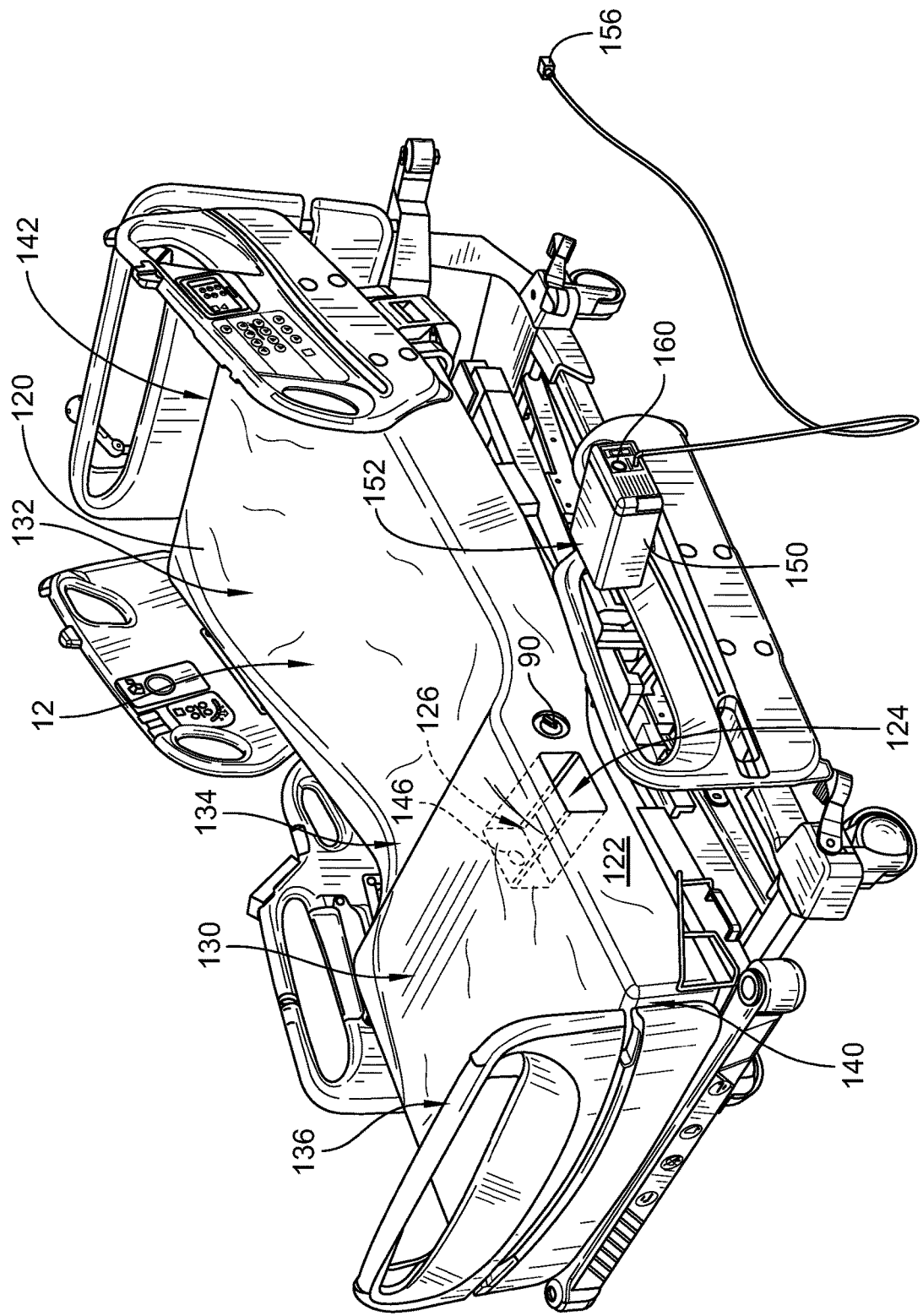
FIG. 5 is a perspective view of the patient support apparatus of FIG. 1 having a support surface in accordance with an embodiment and a pneumatic blower coupled thereto.

FIG. 5 illustrates another embodiment of a support surface 120. The support surface 120 is similar to the support surface 16 and includes several elements that are referenced with the same reference number. The support surface 120 includes a side 122 having an opening 124. A cavity 126 extends from the opening 124 and into the support surface 120. The cavity 126 is illustrated in a thigh section 130 of the support surface 120; however, in other embodiments, the cavity 126 may be formed in a head section 132, a seat section 134, or a foot section 136 of the support surface 120. The cavity 126 is formed in a section of the support surface 120 where a caregiver will have access to the cavity 126. Optionally, the cavity 126 may be formed in a foot end 140 or a head end 142 of the support surface 120. An inlet port 146 (shown in dashed lines) is housed within the cavity 126. In the illustrative embodiment, the inlet port 146 extends from a back wall 148 of the cavity 126. The inlet port 146 is in fluid communication with the microclimate system 12. Air flow into the inlet port 146 is delivered to the microclimate system 12. The inlet port 146 is also in fluid communication with the bladders 30, 32 so that air flow into the inlet port 146 may be delivered to the bladders 30, 32. A valve (not shown) may be positioned downstream from the inlet port 146 to direct air flow to one of the microclimate system 12, the bladders 30, or the bladders 32. Alternatively or additionally, the support surface 120 may include a plurality of inlet ports 146, wherein each inlet port 146 is in fluid communication with one of the microclimate system 12, the bladders 30, or the bladders 32.

An air box or pneumatic blower 150 is configured to be positioned within the cavity 126. By positioning the blower 150 in the cavity 126, space on the footboard of the bed 10 is not required. Additionally, the blower 150 may be added only when needed to save money and resources within the healthcare facility. Moreover, the blower 150 has a smaller more compact size, which saves storage space within the healthcare facility. In some embodiments, the blower 150 may be stored in the patient room. The blower 150 can be positioned within the cavity 126 while a patient is on the support surface 120. The blower 150 includes an outlet port 152. In some embodiments, the blower 150 may include a plurality of outlet ports 152. The blower 150 is configured to be inserted into the cavity 126 so that the outlet port 152 fluidly couples to the inlet port 146. Optionally, the plurality of outlet ports 152 fluidly couple to the plurality of inlet ports 146. The blower 150 controls airflow from the outlet port 152 into the inlet port 146 and, consequently, into the microclimate system 12, the bladders 30, and the bladders 32. In an embodiment having a plurality of outlet ports 152, the blower 150 may have a valve to control air flow to one of the outlet ports 152, thereby controlling air flow to one of the microclimate system 12, the bladders 30, or the bladders 32.

When a patient is in need of additional therapy, the blower 150 may be inserted into the cavity 126 to provide air flow to the microclimate system 12, the bladders 30, and the bladders 32. The blower 150 is illustrated with a power cord 156 that plugs into a wall socket. In some embodiments, the blower 150 may be battery operated. In other embodiments, the blower 150 may electrically couple to the support surface 120 when the blower 150 is inserted into the cavity 126. Such coupling may be achieved with a plug on the blower 150 that engages an outlet in the cavity 126 when the blower 150 is inserted into the cavity 126. If a patient is not in need of therapy, the blower 150 can be removed from the cavity 126. In one embodiment, the walls of the cavity 126 are formed from a stiff material that maintains a shape of the cavity 126 even if a patient is on the support surface 120. That is, the cavity 126 is left open and does not collapse. In some embodiments, the cavity 126 may be filled, for example, with a foam block, when the blower 150 is not in use.

The blower 150 includes an interface 160 that enables a caregiver to control operation of the blower 150. An example of an interface for a blower is provided below. The support surface 120 also includes an end of life indicator 90 that operates as described above. In some embodiments, operating the blower 150 may affect the life span of the support surface 120. Accordingly, the end of life detector of the end of life indicator 90 may track usage of the blower 150. For example, the end of life detector may include a timer that is activated when the blower 150 is installed within the cavity 126. The timer may be stopped when the blower 150 is removed from the cavity 126.

Referring to FIG. 6, a patient support surface 200 is provided that is similar to the patient support surface 16. Elements of the patient support surface 200 that are the same as the elements described with respect to patient support surface 16 are referenced using the same reference numbers. The patient support surface 200 includes an airbox or pneumatic blower 202 positioned within the patient support surface 200. The blower 202 is fluidly coupled to the microclimate system 12 and the bladders 30, 32. As described above valves may be positioned within the blower 202 or the microclimate system 12 to control the flow of air to one of the microclimate system 12, the bladders 30, or the bladders 32. In some embodiments, the blower 202 is permanently housed in the support surface 200 and configured to be discarded or recycled when the support surface 200 is replaced. In some embodiments, the blower 202 may be accessible via an opening in the support surface 200 to provide maintenance for the blower 202 and/or to replace the blower 202 if the blower becomes damaged before the end of life of the support surface 200. In some embodiments, when the support surface 200 reaches its end of life, the blower 202 may be removed from the support surface 200 and reused in a new support surface 200.

By integrating the blower 202 into the support surface 200, the microclimate system 12 becomes available in all support surfaces 200, thereby eliminating the need for a caregiver to find a blower that may be in storage. Additionally, the blowers 202 will not become lost within the healthcare facility, thereby reducing inventory and increasing costs. With the blower 202 built into the support surface 200, patients do not need to wait for a blower 202 to receive therapy. Moreover, an end of life indicator that operates based on usage, e.g. tracks use when the system is powered, will automatically begin tracking usage when the support surface 200 is powered, rather than requiring a blower to be added to the support surface 200. The blower 202 also avoids becoming contaminated during use because the blower 202 is incorporated into the support surface 200 and not exposed to the healthcare facility. Further, the blower 202 provides quiet operation since noises from the blower 202 are filtered by the foam and the bladders within the support surface 200.

In some embodiments, an interface 204 may be provided on a side 206 of the support surface 200 to enable a caregiver to control the blower 202. Another interface 210 is provided on the side 206 of the support surface 200. Referring to FIG. 7, the interface 210 includes the dial 82 and the plurality of indicators 84 that may be selected by the dial 82 as described above. The interface 210 is illustrated without an end of life indicator; however, it should be appreciated that the interface 210 may include an end of life indicator as shown in the interface 80 as described above.

Referring to FIG. 8, a controller 220 is provided that may be used with any of the support surfaces described herein. The controller 220 is configured to control the microclimate system 12. The controller 220 is positioned on a power cord 222, e.g. the power cord of any of the blowers described herein or the power cord of any of the support surfaces described herein. The controller 220 is configured to be operated by either the caregiver or the patient. That is, the controller 220 may be configured to be within reach of the patient when the patient is supported on a support surface. The controller 220 may include a meter 224 that indicates a remaining life span of the support surface 200. The meter 224 may include a plurality of LED colored bars 226 indicating the remaining life of the support surface. For example, the meter 224 may include eight bars 226 that are all lit green when the support surface 200 has a first predetermined life span remaining. As the life span decreases, fewer bars 226 may be lit. As an example, when only 4-5 bars 226 are lit corresponding to a second predetermined life span remaining that is less than the first predetermined life span, the bars 226 may be lit in yellow. As another example, when only 3 bars 226 or fewer are lit corresponding to a third predetermined life span less than the second predetermined life span, the bars 226 may be illuminated in red. When only one bar 226 is lit, the bar may flash red.

The controller 220 may include a power switch 228 to turn the microclimate system 12 on and off. The power switch may be a push button switch, but may take the form of any switch. An intensity button may enable a user to control the intensity of the microclimate system 12. That is, an amount of airflow from the microclimate system 12 may be increased or decreased with the button. A meter may be provided to indicate a current intensity of the microclimate system 12. The meter may only be visible when the microclimate system 12 is turned on. Additionally, the meter may include various colors to display the intensity of the microclimate system 12. For example, when the microclimate system 12 is set at a low airflow, the meter may light up 1-5 bars in a green color. When the airflow is increased, the meter may light up an additional 1-4 bars in a yellow color. When the airflow is further increased, the meter may light up an additional 1-3 bars in a red color. Accordingly, the intensity of the microclimate system 12 may be indicated both through the number of illuminated bars and the color of the bars. In some embodiments, the meter may only include a number of bars. In some embodiments, the meter may only include colors. In even further embodiments, the meter may have a numerical indicator.

Figure 9:
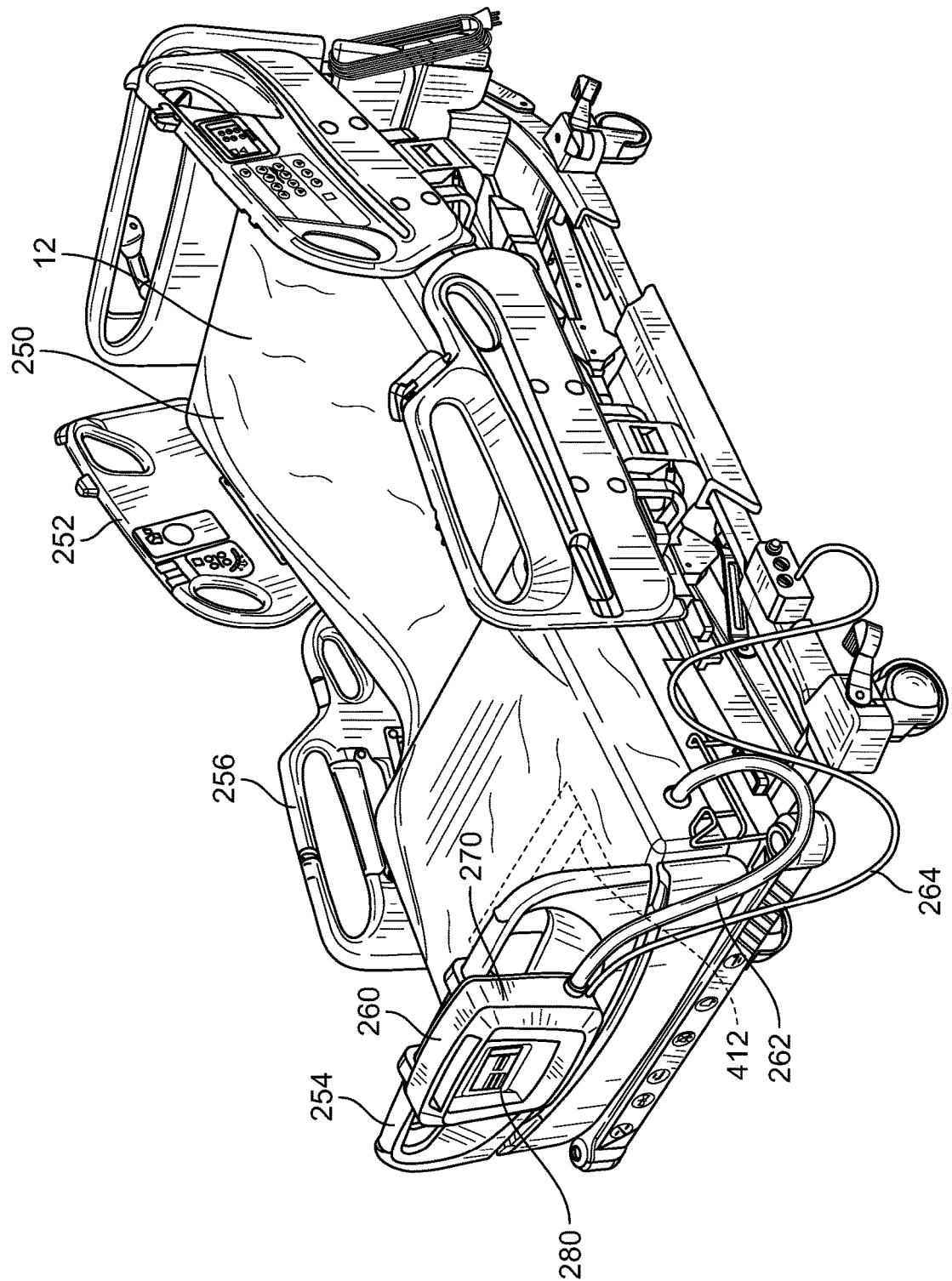
FIG. 9 is a perspective view of the patient support apparatus of FIG. 1 having a support surface in accordance with an embodiment and a pneumatic blower coupled thereto.

A support surface 250 is illustrated in FIG. 9. The support surface 250 includes elements that are the same as the elements of the support surface 16 and referenced with the same reference number. The support surface 250 is positioned on a frame 252 having a foot end 254. An airbox or pneumatic blower 260 is coupled to the foot end 254. The blower 260 may be removably coupled to the foot end 254. In some embodiments, the blower 260 may be coupled to a siderail 256 of the frame 252. The blower 260 is fluidly coupled to the microclimate system 12 and the bladders 30, 32 via a hose 262. As set forth above, multiple hoses 262 may couple the blower 260 to the microclimate system 12 and the bladders 30, 32. Optionally, the blower 260 and/or the support surface 250 may include at least one valve to direct air flow from the blower 260 to the microclimate system 12, the bladders 30, or the bladders 32. The blower 260 also includes a power cord 264 is illustrated as electrically coupling the blower 260 to a power source on the frame 252. Alternatively, the power cord 264 may be electrically coupled to a wall outlet.

The blower 260 includes a housing 270. The power cord 264 and the hose 262 extend from the housing 270. The housing 270 includes an interface 280 that may be used by a caregiver to control the blower 260. In particular, with the interface 280, the caregiver can control air flow to the microclimate system 12, the bladders 30, and the bladders 32. While illustrated in use with the support surface 250, the interface 280 may be used with any of the support surfaces described or illustrated herein. The interface 280 may be incorporated into any of the blowers and/or any of the support surfaces described or illustrated herein.

As shown in FIG. 10, the interface 280 may include a screen 282, e.g. an LED screen. In the illustrated embodiment, the screen 282 is a touch screen that enables the caregiver to select from various operational settings. The screen 282 includes a button 284 to control a pressure of the body bladders 30. The button 284 enables alternating pressure within the body bladders 30. That is, the blower 260 alternates inflating and deflating the body bladders 30 to increase and decrease an air pressure within the body bladders 30, thereby increasing and decreasing a firmness of the support surface 250. By alternating the pressure within the body bladders 30 a likelihood of the patient acquiring pressure ulcers may be reduced. In some embodiments, the blower 260 gradually increases the pressure of the body bladders 30 and then gradually decreases the pressure of the body bladders 30. In other embodiments, the increase and decrease in pressure may occur more rapidly to provide pulses to the patient. In some embodiments, all of the body bladders 30 are inflated and deflated simultaneously, whereas in other embodiments, some body bladders 30 are inflated while others are deflated to rotate the patient. The button 284 may open a second screen that enables the caregiver to select specific pressure levels and/or otherwise control the pressure within the body bladders 30.

A button 286 is provided to control the microclimate system 12. For example, the button 286 may turn the microclimate system 12 on and off. Alternatively, the button 286 may open a microclimate screen that enables the caregiver to select an amount of airflow through the microclimate system 12. By selecting the button 286 the blower 260 is activated to discharge airflow to the microclimate system 12 to prevent dry skin in injury prone areas of the patient, e.g. areas that may develop pressure ulcers.

A button 288 activates a max inflate operation of the support surface 250. By selecting the max inflate operation, all of the body bladders 30 are inflated to a maximum capacity. Additionally, the bladders 32 may also be inflated to a maximum capacity. When the bladders 30 are at maximum capacity, the support surface 250 is at a maximum firmness which assists the caregiver in repositioning the bed.

A button 290 enables a comfort adjustment operation of the support surface 250. Activating the button 290 may activate a comfort screen that enables the caregiver to selectively inflate and deflate the body bladders 30. The body bladders 30 may be adjusted per zones of the support surface 250. That is a head section, a torso section, a seat section, and a foot section of the support surface 250 may be individually controlled to inflate or deflate each section to a different pressure. For example, for patient comfort, the head section of the support surface 250 may be inflated while deflating the seat section, thereby raising the patient's head. Likewise, the foot section may be inflated to a greater capacity than the seat section to raise the patient's feet. In some embodiments, the bladders 32 may also be inflated or deflated to turn the patient onto one side.

A CPR button 292 activates a CPR function of the support surface 250. Like button 288, the CPR button 292 inflates all of the bladders 30 to a maximum pressure. However, the CPR button 292 also stops all other therapies currently active in the support surface 250, for example, the microclimate system 12, heaters, and any therapy that may vibrate or pulse the support surface 250. By inflating the bladders 30 to a maximum pressure, the support surface 250 is at a maximum firmness, which is ideal for performing CPR on a patient.

Part of the screen 282 also includes an on button 300 and an off button 302 for a patient pendant (described in more detail below). When the on button 300 is selected, the patient pendant enables the patient to individually control various comfort features of the support surface. When the off button 302 is selected, the patient pendant is disabled and the patient is not capable of controlling any support surface functions.

A home button 304 returns the interface 280 to the screen 282 if the interface has been changed to a different screen as described above. An alarm button 306 alerts other caregivers, for example, at the nurse's station, of emergencies. Such emergencies may include a patient who is coding, a patient who is having a severe reaction to medication or the like, a patient who has become ill, a patient who has become violent, etc. A settings button 308 activates a settings screen that enables the caregiver to alter various settings of the interface 280, the support surface 250, or any other device coupled to the support surface 250.

An exemplary patient pendant 320 is illustrated in FIG. 11 and includes support surface firmness controls 322. The firmness controls 322 control an amount of pressure in the body bladders 30 by inflating or deflating the body bladders 30. A button 324 is provided to increase a pressure of the body bladders 30 by supplying additional air flow to the body bladders 30 from the blower 260. Another button 326 is provided to decrease a pressure of the body bladders 30 by releasing air from the body bladders 30. The button 324 is includes a plus sign and the button 326 includes a minus sign. A meter 328 displays the current firmness of the support surface 250. The meter 328 includes a plurality of bars 330 that are lit, e.g. with LEDs, to display the current firmness. If no bars 330 are lit, the support surface 250 is at a lowest level of firmness. As the button 324 is activated, the number of lit bars 330 increases corresponding to the amount of pressure increase. If all of the bars 330 are lit, the support surface 250 is at a maximum firmness. As the button 326 is activated, fewer bars 330 remain lit to correspond to a decrease in pressure.

The pendant 320 also includes an alternating pressure control 340. The alternating pressure control 340 controls alternations in pressure within the body bladders 30 as related to the alternating pressure function described above. The alternating pressure control 340 may control a rate at which the body bladders 30 alternate in pressure. The alternating pressure control 340 may also control a variance in pressures between max inflate and max deflate. By activating, the alternating pressure control 340, a minimum setting, a normal setting, or a maximum setting may be selected. The selected setting is indicated by one of three lights (LEDs) 342 provided next to the alternating pressure control 340. A light 342a indicates the minimum setting, a light 342b indicates the normal setting, and a light 342c indicates the maximum setting. In some embodiments, the maximum setting alternates between inflated and deflated faster than the normal setting, which, in turn, alternates between inflated and deflated faster than the minimum setting. In some embodiments, the maximum setting inflates and deflates over a greater pressure range than the normal setting, which inflates and deflates over a greater pressure range than the minimum setting.

A sleep mode button 350 positions the support surface 250 for a comfortable sleeping position. For example, the sleep mode button 350 may inflate and deflate certain body bladders 30 to comfortably position the patient for sleeping. In some embodiments, the sleep settings are patient specific and programmed at the time the patient is admitted pursuant to the patient's requests. In some embodiments, the sleep mode button 350 may also raise and lower parts of the bed, e.g. the head section or the foot section.

Referring to FIG. 12, another patient pendant 370 enables patient control over various features of the support surface 250. A massage control 372 includes an activation button 374. Selecting the activation button 374 cycles the massage control 372 between vibrations, pulses, and off. For example, pressing the button 374 a first time activates vibration mode, wherein the body bladders 30 are vibrated with rapid air flow. The vibration mode is indicated with an indicator 378 that is lit when the vibration mode is selected. Pressing the button 374 a second time activates the pulsation mode, wherein air flow is pulsed through the body bladders 30. The pulsation mode is indicated with an indicator 380 that is lit when the pulsation mode is selected. Pressing the button 374 a third time deactivates the massage control and both indicators 378 and 380 become unlit. The intensity of the massage control may be altered with an increase button 382 and a decrease button 384, wherein the increase button 382 increases a rate of vibration or pulses, and the decrease button 384 decreases the rate of vibrations pulses. An LED meter 386 indicates a level of intensity between maximum intensity 388 and minimum intensity 390.

A microclimate control 400 toggles the microclimate system 12 between various intensities. In some embodiments, the microclimate control 400 is only activated when a caregiver activates the microclimate system 12, e.g. from the interface 280 as described above. In some embodiments, the patient may activate the microclimate system 12 with the microclimate control 400. That is, activating the microclimate control 400 may activate the microclimate system 12 and then allow the patient to toggle through the intensity levels before the microclimate system 12 is deactivated after the patient has toggled through each intensity level. For example, pressing the microclimate control 400 a first time, places the microclimate system 12 at a minimum intensity, as indicated by light 402, wherein the microclimate system 12 provides a low level of air flow to the patient. Pressing the microclimate control 400 a second time, places the microclimate system 12 into normal operation, as indicated by light 404. Pressing the microclimate control 400 a third time places the microclimate system 12 at a maximum intensity, as indicated by light 406, and wherein a maximum amount of air flow is provided to the microclimate system 12. In an embodiment where a caregiver must activate the microclimate system 12, pressing the microclimate control a fourth time returns the microclimate system 12 to the minimum intensity. In another embodiment, pressing the microclimate control 400 a fourth time may deactivate the microclimate system 12.

A foot warming button 410 activates a foot warmer 412 within the support surface 250. The foot warmer 412 is illustrated in FIG. 9 as being incorporated into the support surface 250. However, the foot warmer 412 may be an additional component that is positioned on the support surface 250. In some embodiments, the support surface 250 includes other warmers, for example, a seat warmer and/or a back warmer. Any warmers incorporated into the support surface 250 may be controlled by a patient pendant, e.g. pendant 370. An indicator 414 is lit when the foot warmer is activated. In some embodiments, an intensity of heat from the foot warmer from a low heat to a high heat may be controlled with the pendant 370.

Figures 13, 14:
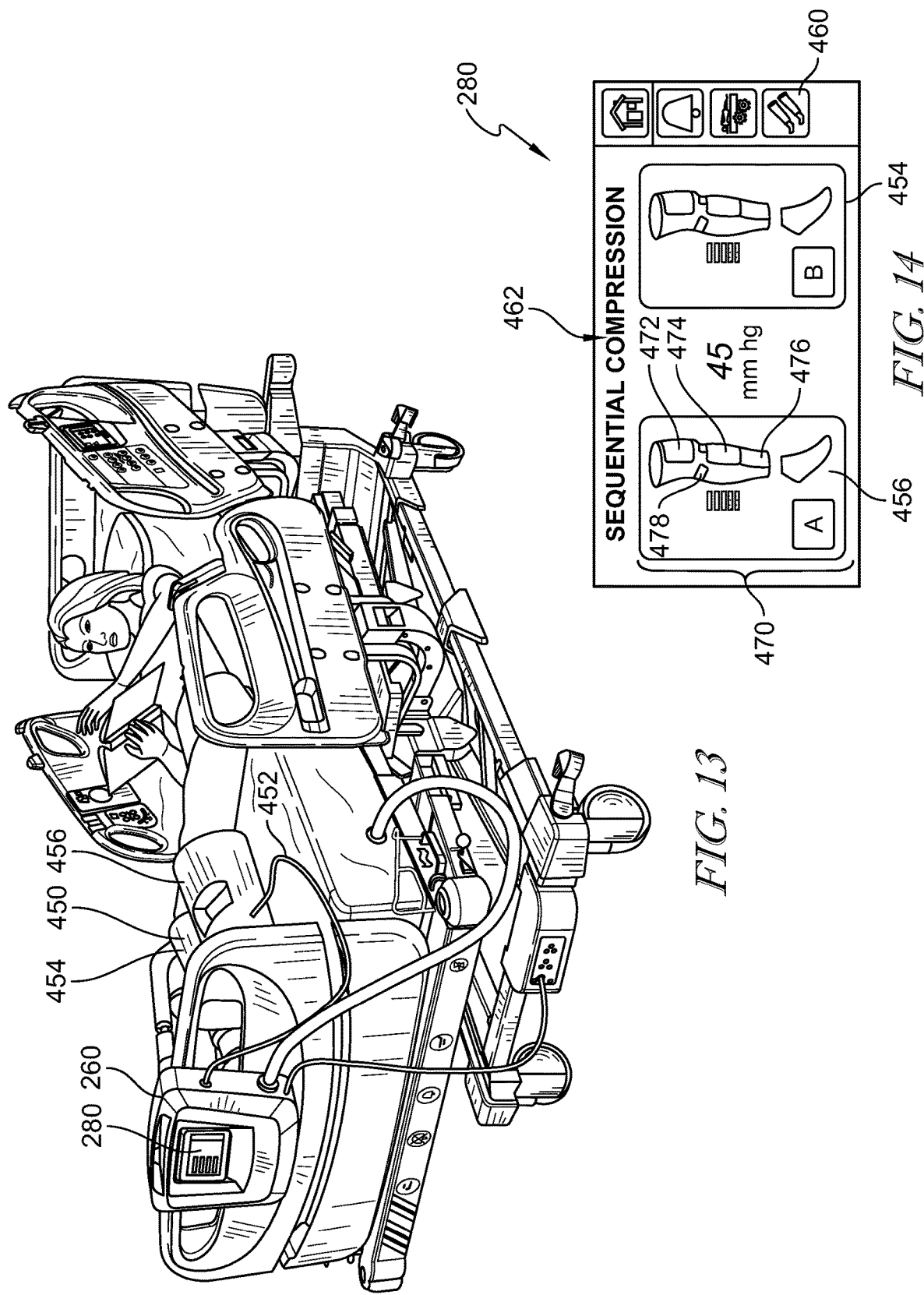
FIG. 13 is a view of a patient support apparatus having a pneumatic blower coupled to a frame thereof and a compression sleeve fluidly coupled to the pneumatic blower.
FIG. 14 is a schematic view of a screen of a user interface that is configured to control air flow to the compression sleeve shown in FIG. 13.

In FIG. 13, a compression sleeve 450 is coupled to the blower 260 via a hose 452. The compression sleeve 450 is illustrated on the patient's legs to prevent blood clots and/or pressure ulcer in the patient's legs. The compression sleeve 450 includes a right sleeve 454 and a left sleeve 456. When the compression sleeve 450 is coupled to the blower 260 an icon or button 460 appears on the interface 280, as illustrated in FIG. 14. Selecting the icon 460 activates compression screen 462 on the interface 280. The screen 462 illustrates the right sleeve 454 and the left sleeve 456. Through screen 462 the caregiver can alter a pressure that is applied to the sleeve 450. In some embodiments, a selected pressure is applied to both the right sleeve 454 and the left sleeves 456. In some embodiments, different pressures may be applied to the right sleeve 454 and the left sleeve 456. Each sleeve 454 and 456 includes several zones 470, for example, an upper leg zone 472, a first lower leg zone 474, a second lower leg zone 476, and a calf zone 478. In some embodiments, each zone 470 may be supplied with the same pressure. In other embodiments, the zones 470 may each be supplied with a different pressure depending on the needs of the patient.

Referring to FIG. 15, a weigh scale 500 is incorporated into the support surface 250. The weigh scale 500 may be positioned within the support surface 250. Alternatively, the weigh scale 500 may be positioned under the support surface 250. The weigh scale 500 includes load cells 502 that monitor a weight of a patient on the support surface 250. The load cells 502 are electrically coupled to a transmitter 504. The transmitter 504 is wirelessly connected to the interface 280. When the weigh scale 500 is operational, the transmitter 504 sends signals to the interface 280 indicative of a weight measured by the load cells 502. The transmitter 504 may include a radio-frequency identification tag to identify the support surface 250 at a remote location or at the interface 280. In some embodiments, the transmitter 504 may communicate with a cloud server via wireless connections, Bluetooth® connections or other wireless capabilities. As illustrated in FIG. 16, the interface 280 includes a screen 506 that enables an operator to control the weigh scale 500. An icon 510 allows the caregiver to wirelessly connect the interface 280 to the weigh scale 500 so that the interface 280 may receive signals from the weigh scale 500. An icon 512 syncs the interface to the weigh scale 500 to receive a signal from the transmitter 504 indicative of the patient's weight. The screen 506 displays the patient's weight when the signal is received from the transmitter 504. The screen 506 also displays a date and time that the signal was received.

As set forth above, some end of life indicators may track the use of a support surface, e.g. support surface 250, based on an amount of time that the support surface 250 is in use. In some embodiments, the weigh scale 500 may detect that a patient is on the support surface 250. The weigh scale 500 then sends a signal to the end of life indicator instructing the end of life indicator to begin tracking time with a timer. When the weigh scale 500 detects that the patient is no longer on the support surface 250, the weigh scale 500 sends a signal to the end of life indicator instructing the end of life indicator to stop the timer. In one example, the life span of the support surface may be three years. Accordingly, if the weigh scale 500 detects that a patient has been on the support surface for 2 hours, the end of life indicator reduces remaining life span of the support surface 250 by 2 hours. That is, by communicating with the weigh scale 500, the end of life indicator tracks an actual usage of the support surface 250 and alerts the caregiver when the usage reaches a predetermined time. In some embodiments, the end of life indicator may also factor the weight of a patient in determining a remaining useful life of the support surface 250. For example, the support surface 250 may have a useful life of 7 years for patients under 200 pounds, and a useful life of only 5 years for patients over 200 pounds. By receiving a signal indicative of the patient's weight, the end of life indicator may more accurately determine the remaining life span of the support surface 250.

The weigh scale 500 provides bed entry and bed exit features that may be utilized in conjunction with caregiver input to track a use of the support surface 250. A bed entry signal from the weigh scale triggers a continuous timer that is started and runs as long as the patient is on the support surface 250. The timer pauses when a bed exit signal is delivered from the weigh scale 500. In some embodiments, the weigh scale 500 also determines the weight of the patient. In other embodiments, the patient weight may be entered by the caregiver. Each block of support surface occupancy is recorded along with the patient's weight to provide a usage profile. The usage profile provides the healthcare facility with real-world use data that may be used to determine surface performance trends in the support surface over time.

Figures 17, 18:
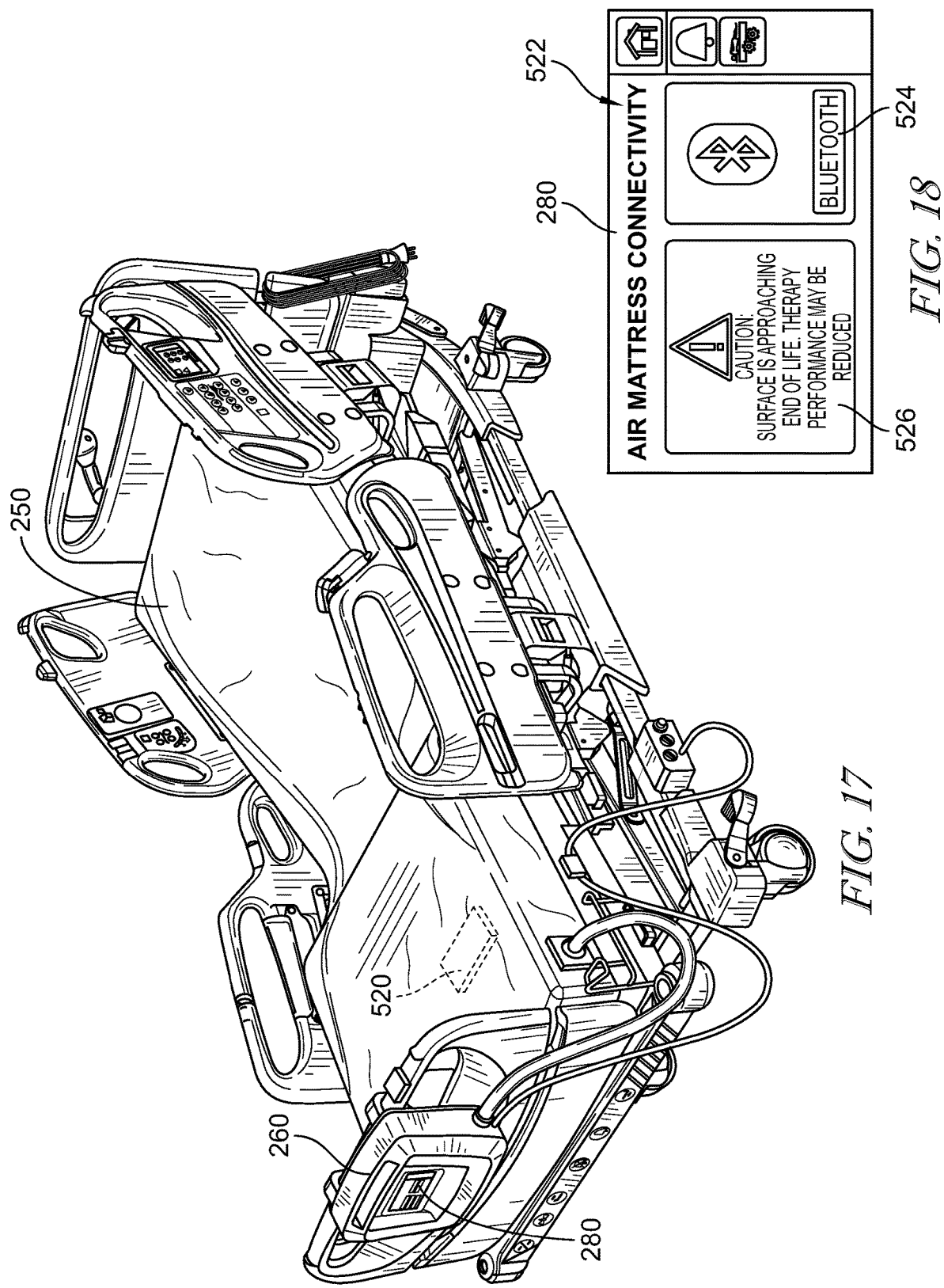
FIG. 17 is a perspective view of a patient support apparatus in accordance with an embodiment and having an end of life monitor incorporated into a support surface thereof.
FIG. 18 is a schematic view of a screen for monitoring the end of life monitor of FIG. 17.

As shown in FIG. 17, a transmitter 520 is positioned with the support surface 250. The transmitter 520 may be a near field communication device or any other transmitter capable of wirelessly communicating with the interface 280. In some embodiments, the transmitter 520 may also communicate with a remote hub, for example, a nurse's station. The transmitter 520 is electrically coupled to an end of life indicator incorporated with the support surface 250. As described herein, the end of life end indicator may be the weigh scale 500 described in FIG. 15, an electrical timer and/or a chemical timer. In some embodiments, the electrical and/or chemical timer may count down a useful life of the support surface 250. In other embodiments, the electrical timer may track an amount of time that a patient is on the support surface 250. In yet another embodiment, the electrical timer may track an amount of time that the support surface 250 is receiving power from a power supply or an amount of time that the support surface 250 is turned on.

The transmitter 520 is configured to communicate with the end of life indicator to receive a signal indicative of a remaining useful life of the support surface 250. The transmitter 520 is further configured to wirelessly communicate with the interface 280 to display an alert regarding the remaining useful life of the support surface 250. The transmitter 520 may include a radio-frequency identification tag to identify the support surface 250 at a remote location or at the interface 280. In some embodiments, the transmitter 520 may communicate with a cloud server via wireless connections, Bluetooth® connections or other wireless capabilities. For example, the interface 280 may have a screen 522 as illustrated in FIG. 18. The screen 522 includes a wireless connection button 524 that may be activated to communicatively couple the interface 280 to the transmitter 520. That is, the button 524 may be activated so that the interface 280 begins receiving a wireless signal from the transmitter 520. In other embodiments, the interface 280 is in constant communication with the transmitter 520 while both the interface 280 and the transmitter 520 are powered. When the transmitter 520 is in communication with the interface 280, the screen 522 displays an icon 526 indicating the remaining life of the support surface 250 as determined from the signal from the transmitter 520.

FIG. 18 illustrates a warning that the support surface 250 is approaching an end of its useful life. This warning may be displayed when the support surface 250 has a predetermined remaining useful life, e.g. 1 year, 6 months, etc. In some embodiments, the icon 526 may display an estimated remaining life in a numerical value. For example, the icon 526 may display the words "7 years, "5 years," "6 months," etc. Alternatively or additionally, the icon 526 may display a color indicative of the remaining life. For example, the color green may indicated that the support surface 250 has over 5 years of remaining useful life, the color yellow may indicate that the support surface 250 has between 1 year and 5 years of remaining useful life, and the color red may indicate that the support surface 250 has less than 1 year of remaining useful life. In some embodiments, numerical figures may be used in conjunction with colors. In yet another embodiment, the icon 526 may display a meter indicative of the remaining useful life of the support surface 250. The meter may be used in conjunction with numerical figures and/or colors. In some embodiments, the screen 522 may display a predicted age of the support surface 250 based on usage, an actual age of the support surface 250, a manufacturing date, an installation date, fault codes, error messages, and/or usage data, e.g. number of uses, average patient weight, mean patient weight, average time of use, and/or mean time of use.

In some embodiments, a serial number of the support surface 250 is recorded at a time of manufacture. This number is then stored and made available to the healthcare facility so that the healthcare facility can track a usage of the support surface 250. Once the support surface 250 receives power, e.g. the support surface is plugged in or turned on, a continuous timer tracks the time that the support surface 250 is in use. Once the support surface 250 is powered down, e.g. unplugged or turned off, the timer stops and records a total usage time. The total usage time is associated with the serial number and data related to the total usage is transmitted to a remote hub of the healthcare facility allowing the usage data of all support surfaces 250 to be associated with the serial number of the support surface 250 and recorded by the healthcare facility.

Figure 19:
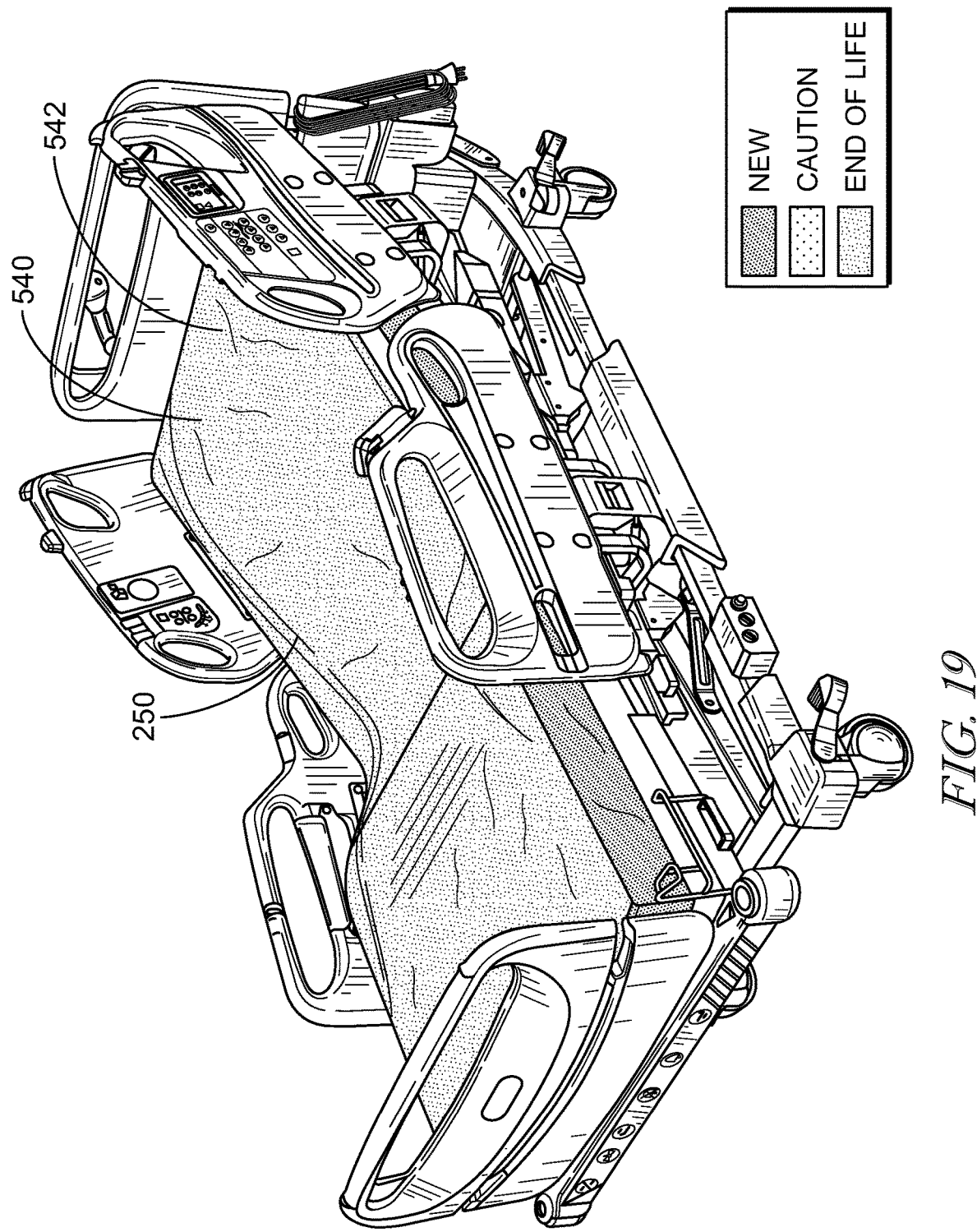
FIG. 19 is a perspective view of a patient support apparatus having a support surface with an end of life indicator incorporated into a top face of the support surface.

Referring to FIG. 19, an end of life indicator 540 is incorporated into a top face 542 of the support surface 250. The end of life indicator 540 is configured to change a color of the top face 542 to indicate a remaining useful life of the support surface 250. For example, as new support surface 250, the top face 542 may be blue. As the support surface 250 ages, the top face 542 may alter to a light blue color indicating caution. When the support surface 250 has reached its end of life, the top face 542 may turn to a grey color. In some embodiments, other colors such as green, yellow, and red may be provided. In some embodiments, the top face 542 remains blue when it has over a first predetermined remaining useful life, e.g. over 5 years. The top face 542 may turn light blue when the remaining useful life is between the first predetermined remaining useful life and a second predetermined remaining useful life, e.g. 1-5 years. The top face 542 may turn grey when the remaining useful life is below the second predetermined remaining useful life, e.g. less than 1 year.

In some embodiments, the top face 542 is filled with a base chemical that changes color when exposed to a catalyst. Upon installing the support surface 250, a seal is broken to release the catalyst into the top face 542, thereby mixing the catalyst with the base chemical. Due to the chemical properties, the base chemical changes colors over time. For example, the base chemical may be configured to fully change colors over the span of 7 years. As such, by monitoring the color of the top face 542, the remaining life of the support surface can be determined over the course of 7 years. In other embodiments, the chemical may change colors over a different time span, e.g. 5 years, thereby altering the time span over which the remaining life of the support surface 250 is indicated. The chemical may be selected based on an expected life span of the support surface 205. For example, if the expected life span of the support surface 250 is 5 years, a chemical that changes colors over 5 years may be selected. In some embodiments, the chemical erodes over time. In some embodiments, the chemical grows over time.

In some embodiments, the top face 542 includes a thin filament, for example, liquid crystals, that may be controlled to display various colors. In such an embodiment, the support surface 250 may include a weigh scale and/or electrical timer, as described above. Based on signals from the weigh scale and/or electrical timer, filament may be altered in color to indicate the remaining life span of the support surface. As set forth above, such a display may include a green, yellow, red color scheme. It should be appreciated that any color scheme may be utilized.

Figure 21:
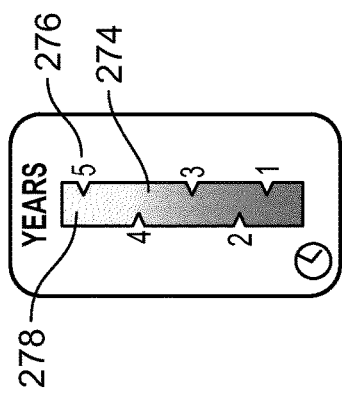
FIG. 21 is a front elevation view of the end of life indicator of FIG. 20.
Figure 20:
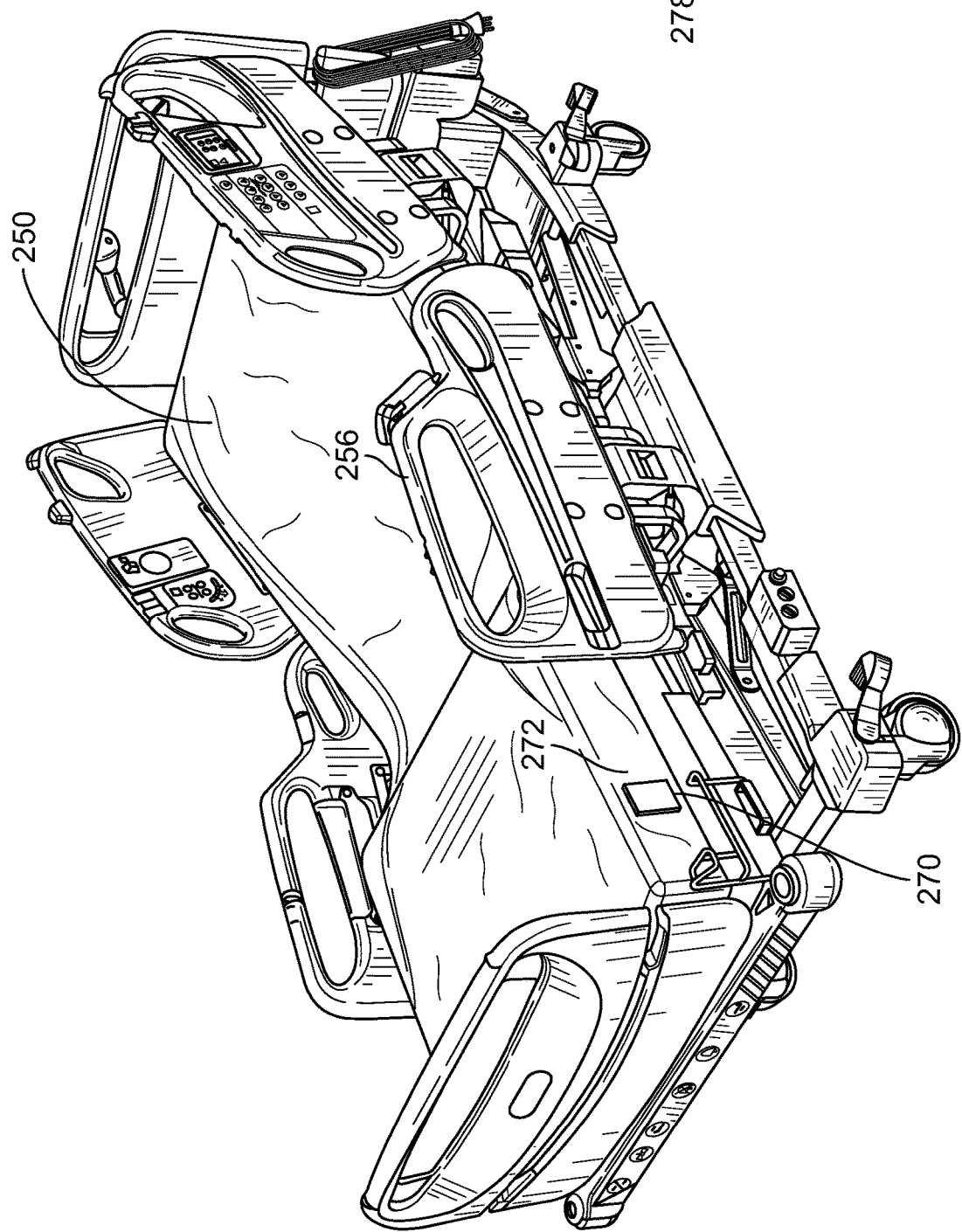
FIG. 20 is a perspective view of a patient support apparatus having a support surface with an end of life indicator incorporated into a side of the support surface.

It may be desired that the support surface 250 include an end of life indicator 270 on a side 272 of the support surface 250 as illustrated in FIG. 20. The end of life indicator 270 is positioned on the side 272 of the support surface 250 so that the end of life indicator 270 is not obstructed by the siderail 256. The end of life indicator 270 is positioned such that the end of life indicator 270 is visible to a caregiver. As illustrated in FIG. 21, the end of life indicator 270 includes a meter 274. The meter 274 may be chemically actuated as described above. In some embodiments, the meter 274 may be electrically actuated by LEDs or the like and display an input from a weigh scale or electrical timer.

The meter 274 includes a series of marks 276 illustrated as 5 years, 4 years, 3 years, 2 years, and 1 year. It should be appreciated that the meter 274 may display other time spans. As the remaining life of the support surface 250 decreases a colored bar 278 of the meter 274 drops. That is the colored bar 278 starts at the 5 year mark 276 and after 1 year of use, the colored bar drops to the 4 year mark 276, etc. Throughout the life of the support surface 250 the colored bar 278 continues to drop corresponding to an elapsed time until the colored bar 278 is extinguished at 0 years indicating that the support surface 250 should be replaced. In some embodiments, the colored bar 278 may also change colors. For example, at the 5 year mark 276, the colored bar 278 may be green; at the 3 year mark 276, the colored bar 278 may be yellow; and at the 1 year mark 276, the colored bar 278 may be red.

Figure 22:
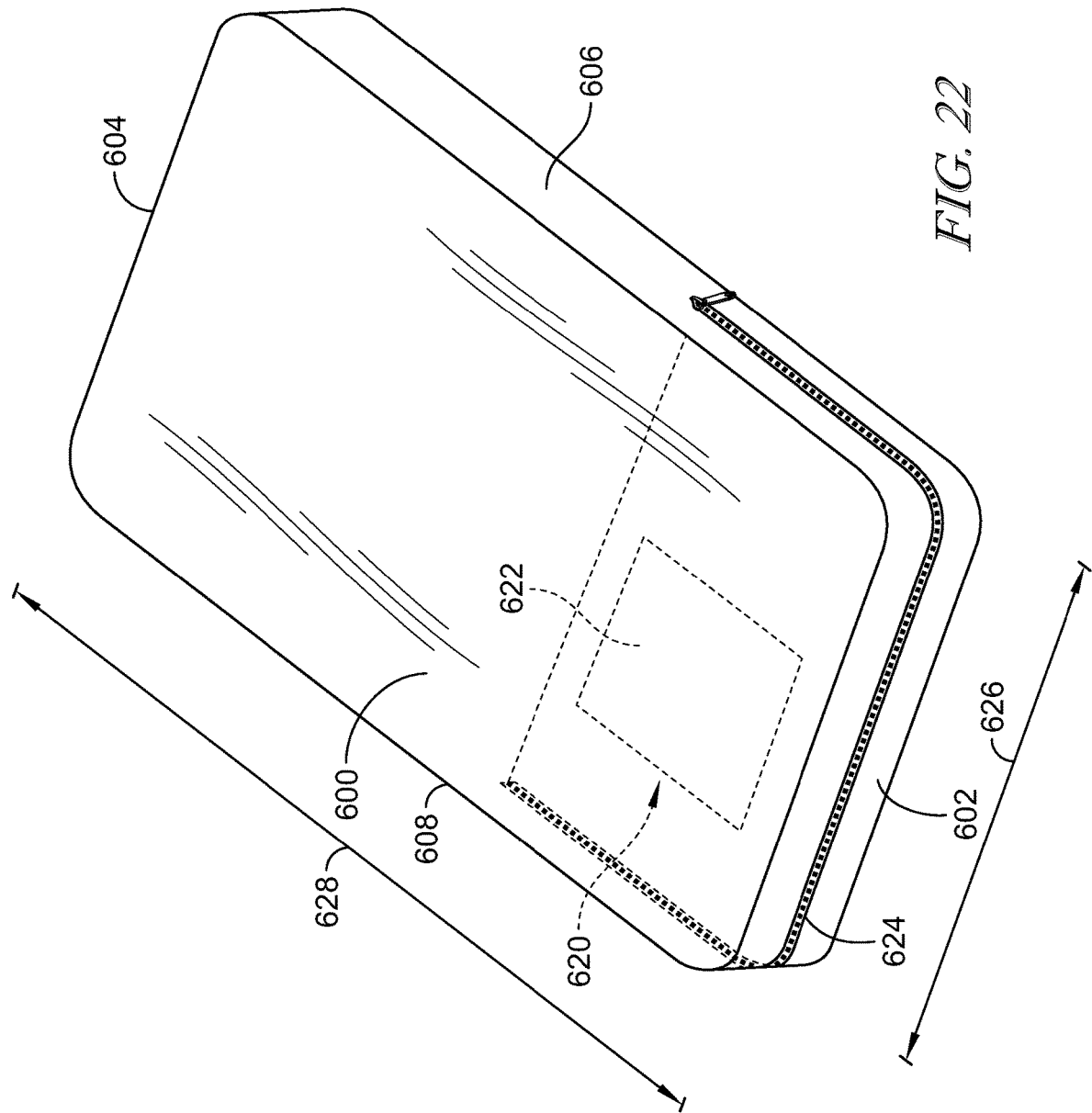
FIG. 22 is a top perspective view of a patient support surface having an x-ray sleeve extending from a first side to a second side along a head end of the support surface.

Referring to FIG. 22, a support surface 600 includes a head end 602, an opposite foot end 604, a right side 606, and a left side 608. An x-ray cassette sleeve 620 is positioned within the support surface 600 and configured to retain an x-ray cassette 622. The sleeve 620 is sealed with zipper 624. In some embodiments, a fastening mechanism other than zipper 624 may be utilized, e.g. hook and loop fasteners, etc. The zipper 624 extends along the entire length 626 of the head end 602. The zipper 624 also extends partially along a length 628 of the right side 606 and partially along the length 628 of the left side 608.

Figure 23:
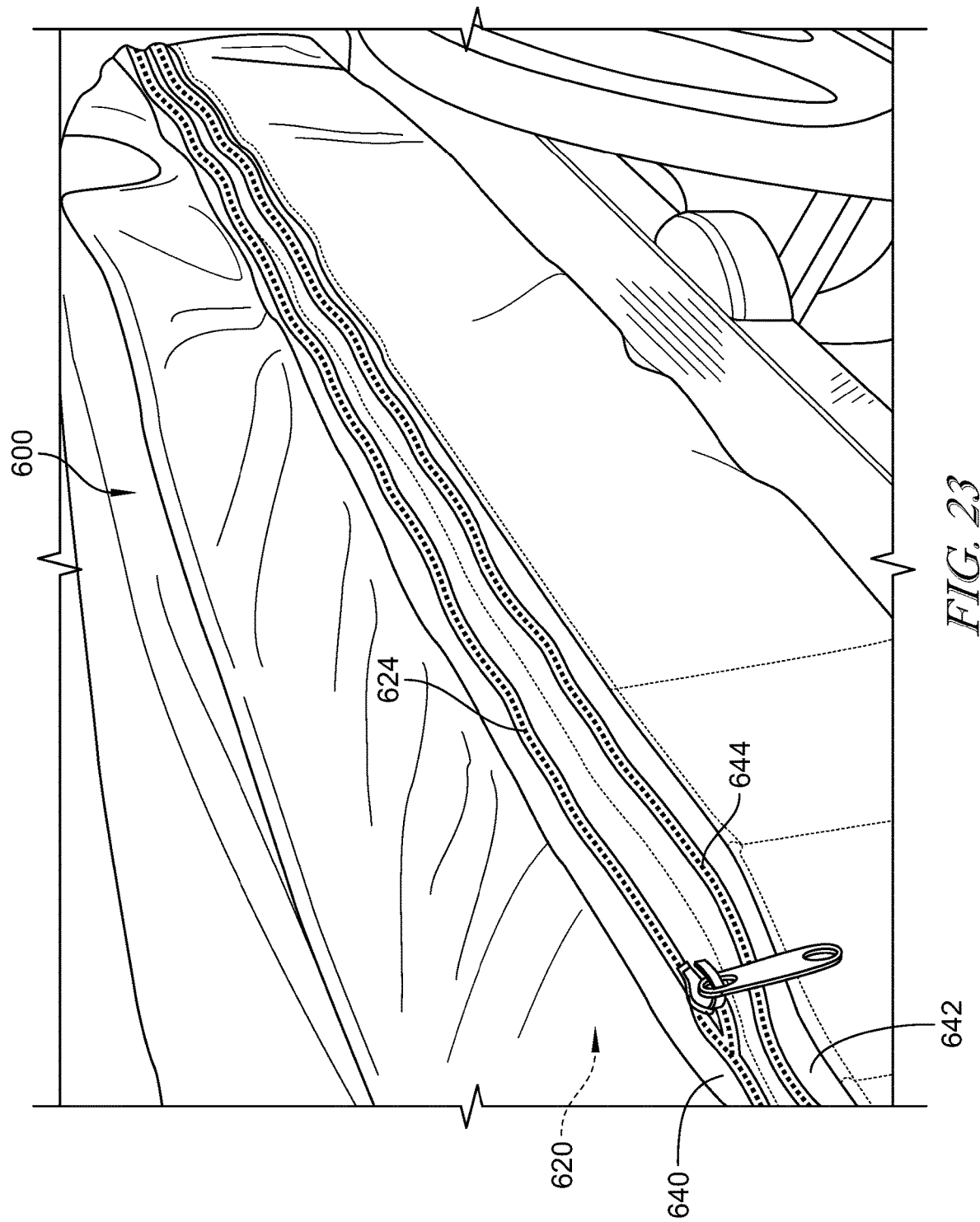
FIG. 23 is a perspective view of a portion of the x-ray sleeve shown in FIG. 22 and illustrating a zipper that fluidly seals the x-ray sleeve to prevent bodily fluids from entering the x-ray sleeve.

As illustrated in FIG. 23, the support surface 600 includes an upper ticking 640 that is sealed to a lower ticking 642 with a zipper 644. The zipper 644 may be actuated to separate the upper ticking 640 from the lower ticking 642 to expose an inside of the support surface 600, for example, bladders and other components described above. The zipper 624 is positioned between the upper ticking 640 and the zipper 644. In some embodiments, the zipper 624 has a different color than the zipper 644 to distinguish the sleeve 620 from the ticking connection. In some embodiments, the zipper 624 and the zipper 644 may have different sizes to distinguish the zippers 624, 644.

Figure 25:
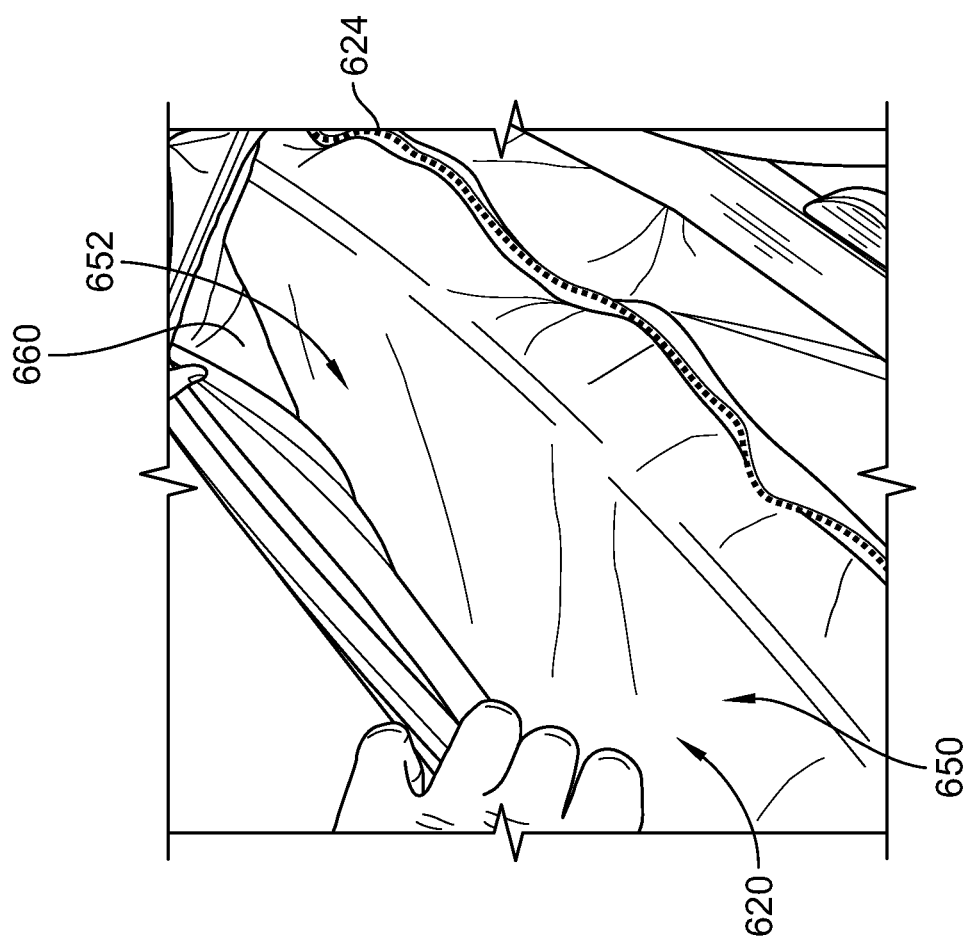
FIG. 25 is a perspective view of a portion of the x-ray sleeve shown in FIG. 22 and illustrating a cavity that is configured to receive an x-ray cassette therein, wherein the x-ray cassette may be positioned under the chest, abdomen, or hips of a patient on the support surface.
Figure 24:
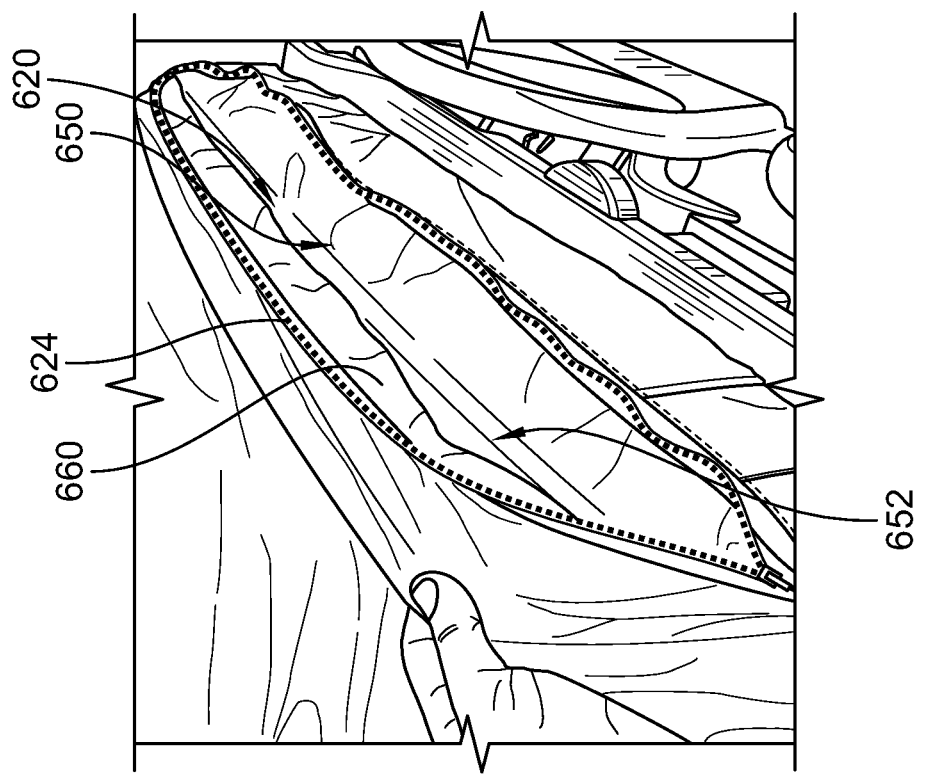
FIG. 24 is perspective view of a portion of the x-ray sleeve shown in FIG. 22 and illustrating the lining of the x-ray sleeve.

FIGS. 24 and 25 illustrate the sleeve 620 in an open configuration that enables insertion and removal of the cassette 622. The sleeve 620 includes an opening 650 that is sealed by the zipper 624. A cavity 652 extends from the opening 650 into the support surface 600. The cavity 652 is configured to receive the cassette 622. The opening 650 extends partially along both sides 606, 608 of the support surface 600 and entirely along the head end 602 of the support surface 600 to provide access to the sleeve 620 by a caregiver. In some embodiments, the caregiver may insert and remove the cassette 622 from the sleeve 620 while a patient is positioned on the support surface 600.

The sleeve 620 includes an inner liner 660 that is bonded or welded to a rip stop material 662 of the zipper 624 to seal the sleeve 620. In some embodiments, the liner 660 is welded with ultrasonic welding or radio-frequency welding. The liner 660 is formed from a water resistant material, e.g. thermoplastic. When the zipper 624 is closed, the sleeve 620 is fluidly sealed to prevent fluid such as bodily fluids from entering the sleeve 620. Accordingly, the sleeve 620 prevents exposure of the cassette 622 to fluids which may damage the cassette.

The sleeve 620 is able to open on three sides to allow for wiping down the sleeve 620 without having to remove the support surface 600 from service. Caregivers can access the sleeve 620 from either the right side 606, the left side 608, or the head end 602. Additionally, the sleeve 620 is larger than conventional sleeves allowing coverage from the head to the seat/hip of the patient allowing for chest, abdominal, and hip x-rays. In some embodiments, the sleeve 620 may extend all the way to the foot end 604 of the support surface 600. Because the sleeve 620 is placed above a core of the support surface 600, the sleeve 620 does not interfere with a microclimate system that may be incorporated into the support surface 600. The two separate compartments (the sleeve 620 and the core) of the support surface 600 enable each compartment to accept a fully enclosed fire sock, thereby enabling the support surface 600 to pass a flame test. The sleeve 620 can be installed in a support surface 600 with or without a topper.

Figure 26:
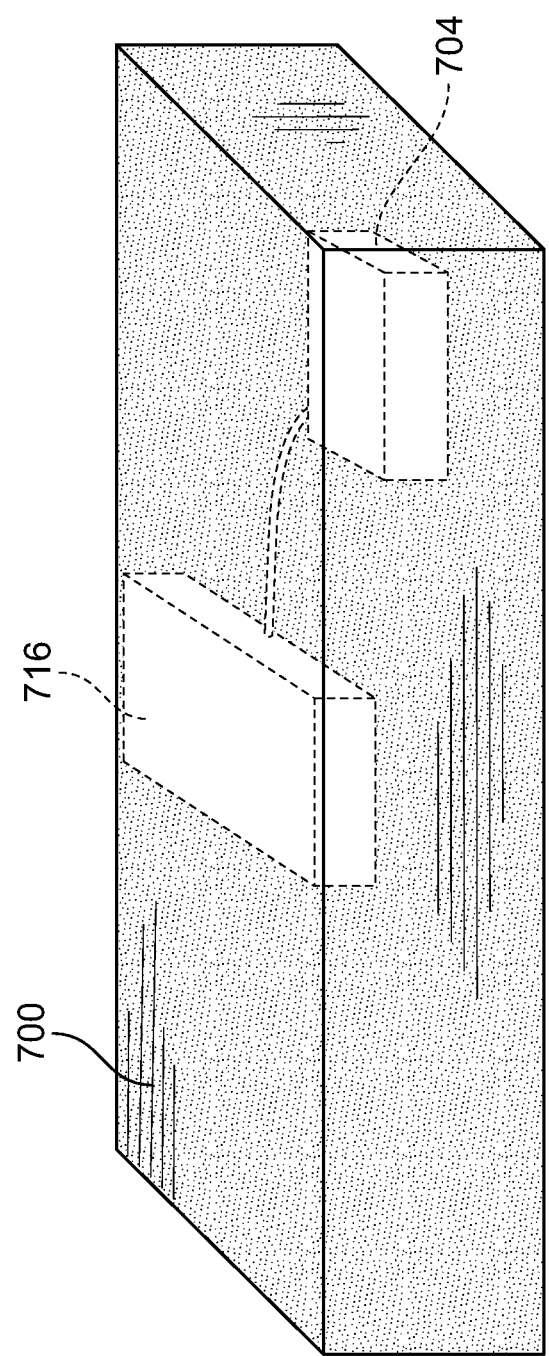
FIG. 26 is a perspective view of a patient support surface having a touch sensor positioned therein to detect bottoming out of the support surface, wherein the touch sensor is electrically coupled to an electronic controller positioned within the support surface and configured to alert a caregiver when the support surface has bottomed out.

As illustrated in FIGS. 26 and 27, a support surface 700 includes a touch sensor 716 coupled to an electronic controller 704. A base foam 710 is provided and a plurality of air bladders 712 are positioned above the base foam 710. An upper ticking 714 of the support surface 700 extends across the air bladders 712. The patient is configured to lie on the upper ticking 714. A capacitive touch sensor 716 is positioned between the base foam 710 and the air bladders 712. A touch sensor 716 can be used to detect when a patient is within approximately an inch of the touch sensor 716. The touch sensor 716 is a capacitive charge sensor that acts as a switch sending out a signal when it is touched or the human body is within an inch of the touch sensor 716. The touch sensor can detect through plastic, glass, paper, or fabric. The touch sensor 716 is therefore capable of detecting through air, bladders, and ticking material. Conductive materials can also be attached to the sensor to increase the sensing area. The touch sensor 716 can be positioned only under the entire area of the support surface 700 or regionalized where the patient is likely to bottom out.

When the patient is not within one inch of the touch sensor 716, the touch sensor delivers a first voltage to the electronic controller 704. As illustrated in FIG. 28, a weight of the patient has caused the air bladders 712 to deform and bottom out. The patient's sacrum 718 is illustrated within one inch of the touch sensor 716. Accordingly, the touch sensor 716 sends a second voltage, e.g. 5V, to the electronic controller 704. Upon receiving the second voltage, the electronic controller 704 sends an audible or visual alert to the caregiver indicating that the patient has bottomed out.

The touch sensor 716 may monitor the patient to determine whether the patient has bottomed out, e.g. come in contact with or close to the base foam 710. The touch sensor 716 enables the caregiver to do a "hand check" without actually having to position their hand under the patient. This enables better comfort for the patient, who does not require unnecessary prodding by the caregiver. In some embodiments, the caregiver is alerted either audibly or visually if the patient has bottomed out.

Figure 29:
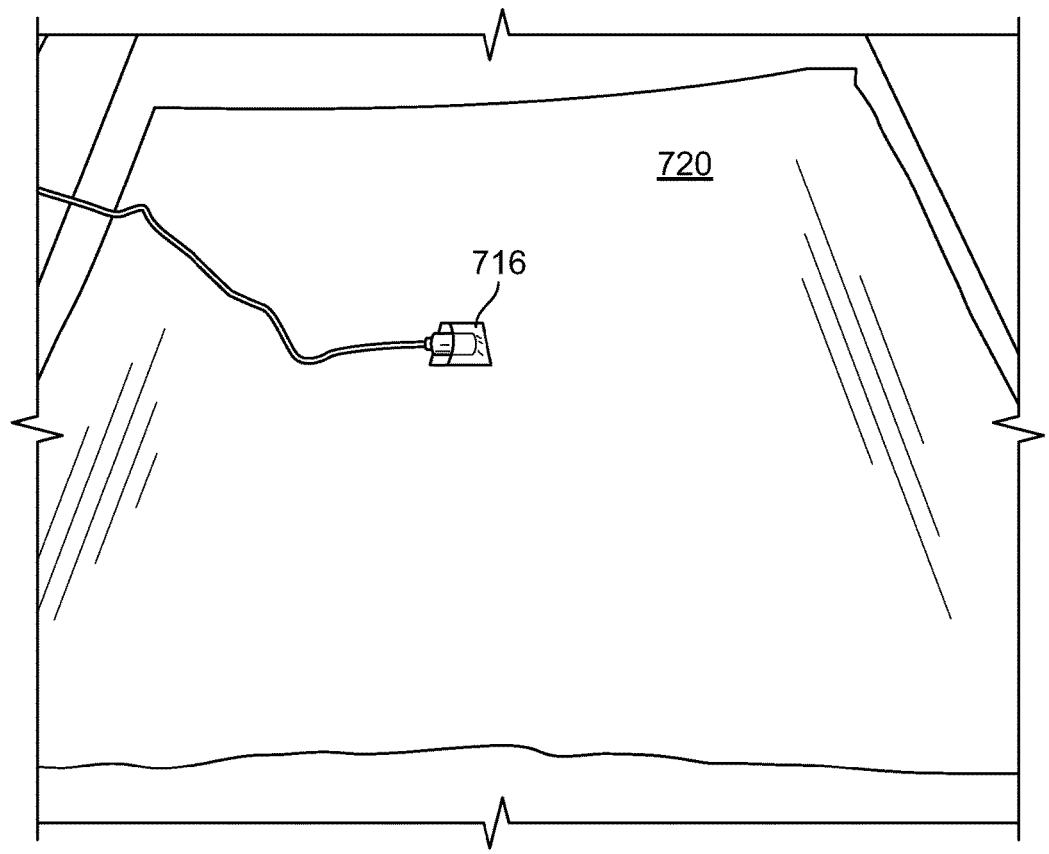
FIG. 29 is a perspective view of a conductive fabric that may be used with the touch sensor shown in FIG. 26 to expand a sensing area of the touch sensor across an entire area of the support surface.
Figure 30:
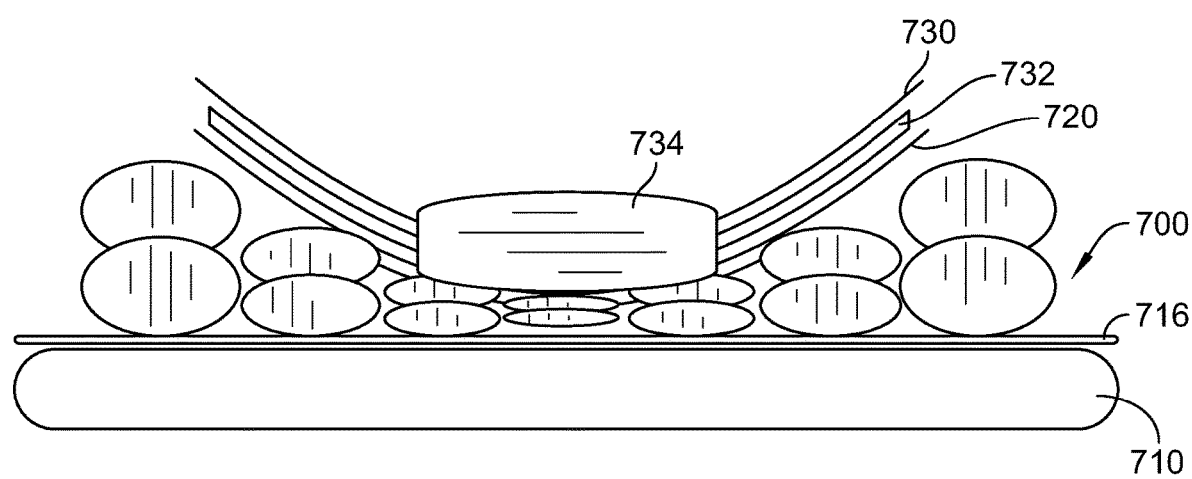
FIG. 30 is a cross-sectional view of another embodiment of the support surface shown in FIG. 26 that incorporates both a touch sensor and a conductive fabric to detect bottoming out of the support surface.

FIG. 29 illustrates a conductive fabric 720 that is configured to be used with the touch sensor 716. Referring to FIG. 30, the support surface 700 includes the fabric 720 and the touch sensor 716. The fabric 720 is positioned below an upper ticking 730 of the support surface 700. A spacer 732 is positioned between the upper ticking 730 and the fabric 720 to isolate the patient from the fabric 720. The air bladders 712 are positioned between the touch sensor 716 and the fabric 720. The touch sensor 716 is positioned over the base foam 710. As a load 734 is applied to the support surface 700, the fabric 720 is moved closed to the touch sensor 716. The fabric 720 is configured to activate the touch sensor 716 when the fabric 720 is within 0.5 inches of the touch sensor 716. When the fabric 720 is within 0.5 inches of the touch sensor 716, the touch sensor 716 sends a voltage to the electronic controller 704 indicating that the support surface 700 has bottomed out.

When bottoming out is detected, the support surface 700 may make pressure adjustments with the bladders 712 to raise the patient from the base foam. Additionally, surface bladder pressures may be optimized for an ideal interface pressure without risking bottoming out by understanding the amount of weight that the support surface 700 can withstand. If the bottoming out condition cannot be corrected by adjusting the pressure of the bladders 712, an alarm may be sent to the caregiver or nurse's station. Further, repeatedly bottoming out may be an indicator that the support surface 700 has become worn. As such the touch sensor 716 may aid in determining an end of life of the support surface 700.

Figure 33:
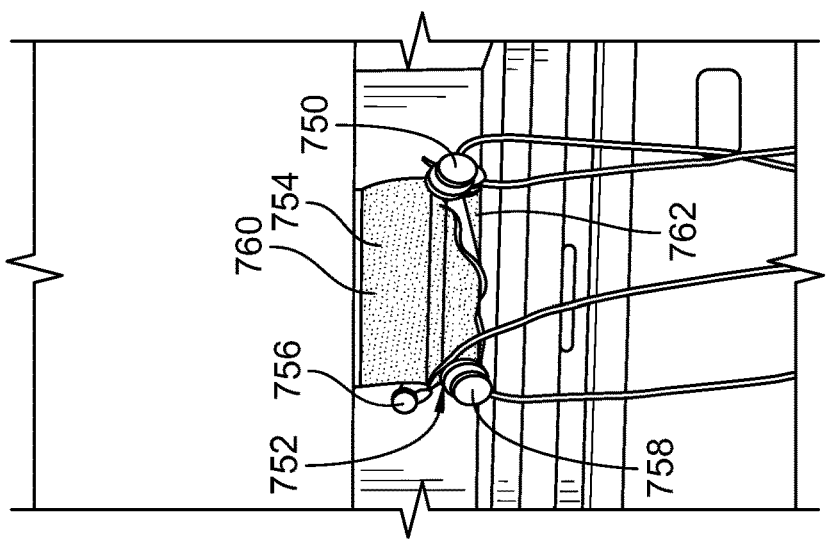
FIG. 33 is a front elevational view of the sensor and foam surface shown in FIG. 31, wherein the foam surface has a load thereon and the sensor is entirely collapsed indicating bottoming out of the foam surface.
Figure 32:
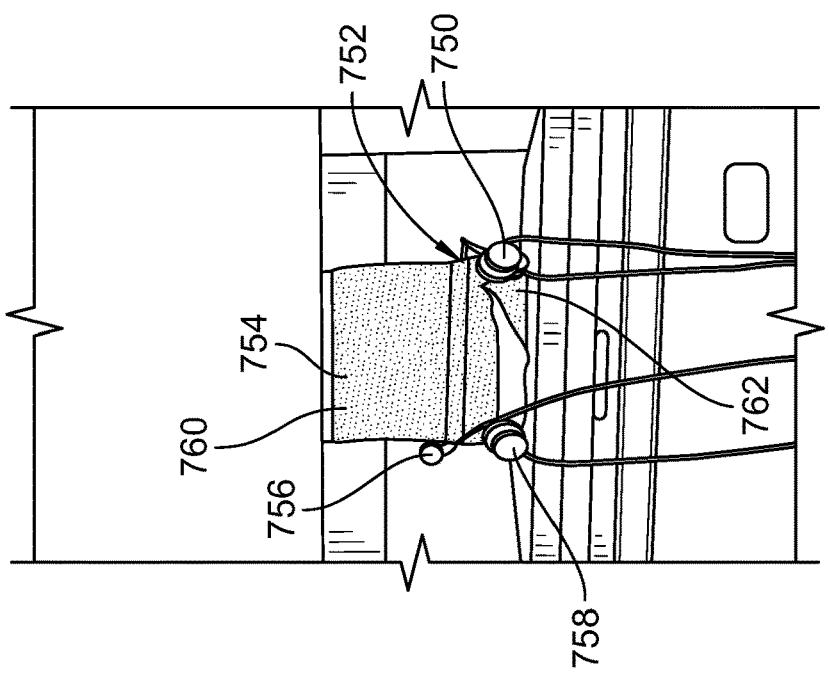
FIG. 32 is a front elevational view of the sensor and foam surface shown in FIG. 31, wherein the foam surface has a load thereon and the sensor is partially collapsed.
Figure 31:
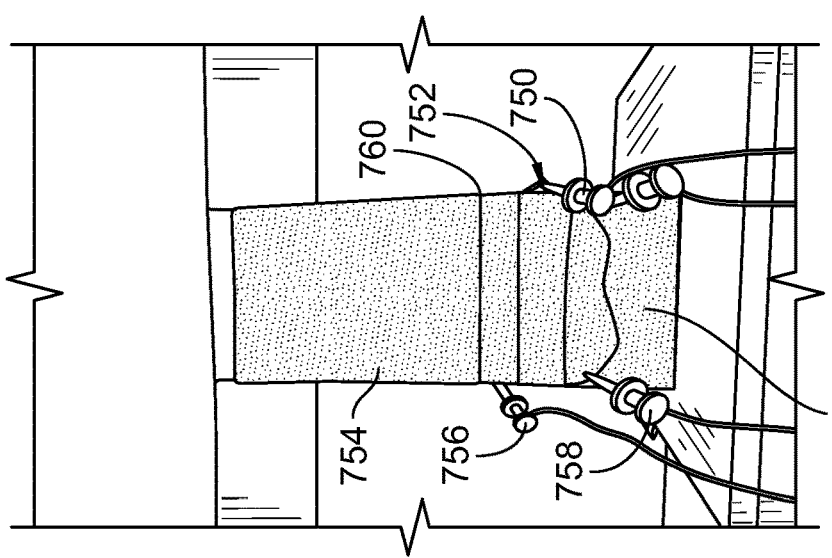
FIG. 31 is a front elevational view of a sensor for detecting bottoming out of a foam surface, wherein the foam surface is illustrated without any load thereon and the sensor is in a fully expanded position.

FIGS. 31-33 illustrate another sensor 750 for determining bottoming out of a support surface. The sensor 750 is positioned within a gap 752 formed in a foam surface 754, e.g. a foam support surface. The gap 752 is formed in approximately the bottom inch of the foam surface 754. If the bottom inch of the foam surface 754 collapses, the patient would be determined as having bottomed out.

The sensor 750 may include a pair of resilient metal conductors 756 and 758 positioned on a top 760 of the gap 752 and a bottom 762 of the gap 752, respectively. The conductors 756, 758 may be spaced from one another by means of insulators. The conductors are adapted to contact one another when at least a portion of the patient's bottoms out. The sensor 750 may also include a waterproof flexible housing which encloses the conductors 756, 758. It will be readily understood that, when the patient lies on the bed, the sensor 750 will be compressed. The compression of the sensor 750 may result in contact at one or more places between the conductors 756, 758 resulting in an electrical indication that the patient has bottomed out. FIG. 31 illustrates the gap 752 in an expanded configuration. In FIG. 32, the gap 752 is shown as beginning to collapse. In FIG. 33, the gap 752 is entirely collapsed. As the gap collapses, the conductors 756, 758 approach one another, thereby generating the electrical signal. The signal increases as the conductors 756, 758 get closer to one another. When a predetermined signal is reached, the foam surface 754 is considered to have bottomed out. At this stage, the caregiver is alerted that the patient has bottomed out. Bottoming out may also indicate that the foam surface 754 has reached its end of life.

The embodiments described in FIGS. 34-60 provide support surfaces having a heel suspension mechanism built into the support surface. In such embodiments, caregivers do not have to locate and place a separate heel wedge for the support surface. The heel suspension mechanisms described herein eliminate the need to create an improvised solution for heel suspension if a wedge cannot be located. The mechanisms also eliminate time spent searching for missing components and allows for more focus on patient care. The heel suspension mechanisms described herein can be optimized to work properly with any support surface that is integrated with. For example, the heel suspension mechanisms described herein may be utilized with any of the support surfaces described herein. The mechanisms improve cleaning of the support surface because the mechanisms may be fully integrated inside a support surface cover. Additionally, the mechanisms eliminate the cost of replacing lost heel wedges.

Referring to FIG. 34, a patient support surface 800 includes a body 802 having a body section 804 and an opposite foot section 806. The patient support surface 800 may be a foam mattress or an air mattress. In some embodiments, the patient support surface 800 may be any of the support surfaces described in FIGS. 1-33. A top face 808 extends from the body section 804 to the foot section 806. The top face 808 is positioned at a first height 810 from a bottom 812 of the support surface 800. A patient 820 is configured to rest on the top face 808 with their feet 822 at the foot section 806 of the support surface 800. A heel suspension mechanism 824 is positioned within the foot section 806 to alter a height of the top face 808. By altering a height of the top face 808, heels 826 of the patient's feet 822 are separated from the top face 808 by a gap 828 (shown in FIG. 35).

The heel suspension mechanism 824 includes a plate 838 having a plurality of grooves 840 formed therein. It should be noted that only one side of the support surface 800 is illustrated; however, it will be appreciated that the support surface 800 may include a plate 838 on both sides of the support surface 800. Optionally, multiple plates 838 may be positioned between the sides of the support surface 800. In the illustrated embodiment, the plate 838 includes three grooves 840a-840c; however, any number of grooves 840 may be contemplated. Each groove 840a-840c is positioned under one of three corresponding sections 842a-842c of the foot section 806. A flexible membrane 844 is coupled to the body 802 and extends along each section 842. A cam assembly 846 is configured to position within one of the grooves 840a-840c. The cam assembly 846 is further configured to be movable to and from any of the grooves 840a-840c so that the cam assembly 846 is positionable under a corresponding section 842a-842c of the foot section 806. The cam assembly 846 includes a rod 848 that is moveable to any of the grooves 840a-840c and sits within the respective groove 840a-840c. A cam 850 having a fixed end 852 and a moving end 854 is coupled to the rod 848. It should be noted that, while only a single cam 850 is illustrated, multiple cams 850 may be positioned along the rod 848 between the sides of the support surface 800. A handle 856 extends from the rod 848. The handle 856 is configured to be rotated so that the moving end 854 of the cam 850 rotates around the fixed end 852 from a first position 860 (shown in FIG. 34) to a second position 862 (shown in FIG. 35).

As illustrated in FIG. 34, when the cam 850 is in the first position 860, the membrane 844 rests on the fixed end 852 of the cam 850 so that the top face 808 of the foot section 806 is retained at the first height 810. As illustrated in FIG. 35, when the cam 850 is rotated to the second position 862, the moving end 854 of the cam 850 moves the membrane 844 upward so that the top face 808 of the foot section 806 is raised to a second height 870 from the bottom 812 of the support surface 800, wherein the second height 870 is greater than the first height 810. Notably, in FIGS. 34-35, the cam assembly 846 is illustrated in the groove 840b, thereby raising section 842b. It will be appreciated that the cam assembly 846 is also movable to grooves 840a and 840c to raise the height of the section 842a or 842c, respectively.

Referring to FIG. 36, a patient support surface 900 includes a body 902 having a body section 904 and an opposite foot section 906. The patient support surface 900 may be a foam mattress or an air mattress. In some embodiments, the patient support surface 900 may be any of the support surfaces described in FIGS. 1-33. A top face 908 extends from the body section 904 to the foot section 906. The top face 908 is positioned at a first height 910 from a bottom 912 of the support surface 900. A patient 920 is configured to rest on the top face 908 with their feet 922 at the foot section 906 of the support surface 900. A heel suspension mechanism 924 is positioned within the foot section 906 to alter a height of the top face 908. By altering a height of the top face 908, heels 926 of the patient's feet 922 are separated from the top face 908 by a gap 928 (shown in FIG. 37).

The heel suspension mechanism 924 includes a plurality of cams 940. In the illustrated embodiment, the heel suspension mechanism 924 includes three cams 940a-940c; however, any number of cams 940 may be contemplated. Each cam 940a-940c is positioned under one of three corresponding sections 942a-942c of the foot section 906. A flexible membrane 944 is coupled to the body 902 and extends along each section 942a-942c. Each cam 940a-940c has a fixed end 952 and a moving end 954. It should be noted that, while only a single cam 940a-940c is illustrated, multiple cams 940a-940c may be positioned between the sides of the support surface 800 and coupled via a rod. A knob 956 is positioned on each cam 940a-940c to rotate the respective cam 940a-940c so that the moving end 954 of the respective cam 940a-940c rotates around the fixed end 952 from a first position 960 (shown in FIG. 36) to a second position 962 (shown in FIG. 37).

As illustrated in FIG. 36, when each cam 940a-940c is in the first position 962, the membrane 944 rests on the fixed end 952 of the each cam 940a-940c so that the top face 908 of the foot section 906 is retained at the first height 910. As illustrated in FIG. 37, when the cam 940b is rotated to the second position 964, the moving end 954 of the cam 940b moves the membrane 944 upward so that the top face 908 of the foot section 906 is raised to a second height 970 from the bottom 912 of the support surface 900, wherein the second height 970 is greater than the first height 910. Notably, in FIG. 37, the cam 940b is illustrated as being rotated, thereby raising section 942b. It will be appreciated that the cams 940a-940c are also rotatable to raise the height of the section 942a or 942c, respectively. In some embodiments, any number of cams 940a-940c may be rotated to alter the height of the top face 908 of the foot section 906.

Referring to FIG. 38, a patient support surface 1000 includes a body 1002 having a body section 1004 and an opposite foot section 1006. The patient support surface 1000 may be a foam mattress or an air mattress. In some embodiments, the patient support surface 1000 may be any of the support surfaces described in FIGS. 1-33. A top face 1008 extends from the body section 1004 to the foot section 1006. The top face 1008 is positioned at a first height 1010 from a bottom 1012 of the support surface 1000. A patient 1020 is configured to rest on the top face 1008 with their feet 1022 at the foot section 1006 of the support surface 1000. A heel suspension mechanism 1024 is positioned within the foot section 1006 to alter a height of the top face 1008. By altering a height of the top face 1008, heels 1026 of the patient's feet 1022 are separated from the top face 1008 by a gap 1028 (shown in FIG. 39).

The heel suspension mechanism 1024 includes a plurality of cams 1040. In the illustrated embodiment, the heel suspension mechanism 1024 includes three cams 1040a-1040c; however, any number of cams 1040 may be contemplated. Each cam 1040a-1040c is positioned under one of three corresponding sections 1042a-1042c of the foot section 1006. Flexible membranes 1044a-1044c are coupled to the body 1002 by a hinge 1046. Each membrane 1044a-1044c extends along a respective section 1042a-1042c. Each cam 1040a-1040c has a fixed end 1052 and a moving end 1054. It should be noted that, while only a single cam 1040a-1040c is illustrated, multiple cams 1040a-1040c may be positioned between the sides of the support surface 1000 and coupled via a rod. A knob 1056 is positioned on each cam 1040a-1040c to rotate the respective cam 1040a-1040c so that the moving end 1054 of the respective cam 1040a-1040c rotates around the fixed end 1052 from a first position 1060 (shown in FIG. 38) to a second position 1062 (shown in FIG. 39).

As illustrated in FIG. 38, when each cam 1040a-1040c is in the first position 1060, each membrane 1044 rests on the fixed end 1052 of the respective cam 1040a-1040c so that the top face 1008 of the foot section 1006 is retained at the first height 1010. As illustrated in FIG. 39, when the cam 1040b is rotated to the second position 1062, the moving end 1054 of the cam 1040b rotates the membrane 1044b upward about its hinge 1046 so that the top face 1008 of the foot section 1006 is raised to a second height 1070 from the bottom 1012 of the support surface 1000, wherein the second height 1070 is greater than the first height 1010. Notably, in FIG. 39, the cam 1040b is illustrated as being rotated, thereby raising section 1042b. It will be appreciated that the cams 1040a-1040c are also rotatable to raise the height of the section 1042a or 1042c, respectively. In some embodiments, any number of cams 1040a-1040c may be rotated to alter the height of the top face 1008 of the foot section 1006.

Referring to FIG. 40, a patient support surface 1100 includes a body 1102 having a body section 1104 and an opposite foot section 1106. A plurality of foam segments 1108 are positioned within the body 1102 from the body section 1104 to the foot section 1106. In some embodiments, the support surface 1100 may be any one of the support surfaces described in FIGS. 1-33. A top face 1110 extends from the body section 1104 to the foot section 1106. The top face 1110 is positioned at a first height 1112 from a bottom 1114 of the support surface 1100. A patient 1120 is configured to rest on the top face 1110 with their feet 1122 at the foot section 1106 of the support surface 1100. A heel suspension mechanism 1124 is positioned within the foot section 1106 to alter a height of the top face 1110. By altering a height of the top face 1110, heels 1126 of the patient's feet 1122 are separated from the top face 1110 by a gap 1128 (shown in FIG. 41).

The heel suspension mechanism 1124 includes a plurality of the air bladders 1128 positioned in the foot section 1106 of the support surface 1100 below foam sections 1108. In the illustrated embodiment, the heel suspension mechanism 1124 includes air bladders 1128a-1128d; however, any number of air bladders 1128 may be incorporated into the heel suspension mechanism 1124. The bladders 1128 that are not incorporated into the heel suspension mechanism 1124 may be foamed filled air bladders. Each air bladder 1128a-1128d is positioned under a respective section 1130a-1130d of the foot section 1106. Each bladder 1128a-1128d is fluidly coupled to a valve 1140 via a respective hose 1142a-1142d. A hand pump 1144 is fluidly coupled to the valve 1140 to supply air flow to the valve 1140. In some embodiments, an electrical pump may be fluidly coupled to the valve 1140. The valve 1140 includes a dial 1146 that is actuated to direct the air flow to one of the air bladders 1128a-1128d. The dial 1146 includes indicators 1148a-1148d that each corresponds to one of the hoses 1142a-1142d and, consequently, the respective bladder 1128a-1128d. The hand pump 1144 is operable to supply air flow to one of the bladders 1128a-1128d via the valve 1140 to inflate the respective bladder 1128a-1128d from a first position 1160 (shown in FIG. 40) to a second position 1162 (shown in FIG. 41).

As illustrated in FIG. 40, when each air bladder 1128a-1128d is in the first position 1160 the top face 1110 of the foot section 1106 is retained at the first height 1112. As illustrated in FIG. 41, when the air bladder 1128b is inflated to the second position 1162, the top face 1110 of the foot section 1106 is raised to a second height 1170 from the bottom 1114 of the support surface 1100, wherein the second height 1170 is greater than the first height 1112. Notably, in FIG. 41, the air bladder 1128b is illustrated as being inflated, thereby raising section 1130b. It will be appreciated that the air bladders 1128a, 1128c, and 1128d are also inflatable to raise the height of the section 1130a, 1130c, and 1130d, respectively. In some embodiments, the valve 1140 may be configured so the multiple combinations of air bladders 1128a-1128d may be inflated to alter the height of the top face 1110 of the foot section 1106.

Figure 42:
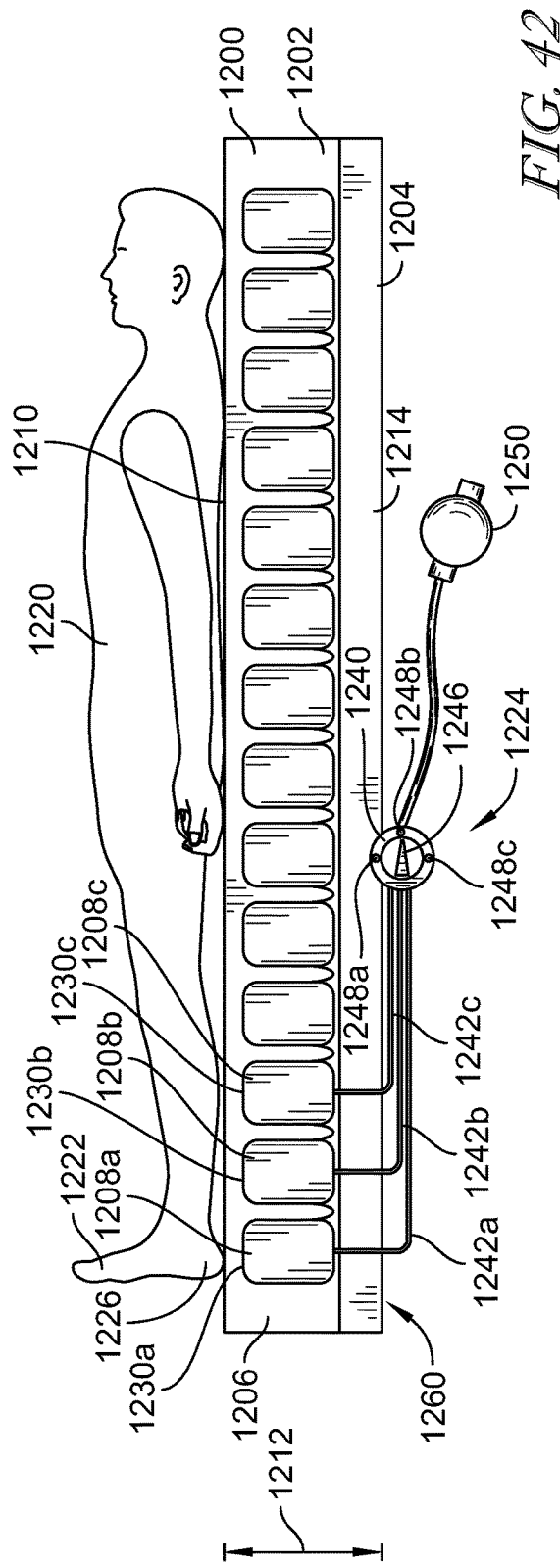
FIG. 42 is a side elevation view of a support surface having another plurality of bladders positioned in a foot end, wherein the plurality of bladders operate as a heel suspension mechanism.

Referring to FIG. 42, a patient support surface 1200 includes a body 1202 having a body section 1204 and an opposite foot section 1206. A plurality of air bladders 1208 are positioned within the body 1202 from the body section 1204 to the foot section 1206. In some embodiments, the support surface 1200 may be any one of the support surfaces described in FIGS. 1-33. A top face 1210 extends from the body section 1204 to the foot section 1206. The top face 1210 is positioned at a first height 1212 from a bottom 1214 of the support surface 1200. A patient 1220 is configured to rest on the top face 1210 with their feet 1222 at the foot section 1206 of the support surface 1200. A heel suspension mechanism 1224 is positioned within the foot section 1206 to alter a height of the top face 1210. By altering a height of the top face 1210, heels 1226 of the patient's feet 1222 are separated from the top face 1210 by a gap 1228 (shown in FIG. 43).

The heel suspension mechanism 1224 includes a plurality of the air bladders 1208 positioned in the foot section 1206 of the support surface 1200. In the illustrated embodiment, the heel suspension mechanism 1224 includes air bladders 1208a-1208c; however, any number of air bladders 1208 may be incorporated into the heel suspension mechanism 1224. The bladders 1208 that are not incorporated into the heel suspension mechanism 1224 may be foamed filled air bladders. Each air bladder 1208a-1208c is positioned under a respective section 1230a-1230d of the foot section 1206. Each bladder 1208a-1208c is fluidly coupled to a release valve 1240 via a respective hose 1242a-1242c. The release valve 1240 is configured to release air from any one of the air bladder 1208a-1208c. The valve 1240 includes a dial 1246 that is actuated to release air flow from any of the air bladders 1208a-1208c to a pump 1250. The dial 1246 includes indicators 1248a-1248c that each corresponds to one of the hoses 1242a-1242c and, consequently, the respective bladder 1208a-1208c. The valve 1240 is operable to release air from any of the bladders 1208a-1208c to deflate the respective bladders 1208a-1208c from a first position 1260 (shown in FIG. 42) to a second position 1262 (shown in FIG. 43).

Figure 43:
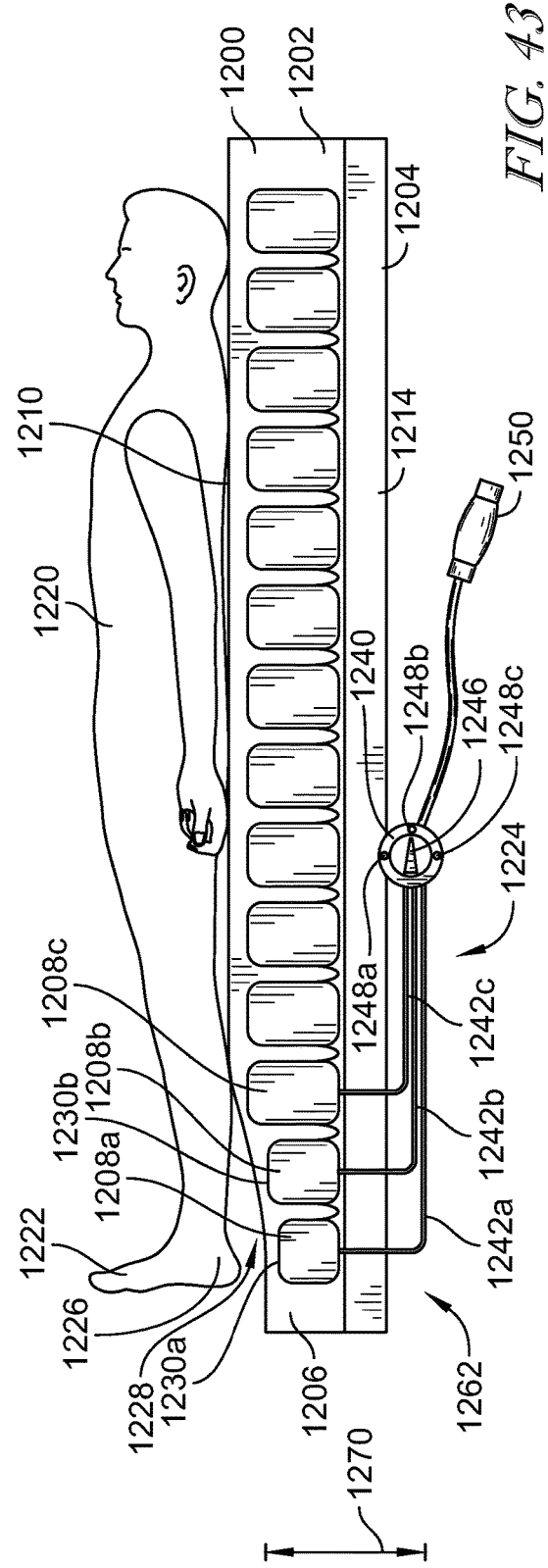
FIG. 43 is a side elevation view similar to FIG. 42, wherein one of the plurality of bladders is actuated to raise the foot end of the support surface.

As illustrated in FIG. 42, when each air bladder 1208a-1208c is in the first position 1260 the top face 1210 of the foot section 1206 is retained at the first height 1212. As illustrated in FIG. 43, when the air bladders 1208a and 1208b are deflated to the second position 1262, the top face 1210 of the foot section 1206 is lower to a second height 1270 from the bottom 1214 of the support surface 1200, wherein the second height 1270 is less than the first height 1212. Notably, in FIG. 41, the air bladder 1208a is illustrated as being deflated approximately 50% and the air bladder 1208b is illustrated being deflated approximately 25%, thereby lowering sections 1230a and 1230b. It will be appreciated that any number of air bladders 1208a-1208c may be deflated to any pressure to lower the height of the sections 1230a-1230c, respectively, thereby lowering the top face 1210 of the foot section 1206.

Figure 44:
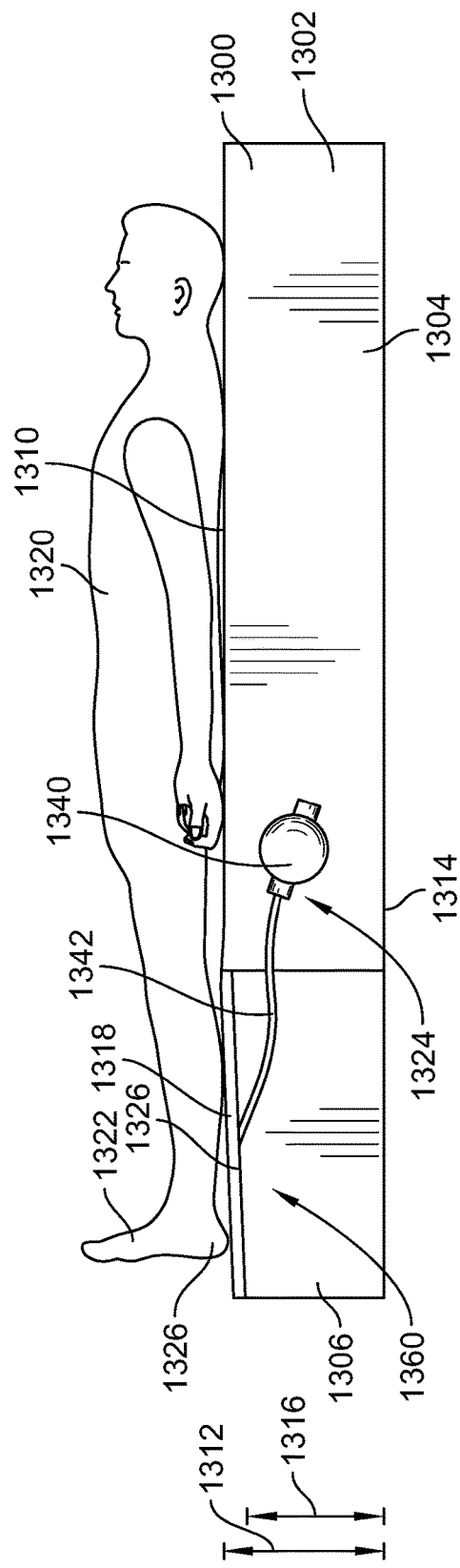
FIG. 44 is a side elevation view of a support surface having an air bladder positioned in a foot end, wherein the air bladder operates as a heel suspension mechanism.

Referring to FIG. 44, a patient support surface 1300 includes a body 1302 having a body section 1304 and an opposite foot section 1306. The patient support surface 1300 may be a foam mattress or an air mattress. In some embodiments, the patient support surface 1300 may be any of the support surfaces described in FIGS. 1-33. A top face 1310 extends from the body section 1304 to the foot section 1306. The top face 1310 is positioned at a first height 1312 from a bottom 1314 of the support surface 1300. The top face 1310 angles at the foot section 1306 from the first height 1312 to a second height 1316 forming an angled surface 1318. A patient 1320 is configured to rest on the top face 1310 with their feet 1322 on the angled surface 1318. A heel suspension mechanism 1324 is positioned within the foot section 1306 under the angled surface 1318 to alter a height of the angled surface 1318. By altering a height of the angled surface 1318, heels 1326 of the patient's feet 1322 are separated from the top face 1310 by a gap 1328 (shown in FIG. 45).

Figure 45:
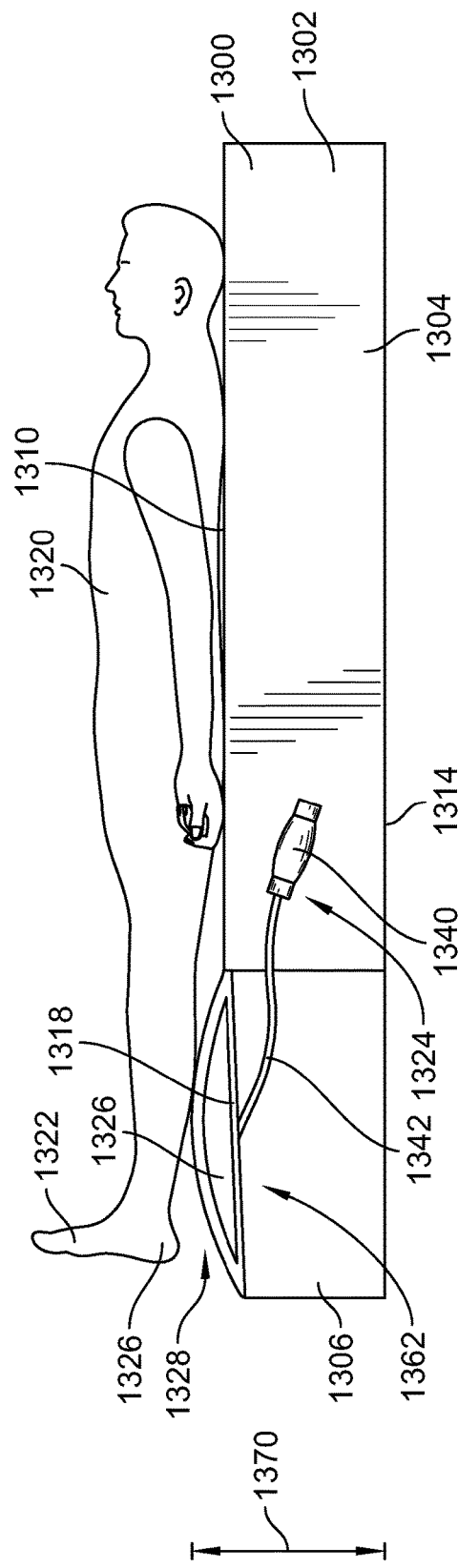
FIG. 45 is a side elevation view similar to FIG. 44, wherein the air bladder is actuated to raise the foot end of the support surface.

The heel suspension mechanism 1324 includes an air bladder 1326 positioned under the angled surface 1318 of the top face 1310 of the support surface 1300. The air bladder 1326 is fluidly coupled to a hand pump 1340 via a hose 1342. The hand pump 1340 is configured to inflate the air bladder 1326. The valve 1340 is operable to provide air to the air bladder 3126 to inflate the air bladder 1326 from a first position 1360 (shown in FIG. 44) to a second position 1362 (shown in FIG. 45). As illustrated in FIG. 44, when the air bladder 1326 is deflated to the first position 1362 the angled surface 1318 is retained in a first position 1364. As illustrated in FIG. 45, when the air bladder 1326 is inflated to the second position 1362, the angled surface 1318 is raised to a second position 1366, wherein the second position 1366 raises the height top the top face 1310.

Referring to FIG. 46, a patient support surface 1400 includes a body 1402 having a body section 1404 and an opposite foot section 1406. The patient support surface 1400 may be a foam mattress or an air mattress. In some embodiments, the patient support surface 1400 may be any of the support surfaces described in FIGS. 1-33. A top face 1410 extends from the body section 1404 to the foot section 1406. The top face 1410 is positioned at a first height 1412 from a bottom 1414 of the support surface 1400. The top face 1410 angles at the foot section 1406 from the first height 1412 to a second height 1416 forming an angled surface 1418. A patient 1420 is configured to rest on the top face 1410 with their feet 1422 on the angled surface 1418. A heel suspension mechanism 1424 is positioned within the foot section 1406 under the angled surface 1418 to alter a height of the angled surface 1418. By altering a height of the angled surface 1418, heels 1426 of the patient's feet 1422 are separated from the top face 1410 by a gap 1428 (shown in FIGS. 47 and 48).

A microclimate system 1430 is positioned under the top face 1410 of the body section 1404. The microclimate system 1430 includes a bladder 1432 configured to force air over the top face 1410 of the body section 1404. In some embodiments, the bladder 1432 may extend into the foot section 1406. The microclimate system 1430 is fluidly coupled to a valve 1436 via a hose 1438. The valve 1436 is fluidly coupled to a pump 1440 via a hose 1442. The pump 1440 is configured to provide air flow to the microclimate system 1430.

The heel suspension mechanism 1424 includes air bladders 1450a-1450b positioned under the angled surface 1418 of the foot section 1406 of the support surface 1400. The air bladders 1450a-1450b are fluidly coupled to the pump 1440 via respective hoses 1452a-1452b. The valve 1436 includes a dial 1454 having indicators 1456a-1456c. The dial 1454 is turned to one of the indicators 1456a-1456b to provide air flow to the air bladder 1450a-1450b, respectively, to inflate the corresponding air bladder 1450a-1450b from a first position 1460a-1460b to a second position 1462a-1462b (shown in FIGS. 47 and 48). The dial 1454 may also be turned to the indicator 1456c to provide air flow to the microclimate system 1430.

As illustrated in FIG. 46, when the air bladders 145a-1450b are deflated to the first position 1460a-1460b the angled surface 1418 is retained in a first position 1464. FIG. 46 also illustrates the dial 1454 turned to the indicator 1456c to provide air flow to the microclimate system 1430. As illustrated in FIG. 47, when the dial 1454 is turned to the indicator 1456a, the pump 1440 provides air flow to the air bladder 1450a to inflate the air bladder 1450a to the second position 1464a, to raise the angled surface 1418. As illustrated in FIG. 48, when the dial 1454 is turned to the indicator 1456b, the pump 1440 provides air flow to the air bladder 1450b to inflate the air bladder 1450b to the second position 1464b, to raise the angled surface 1418. It will be appreciated that the dial 1454 may be configured to supply air flow to any combination of air bladders 1450a-1450b and microclimate system 1430.

Referring to FIG. 49, a patient support surface 1500 includes a body 1502 having a body section 1504 and an opposite foot section 1506. The patient support surface 1500 may be a foam mattress or an air mattress. In some embodiments, the patient support surface 1500 may be any of the support surfaces described in FIGS. 1-33. A top face 1508 extends from the body section 1504 to the foot section 1506. The top face 1508 is positioned at a first height 1510 from a bottom 1512 of the support surface 1500. A patient 1520 is configured to rest on the top face 1508 with their feet 1522 at the foot section 1506 of the support surface 1500. A heel suspension mechanism 1524 is positioned within the foot section 1506. The heel suspension mechanism 1524 is movable onto the top face 1508 so that heels 1526 of the patient's feet 1522 are separated from the top face 1508 by a gap 1528 (shown in FIG. 50).

The heel suspension mechanism 1524 includes a wedge 1538, for example, a foam wedge, that is positioned at an end 1540 of the foot section 1506. The end 1540 of the foot section 1506 includes a notch 1542 formed in the foot section 1506. The wedge 1538 rests in the notch 1542 and is secured to the foot section 1506 via a strap 1544. The strap 1544 retains the wedge 1538 in the notch 1542 in a first position 1560. The wedge 1538 is configured to be flipped over onto the top face 1508 of the foot section 1506 to a second position 1562 (shown in FIG. 50). As illustrated in FIG. 49, when the wedge 1538 is in the first position 1560, a top 1570 of the wedge 1538 is at the first height 1510 and level with the top face 1508. As illustrated in FIG. 50, when the wedge 1538 is flipped to the second position 1562, an outer side 1572 of the wedge 1538 is positioned on the top face 1508 so that an inner side 1574 of the wedge 1538 faces upward and is positioned at a second height 1576 that is greater than the first height 1510. The patient's feet 1522 are configured to rest on the inner side 1574 of the wedge 1538 to elevate the patient's heels 1526 when the wedge 1538 is in the second position 1562.

Referring to FIG. 51, a patient support surface 1600 includes a body 1602 having a body section 1604 and an opposite foot section 1606. The patient support surface 1600 may be a foam mattress or an air mattress. In some embodiments, the patient support surface 1600 may be any of the support surfaces described in FIGS. 1-33. A top face 1608 extends from the body section 1604 to the foot section 1606. The top face 1608 is positioned at a first height 1610 from a bottom 1612 of the support surface 1600. A patient 1620 is configured to rest on the top face 1608 with their feet 1622 at the foot section 1606 of the support surface 1600. A heel suspension mechanism 1624 is positioned within the foot section 1606. The heel suspension mechanism 1624 is movable onto the top face 1608 so that heels 1626 of the patient's feet 1622 are separated from the top face 1608 by a gap 1628 (shown in FIG. 52).

The heel suspension mechanism 1624 includes a wedge 1638, for example a foam wedge, that is positioned at an end 1640 of the foot section 1606. The end 1640 of the foot section 1606 includes a notch 1642 formed in the foot section 1606. The wedge 1638 rests in the notch 1642 in a first position 1660. The wedge 1638 is configured to be slid onto the top face 1608 of the foot section 1606 to a second position 1662 (shown in FIG. 52). As illustrated in FIG. 51, when the wedge 1638 is in the first position 1660, a top 1670 of the wedge 1638 is at the first height 1610 and level with the top face 1608. As illustrated in FIG. 52, when the wedge 1638 is slid into the second position 1662, the top 1670 of the wedge 1638 is positioned at a second height 1674 that is greater than the first height 1610. The patient's feet 1622 are configured to rest on the top 1670 of the wedge 1638 to elevate the patient's heels 1626 when the wedge 1638 is in the second position 1662.

Figure 53:
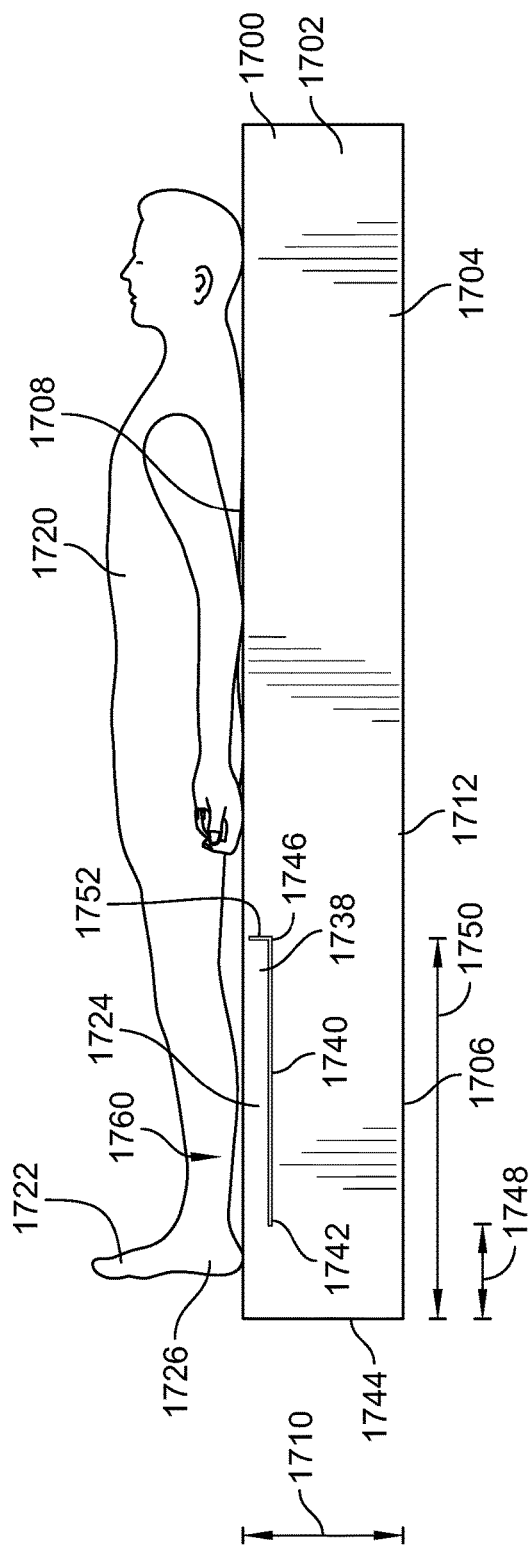
FIG. 53 is a side elevation view of a support surface having a cutout positioned in a foot end, wherein the cutout operates as a heel suspension mechanism.

Referring to FIG. 53, a patient support surface 1700 includes a body 1702 having a body section 1704 and an opposite foot section 1706. The patient support surface 1700 may be a foam mattress or an air mattress. In some embodiments, the patient support surface 1700 may be any of the support surfaces described in FIGS. 1-33. A top face 1708 extends from the body section 1704 to the foot section 1706. The top face 1708 is positioned at a first height 1710 from a bottom 1712 of the support surface 1700. A patient 1720 is configured to rest on the top face 1708 with their feet 1722 at the foot section 1706 of the support surface 1700. A heel suspension mechanism 1724 is positioned within the foot section 1706. The heel suspension mechanism 1724 is movable under the patient's feet 1722 so that heels 1726 of the patient's feet 1722 are separated from the top face 1708 by a gap 1728 (shown in FIG. 54).

Figure 54:
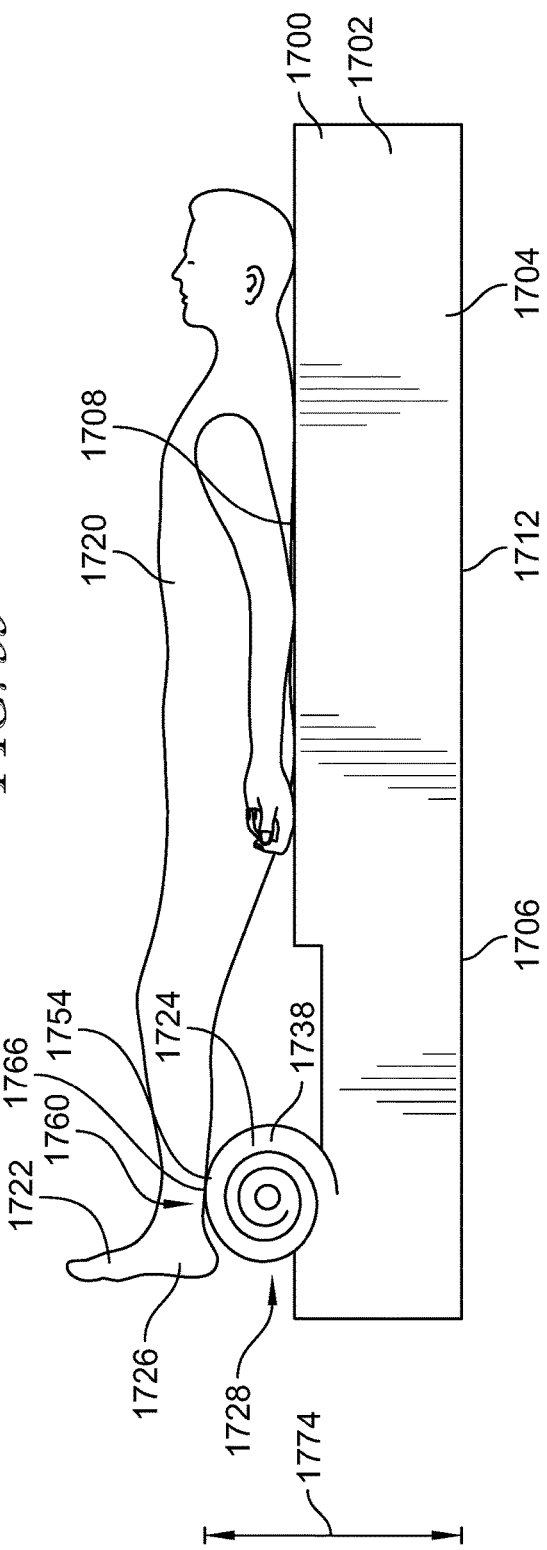
FIG. 54 is a side elevation view similar to FIG. 53, wherein the cutout is actuated to raise the foot end of the support surface.

The heel suspension mechanism 1724 includes a cutout 1738 in the foot section 1706. The cutout 1738 includes a bottom cut 1740 that begins at a location 1742 spaced from an end 1744 of the foot section 1706 and extends toward the body section 1704 to location 1746. The location 1742 is spaced a first distance 1748 from the end 1744, and the location 1746 is spaced a second distance 1750 from the end 1744. The second distance 1750 is greater than the first distance 1748. A cut 1752 extends from the bottom cut 1740 through the top face 1708 at the location 1746. In some embodiments, the bottom cut 1740 and the cut 1752 may be sealed with a zipper. The cutout 1738 is configured to be rolled from the location 1746 toward the end 1744 to form a rolled cutout 1754 (shown in FIG. 54). As illustrated in FIG. 53, when the cutout 1738 is in a first unrolled position 1760, a top 1762 of the cutout 1738 is at the first height 1710 and level with the top face 1708. As illustrated in FIG. 54, when the cutout 1738 is rolled into a second position 1762 to form the rolled cutout 1754, a portion 1764 of a bottom 1766 of the cutout 1738 is positioned at a second height 1774 that is greater than the first height 1710. The patient's feet 1722 are configured to rest on the rolled cutout 1754 to elevate the patient's heels 1726 when the cutout 1738 is in the second position 1762.

Referring to FIG. 55, a patient support surface 1800 includes a body 1802 having a body section 1804 and an opposite foot section 1806. The patient support surface 1800 may be a foam mattress or an air mattress. In some embodiments, the patient support surface 1800 may be any of the support surfaces described in FIGS. 1-33. A top face 1808 extends from the body section 1804 to the foot section 1806. The top face 1808 is positioned at a first height 1810 from a bottom 1812 of the support surface 1800. A patient 1820 is configured to rest on the top face 1808 with their feet 1822 at the foot section 1806 of the support surface 1800. A heel suspension mechanism 1824 is positioned within the foot section 1806. The heel suspension mechanism 1824 is movable onto the top face 1808 so that heels 1826 of the patient's feet 1822 are separated from the top face 1808 by a gap 1828 (shown in FIG. 56).

The heel suspension mechanism 1824 includes a cutout 1838 in the foot section 1806. The cutout 1838 includes a bottom cut 1840 that begins at an end 1844 of the foot section 1806 and extends toward the body section 1804 to location 1846 that is spaced a distance 1848 from the end 1844. A zipper 1836 extends along the bottom cut 1840 to secure the cutout 1838 to the foot section 1806, when the heel suspension mechanism 1824 is not in use. The cutout 1838 is configured to be folded from a first position 1860 to a second position 1862 (shown in FIG. 56). As illustrated in FIG. 55, when the cutout 1838 is in the first position 1860, a top 1862 of the cutout 1838 is at the first height 1810 and level with the top face 1808. As illustrated in FIG. 56, when the cutout 1838 is folded into the second position 1862, a bottom 1866 of the cutout 1838 is positioned at a second height 1874 that is greater than the first height 1810. The patient's feet 1822 are configured to rest on the bottom 1866 of the cutout 1838 to elevate the patient's heels 1826 when the cutout 1838 is in the second position 1862. An additional foam pad 1880 may be placed on the bottom 1866 of the cutout 1838 to further raise the patient's heels 1826 and to protect the patient's feet 1822 from the zipper 1836.

Figure 57:
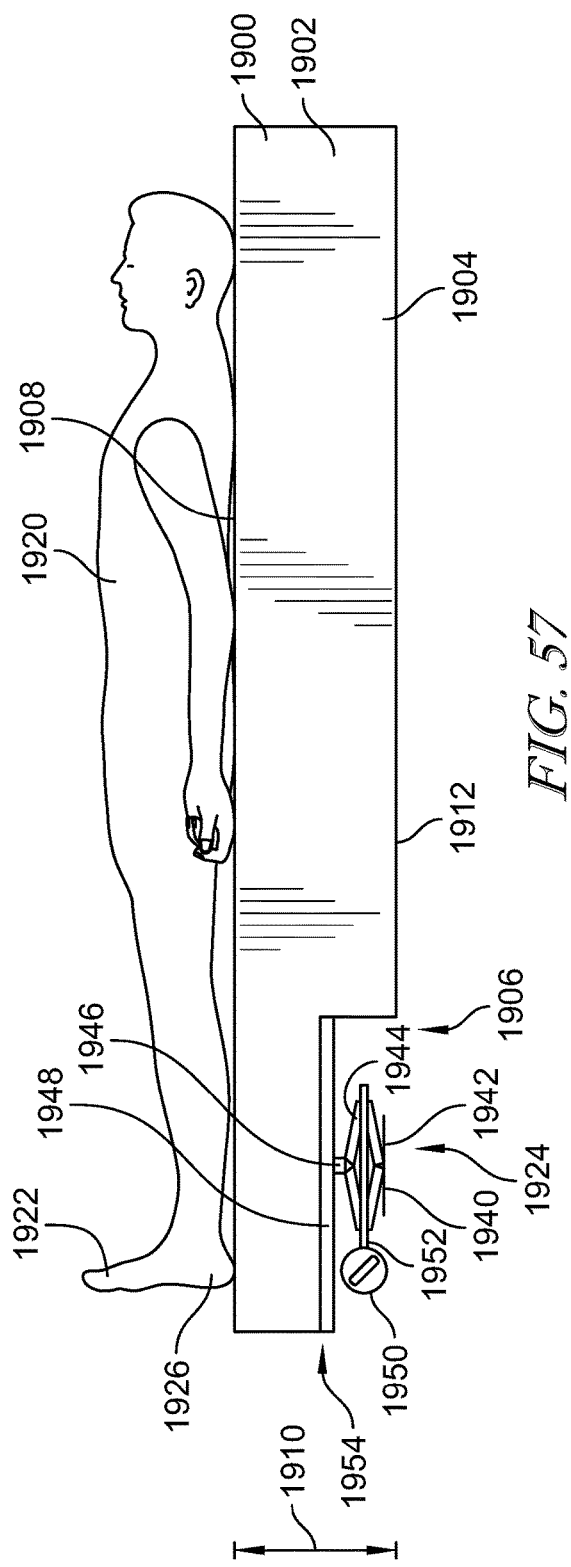
FIG. 57 is a side elevation view of a support surface having a jack positioned in a foot end, wherein the jack operates as a heel suspension mechanism.

Referring to FIG. 57, a patient support surface 1900 includes a body 1902 having a body section 1904 and an opposite foot section 1906. The patient support surface 1900 may be a foam mattress or an air mattress. In some embodiments, the patient support surface 1900 may be any of the support surfaces described in FIGS. 1-33. A top face 1908 extends from the body section 1904 to the foot section 1906. The top face 1908 is positioned at a first height 1910 from a bottom 1912 of the support surface 1900. A patient 1920 is configured to rest on the top face 1908 with their feet 1922 at the foot section 1906 of the support surface 1900. A heel suspension mechanism 1924 is positioned within the foot section 1906. The heel suspension mechanism 1924 is movable to raise the foot section 1906 so that heels 1926 of the patient's feet 1922 are separated from the top face 1908 by a gap 1928 (shown in FIG. 58).

The heel suspension mechanism 1924 includes a jack 1940 positioned below the foot section 1906. The jack 1940 includes a base 1942 and expandable arms 1944 extending from the base 1942 to a top post 1946. The top post 1946 is coupled to a flexible membrane 1948 that extends along the bottom 1912 of the support surface 1900 at the foot section 1906. A handle 1950 is coupled to a screw 1952 that is threaded to the expandable arms 1944. When the handle 1950 is rotated a first direction, the screw 1952 is actuated to lower the expandable arms 1944 to a collapsed position 1954 (shown in FIG. 57). When the handle 1950 is rotated an opposite second direction, the screw 1952 is actuated to raise the expandable arms 1944 to a raised position 1956 (shown in FIG. 58). In some embodiments, the expandable arms 1944 may be hydraulically actuated.

Figure 58:
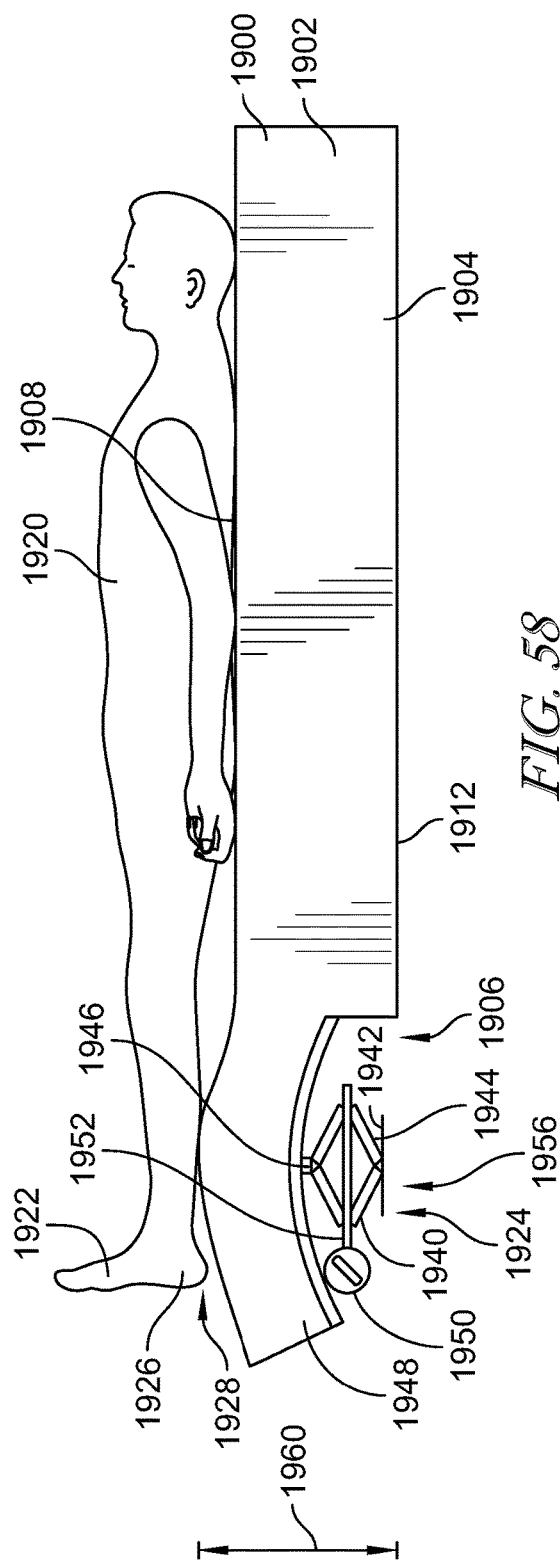
FIG. 58 is a side elevation view similar to FIG. 57, wherein the jack is actuated to raise the foot end of the support surface.

As illustrated in FIG. 57, when the expandable arms 1944 are in the collapsed position 1954, the top face 1808 of the foot section 1906 is positioned at the first height 1810. As illustrated in FIG. 58, when expandable arms 1944 are in the raised position 1956, the top post 1946 of the jack 1940 pushes the membrane 1948 upward to push against the bottom 1912 of the support surface 1900 at the foot section 1906, thereby raising the top face 1908 at the foot section 1906 to a second height 1960 that is greater than the first height 1910.

Referring to FIG. 59, a patient support surface 2000 includes a body 2002 having a body section 2004 and an opposite foot section 2006. The patient support surface 2000 may be a foam mattress or an air mattress. In some embodiments, the patient support surface 2000 may be any of the support surfaces described in FIGS. 1-33. A top face 2008 extends from the body section 2004 to the foot section 2006. The top face 2008 is positioned at a first height 2010 from a bottom 2012 of the support surface 2000. A patient 2020 is configured to rest on the top face 2008 with their feet 2022 at the foot section 2006 of the support surface 2000. A heel suspension mechanism 2024 is positioned within the foot section 2006. The heel suspension mechanism 2024 is movable to raise the foot section 2006 so that heels 2026 of the patient's feet 2022 are separated from the top face 2008 by a gap 2028 (shown in FIG. 60).

The heel suspension mechanism 2024 includes an elevating assembly 2040 positioned below the body 2002. The elevating assembly 2040 includes a base 2042 that extends along the bottom 2012 of the support surface 2000. An arm 2044 extends from the base 2042 to a top plate 2046. The top plate 2046 is coupled to a flexible membrane 2048 that extends along the bottom 2012 of the support surface 2000 at the foot section 2006. The arm 2044 is extendable from the base 2042. In some embodiments, the arm 2044 is hydraulically lifted from the base 2042. In some embodiments, the arm 2044 is telescopically extended from the base 2042. The arm 2044 may be actuated to lower the top plate 2046 to a collapsed position 2054 (shown in FIG. 59). The arm 2044 may also be actuated to raise the top plate 2046 to a raised position 2056 (shown in FIG. 60). As illustrated in FIG. 59, when the top plate 2046 is in the collapsed position 2054, the top face 2008 of the foot section 2006 is positioned at the first height 2010. As illustrated in FIG. 60, when the top plate 2046 is in the raised position 2056 the top face 2008 at the foot section 2006 is raised to a second height 2060 that is greater than the first height 2010.

Figure 61:
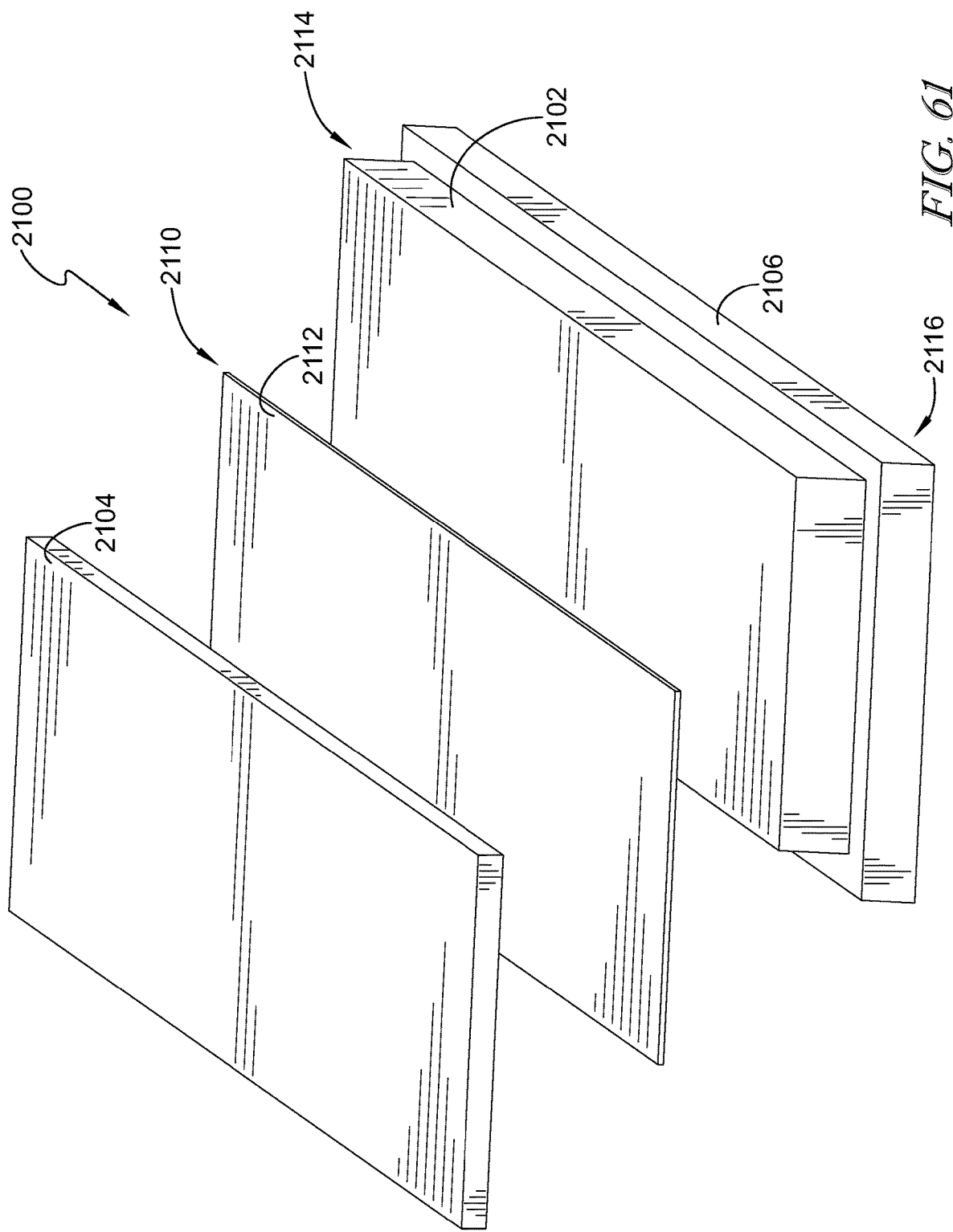
FIG. 61 is a top perspective view of a patient support apparatus in accordance with another embodiment.

Referring to FIG. 61 a patient support apparatus 2100 is embodied as a mattress 2100 having a top cover 2104, one or more support elements 2102, and a bottom cover 2106. The mattress 2100 may be any of the mattresses described herein. The top and bottom covers 2104 and 2106 attach together, such as with a zipper to form a coverlet or casing having an interior region in which the support elements 2102 are received. In the illustrative example, support element 2102 is shown as a single foam block, but, in other embodiments, includes multiple foam elements or an inflatable bladder. The top cover 2104 may be a non-permeable cover, e.g. a plastic cover that is not permeable to liquid. In other embodiments, the top cover 2104 is a fabric cover that may be permeable to liquids. In still other embodiments, the top cover 2104 is made of a moisture vapor permeable material that is permeable to air and moisture vapor but impermeable to liquids.

A fluid ingress detection system 2110 is positioned between the top cover 2104 and other support elements of the mattress 2100. The fluid ingress detection system 2110 generally includes a flexible substrate 2112. The flexible substrate 2112 includes a hydrophobic material, such as plastic. In some embodiments, the flexible substrate 2112 may include a synthetic resin. In some embodiments, the flexible substrate 2112 may include a thermoplastic polymer material. The flexible substrate 2112 is substantially rectangular and extends from a head end 2114 of the mattress 2100 to a foot end 2116 of the mattress 2100 and extends laterally across the width of the mattress 2100. Thus, the flexible substrate 2112 extends entirely between the support elements 2102 of the mattress 2100 and the top cover 2104.

Figure 62:
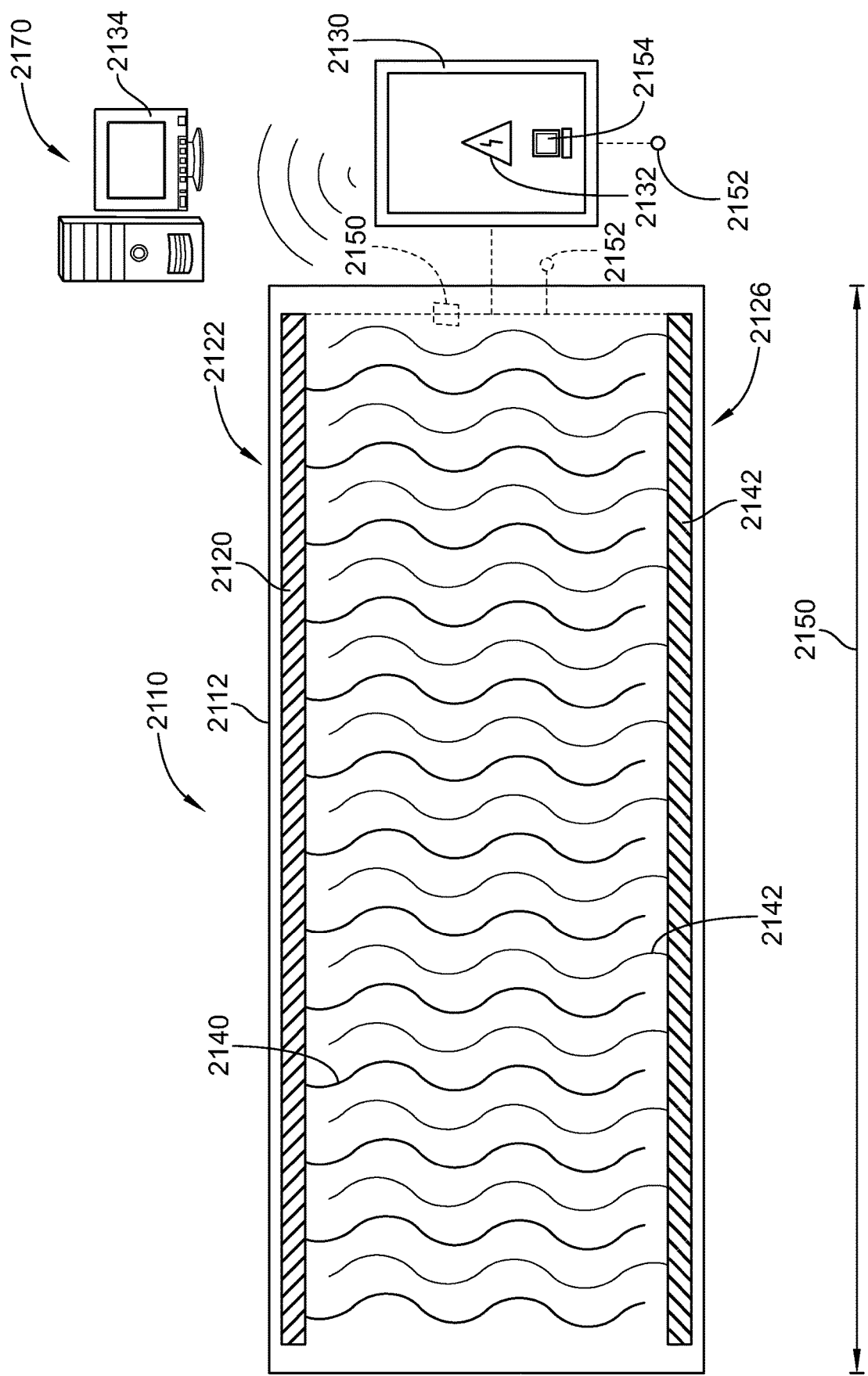
FIG. 62 is a top plan view of the fluid ingress detection system shown in FIG. 61.

As illustrated in FIG. 62, the flexible substrate 2112 includes a conductive trace 2120 extending along a first side 2122 of the flexible substrate 2112. A conductive trace 2124 extends along a second side 2126 of the flexible substrate 2112. The conductive trace 2120 and the conductive trace 2124 may include conductive threads woven on the flexible substrate 2112. In some embodiments, the conductive trace 2120 and the conductive trace 2124 include conductive ink printed on the flexible substrate 2112. The conductive trace 2120 and the conductive trace 2124 may be electrically coupled to a controller 2130. In some embodiments, the controller 2130 includes an alarm 2132 that may be an audible or visual alarm. In some embodiments, the controller 2130 is electrically or wirelessly coupled to a remote alarm 2134, e.g. an alarm at a nurse's station 2170.

A plurality of conductive segments 2140 extend from the conductive trace 2120. The segments 2140 may include conductive threads woven on the flexible substrate 2112. In some embodiments, the segments 2140 include conductive ink printed on the flexible substrate 2112. The segments 2140 extend from the conductive trace 2120 toward the conductive trace 2124. The segments 2140 do not contact the conductive trace 2124. Another plurality of conductive segments 2142 extend from the conductive trace 2124. The segments 2142 may include conductive threads woven on the flexible substrate 2112. In some embodiments, the segments 2142 include conductive ink printed on the flexible substrate 2112. The segments 2142 extend from the conductive trace 2124 toward the conductive trace 2120. The segments 2142 do not contact the conductive trace 2120. A moisture absorbent material may overlie the first conductive trace 2120, the second conductive trace 2124, and the segments 2140 and 2142.

The segments 2140 and the segments 2142 alternate along a length 2150 of the flexible substrate 2112 from the head end 2114 to the foot end 2116. Thus, the segments 2140 are interleaved or interdigitated with the segments 2142. Each pathway 2140 is positioned adjacent to a pathway 2142, and each pathway 2142 is positioned adjacent to a pathway 2140. An open circuit is formed between the conductive trace 2120 and the conductive trace 2124 when the flexible substrate is dry. The controller 2130 measures an impedance between the adjacent segments 2140 and 2142. In some embodiments, the controller 2130 is calibrated to measure a baseline impedance between the segments 2140 and 2142. That is, the impedance between the segments 2140 and 2142 is constant, within a range, when the flexible substrate 2112 remains dry. The presence of a threshold amount of liquid, such as cleaning solution or incontinence, on the flexible substrate 2112 forms a closed circuit with the conductive trace 2120 and the conductive trace 2124 due to the flexible substrate 2112 being wet. The impedance between the conductive trace 2120 and the conductive trace 2124 changes when the flexible substrate is wet.

If fluid permeates through the top cover 2104, the liquid is collected on the flexible substrate 2112. In some embodiments, the liquid permeates through the top cover 2104 because of a tear in the top cover 2104. In some embodiments, the liquid permeates through the top cover 2104 because the top cover 2104 has become worn. When the liquid permeates through the top cover 2104, the liquid settles on the flexible substrate 2112. As a result of the liquid bridging the gap between adjacent segments 2140 and 2142, the liquid changes the impedance between the segments 2140 and 2142. The change in impedance is detected by the controller 2130. In particular, the liquid bridging between segments 2140, 2142 causes the impedance to be reduced significantly, thereby changing an open circuit (i.e. dry) condition to a closed circuit (i.e. wet) condition. In response, the controller 2130 sends an alert that the top cover 2104 has been compromised and that liquid is ingressing into the mattress 2100.

In some embodiments, a passive RFID tag 2150 may be situated on the flexible substrate 2112 and in electrical communication with the conductive trace 2120 and the conductive trace 2124. An antenna 2152 receives wireless energy emitted by the RFID tag 2150 indicating whether the flexible substrate is dry or wet. In some embodiments, a reader 2154 of the controller 2130 supplies power to the antenna, which produces an electromagnetic field that powers the passive RFID tag 2150. The reader 2154 receives signals from the antenna, which signals contain back scattered data from the passive RFID tag 2150, and transmits a notification message in response to at least one of the signals from the antenna indicating that the flexible substrate 2112 is wet. The reader may be communicatively coupled to a network 2160 of a healthcare facility and configured to communicate wirelessly with the network 2160.

In some embodiments, the alarm 2132 may be activated when the impedance between the conductive trace 2120 and the conductive trace 2124 changes. The alarm 2132 may be a visual alarm or an audible alarm. The alarm 2132 may be provided on the patient support apparatus 2100. In other embodiments, the alarm 2134 is remote from the patient support apparatus 2100, e.g. at a nurse's station 2170.

The liquid detection by system 2110 prevents caregivers from having to perform hand checks to determine whether a mattress interior has been soiled due to a compromised top cover 2104. Once the liquid permeates through the top cover 2104, the caregiver is alerted in real time. Accordingly, the caregiver can attend to the liquid within the mattress 2100 in a quicker manner, rather than the liquid settling into the mattress 2100. By attending to liquid ingress into the mattress 2012 in a timelier manner, a life-span of the mattress 2100 may be extended with only the top cover 2104 needing to be replaced. Additionally, the mattress 2100 may be properly cleaned upon learning of the liquid ingress, so that infections may be prevented when the mattress 2012 is used.

Figure 63:
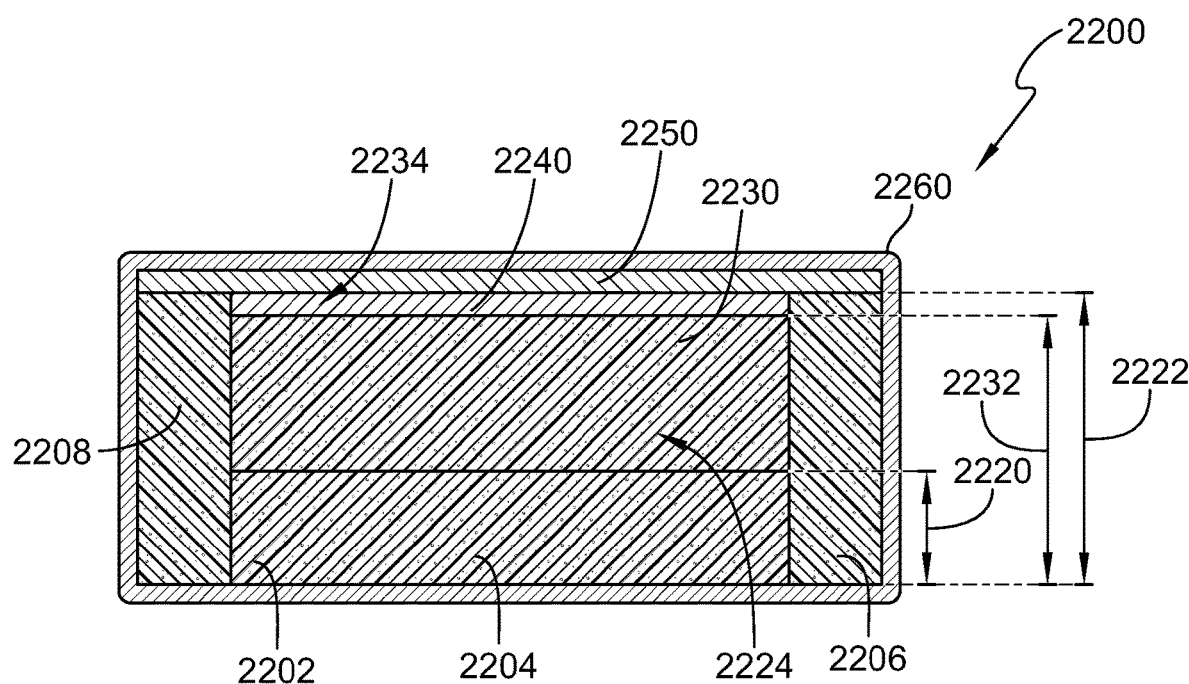
FIG. 63 is a side cross-sectional view of a mattress in accordance with an embodiment.

Referring now to FIG. 63, a mattress 2200 includes a foam base 2202 having a bottom section 2204, a head section 2206, and a foot section 2208. The bottom section 2204 extends between the head section 2206 and the foot section 2208. The bottom section 2204 has a height 2220 and the head section 2206 and foot section 2208 have a height 2222 that is greater than the height 2220. A cavity 2224 is formed in the foam base 2202 between the head section 2206 and foot section 2208 and above the bottom section 2204. In some embodiments, the foam base 2202 may also include side sections (not shown) that extend to the height 2222 so that the cavity 2224 is enclosed on all sides.

A foam layer 2230 is positioned within the cavity 2224 and extends from the head section 2206 to the foot section 2208. In the illustrated embodiment, the foam layer 2230 is a separate layer from the foam base 2202. In other embodiments, the foam layer 2230 may be integrally formed with the foam base 2202. The foam layer 2230 extends to a height 2232 that is less than the height 2222 of the head section 2206 and the foot section 2208. A cavity 2234 is defined between the head section 2206 and the foot section 2208 and above the foam layer 2230. The cavity 2234 is sized so that a patient can lie across the mattress 2200 without having pressure points developed due to the difference in height between the foam layer 2230 and the head section 2206 and foot section 2208.

A therapeutic layer 2240 is positioned within the cavity 2234. The therapeutic layer 2240 is inflatable from a deflated position to an inflated position. When a patient does not require therapeutic treatment, the therapeutic layer 2240 is deflated. If the patient requires therapeutic treatment, e.g. to treat ulcers or bed sores, the therapeutic layer 2240 is inflated.

A protective layer 2250 is positioned over the therapeutic layer 2240. The protective layer 2250 extends over the head section 2206 and the foot section 2208 of the foam base 2202. The protective layer 2250 made be formed from three-dimensional spacers. In some embodiments, the protective layer 2250 is formed from a non-woven fabric layer. In other embodiments, the protective layer 2250 is formed from a layer of foam. It will be appreciated that the protective layer 2250 may be made from a combination of materials. The therapeutic layer 2240 is positioned adjacent the protective layer 2250, so that when the therapeutic layer 2240 is deflated, the protective layer 2240 continues to provide a level surface for the patient. That is, the protective layer 2250 is formed so that is does not dip into the cavity 2234 when the therapeutic layer 2240 is deflated.

A cover 2260 is positioned around the mattress 2200. The cover 2260 encloses the foam base 2202, the foam layer 2230, the therapeutic layer 2240, and the protective layer 2250. The cover 2260 may include a zipper or other fastening mechanism to seal the cover 2260 around the mattress 2200. In some embodiments, the cover 2260 is formed from a water impermeable material to prevent liquids, such as patient sweat, from saturating the layers of the mattress 2200.

Figure 64:
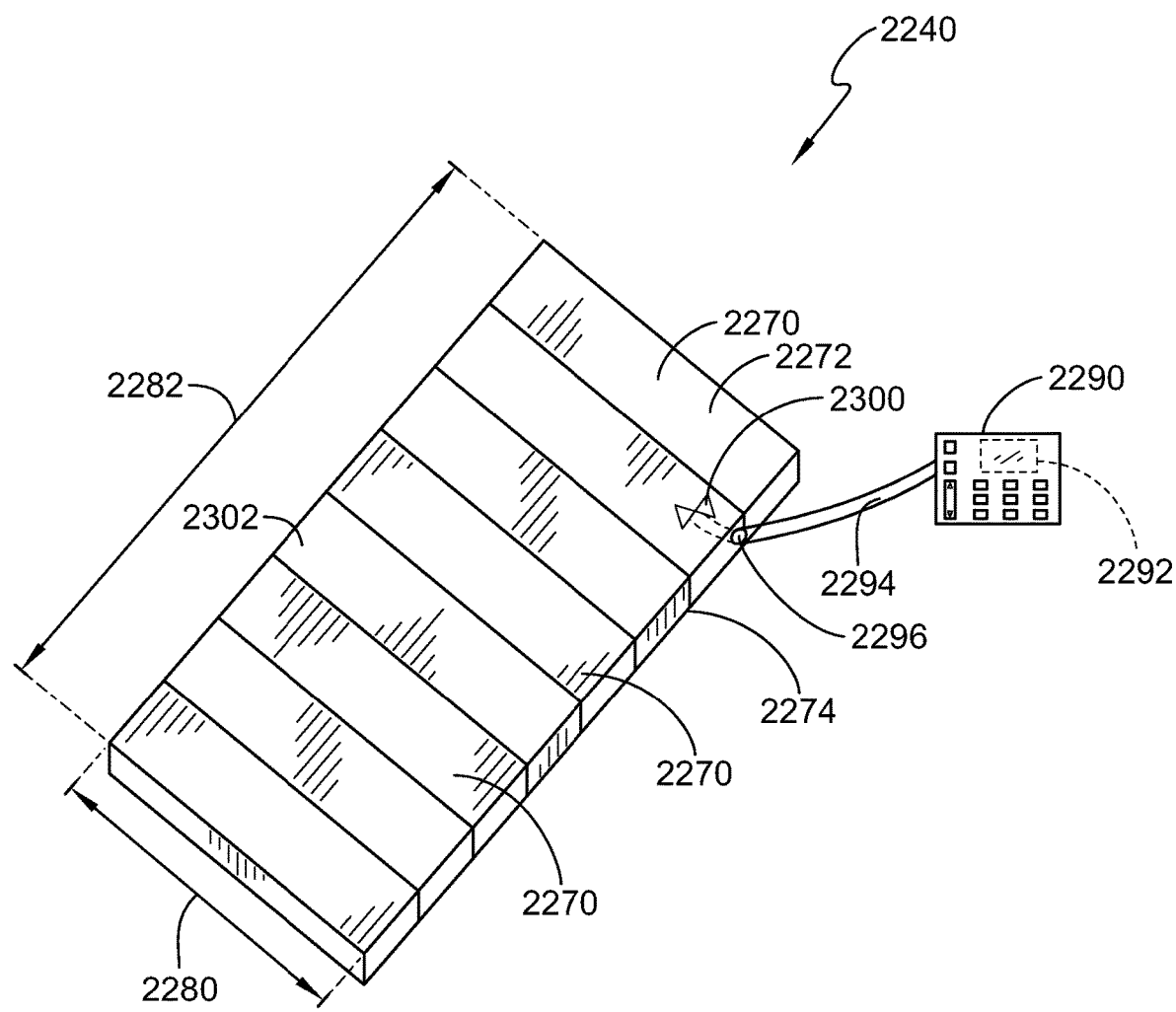
FIG. 64 is a top perspective view of a therapeutic layer of the mattress shown in FIG. 63 and coupled to a control unit with a hose.

Referring now to FIG. 64, the therapeutic layer 2240 is formed from a plastic material that may be welded with laser or radio-frequency welding. The therapeutic layer 2240 includes a plurality of bladders 2270. The bladders 2270 may be formed be welding a top layer 2272 of the therapeutic layer 2240 to a bottom layer 2274 of the therapeutic layer 2240. The bladders 2270 are illustrated as extending along a width 2280 of the therapeutic layer 2240; however, the bladders 2270 may be formed to extends along a length 2282 of the therapeutic layer 2240. In some embodiments, the bladders 2270 may have other configurations, e.g. an array.

A control unit 2290 is configured to couple to the therapeutic layer 2240. The control unit 2290 includes a blower 2292 that is fluidly coupled to the therapeutic layer 2240 via a hose 2294. The hose 2294 is coupled to an inlet 2296 of the therapeutic layer 2240. In one embodiment, a healthcare facility may have a plurality of mattresses 2200, and a lesser number of control units 2290. That is, the control unit 2290 is only required when a particular patient requires therapeutic treatment. Accordingly, the healthcare facility can save costs by having control units 2290 for only those patients that require therapy. Patient's that do not require therapy can utilize the mattress 2200 with the therapeutic layer 2240 in the deflated position. When a patient requires therapy, the control unit 2290 is attached to the therapeutic layer 2240 to inflate the therapeutic layer 2240.

In the illustrated embodiment, the therapeutic layer 2240 includes a valve 2300. The valve 2300 is configured to direct airflow to particular bladders 2270 via a series of hoses (not shown). In that way, not all of the bladders 2270 are required to be simultaneously inflated. Rather, individual bladders 2270 may be inflated based on the patient's therapeutic needs. For example, a bladder 2302 in a seat section 2304 of the therapeutic layer 2240 may be inflated to provide pressure relief to a patient's sacrum. In other embodiments, the therapeutic layer 2240 does not include a valve 2300, and all of the bladders 2270 are simultaneously inflated.

Figure 65:
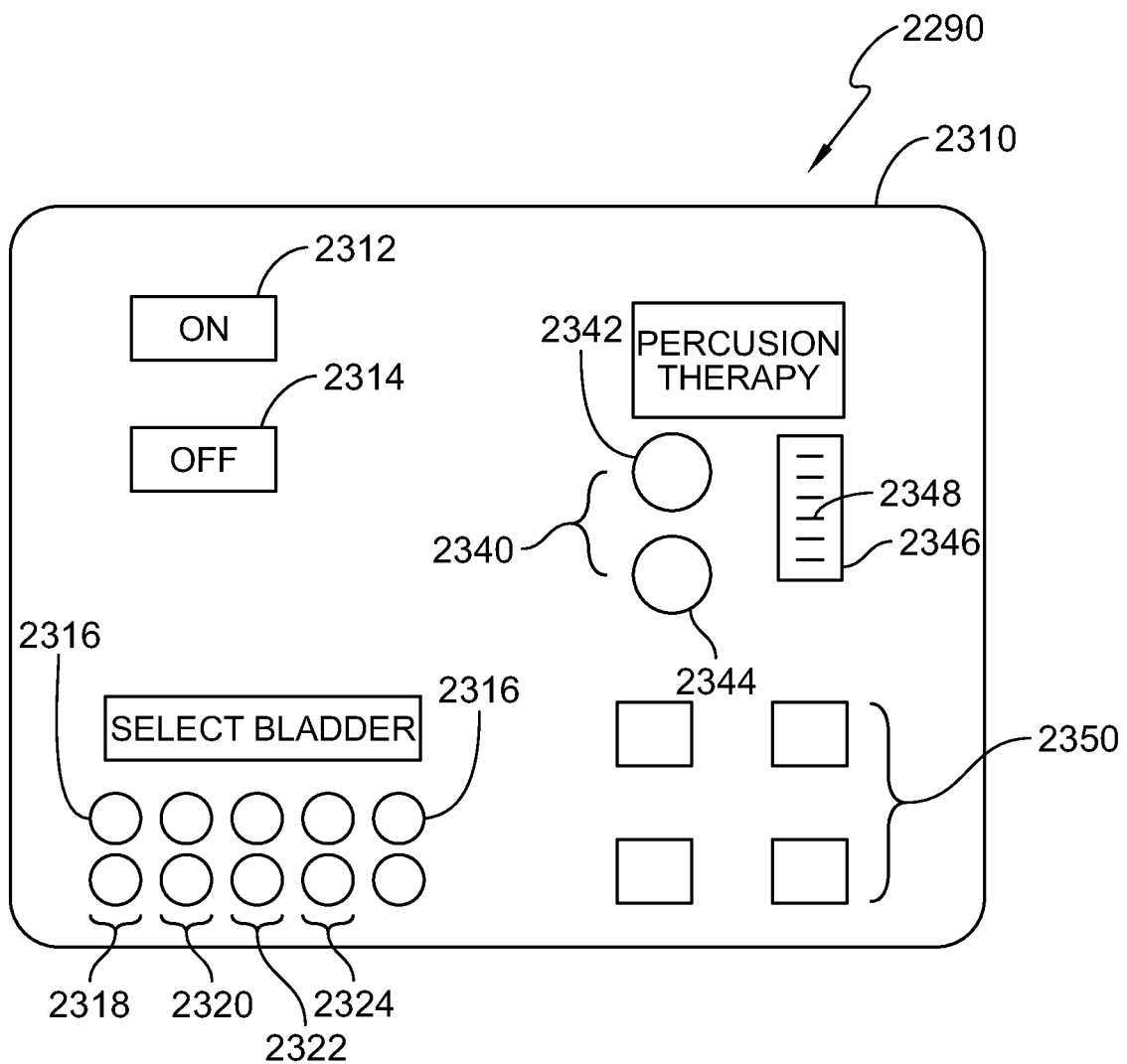
FIG. 65 is a front elevation view of the control unit shown in FIG. 64.

FIG. 65 shows an example of a display 2310 for the control unit 2290. It will be appreciated that the display 2310 may include user input buttons, e.g. membrane switches, or a touchscreen display. The display 2310 includes user inputs to turn the control unit 2290 on and off. In the illustrated embodiment, the display 2310 includes an "on" input 2312 and an "off" input 2314. It will be appreciated that inputs 2312 and 2314 may be replaced with a single power input.

In an embodiment where the therapeutic layer 2240 includes the valve 2300, a plurality of inputs 2316 may be provided for selecting particular bladders to inflate. For example, the inputs 2316 may include buttons 2318 for inflating a head section, buttons 2320 for inflating a torso section, buttons 2322 for inflating a seat section, and buttons 2324 for inflating a foot section. Other inputs 2316 may be provided for specific therapies, e.g. legs sores, or back sores. Another input 2316 may be provided for inflating all bladders 2270.

In some embodiments, the control unit 2290 may provide percussion therapy by sending impulses or vibrations to the bladders 2270. In such an embodiment, the display 2310 includes inputs 2340 for controlling the percussion therapy. The display 2310 includes an input 2342 for increasing the percussion therapy and an input 2344 for decreasing the percussion therapy. The display 2310 may also include a meter 2346 having a plurality of icons 2348 that indicate a level of the percussion therapy.

The display 2310 may also include additional inputs 2350 for controlling other aspects of the therapeutic layer 2240. For example, the therapeutic layer 2240 may enable microclimate control.

Figure 66:
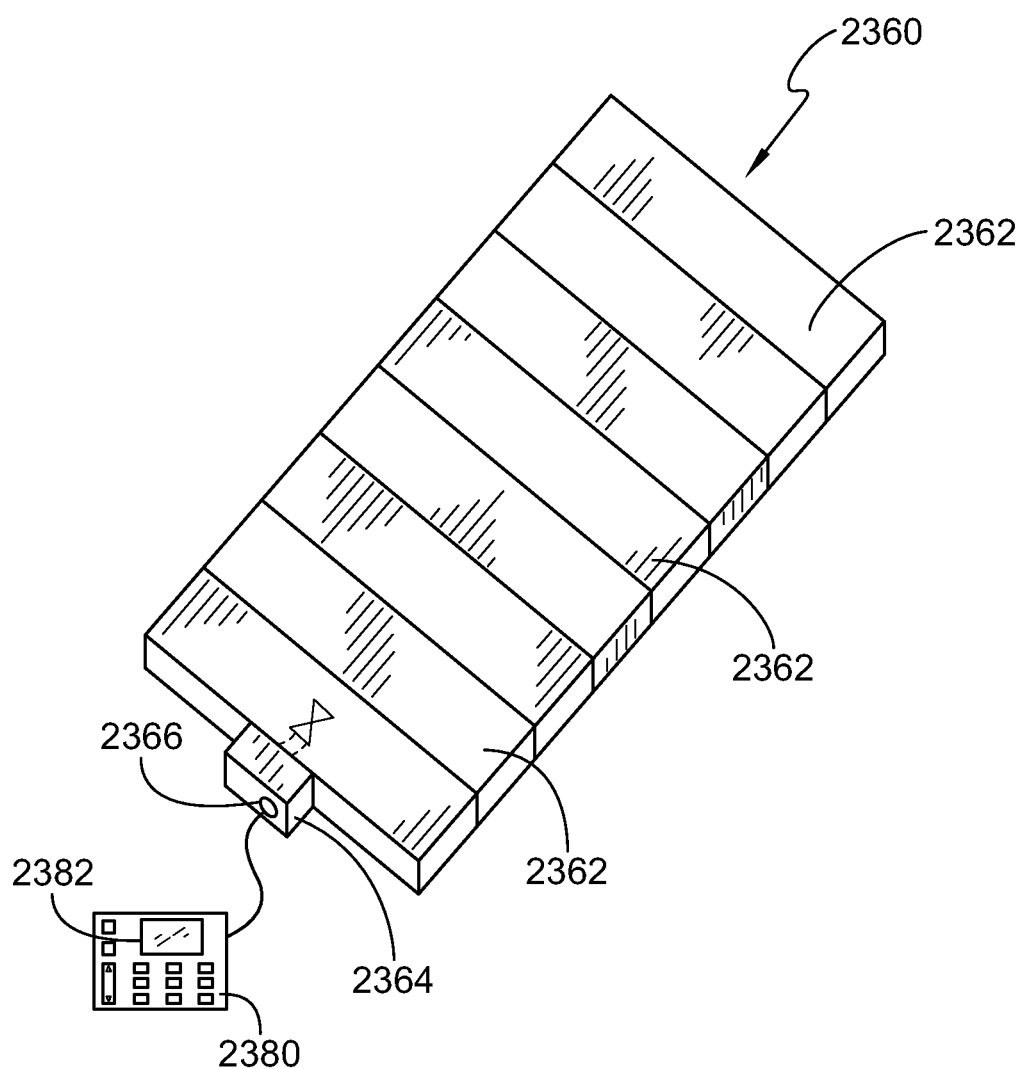
FIG. 66 is a top perspective view of another embodiment of a therapeutic layer having a blower coupled to a control unit.

Referring now to FIG. 66, another embodiment of a therapeutic layer 2360 may be used with the mattress 2200. The therapeutic layer 2360 includes a plurality of bladders 2362 that may be formed by laser or radio-frequency welding, as described above. The therapeutic layer 2360 includes a blower 2364 that is coupled to an end or side of the therapeutic layer 2360. The blower 2364 extends through the cover 2260 and includes a power input 2366. The blower 2364 is in fluid communication with each of the bladders 2362. In some embodiments, a valve 2364 selectively fluidly couples the bladders 2362 to the blower 2364, as described above.

Another embodiment of a control unit 2380 is configured to plug into the power input 2366 to supply power to the blower 2364. The control unit 2380 may be configured with a display 2382, e.g. the display 2310 describe above. As set forth above, the control unit 2380 is attached to the therapeutic layer 2360 when the patient requires therapeutic treatment.

Figure 67:
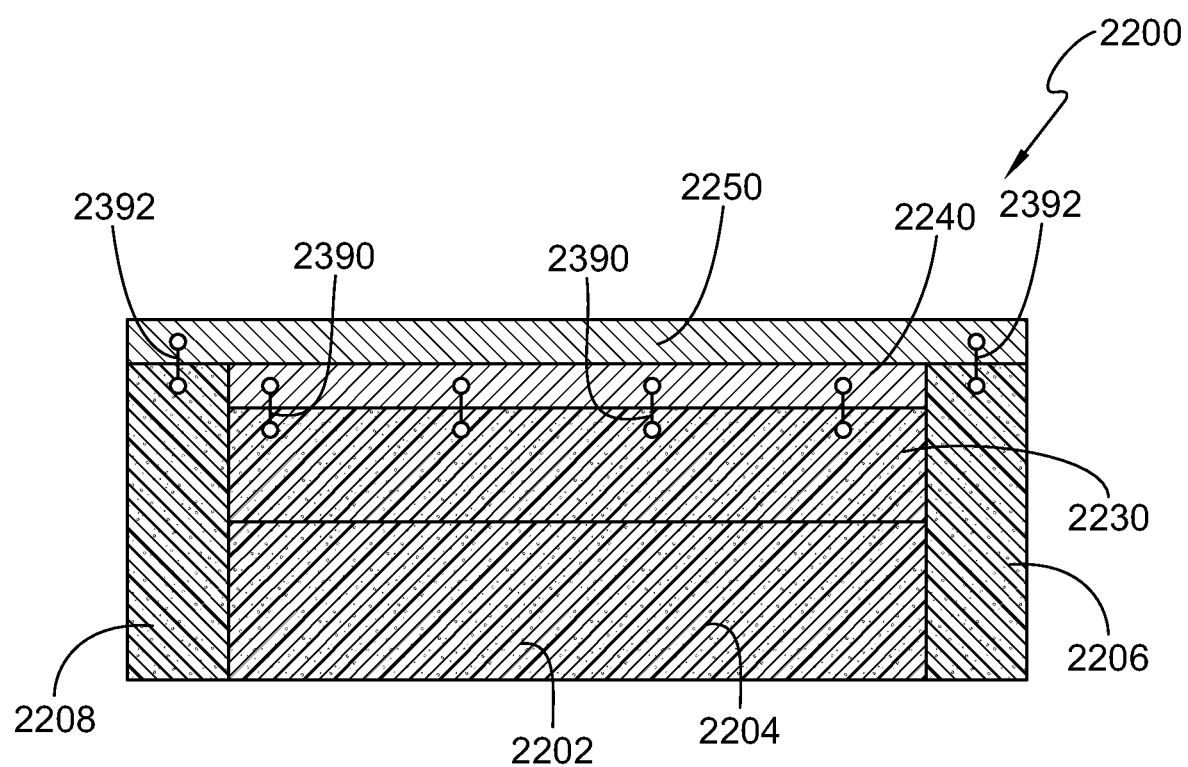
FIG. 67 is a side cross-sectional view of the mattress shown in FIG. 63 having the therapeutic layer and protective layer coupled to the foam base with a fastener.

Referring to FIG. 67, to prevent bunching of the therapeutic layer 2240 and the protective layer 2250, each of these layers may be coupled to the foam base 2202 and/or the foam layer 2230. In the illustrated embodiment, the therapeutic layer 2240 is coupled to the foam layer 2230 with fasteners 2390, e.g. snaps, zippers, buckles, etc. The therapeutic layer 2240 may also be coupled to any of the bottom section 2204, head section 2206 and/or foot section 2208 of the foam base 2202. In the illustrated embodiment, the protective layer 2250 is coupled to the head section 2206 and the foot section 2208 with fasteners 2392, e.g. snaps, zippers, buckles, etc. The protective layer 2250 may also be coupled to the foam layer 2230 or the bottom layer 2204 of the foam base 2202. In some embodiments, the protective layer 2250 and the therapeutic layer 2240 may be coupled.

The mattress 2200 provides a surface for a patient that may be used with or without therapy. In an example where a patient is admitted to a healthcare facility and requires therapy, the patient may be placed on a mattress 2200 with the therapeutic layer 2240 already inflated. If the patient later does not require therapy, the therapeutic layer 2240 may be deflated without having to move the patient. In an example where a patient is admitted to a healthcare facility and does not require therapy, the patient may be placed on a mattress 2200 with the therapeutic layer 2240 deflated. If the patient later requires therapy, the therapeutic layer 2240 may be inflated without having to move the patient. Accordingly, the mattress 2200 facilitates not having to move a patient once the patient is admitted to the healthcare facility.

Figure 68:
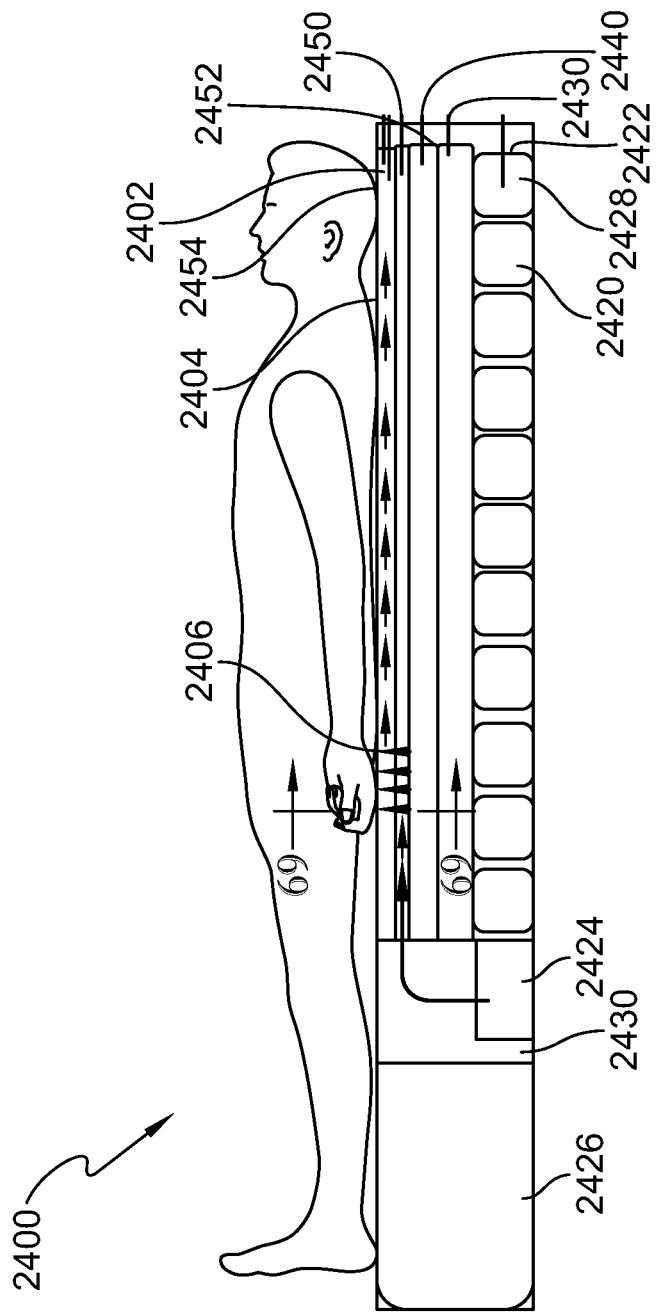
FIG. 68 is a side cross-sectional view of another embodiment of a patient support apparatus.

Referring now to FIG. 68, a patient support apparatus 2400 includes a microclimate management (MCM) feature 2402 in a surface 2404 of the apparatus 2400 to remove heat and moisture from the skin-surface interface. Removing heat and moisture has been shown to lower the risk of pressure injury (PI) development. Lab studies have shown that more heat removal leads to greater protection against ischemia and ischemic necrosis. At the sacrum and pelvis in general nearly 60% of PIs occur over less than 10% of the body's surface area. Given a severity and prevalence of PIs in this area, the MCM 2402 is configured to direct air to a seat section 2406 of the patient support apparatus 2400.

The patient support apparatus 2400 includes a base 2420 that may be formed from a foam material. In other embodiments, the base 2420 is formed from air bladders or other suitable cushion materials. The base 2420 is illustrated as a plurality of blocks 2428; however the base 2420 may be one continuous piece. The base 2420 extends from a head end 2422 of the apparatus 2400 to the seat section 2406. A blower assembly 2424 is positioned adjacent the base 2420 between the base 2420 and a foot end member 2426 of the apparatus 2400. The foot end member 2426 may also be formed from a foam material. In other embodiments, the foot end member 2426 is formed from air bladders or other suitable cushion materials. Another foam layer or cushion 2430 is positioned above the blower assembly 2424 adjacent the foot end member 2426. Another foam layer 2440 is positioned over the base 2420. In some embodiments, the layer 2440 may be formed from air bladders or other suitable cushion materials. A visco foam layer 2442 is positioned over the layer 2440.

A manifold 2450 extends over the visco foam layer 2442. An outlet of the blower assembly 2424 is configured to direct airflow from the blower assembly 2424, through a passageway in the cushion 2430, and into the manifold 2450. The manifold 2450 directs the air flow into a patient three dimensional spacer 2452 that is positioned between the manifold 2450 and a top surface 2454 of the apparatus 2400. A top surface 2456 of the patient three dimensional spacer 2452 forms the top surface 2454 of the apparatus 2400. The air flow is directed into the seat section 2406 of the patient support apparatus 2400.

Figure 69:
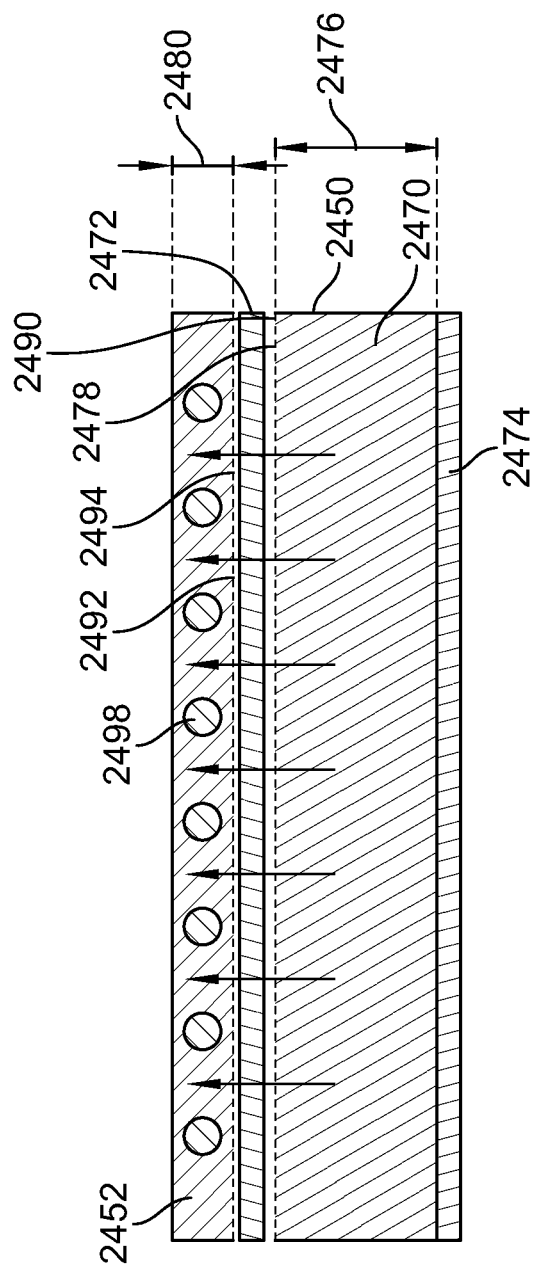
FIG. 69 is a foot end cross-sectional view taken about line 69-69 in FIG. 68.
Figure 70:
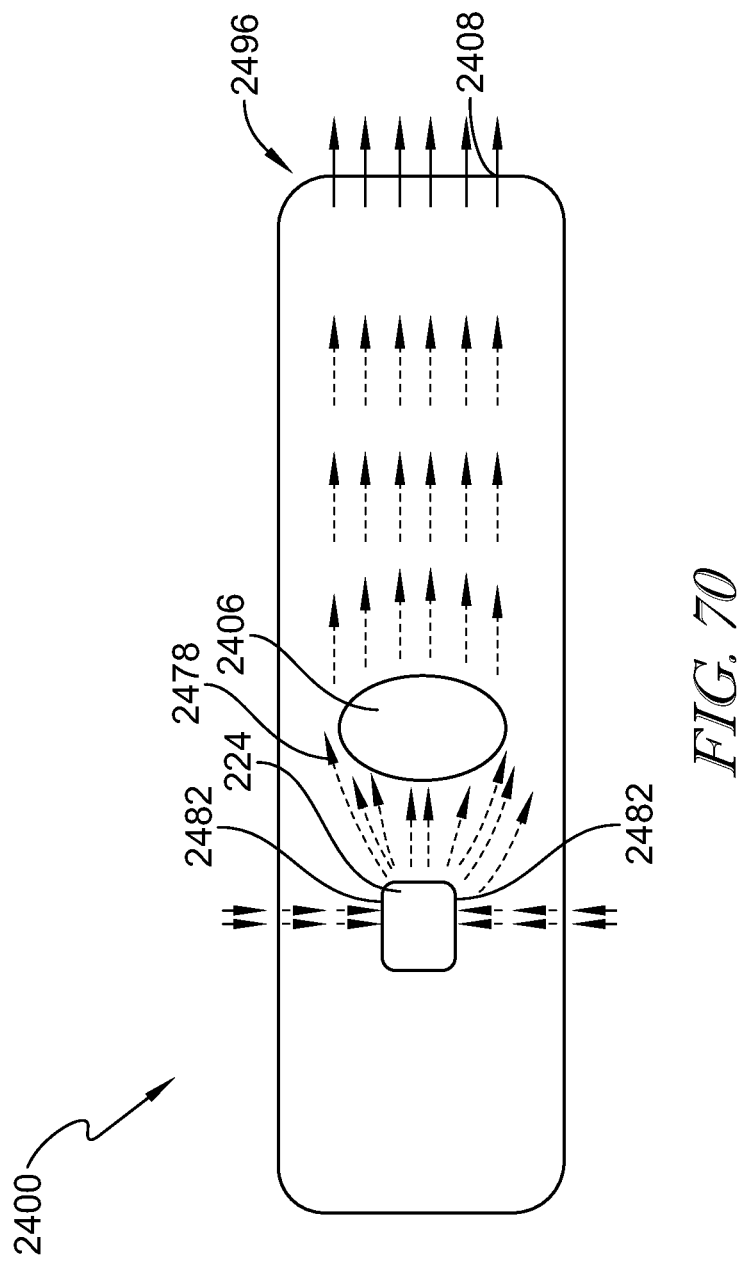
FIG. 70 is a top schematic view of airflow through the patient support apparatus shown in FIG. 68.

As illustrated in FIG. 69, the manifold 2450 includes a manifold three dimensional spacer 2470 that is positioned between a top fabric layer 2472 and a bottom fabric layer 2474. The manifold three dimensional spacer 2470 has a thickness 2476. Apertures 2478 are formed in a top surface 2490 of the manifold three dimensional spacer 2470. The apertures 2478 are formed in the seat section 2406 of the apparatus 2400 and configured to direct the air flow from the blower assembly 2424 through the top surface 2490 of the manifold three dimensional spacer 2470 at the seat section 2406. As illustrated in FIG. 70, air enters the blower assembly 2424 through sides 2482 of the apparatus 2400 and is discharged in the manifold three dimensional spacer 2470. The air exits the manifold 2450 through the apertures 2478.

Referring back to FIG. 69, the patient three dimensional spacer 2452 is positioned over the manifold 2450 and has a thickness 2480 that is less than the thickness 2476 of the manifold three dimensional spacer 2452. The air flows through the top fabric layer 2472 and into the patient three dimensional spacer 2452 through apertures 2492 formed in a bottom surface 2494 of the patient three dimensional spacer 2452. As shown in FIG. 70, the air flows around the patient's sacrum and pelvis 2484 and travels to a head end 2496 of the patient three dimensional spacer 2452. The air exits the patient support apparatus 2400 through apertures 2498 (shown in FIG. 69) formed in the head end 2496 of the patient three dimensional spacer 2452.

The apparatus provides a system for directing the air flow into the region of interest (ROI). The manifold 2450 is constructed by introducing the layer of 3-D spacer material 2452 between the two fabric materials 2472, 2474. The manifold three dimensional spacer 2452 is chosen to provide a medium to allow sufficient air flow. The manifold three dimensional spacer 2452 is configured to prevent severe occlusion of the air flow path through the fabric 2472, 2474 when a patient load is applied. The top fabric layer 2472 has a pattern of holes punched out of the appropriate location where the most therapy is needed (i.e. the seat section 2406). The remaining unaltered top fabric layer 2472 and bottom fabric layer 2474 act as a wall to facilitate preventing air leakage from the manifold 2450.

Figure 72:
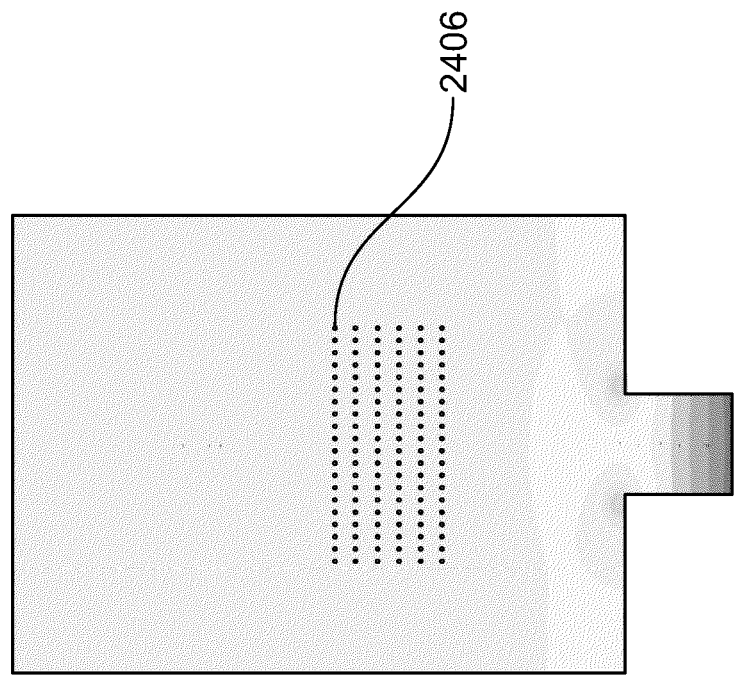
FIG. 72 is a schematic view of pressure in the patient three dimension spacer shown in FIG. 68.
Figure 71:
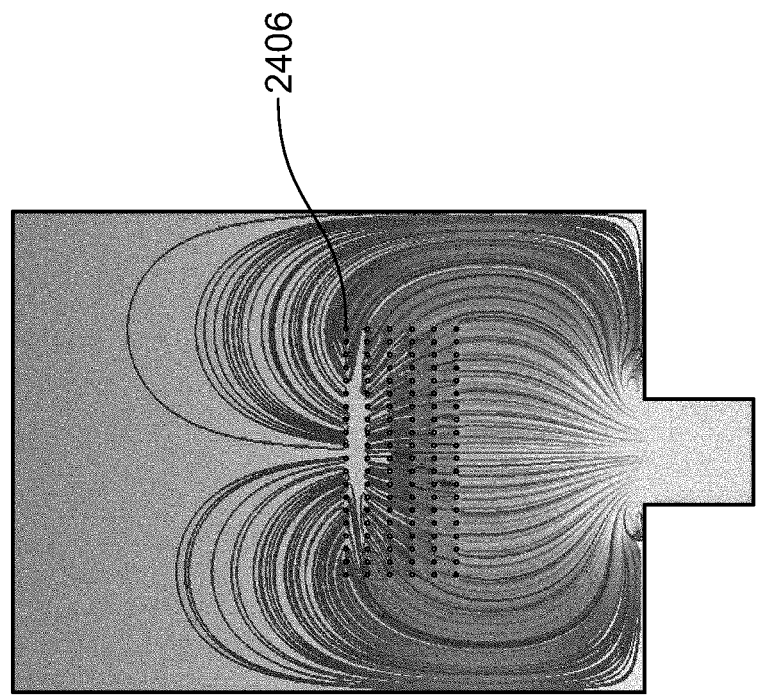
FIG. 71 is a schematic view of airflow through the patient three dimensional spacer shown in FIG. 68.

The apparatus 2400 is configured to provide a low-pressure system that can be used to provide the air flow for MCM therapy. A location of the therapy can be controlled by the design so that therapy is provided by the MCM where therapy is required the most. FIG. 71 shows a computation fluid dynamics simulation of a velocity particle track. This simulation illustrates the air flow converging at the seat section 2406. A pressure spectrum, shown in FIG. 72 illustrates a substantially uniform pressure that facilitates ease of controlling the air flow. A low pressure air source can be utilized by the patient support apparatus 2400 to provide sufficient air flow to the target region.

Figure 73:
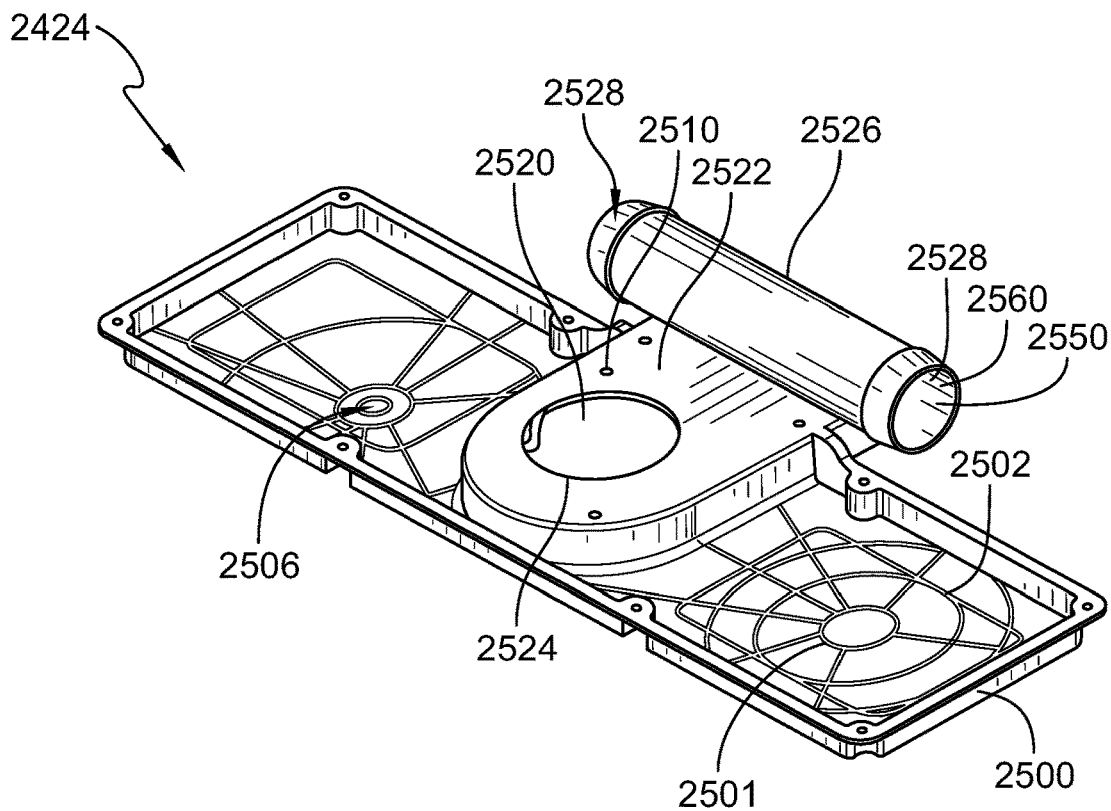
FIG. 73 is a top perspective view of a base of a blower assembly housing.

Referring to FIG. 73, the blower assembly 2424 includes a base 2500 having a bottom 2502 and side walls 2504 extending from the bottom 2502 to form a cavity 2506. A center platform 2510 extends upward from the bottom 2502 to a height that is greater than a height of the side walls 2504. An opening 2520 is formed in a top surface 2522 of the platform 2510 and extends into a vacuum chamber 2524.

The vacuum chamber 2524 is fluidly connected to an inlet assembly 2526. The inlet assembly 2526 extends along a side 2528 of the base 2500. The inlet assembly 2526 includes a pair of opposite inlets 2528. In some embodiments, the inlet assembly 2526 includes only one inlet 2528. In other embodiments, the inlet assembly 2526 may include any number of inlets 2528. Each inlet 2528 includes an opening 2550 that extends into a passageway 2560. The passageway 2560 in the illustrated embodiment extends between the openings 2550 of the inlets 2528. The passageway 2560 is in fluid communication with the vacuum chamber 2524.

Figure 74:
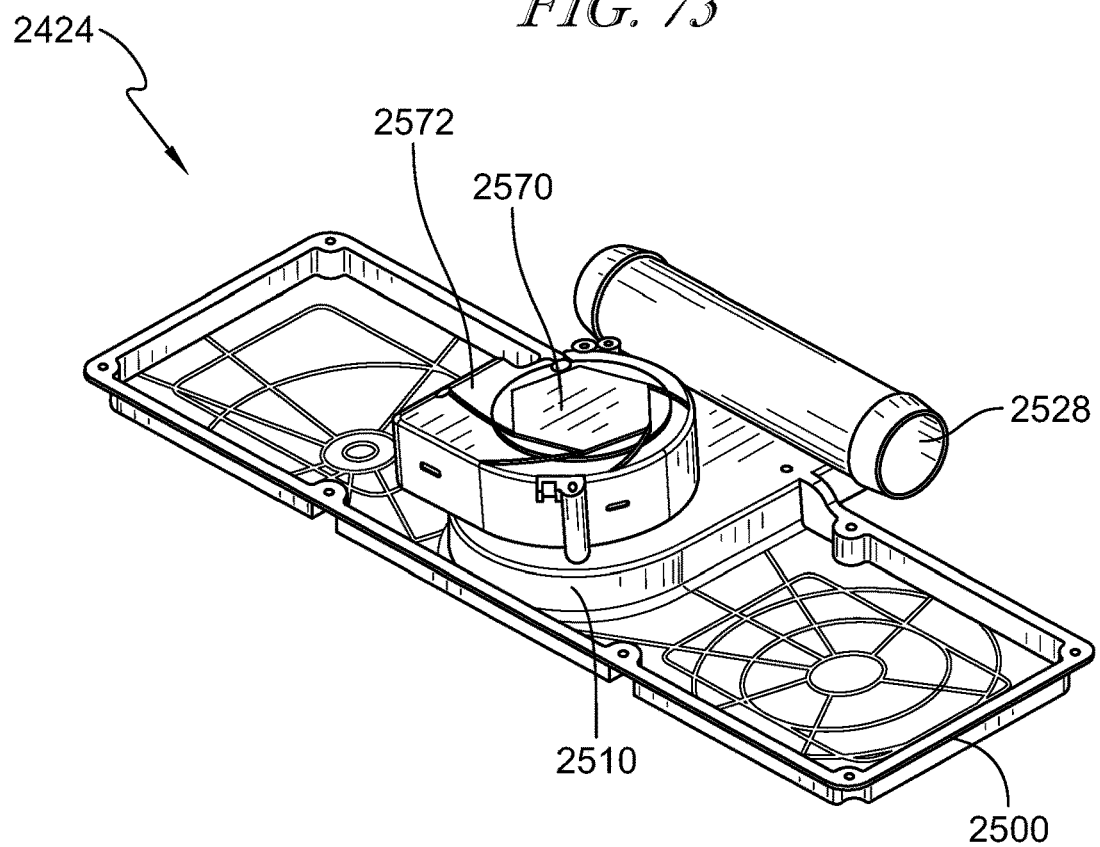
FIG. 74 is a top perspective view of a blower coupled to the base of the blower assembly housing shown in FIG. 73.

Referring now to FIG. 74, a blower 2570 is positioned over the opening 2520 and sealed to the platform 2510. The blower 2570 includes an inlet that is in fluid communication with the vacuum chamber 2524. Accordingly, the blower 2570 is sealed to the vacuum chamber 2524. The blower 2570 also includes an outlet 2572 that opens over the base 2500. Although not shown, it should be appreciated that the blower 2570 includes a fan that draws air into the inlet of the blower 2570. That is, air enters the blower assembly 2424 through the inlets 2528, passes through the passageway 2560 to the vacuum chamber 2524, and into the blower 2570 through the inlet. The blower 2570 then discharges the air through the outlet 2572 over the base 2500.

Figure 75:
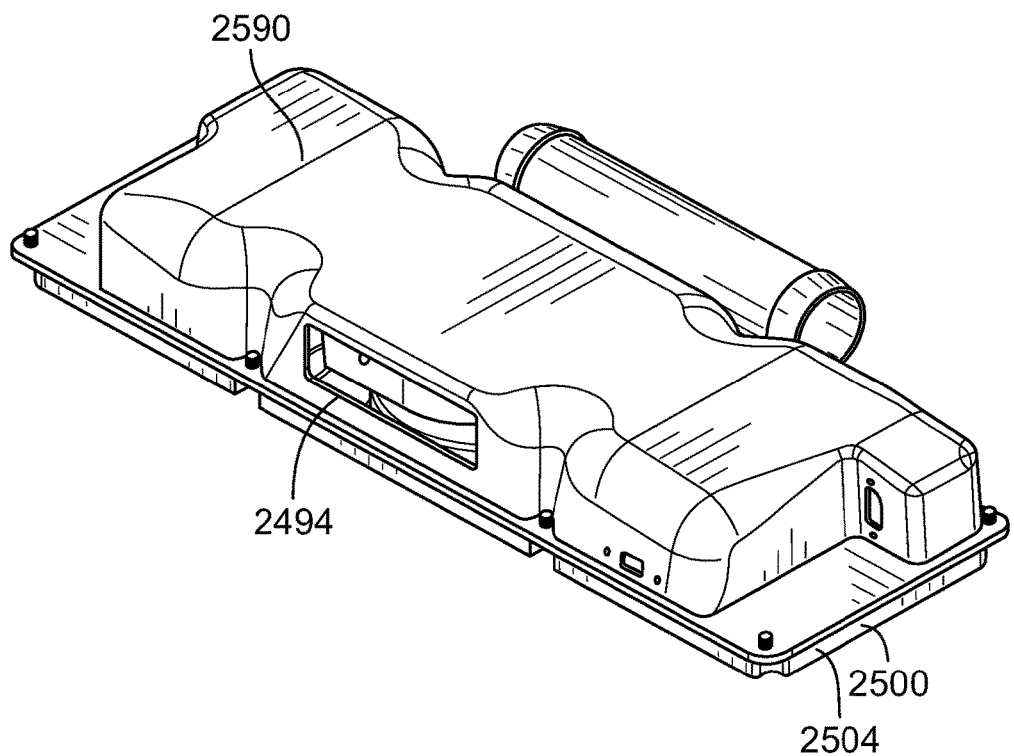
FIG. 75 is a top perspective view of the blower assembly housing having a cover coupled to the base.

As illustrated in FIG. 75, a top cover 2590 is sealed to the side walls 2504 of the base 2500 to form a pressurized chamber 2592. The blower 2570 is positioned within the pressurized chamber 2592. Accordingly, the inlet of the blower 2570 is in fluid communication with the vacuum chamber 2524 and the outlet 2572 of the blower 2570 is in fluid communication with the pressurized chamber 2592. The blower 2570 receives air from the vacuum chamber 2524 and discharges air into the pressurized chamber 2592. The top cover 2590 includes an opening 2594 that defines an exhaust 2596 of the blower assembly 2424.

Figure 76:
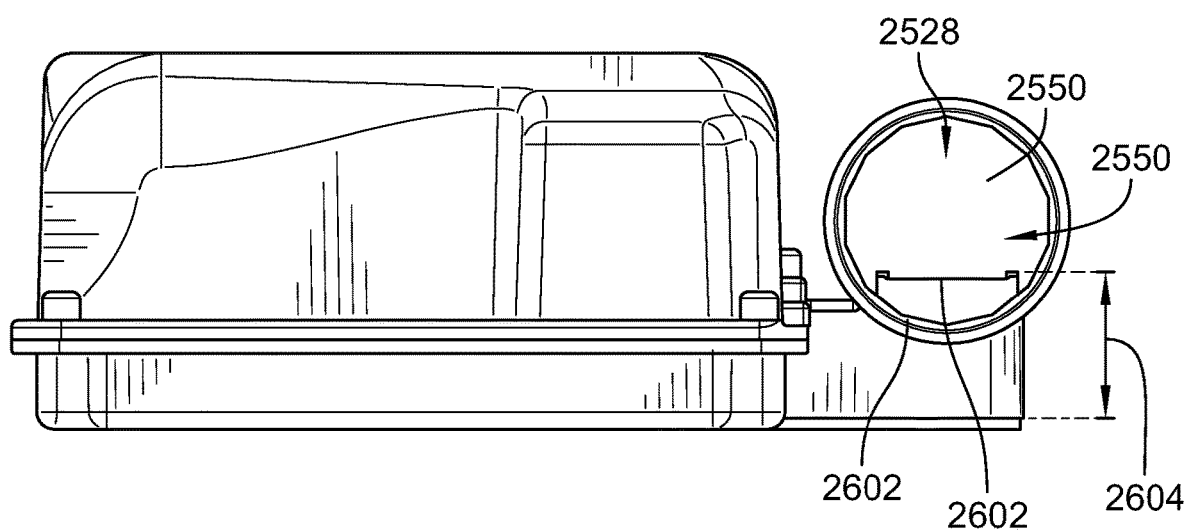
FIG. 76 is a side elevation view of the blower assembly housing.

As illustrated in FIG. 76, each inlet 2528 includes an opening 2550 that extends into a passageway 2560. A ridge 2600 is formed across a bottom 2602 of the inlet 2528. The ridge 2600 extends across a portion of the opening 2550 so that the ridge 2600 covers that portion of the opening 2550. The ridge 2600 is configured to facilitate preventing the ingress of fluids into the passageway 2560. That is, while air may pass over the ridge 2600 and into the passageway 2560, liquids are blocked from entering the passageway 2560 by the ridge 2600. A height 2604 of the ridge 2600 is selected based on an air flow criteria for the blower assembly 2424.

In operation, the blower assembly 2424 draws air from the sides of the patient support apparatus 2400, as shown in FIG. 70. The air enters the inlets 2528 and passes into the vacuum chamber 2524. The blower 2570 is operated to draw the air from the vacuum chamber 2524 and discharged the air into the pressurized chamber 2592 at a predetermined pressure. The pressurized air exits the pressurized chamber 2592 through the exhaust 2596. From the exhaust 2596, the air travels through a plenum or hose into the manifold three dimensional spacer 2452. The pressurized air in the manifold three dimensional spacer 2452 passes through the apertures 2478 and the apertures 2492 and into the patient three dimensional spacer 2452 at the patient's sacrum and pelvis 2484. The pressurized air then flows through the patient three dimension spacer 2452 to the apertures 2498 formed in the head end 2496. The pressurized air exits the patient support apparatus 2400 through the apertures 2498.

Figure 77:
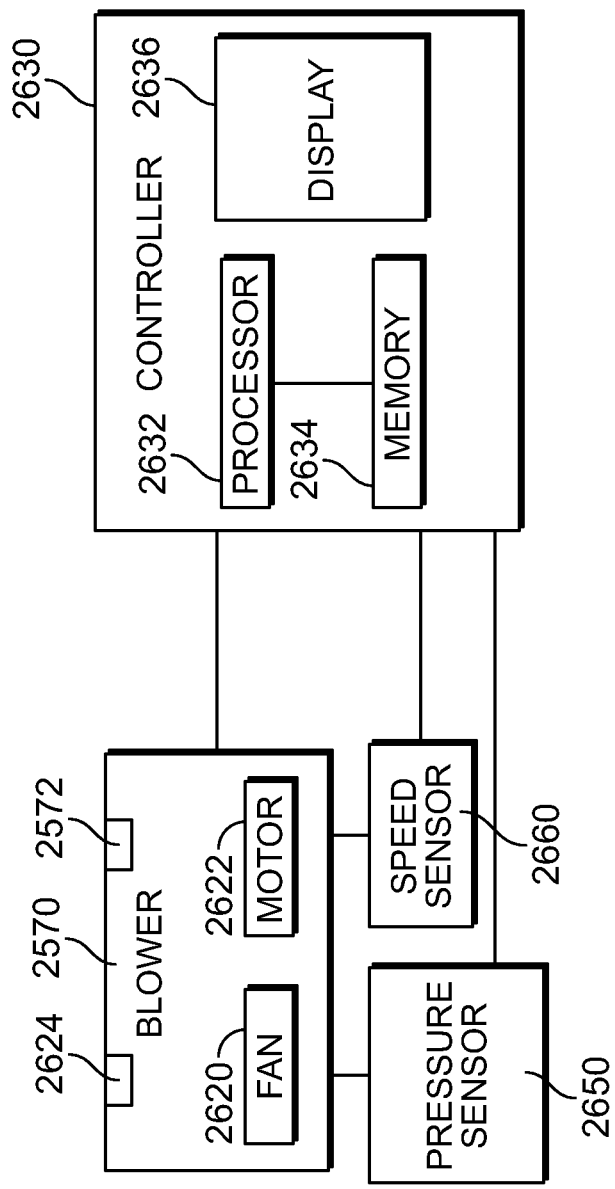
FIG. 77 is a schematic view of the blower assembly coupled to a control system.

As illustrated in FIG. 77, the blower 2570 of the blower assembly 2424 includes fan 2620 that is driven by a motor 2622 to draw air into an inlet 2624 and discharge pressurized air through the outlet 2572. A controller 2630 includes a processor 2632 and a memory 2634 electronically coupled to the processor 2632. The memory includes instructions that are carried out by the processor 2632 to control the motor 2622. For example, the blower 2570 may be configured to operate such that the discharged air has a predetermined pressure. The processor 2632 carries out instructions to rotate the fan 2620 at an optimal speed for maintaining the predetermined pressure. In some embodiments, the predetermined pressure may be a predetermined pressure range. A display 2636 may be configured to display the operating speed and discharge pressure of the blower 2570. The display 2636 may be a touch screen display or include other user inputs. Accordingly, the display or other user inputs may be operable to set the predetermine discharge pressure, as well as, other parameters of the blower assembly 2424.

A pressure sensor 2650 is provide to monitor the discharge pressure at the outlet 2572. In some embodiments, the pressure sensor 2650 may be configured to detect the discharge pressure at the exhaust 2596 of the blower assembly 2424. If the pressure sensor 2650 detects that the discharge pressure is outside of the predetermined pressure range or that a predetermined pressure is not being maintained, the controller 2630 may alter a speed of the motor 2622 to help maintain the predetermine pressure or pressure range.

Figure 78:
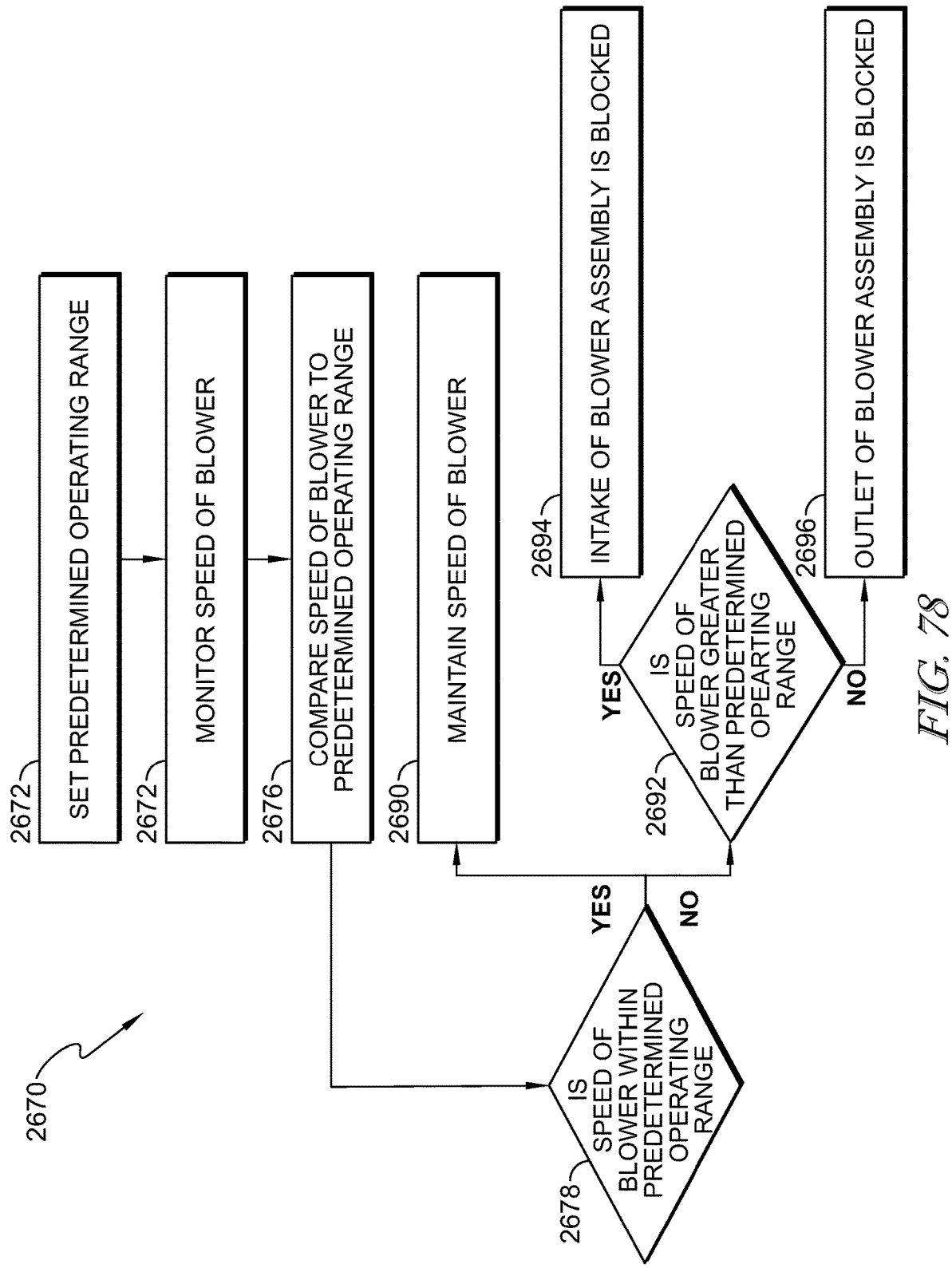
FIG. 78 is a flowchart for a method of detecting blockages in the blower assembly.

A speed sensor 2660 may also be provided to monitor the speed of the motor 2622. By monitoring the motor speed, the controller 2630 may be operable to detect blockages in the blower assembly 2424. Referring to FIG. 78, a method 2670 is illustrated for determining blockages in the blower assembly 2424. At block 2672, a predetermined operating range is set for the blower assembly 2424. The predetermined operating range may include a predetermined discharge pressure and/or a predetermined speed of the motor 2622. At block 2674, a speed of the motor 2622 is monitored by the speed sensor 2660. The speed of the motor 2622 is then compared to the predetermined speed range, at step 2676.

The controller 2630 determines whether the motor 2622 is operating within the predetermined range, at block 2678. If the motor 2622 is operating within the predetermined operating range, the motor 2622 continues to operate within the predetermined parameters, at block 2690. If the motor 2622 is not operating within the predetermined range, the controller 2630 determines whether the motor 2622 is operating at a speed greater than the predetermined operating range, at block 2692. If the motor 2622 is operating at a speed greater than the predetermined operating speed, the controller determines that an inlet 2624 of the blower 2570 is blocked, at block 2694. In some embodiments, a greater operating speed may be indicative of the inlets 2528 of the blower assembly 2424 being blocked. In some embodiments, both the inlets 2528 and the inlet 2624 may be blocked. If the controller 2630 determines that the motor 2622 is not operating at a speed greater than the predetermined operating range, the motor 2622 must be operating at a speed less than the predetermined operating range. At block 2696, the controller 2630 determines that the outlet 2572 of the blower 2570 is blocked. In some embodiments, a lower operating speed may be indicative of the exhaust 2596 of the blower assembly 2424 being blocked. In some embodiments, both the outlet 2572 and the exhaust 2596 may be blocked.

Figure 79:
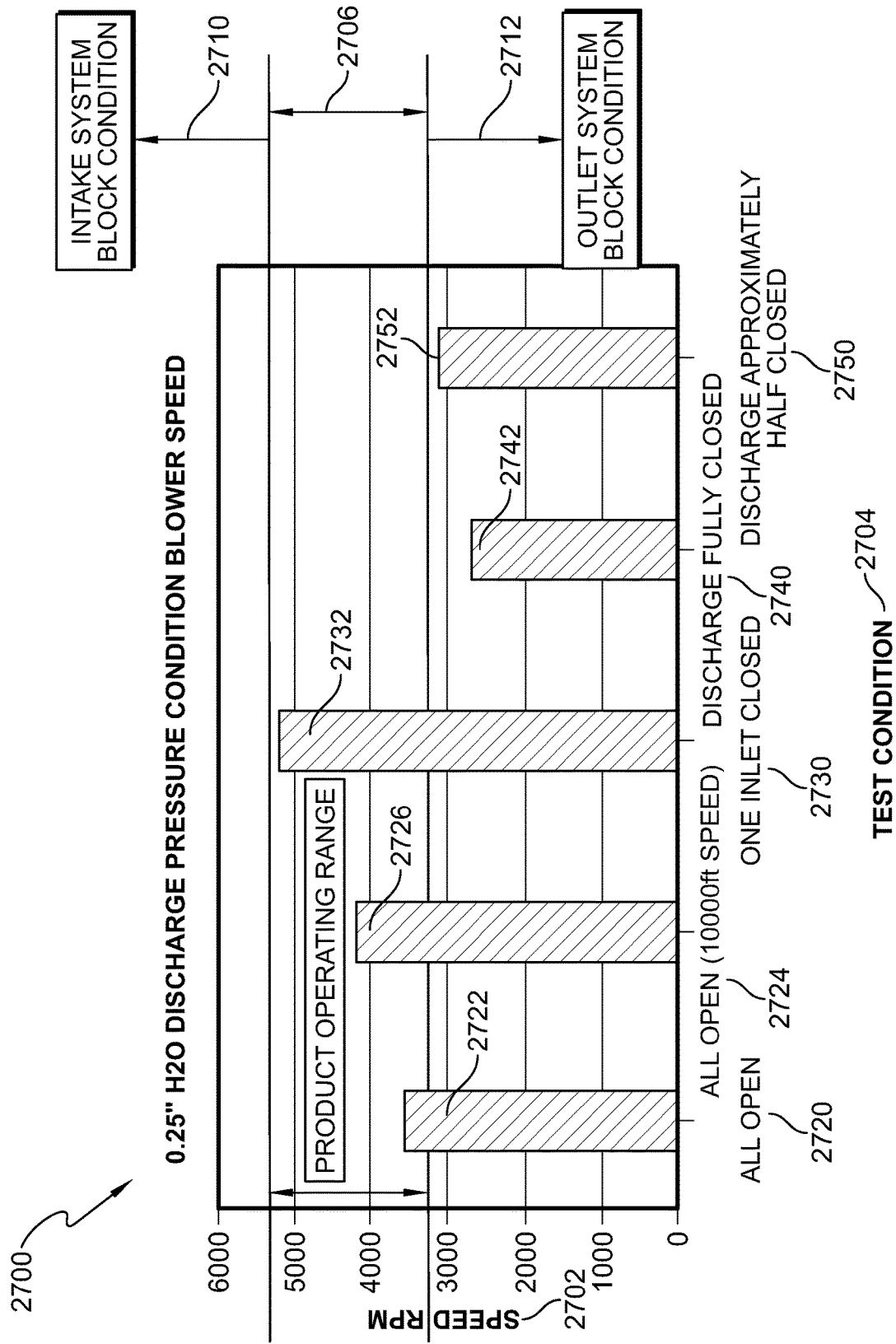
FIG. 79 is a graph illustrating a speed of the blower during various conditions.

Referring now to FIG. 79, a graph 2700 illustrates a fan operating speed 2702 in revolutions per minute (RPM) in view of various operating conditions 2704. An operating range 2706 of the blower assembly 2424 is between approximately 3100 RPM and approximately 5100 RPM, in the illustrated embodiment. An operating speed greater than approximately 5100 RPM is indicative of an intake system block condition 2710. An operating speed less than approximately 3100 RPM is indicative if an exhaust system block condition 2712.

In a condition 2720 wherein all inlets and outlets are open, the fan operates within the operating range 2706 at a speed 2722 of approximately 3500 RPM. In a condition 2724 wherein all inlets and outlets are open and the fan is operating at approximately 10,000 foot speed, the fan operates within the operating range 2706 at a speed 2726 of approximately 4100 RPM. In a condition 2730 wherein one inlet is closed, the fan operates at an intake system block condition 2710 at a speed 2732 of approximately 5100 RPM. In a condition 2740 wherein the outlet is fully closed, the fan operates at the exhaust system block condition 2712 at a speed 2742 of approximately 2800 RPM. In a condition 2750 wherein the outlet is partially closed, the fan operates in the exhaust system block condition 2712 at a speed 2752 of approximately 3100 RPM. Accordingly, by monitoring a speed of the blower assembly 2424, an operating condition of the blower assembly 2424 may be determined.

Figure 80:
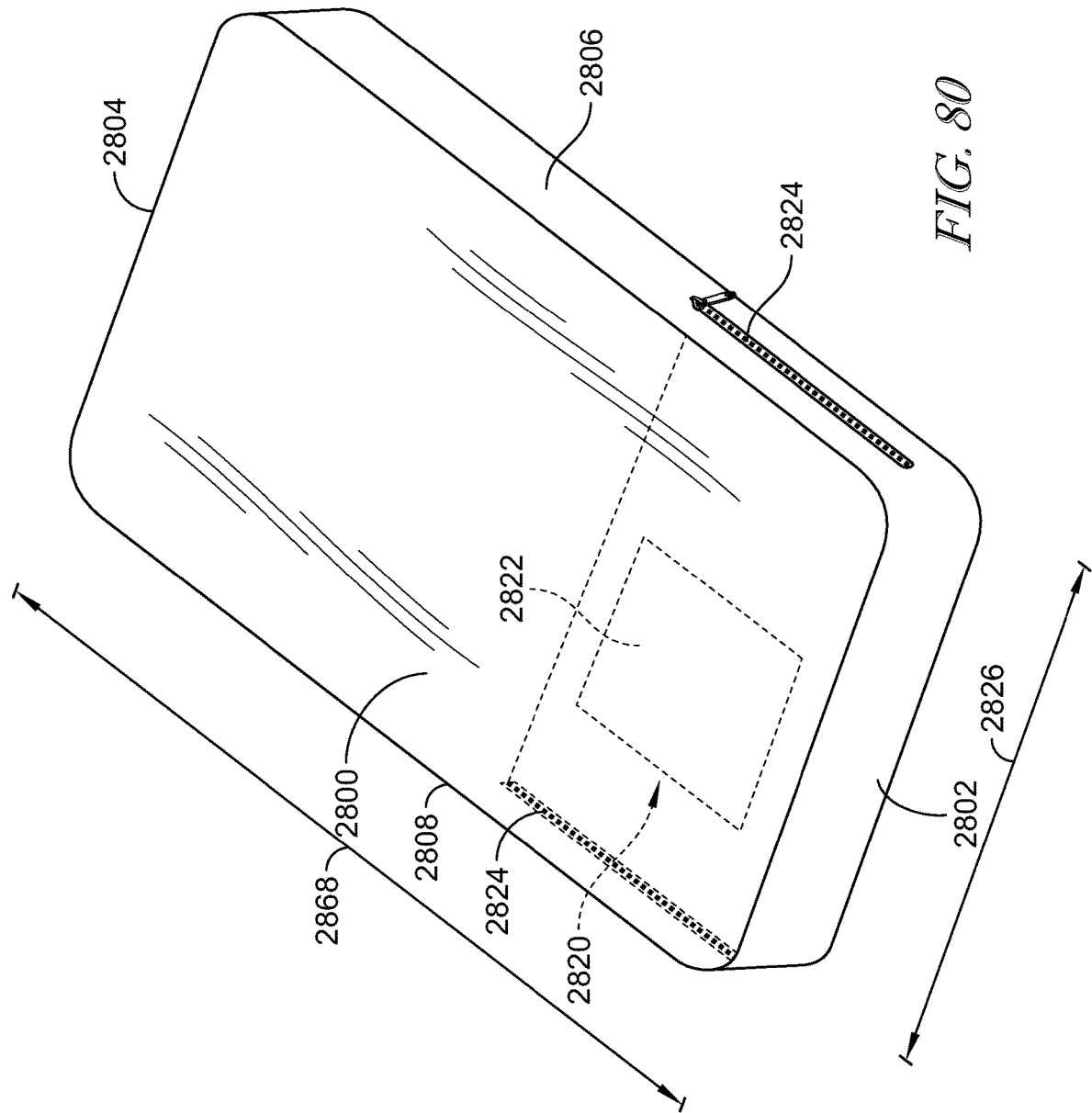
FIG. 80 is a top perspective view of a patient support surface having an x-ray sleeve extending along a first side and a second side of the support surface.

Referring to FIG. 80, a support surface 2800 includes a head end 2802, an opposite foot end 2804, a right side 2806, and a left side 2808. An x-ray cassette sleeve 2820 is positioned within the support surface 2800 and configured to retain an x-ray cassette 2822. The sleeve 2820 is sealed with a pair of zippers 2824. In some embodiments, a fastening mechanism other than zippers 2824 may be utilized, e.g. hook and loop fasteners, etc. Each zipper 2824 extends partially along a length 2828 of the right side 2806 and partially along the length 2828 of the left side 2808, respectively. In the illustrative embodiment, the zippers 2824 do not extend along the head end 2802 or the foot end 2804 of the support surface 2800.

Figure 81:
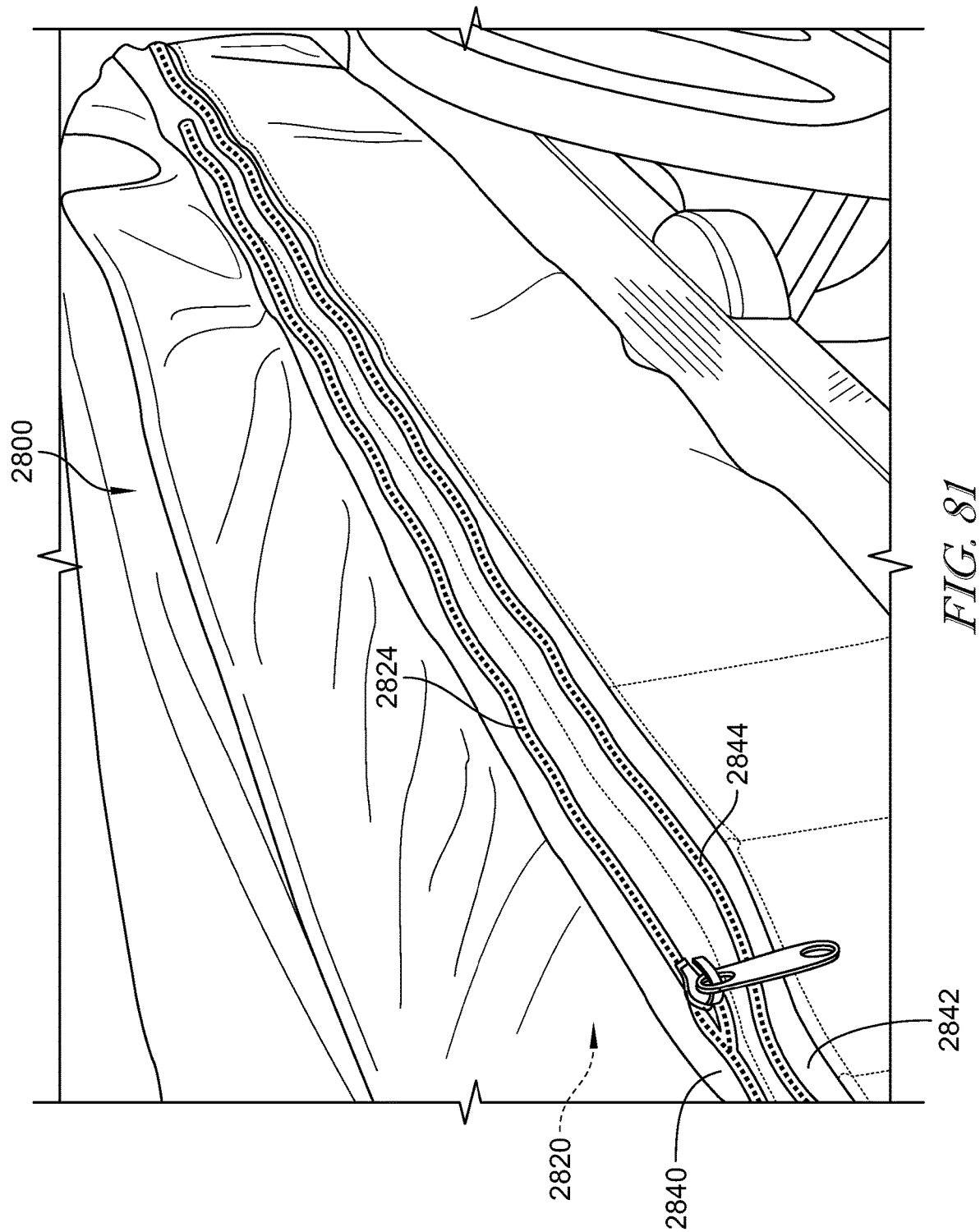
FIG. 81 is a perspective view of a portion of the x-ray sleeve shown in FIG. 80 and illustrating a zipper that fluidly seals the x-ray sleeve to prevent bodily fluids from entering the x-ray sleeve.

As illustrated in FIG. 81, the support surface 2800 includes an upper ticking 2840 that is sealed to a lower ticking 2842 with a zipper 2844. The zipper 2844 may be actuated to separate the upper ticking 2840 from the lower ticking 2842 to expose an inside of the support surface 2800, for example, bladders and other components described herein. Each zipper 2824 is positioned between the upper ticking 2840 and the zipper 2844. In some embodiments, the both zippers 2824 have a different color than the zipper 2844 to distinguish the sleeve 2820 from the ticking connection. In some embodiments, each zipper 2824 and the zipper 2844 may have different sizes to distinguish the zippers 2824, 2844.

Figure 83:
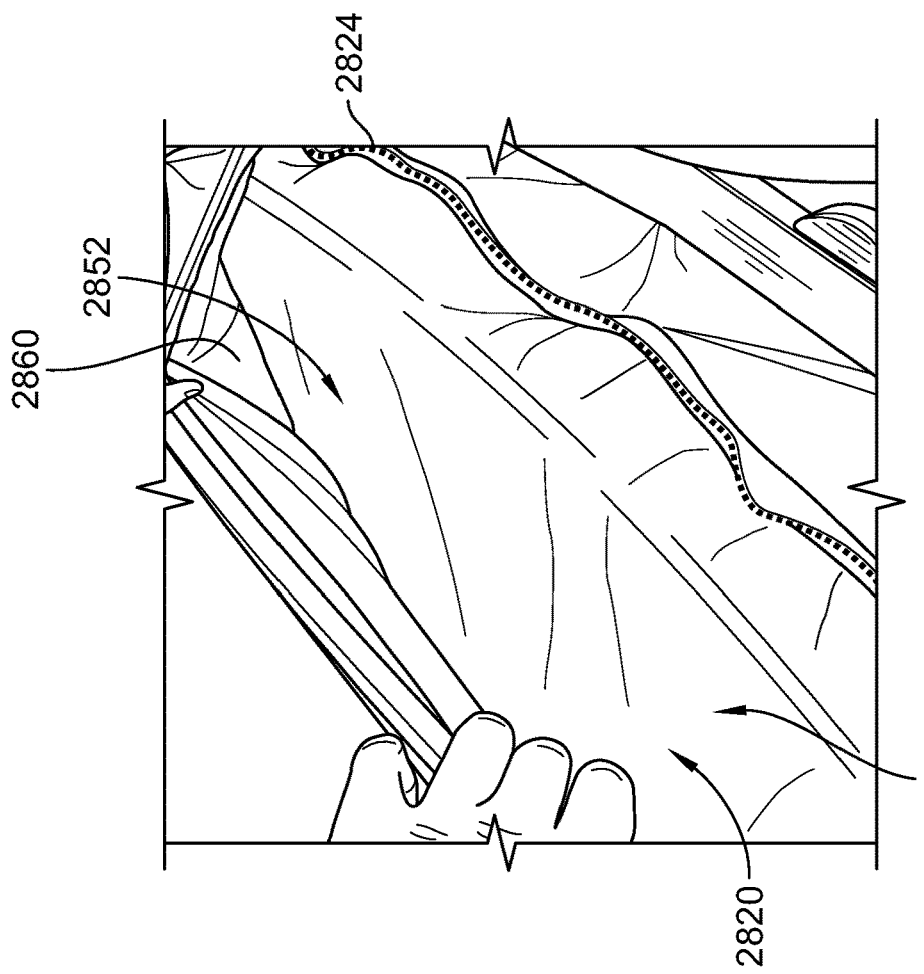
FIG. 83 is a perspective view of a portion of the x-ray sleeve shown in FIG. 80 and illustrating a cavity that is configured to receive an x-ray cassette therein, wherein the x-ray cassette may be positioned under the chest, abdomen, or hips of a patient on the support surface.
Figure 82:
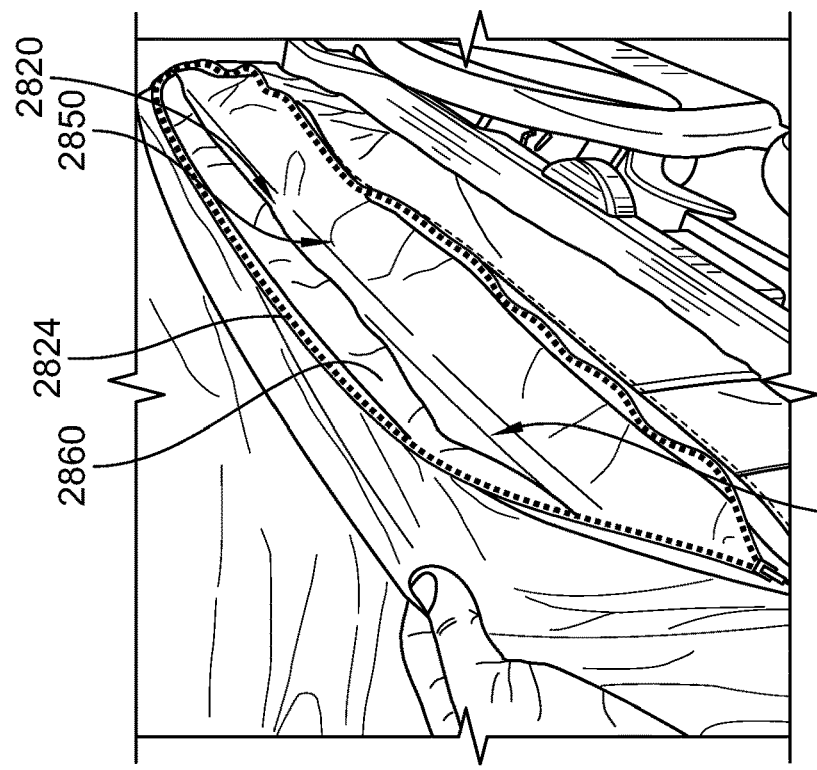
FIG. 82 is perspective view of a portion of the x-ray sleeve shown in FIG. 80 and illustrating the lining of the x-ray sleeve.

FIGS. 82 and 83 illustrate the sleeve 2820 in an open configuration that enables insertion and removal of the cassette 2822. The sleeve 2820 includes an opening 2850 on both the right side 2806 and the left side 2808 that is sealed by a respective zipper 2824. A cavity 2852 extends into the support surface 2800 between the openings 2850. The cavity 2852 is configured to receive the cassette 2822. Each opening 2850 extends partially along one of the sides 2806 and 2808 of the support surface 2800 to provide access to the sleeve 2820 by a caregiver. In some embodiments, the caregiver may insert and remove the cassette 2822 from the sleeve 2820 while a patient is positioned on the support surface 2800.

The sleeve 2820 includes an inner liner 2860 that is bonded or welded to a rip stop material 2862 of each zipper 2824 to seal the sleeve 2820. In some embodiments, the liner 2860 is welded with ultrasonic welding or radio-frequency welding. The liner 2860 is formed from a water resistant material, e.g. thermoplastic. When the zippers 2824 are closed, the sleeve 2820 is fluidly sealed to prevent fluid such as bodily fluids from entering the sleeve 2820. Accordingly, the sleeve 2820 prevents exposure of the cassette 2822 to fluids which may damage the cassette.

The sleeve 2820 is able to open on both sides 2806 and 2808 to allow for wiping down the sleeve 2820 without having to remove the support surface 2800 from service. Caregivers can access the sleeve 2820 from either the right side 2806 or the left side 2808. Additionally, the sleeve 2820 is larger than conventional sleeves allowing coverage from the head to the seat/hip of the patient allowing for chest, abdominal, and hip x-rays. In some embodiments, the sleeve 2820 may extend all the way to the foot end 2804 of the support surface 2800. Because the sleeve 2820 is placed above a core of the support surface 2800, the sleeve 2820 does not interfere with a microclimate system that may be incorporated into the support surface 2800. The two separate compartments (the sleeve 2820 and the core) of the support surface 2800 enable each compartment to accept a fully enclosed fire sock, thereby enabling the support surface 2800 to pass a flame test. The sleeve 2820 can be installed in a support surface 2800 with or without a topper.

Referring to FIG. 84, an x-ray cassette sleeve 2900 includes a pocket 2902 that is formed from fabric. The fabric may be coated with a plastic coating, for example polyurethane. The pocket 2902 includes open ends 2904, as shown in FIG. 85. A cavity extends between the open ends 2904. Each of a pair of end panels 2906 is coupled to an end 2904 of the pocket 2902. In some embodiments, the panels 2906 are welded to the pocket 2902, for example through radio-frequency welding. The panels 2906 include openings 2908 that extend through the panel 2906. When the panels 2906 are welded to the pocket 2902, as shown in FIG. 86, the openings 2908 in the panel 2906 are aligned with the open ends 2904 of the pocket 2902. As shown in FIG. 85, an upper coupling member 2920 and a lower coupling member 2922 include a pocket flange 2924 and a panel flange 2926. The pocket flanges 2924 are welded to the pocket 2902 at the ends 2904. The panel flanges 2926 are welded to the end panels 2906 so that the open end 2904 of the pocket 2902 is aligned with the opening 2908 of the panel 2906, as shown in FIG. 87. A zipper 2928 is welded to each of the upper coupling member 2920 and the lower coupling member 2922. The weld seals the coupling members 2920 and 2922 the zipper 2928 so that fluids cannot flow into the pocket 2902. FIG. 89 illustrates tabs 2930 of each coupling member 2920, 2922 welded together over an end 2932 of the zipper 2928. The welded tabs 2930 seal the ends 2932 of the zipper 2928. As shown in FIG. 88, the zipper 2928 is welded to the panels 2906 and closes the opening 2908. When in a zipped condition, unzipping the zipper 2928 opens the respective opening 2908 to permit insertion of an x-ray cassette into pocket 2902.

Figure 90:
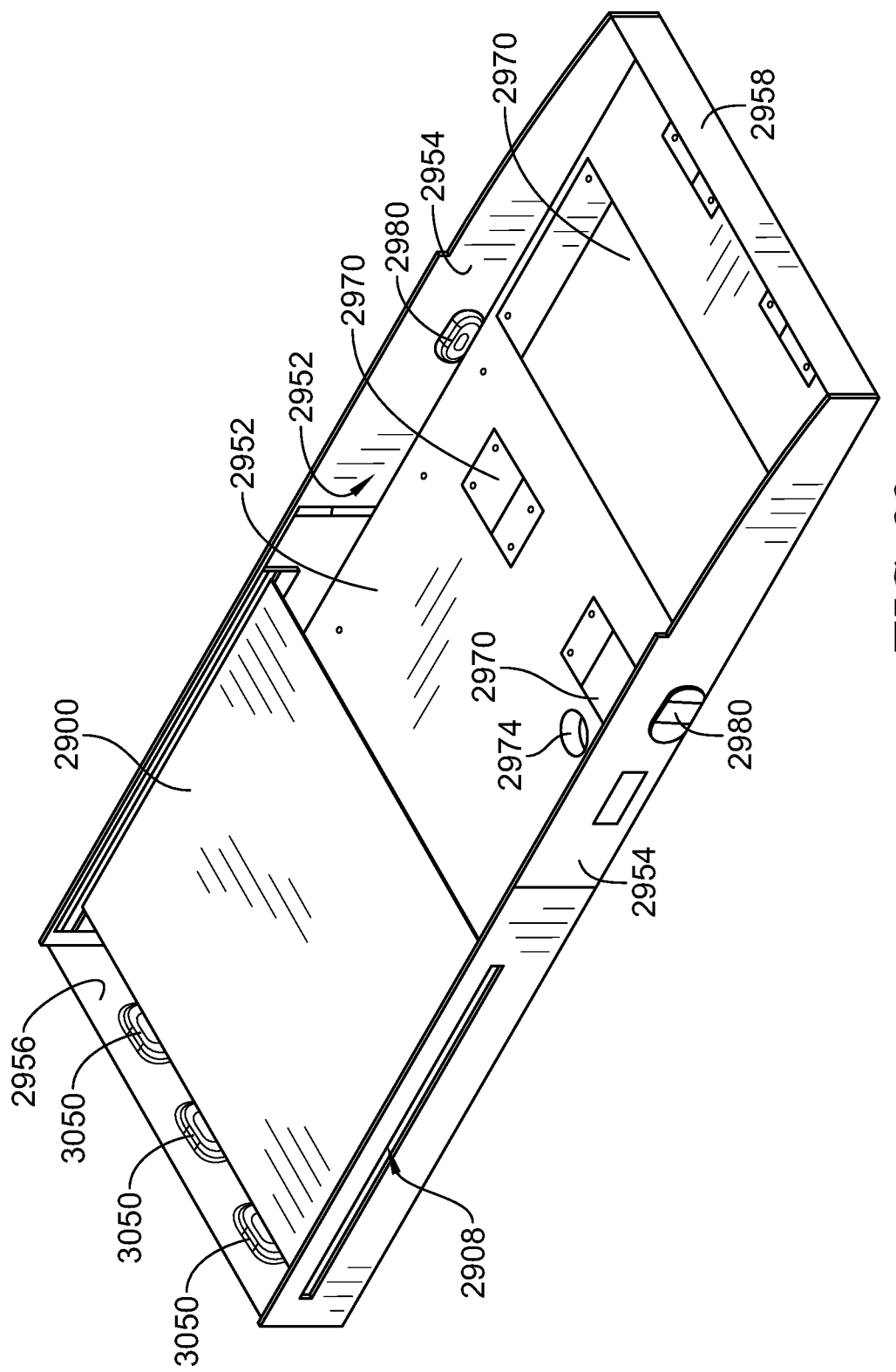
FIG. 90 is a top perspective view of the x-ray sleeve shown in FIG. 84 welded into a bottom cover of a mattress.

Referring to FIG. 90, the sleeve 2900 is welded to a bottom cover 2950 of a mattress. The bottom cover 2950 includes a bottom panel 2952, a pair of side panels 2954, a head end panel 2956, and a foot end panel 2958. The bottom panel 2952 extends between the side panels 2954 and between the head end panel 2956 and the foot end panel 2958. The sleeve 2900 is welded to the side panels 2954 adjacent the head end panel 2956. Each of the end panels 2906 of the sleeve 2900 is welded to a side panel 2954 of the cover 2950. The sleeve 2900 is welded to the cover 2950 so that the openings 2908 of the sleeve 2900 are accessible from the side panels 2954 of the cover 2950. The welding and the zippers 2928 are substantially fluid-proof to inhibit fluid on the mattress from entering the pocket 2902.

The bottom panel 2952 includes pockets 2970 that are configured to retain components of the mattress. For example, the pockets 2970 may be configured to retain foam blocks (not shown). The pockets 2970 are formed from a fabric material that is welded to the bottom panel 2952. The fabric material is welded on three sides so that an opening is formed on the fourth side. The opening provides access to the pocket 2970 to insert components of the mattress. The bottom panel 2952 also includes an opening 2974 that is sized to receive a power cord (described in detail below). As described below, the power cord extends from a blower in the mattress to outside the mattress so that the blower may receive power from an outlet.

The side panels 2954 include inlets 2980. The inlets 2980 are configured to permit air to be drawn into the mattress by a blower assembly. As illustrated in FIG. 97, each inlet 2980 includes a body 3000 having a sidewall 3002 that defines a cavity 3004. The sidewall 3002 includes an outer flange 3006 that is welded to the side panel 2954 of the cover 2950 to prevent fluid ingress into the mattress. A cover 3008 extends over a portion of an opening 3010 of the cavity 3004. The opening 3010 has an axis 3012. FIG. 98 illustrates a back side 3020 of the body 3000 having an opening 3022. The opening 3022 extends from the back side 3020 to the cavity 3004. The cover 3008 partially blocks the opening 3022 to inhibit fluid from flowing into the opening 3022. During operation of the blower assembly, air flows around the cover 3008 and into the opening 3022.

A plug 3030, shown in FIG. 99, is configured to be inserted into the opening 3022. The plug 3030 includes a medial flange 3032 and an inlet connector 3034 extending from the medial flange 3032. The plug 3030 has a passageway 3044 having an axis 3046 that is co-axial to the axis 3012 of the opening 3010. The inlet connector 3034 is inserted into the opening 3022 so that a lip 3036 of the inlet connector 3034 engages and locks to an opening flange 3038 formed around the opening 3022, as illustrated in FIG. 100. The opening flange 3038 extends into the cavity 3004 causing the medial flange 3032 of the plug 3030 to rest against the back side 3020 of the body 3000, as illustrated in FIG. 101. A blower connector 3040 extends from the medial flange 3032 in a direction opposite the inlet connector 3034. The blower connector 3040 is configured to couple to an inlet of the blower via tubing or other suitable conduit, as discussed below. The blower connector 3040 includes a lip 3042 to secure the blower connector 3040 to the tubing leading to the inlet of the blower assembly. During operation, air flows around the cover 3008 and through the plug 3030 and opening 3022 to the inlet of the blower. The cover 3008 and the opening flange 3038 cooperate to inhibit fluid ingress into the blower.

Figure 93:
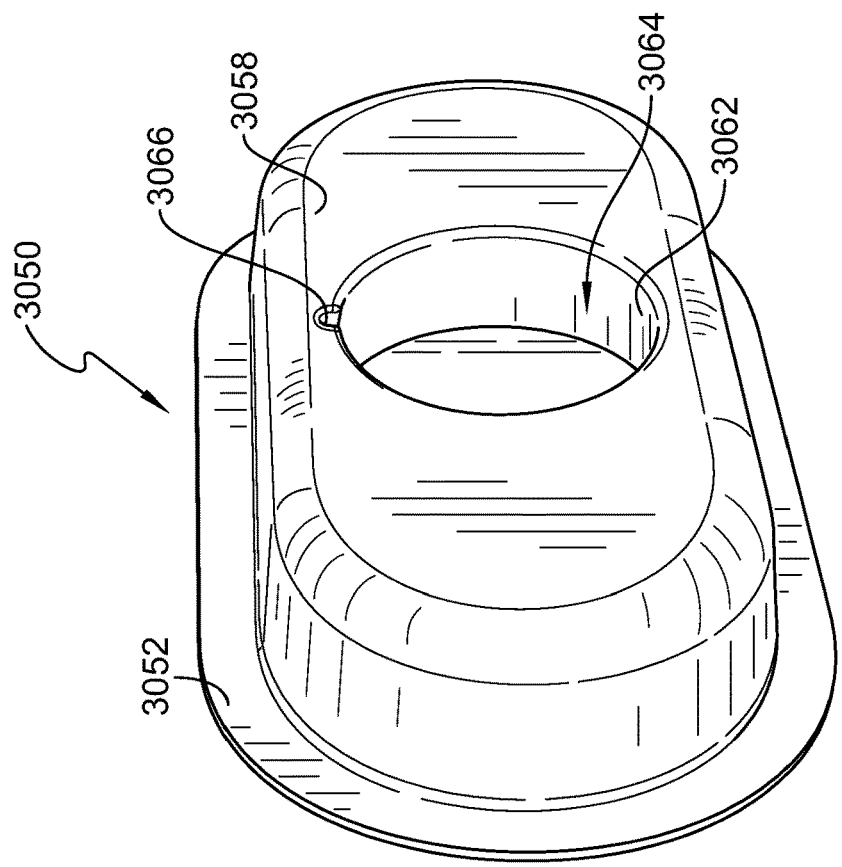
FIG. 93 is a rear perspective view of the outlet having an opening.
Figure 92:
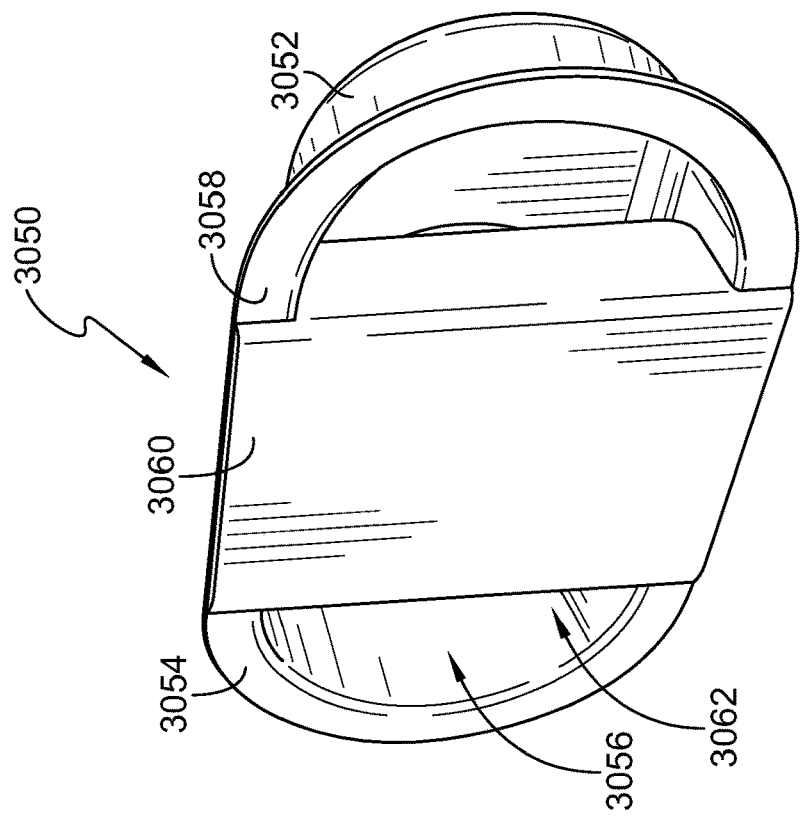
FIG. 92 is a front perspective view of an outlet of a blower assembly having a cover positioned on a front face of the outlet.

The head end panel 2956 includes outlets 3050, as shown in FIG. 90. The outlets 3050 are configured to discharge air from the mattress. As illustrated in FIG. 92, each outlet 3050 includes a body 3052 having a sidewall 3054 that defines a cavity 3056. The sidewall 3054 includes an outer flange 3058 that is welded to the head end panel 2956 of the cover 2950 to prevent fluid ingress into the mattress. A cover 3060 extends over a portion of an opening 3062 of the cavity 3056. The opening 3062 has an axis 3068. FIG. 93 illustrates a back side 3058 of the body 3052 having an opening 3062. The opening 3062 extends from the back side 3058 to the cavity 3056. The cover 3060 partially blocks the opening 3062 to inhibit fluid from flowing into the opening 3062. A sidewall 3064 defining the opening 3062 includes a notch 3066.

Figure 95:
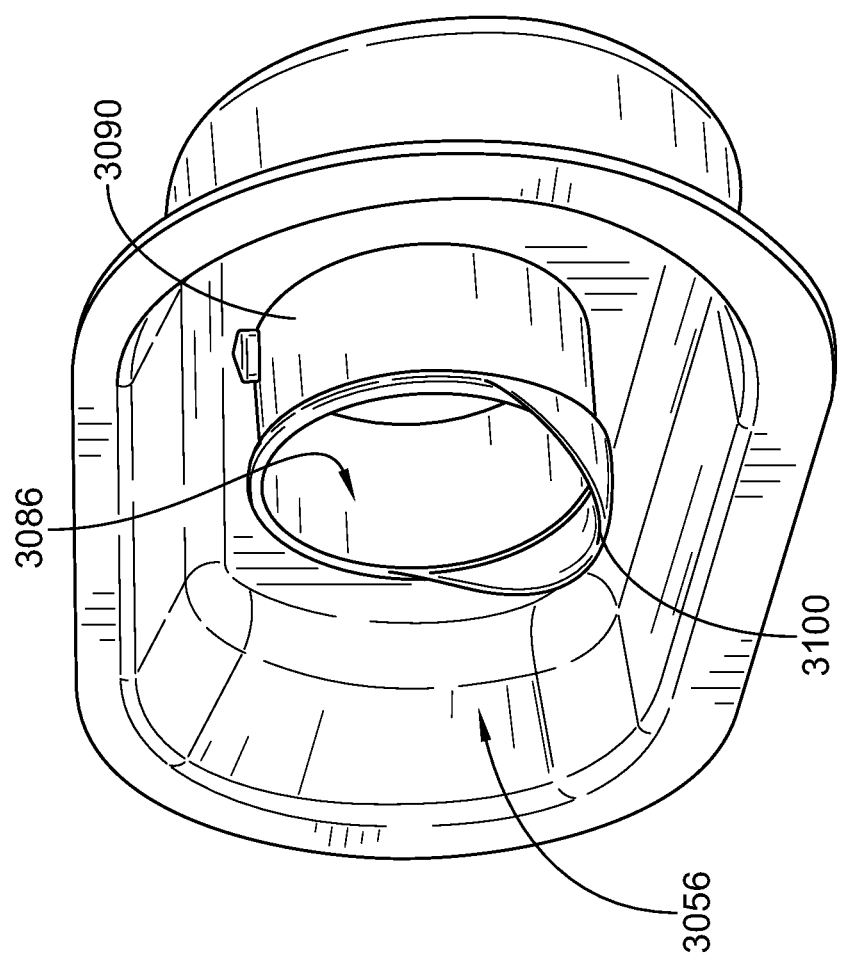
FIG. 95 is a front perspective view of the plug positioned within the opening formed in the outlet.
Figure 94:
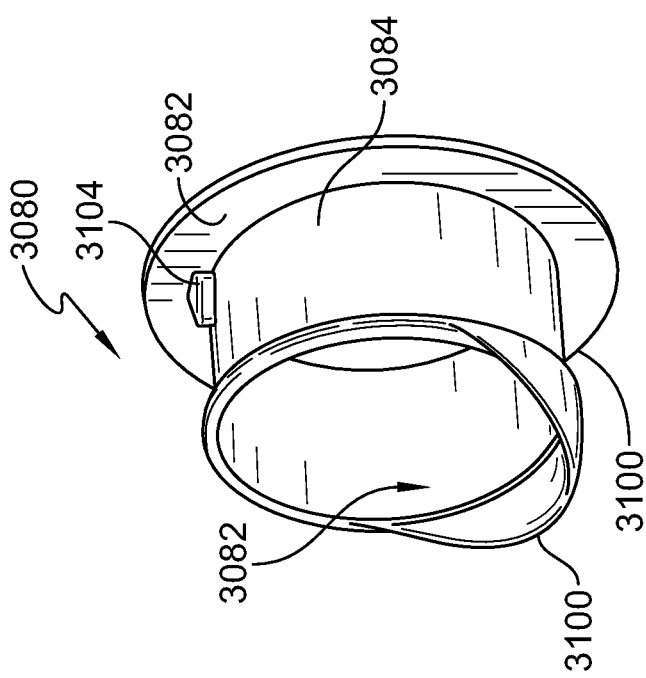
FIG. 94 is a front perspective view of a plug that is configured to be inserted into the opening formed in the outlet.

A plug 3080, shown in FIG. 94, is configured to be inserted into the opening 3062. The plug 3080 includes a flange 3082 and an outlet connector 3084 extending from the flange 3082. The plug 3080 has a passageway 3092 having an axis 3094 that co-axial to the axis 3068 of the opening 3062. The outlet connector 3084 is inserted into the opening 3062 so that a flange 3086 of the outlet connector 3084 engages and locks to an opening flange 3090 formed around the opening 3062, as illustrated in FIG. 95. The opening flange 3090 extends into the cavity 3056 causing the flange 3082 of the plug 3080 to rest against the back side 3058 of the body 3052, as illustrated in FIG. 96. Referring back to FIG. 94, a lip 3100 extends from a bottom end 3102 of the outlet connector 3084 and into the cavity 3056, as shown in FIG. 95. A tab 3104 is provided on the outlet connector 3084 and configured to engage the notch 3066 to prevent the lip 3100 from rotating.

During operation, air is discharged from the mattress through the opening 3062. The cover 3060, the opening flange 3090 and the lip 3100 inhibit fluid ingress into the outlet 3050. When the head end of the mattress is substantially horizontal, fluids are prevented from entering the outlet 3050 by the cover 3060 and the opening flange 3090. However, as the head end of the mattress is raised between a 0 degree and 65 degrees head tilt angle, fluids from the mattress may begin to accumulate in the cavity 3056 of the outlet 3050. The lip 3100 inhibits these fluids from flowing into the opening 3062. That is, the lip 3100 is sized so that fluids gathering in the cavity 3056 will flow out of the cavity along the head end of the mattress before flowing back into the mattress through the opening 3062.

Figure 91:
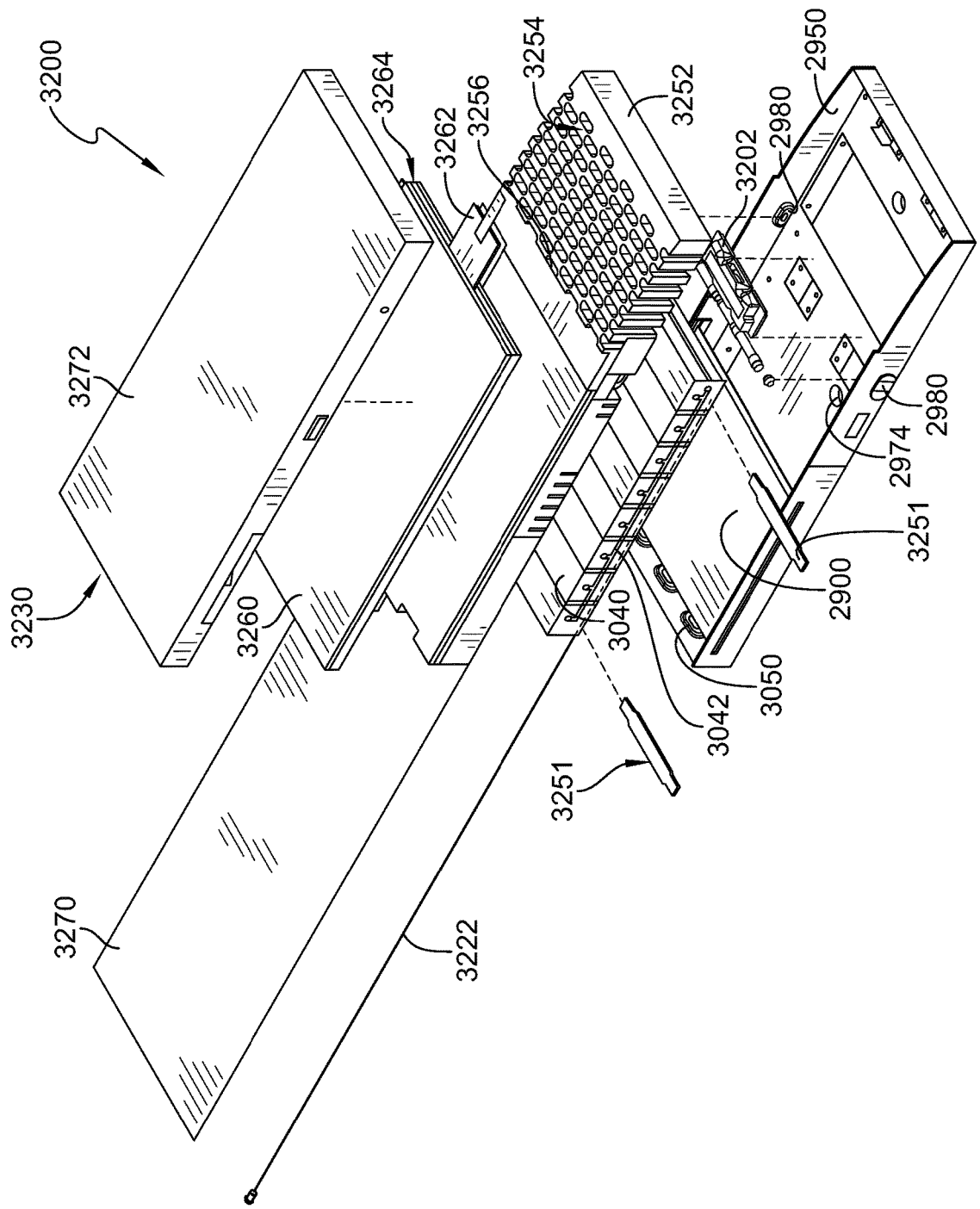
FIG. 91 is an exploded view of a mattress in accordance with an embodiment and having a blower assembly positioned therein.
Figure 102:
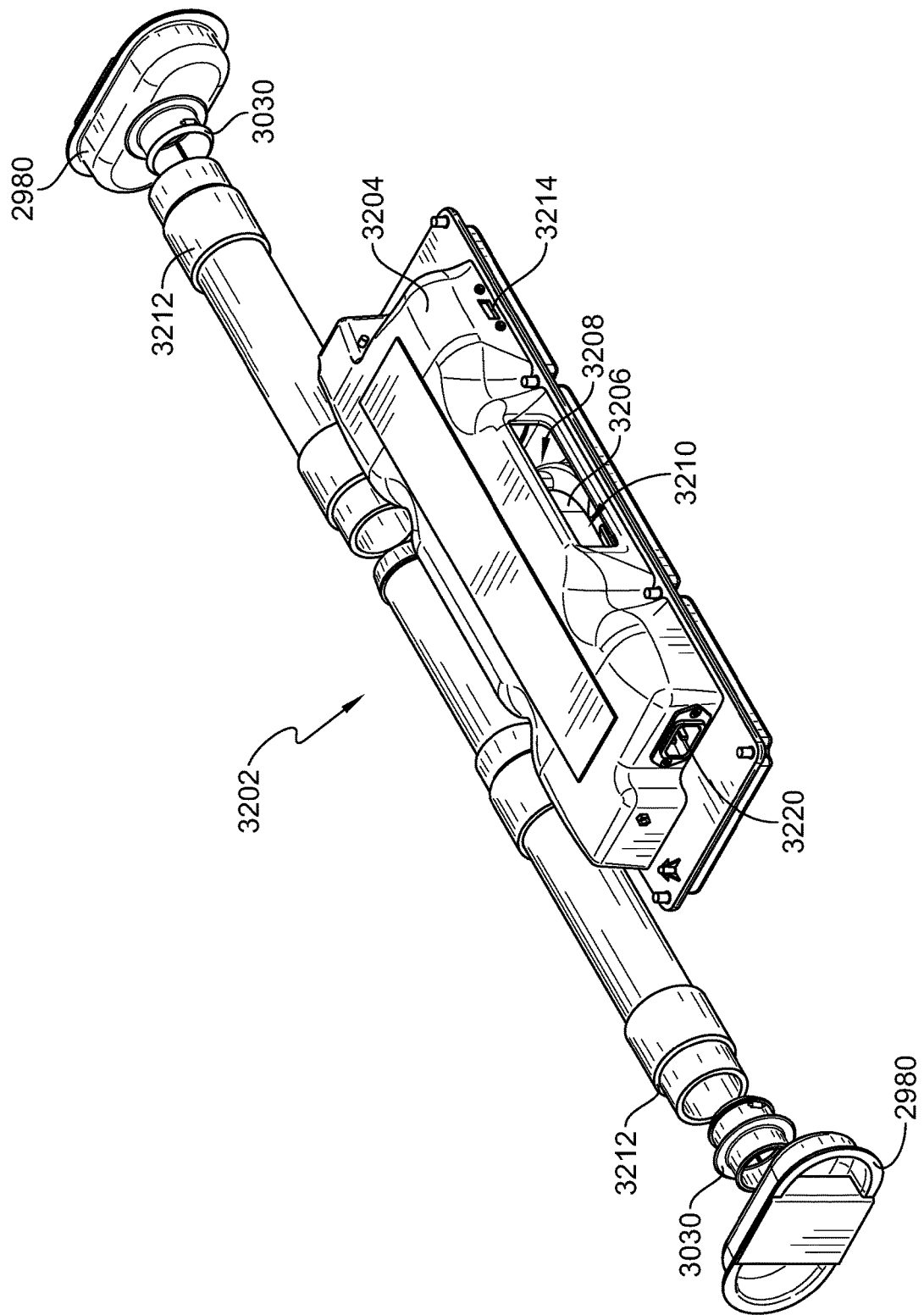
FIG. 102 is a top perspective view of a blower assembly in accordance with an embodiment.

Referring to FIG. 91, a mattress 3200 includes the bottom cover 2950 and the sleeve 2900 welded to the bottom cover 2950. A blower assembly 3202 is positioned within the mattress 3200. The blower assembly 3202 is illustrated in FIG. 102 and includes a housing 3204 that houses a fan (or blower) 3206 in a chamber 3208. A universal serial bus (USB) port 3214 is positioned within the housing 3204 to provide diagnostics access to the blower assembly 3202. The housing 3204 includes an outlet 3210 that is in fluid communication with the outlets 3050 positioned in the head end panel 2956 of the bottom cover 2950. A pair of tubes 3212 extend from the housing 3204 and are in fluid communication with the inlets 2980 formed in the side panels 2954 of the bottom cover 2950. A power outlet 3220 of the housing 3204 is configured to couple a power cord 3222, shown in FIG. 91. FIG. 91 illustrates the cord 3222 extending toward a head end 3230 of the mattress 3200; however, it should be appreciated that, as described below, the cord 3222 extends through the opening 2974 in the bottom panel 2952 of the bottom cover 2950. The opening 2974 is sealed around the cord 3222, as described below, to inhibit fluid ingress through the opening 2974.

Still referring to FIG. 91, foam filled bladders 3240 are positioned adjacent to the blower assembly 3202 and extend between the blower assembly 3202 and the head end panel 2956 of the bottom cover 2950. The bladders 3240 include inlet valves (not shown) that allow ambient air to flow into the bladders 3240. The ambient air passes through the bladders 3240 and exits through exit valves 3242. The bladders 3240 are arranged in a row and extend laterally between the side panels 2954 of the bottom cover 2950. A foam panel 3250 encases the bladders 3240 and the blower assembly 3202. A foot end 3252 of the foam panel 3250 includes apertures 3254 that enable the foot end 3252 of the foam panel 3250 to extend and retract as dictated by extension and retraction of a foot section of a bed frame (not shown). An opening 3256 extends through the foam panel 3250 and is aligned with the outlet 3210 of the blower assembly 3202.

A microclimate management (MCM) layer 3260 is positioned above the foam panel 3250 and zipped to the bottom cover 2950. The MCM layer 3260 is encased in a fire barrier sock. An inlet 3262 of the layer 3260 extends from a foot end 3264 of the layer 3260. The inlet 3262 is configured to be folded downward and extend through the opening 3256 in the foam panel 3250. The inlet 3262 is coupled to the outlet 3210 of the blower assembly 3202. In some embodiments, the inlet 3262 is secured around the outlet 3210 of the blower assembly 3202 with hook and loop fasteners, snaps, or the like.

A fire barrier sock 3270 encases the foam panel 3250 and the bladders 3240. The fire barrier sock 3270 is positioned over the sleeve 2900. The blower assembly 3202 is positioned outside of the sock 3270. A hole is cut in the sock to connect the microclimate management layer 3260 to the blower assembly 3202. The fire sock 3270 is secured to the foam panel 3250 with retaining flanges 3251 coupled to the foam panel 3250. Holes are cut in the sock 3270 to receive ends of the flanges 3251. A top cover 3272 is zipped to the bottom cover 2950 to seal the mattress 3200.

Figure 103:
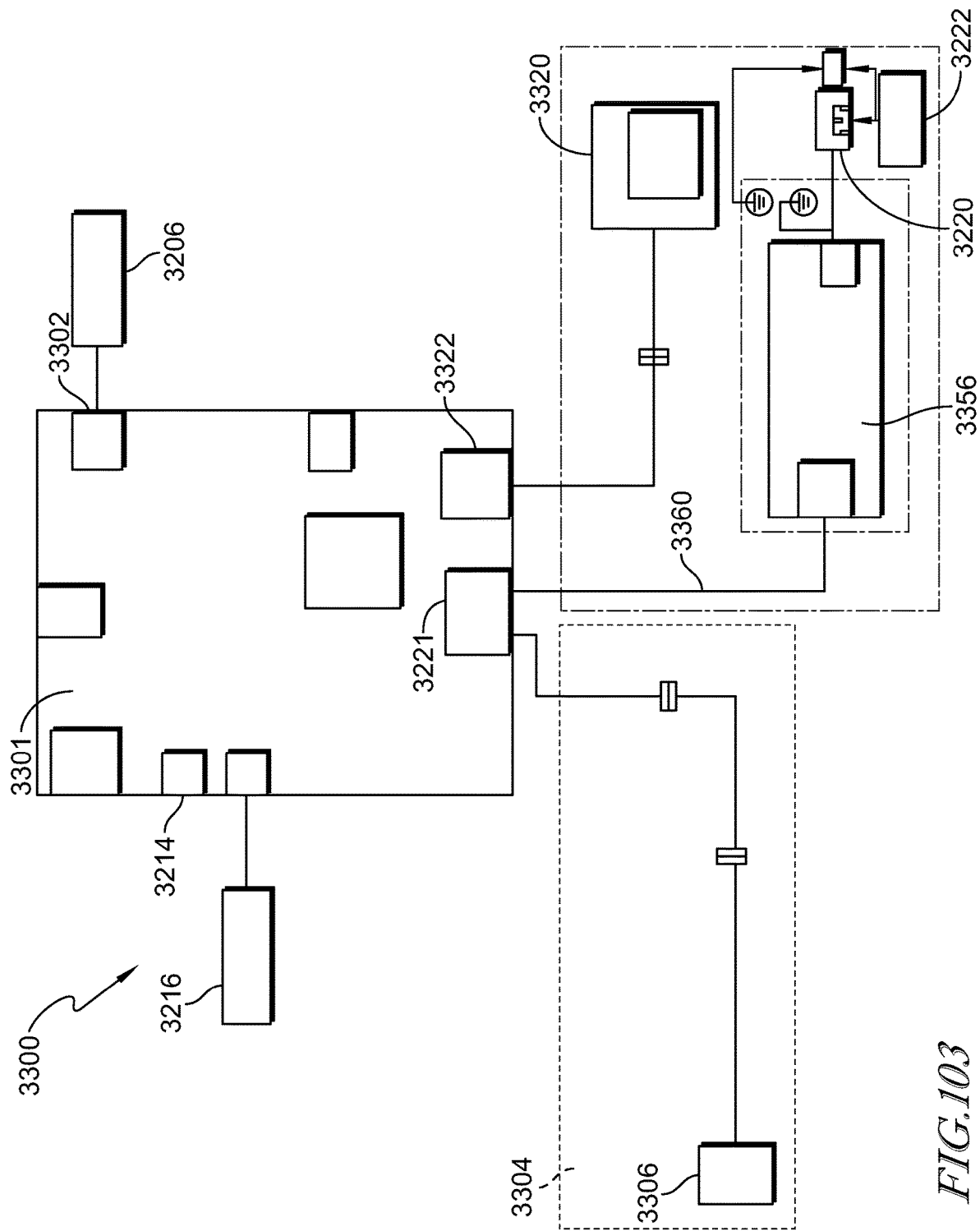
FIG. 103 is a schematic view of a control circuit for use in a mattress having a blower in accordance with an embodiment.

Now referring to FIG. 103, a control circuit 3300 is positioned within the housing 3204 of the blower assembly 3202. The control circuit 3300 includes a control board 3001 with the USB port 3214, which couples to a USB diagnostics device 3216 that receives diagnostics information regarding the blower assembly 3202 to power the blower 3206. Another port 3302 provides power and control signals to the blower assembly 3202. There are two options available for powering the control circuit 3300. First, the control circuit 3300 may be powered from a frame 3304 of a patient support apparatus (not shown). In such an embodiment, a power cable from the frame 3304 is plugged into the outlet 3221 of the housing 3204. The frame 3304 includes a power supply 3306, e.g. 28 volt power supply, from which power is supplied to board 3301 and to blower 3206.

In another embodiment, the control circuit 3300 is powered by an external power source, for example a wall outlet. In such an embodiment, a power cord 3222 is coupled to the wall outlet. The power cord 3222 is joined to an AC/DC power supply 3312, which is coupled to the outlet 3220 of the housing 3204. A ground wire lug 3314 extends from the outlet 3220. To provide a graphical user interface, a user interface device 3320 is coupled to an interface port 3322 of the control circuit 3300. The device 3320 may be coupled to a frame of the patient support apparatus in some embodiments.

Figure 104:
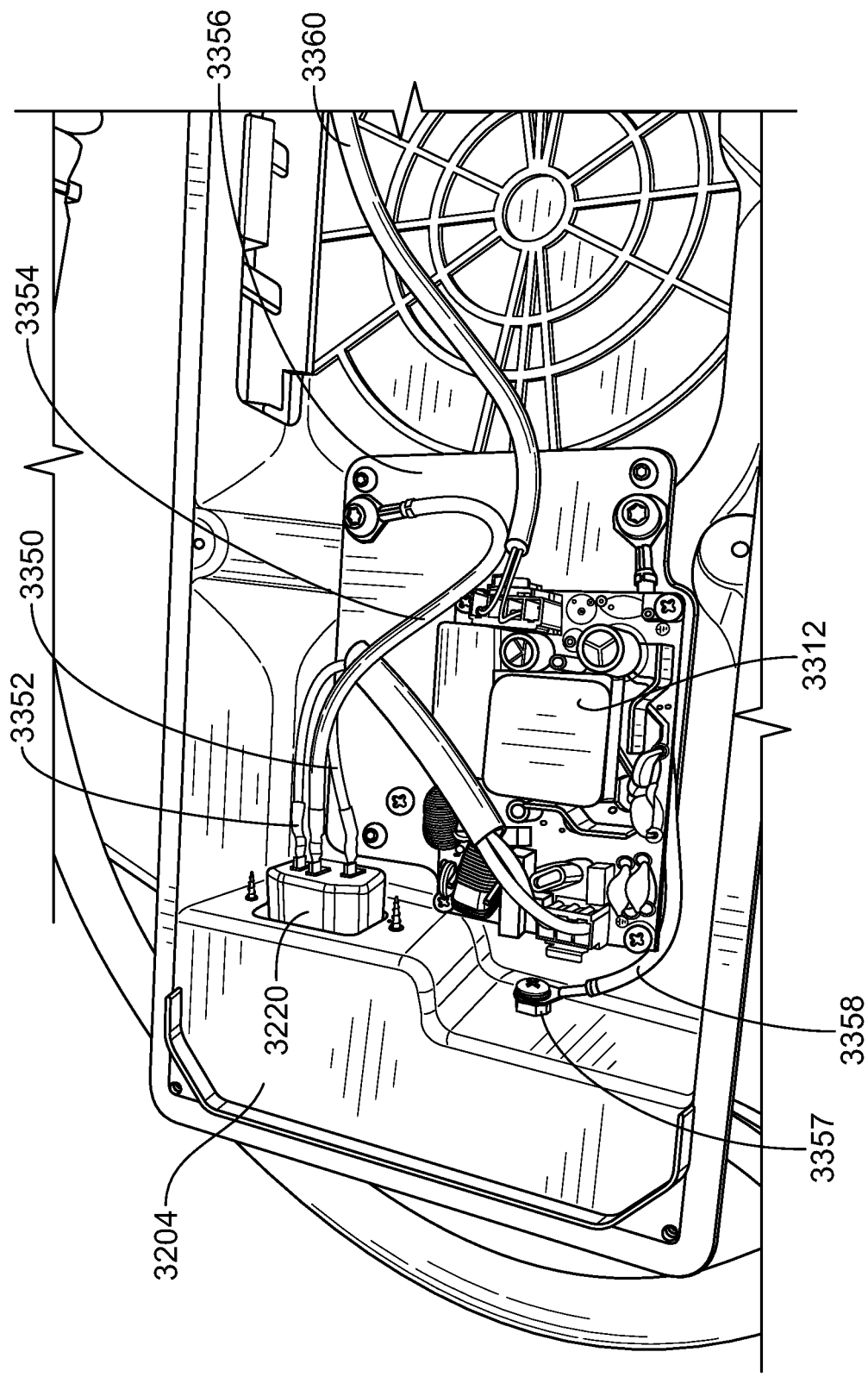
FIG. 104 is top perspective view of a portion of the control circuit installed in a housing of the blower.

As shown in FIG. 104, a positive terminal 3350 and a negative terminal 3352 extend from the outlet 3220 to the power supply 3212 to power the control board 3301. A ground wire 3354 extends from the outlet 3220 to a ground plate 3356. Another ground wire 3358 extends from the ground plate 3356 to a bolt 3357 that extends through the housing 3204. An electrical cable 3360 extends from power supply 3312 to the control board 3301. The electrical cable 3360 supplies power to operate the blower 3206 of the blower assembly 3202 and other components of the control board 3301.

Figure 105:
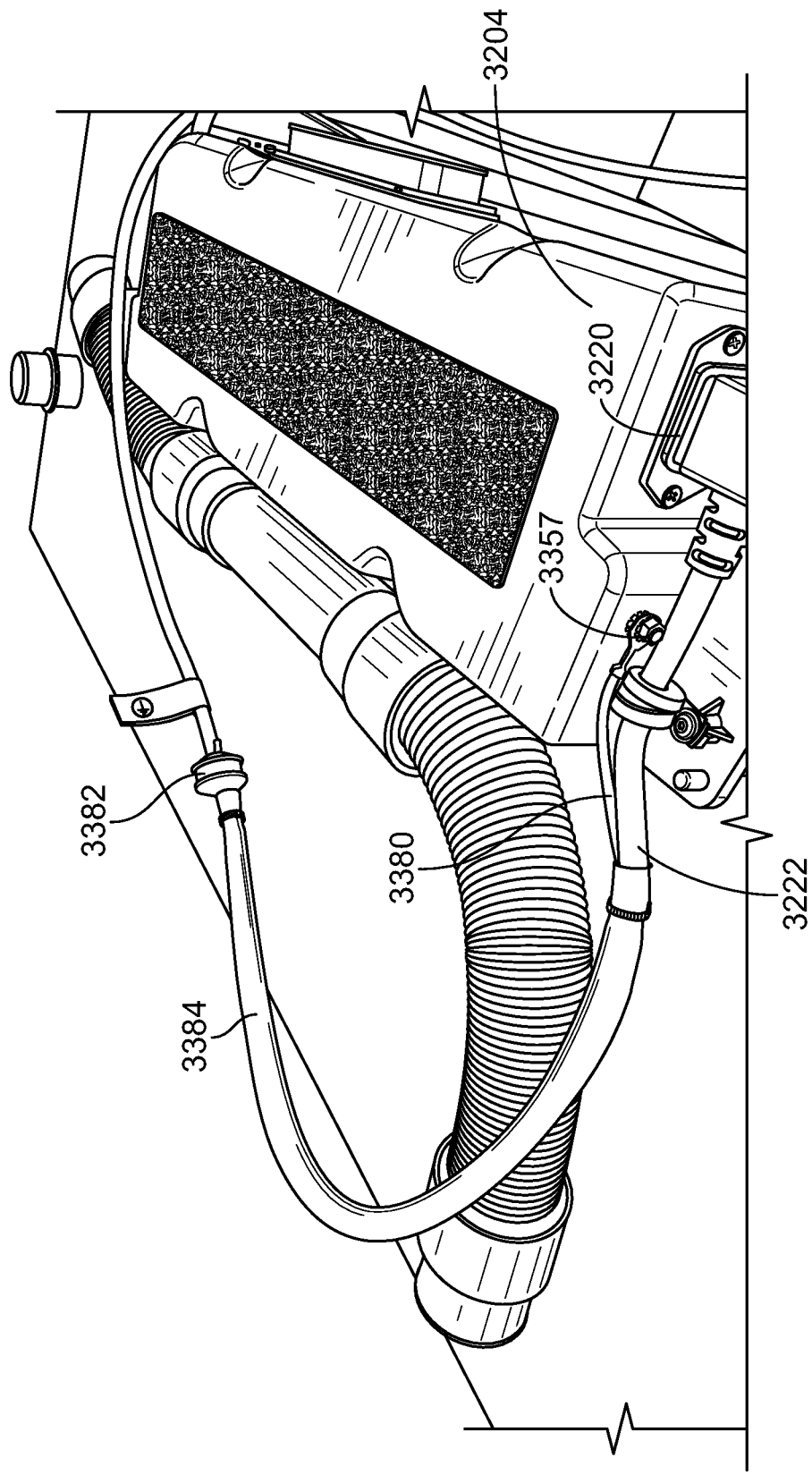
FIG. 105 is a side perspective view of a power cord and ground wire extending from the housing of the blower.
Figure 106:
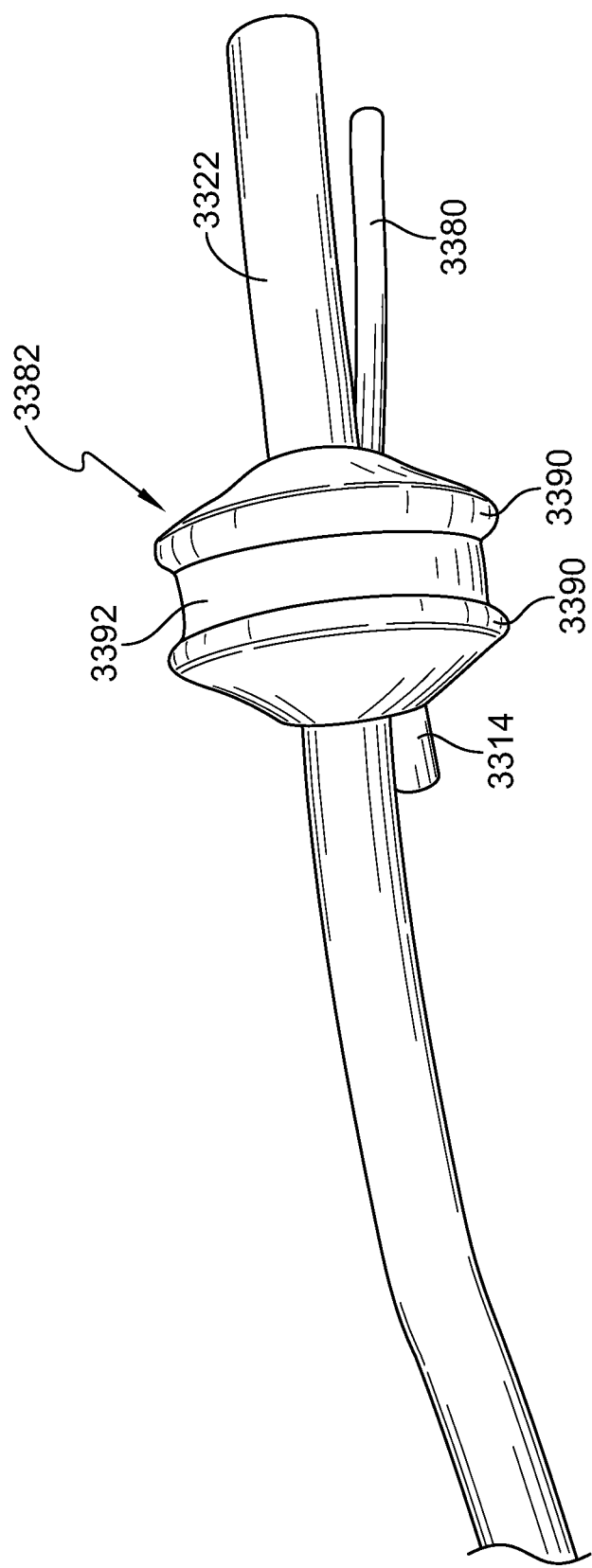
FIG. 106 is a side view of an overmold formed on the power cord.

Referring now to FIG. 105, a ground wire 3380 is joined to the bolt 3357 that extends through the housing 3204 and is routed along the power cord 3222. The ground wire 3380 and the power cord 3222 are sheathed together with a cover 3384 and extend to an overmold 3382. The power cord 3222 passes through the overmold 3382 and extends to the respective plug. As shown in FIG. 106, the ground wire 3380 is inserted into the overmold 3382 and coupled to the ground lug 3314, which extends from the other side of the overmold 3382. The ground lug 3314 provides access for a ground continuity test that runs high current through the ground line and monitors for maximum impedance. In some embodiments, an alligator clip is attached to the ground lug 3380 on the overmold 3382 and the power cord 3222 is plugged into a machine that measures the impedance.

The overmold 3382 includes a pair of ridges 3390 that form a notch 3392. That is, the notch 3392 is formed between the ridges 3390 and configured to retain a clamp or tie. As shown in FIG. 107, a somewhat frusto-conically shaped umbilical 3400 extends from the opening 2974 in the bottom cover 2950 of the mattress 3200. The power cord 3222 extends through the umbilical 3400. As shown in FIG. 108, the umbilical 3400 is pulled over the overmold 3382 and a clamp or tie 3402 is secured around an end of the umbilical and the overmold 3382. The tie 3402 is secured within the notch 3392 so that the ridges 3390 prevent movement of the tie 3402. By coupling the umbilical 3400 to the overmold 3382, the power cord 3222 is permitted to exit the mattress 3200, while maintaining a substantially fluid-proof seal that inhibits ingress of fluids into the mattress 3200.

Although this disclosure refers to multiple embodiments, it will be appreciated that aspects of each embodiment may be utilized with other embodiments described herein.

Although this disclosure refers to specific embodiments, it will be understood by those skilled in the art that various changes in form and detail may be made without departing from the subject matter set forth in the accompanying claims.

The invention claimed is:

1. A patient support apparatus comprising
a support surface including a topper, the topper configured to conduct air along a top face of the support surface so that heat and moisture from a patient lying on the support surface are drawn away from the top face of the support surface,
a pneumatic blower having an outlet port that couples to an inlet port of the support surface, the pneumatic blower conducting air through the inlet port to the topper,
an end of life indicator to indicate when the support surface has reached an end of a useful life of the support surface, and
a user input that is selected in connection with installation of the support surface at a healthcare facility to start the end of life indicator, wherein the end of life indicator is active in response to the pneumatic blower being coupled to the inlet port of the support surface and the end of life indicator is inactive in response to the pneumatic blower being uncoupled from the inlet port of the support surface.

2. The patient support apparatus of claim 1, wherein the end of life indicator is coupled to the support surface.

3. The patient support apparatus of claim 1, further comprising an interface on a side of the support surface, the interface including a dial to select a patient weight range, wherein a plurality of bladders within the support surface are inflated or deflated to adjust the support surface according to a patient weight range selected with the dial.

4. The patient support surface of claim 3, wherein the interface includes the end of life indicator.

5. The patient support surface of claim 3, including a plurality of patient weight ranges, wherein the dial is used to select one of the plurality of patient weight ranges.

6. The patient support surface of claim 5, wherein the plurality of patient weight ranges includes:
a first range,
a second range that is greater than the first range, and
a third range that is greater than the second range.

7. The patient support surface of claim 6, wherein:
when the first range is selected, the plurality of bladders is inflated to a first firmness,
when the second range is selected, the plurality of bladders is inflated to a second firmness, and
when the third range is selected, the plurality of bladders is inflated to a third firmness.

8. The patient support apparatus of claim 7, wherein:
the second firmness is greater than the first firmness, and
the third firmness is greater than the second firmness.

9. The patient support surface of claim 5, wherein the one of the plurality of patient weight ranges is selected based on a weight of the patient.

10. The patient support apparatus of claim 1, wherein the end of life indicator includes a timer that tracks how long the support surface has been in use.

11. The patient support apparatus of claim 1, wherein the end of life indicator includes a timer that tracks a total time that the support surface receives power.

12. The patient support apparatus of claim 1, wherein the end of life indicator includes a transmitter to transmit a signal indicating a remaining life span of the support surface to a user interface.

13. The patient support apparatus of claim 1, wherein the end of life indicator includes a sensor positioned below the support surface, the sensor determining when a patient is within a predetermined range of the sensor.

14. The patient support apparatus of claim 1, wherein the end of life indicator includes:
a sensor positioned below the support surface, and
a conductive material positioned below the topper, and
the sensor determining when the conductive material is within a predetermined range of the sensor.

15. The patient support apparatus of claim 1, further comprising:
a blower assembly configured to position within a cavity in the support surface, wherein the blower assembly includes a housing having a base that forms a vacuum chamber and a top cover sealed to the base to create a pressurized chamber, wherein the blower assembly is controlled by determining whether the blower assembly has a blockage based on a comparison of a monitored speed to a predetermined speed,
an x-ray cassette sleeve in the support surface,
a heel support mechanism built into a foot end of the support surface,
an electronics enclosure positioned within the support surface, wherein a wire extends from the electronics enclosure and is grounded, wherein an overmold is formed on the wire, wherein a terminal extends from the wire through the overmold to provide a ground test point, and
a support surface outlet port extending through the support surface and in fluid communication with an outlet port of the blower assembly, the support surface outlet port having a lip to facilitate preventing the ingress of fluids into the support surface outlet port,
wherein the patient support apparatus further comprises:
a flexible substrate positioned above the at least one support element,
a first conductive trace carried by the flexible substrate, and
a second conductive trace carried by the flexible substrate adjacent to the first conductive trace, wherein an open circuit is formed between the first conductive trace and the second conductive trace when the flexible substrate is dry, wherein the presence of a threshold amount of liquid on the flexible substrate forms a closed circuit with the first conductive trace and the second conductive trace due to the flexible substrate being wet.

16. The patient support apparatus of claim 1, wherein the support surface further comprises:
a therapeutic layer having a plurality of bladders that are configured to inflate,
a protective layer positioned over the therapeutic layer, and
a control unit that is configured to inflate the therapeutic layer, wherein, in a normal mode, the control unit is not coupled to the therapeutic layer and the therapeutic layer is deflated, and, in a therapeutic mode, the control unit is coupled to the therapeutic layer to inflate the therapeutic layer.

17. The patient support apparatus of claim 1, wherein the support surface further comprises:
at least one foam layer,
a manifold positioned having a plurality of apertures, and
a patient three dimensional spacer positioned on the manifold and configured to retain a patient,
wherein the blower assembly is configured to direct air flow into the manifold, wherein the airflow exits the manifold through the plurality of apertures and enters the patient three dimensional spacer.

* * * * *